US008853234B2

(12) United States Patent
Nagasawa et al.

(10) Patent No.: US 8,853,234 B2
(45) Date of Patent: *Oct. 7, 2014

(54) QUINOLONE ANALOGS AND METHODS RELATED THERETO

(75) Inventors: Johnny Yasuo Nagasawa, San Diego, CA (US); Fabrice Pierre, La Jolla, CA (US); Mustapha Haddach, San Diego, CA (US); Michael Schwaebe, San Diego, CA (US); Levan Darjania, Escondido, CA (US); Jeffrey P. Whitten, Santee, CA (US)

(73) Assignee: Senhwa Biosciences, Inc., New Taipei (TW)

( * ) Notice: Subject to any disclaimer, the term of this patent is extended or adjusted under 35 U.S.C. 154(b) by 162 days.

This patent is subject to a terminal disclaimer.

(21) Appl. No.: 13/043,956

(22) Filed: Mar. 9, 2011

(65) Prior Publication Data
US 2011/0218184 A1    Sep. 8, 2011

Related U.S. Application Data

(63) Continuation of application No. 12/245,619, filed on Oct. 3, 2008, now Pat. No. 7,928,100.

(60) Provisional application No. 60/978,042, filed on Oct. 5, 2007, provisional application No. 61/038,681, filed on Mar. 21, 2008, provisional application No. 61/045,933, filed on Apr. 17, 2008.

(51) Int. Cl.
| C07D 498/06 | (2006.01) |
| C07D 498/16 | (2006.01) |
| C07D 471/14 | (2006.01) |
| C07D 513/14 | (2006.01) |

(52) U.S. Cl.
CPC ............ *C07D 513/14* (2013.01); *C07D 498/06* (2013.01); *C07D 498/16* (2013.01); *C07D 471/14* (2013.01)
USPC ............................................ 514/287; 546/64

(58) Field of Classification Search
USPC ........................................... 514/287; 546/64
See application file for complete search history.

(56) References Cited

U.S. PATENT DOCUMENTS

| 4,559,157 | A | 12/1985 | Smith et al. | |
| 4,608,392 | A | 8/1986 | Jacquet et al. | |
| 4,820,508 | A | 4/1989 | Wortzman | |
| 4,938,949 | A | 7/1990 | Borch et al. | |
| 4,992,478 | A | 2/1991 | Geria | |
| 5,703,055 | A | 12/1997 | FelQner et al. | |
| 7,179,805 | B2 | 2/2007 | Grant, III et al. | |
| 7,928,100 | B2 * | 4/2011 | Nagasawa et al. | 514/218 |
| 2007/0099951 | A1 | 5/2007 | Dube et al. | |
| 2009/0093455 | A1 | 4/2009 | Nagasawa et al. | |
| 2010/0305136 | A1 * | 12/2010 | Nagasawa | 514/253.02 |

FOREIGN PATENT DOCUMENTS

| WO | WO-00/59882 | | 10/2000 | | |
| WO | WO-03/050107 | | 6/2003 | | |
| WO | WO-2004/014893 | | 2/2004 | | |
| WO | WO 2006/034113 A2 | | 3/2006 | | |
| WO | WO 2007/019295 A1 | | 2/2007 | | |
| WO | WO 2007/022474 A2 | | 2/2007 | | |
| WO | WO 2007/056113 A2 | | 5/2007 | | |
| WO | WO 2007/146813 A2 | | 12/2007 | | |
| WO | WO 2007/146831 | * | 12/2007 | ........... | C07D 471/14 |
| WO | WO 2008/060693 | * | 5/2008 | ........... | A61K 31/519 |
| WO | WO 2008/060693 A2 | | 5/2008 | | |
| WO | WO-2008/092681 | | 8/2008 | | |
| WO | WO 2008/131134 | * | 10/2008 | ........... | C07D 277/60 |
| WO | WO 2008/131134 A1 | | 10/2008 | | |

OTHER PUBLICATIONS

Ansell et al., Curr Opin Biotechnol (1996) 7:89-94.
Berge et al., J Pharm Sci (1977) 66: 1-19.
Gibson et al., Genome Res (1996) 6:995-1001.
Heid et al., Genome Res (1996) 6:986-994.
International Search Report for PCT/US08/78859, mailed on Dec. 24, 2008, 2 pages.
Jin and Pike, Mol Endocrinol (1996) 10:196-205.
Kriz et al., Analytical Chemistry (1995) 67:2142-2144.
Mei et al., AAPS Journal (2006) 8(3) Article 58.
Shea, Trends in Polymer Sci (1994) 2:166-173.
Vaickus, Crit Rev in *Oncoll Hermatol* (1991) 11 :267-297.
Vlatakis et al., Nature (1993) 361 :645-647.
Written Opinion of the International Searching Authority for PCT/US08/78859, mailed on Dec. 24, 2008, 7 pages.
Supplementary European Search Report and Search Opinion based on European Patent Application No. 08731934.9, mailed on Jul. 22, 2009.
Supplementary European Search Report and Search Opinion based on European Patent Application No. 08835342.0 mailed on Oct. 12, 2010.
European Patent Office Action based on European Patent Application No. 08835342.0 mailed on Nov. 23, 2011.
AU Office Action dated Jun. 28, 2013 for the application AU 2008308485.
CN Office Action dated Aug. 13, 2013 for the application CN 200880119635.6.
EP Office Action dated Aug. 16, 2013 for the application EP 08835342.0.
IL Office Action dated Aug. 9, 2013 for the application IL 204844.
JP Office Action dated Jan. 16, 2014 for the application JP 2010-528194.
MX Office Action dated Aug. 6, 2012 for the application MX/a/2010/003685.
NZ Office Action dated May 17, 2012 for the application NZ 584892.
RU Office Action dated Aug. 22, 2013 for the application RU 2010117225.

* cited by examiner

*Primary Examiner* — Erich A Leeser
(74) *Attorney, Agent, or Firm* — Cooley LLP

(57) ABSTRACT

The present invention provides novel quinolone compounds and pharmaceutical composition thereof which may inhibit cell proliferation and/or induce cell apoptosis. The present invention also provides methods of preparing such compounds and compositions, and methods of making and using the same.

18 Claims, 1 Drawing Sheet

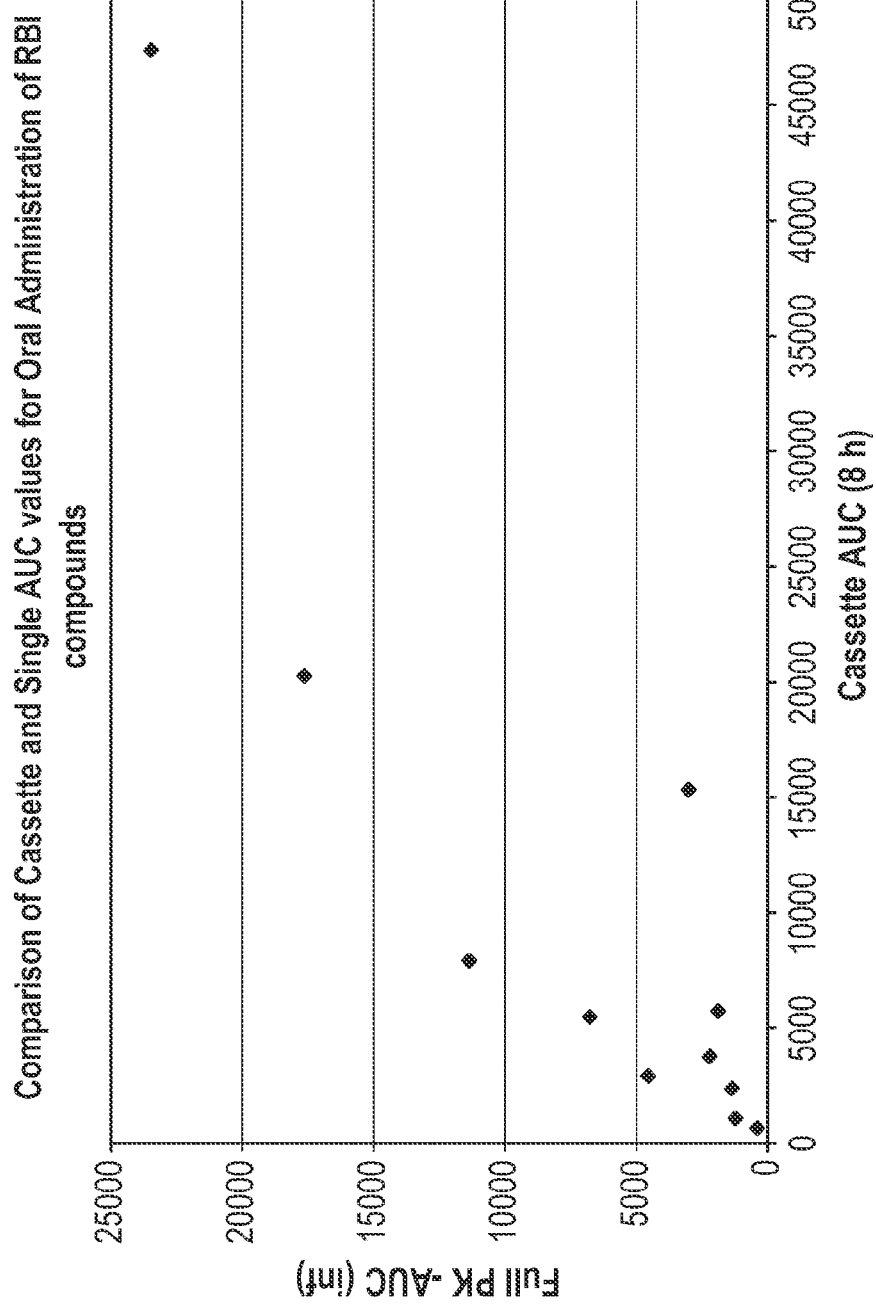

QUINOLONE ANALOGS AND METHODS RELATED THERETO

CROSS-REFERENCE TO RELATED APPLICATIONS

This application is a continuation of U.S. patent application Ser. No. 12/245,619, filed Oct. 3, 2008, which claims the benefit of priority from U.S. Ser. No. 60/978,042, filed Oct. 4, 2007; 61/038,681 filed Mar. 21, 2008; and 61/045,933, filed Apr. 17, 2008. The contents of these applications are hereby incorporated by reference in their entirety.

FIELD OF THE INVENTION

The invention relates to novel quinolone compounds and pharmaceutical compositions thereof. The invention also relates to methods of using and preparing such quinolone compounds and compositions to inhibit cell proliferation and/or induce cell apoptosis.

SUMMARY OF THE INVENTION

The present invention provides novel quinolone compounds and pharmaceutical compositions thereof which may inhibit cell proliferation and/or induce cell apoptosis. The present invention also provides methods of preparing such quinolone compounds and compositions, and methods of treating cell proliferation disorders by administering the same.

In one aspect, the present invention provides a compound of Formula (I),

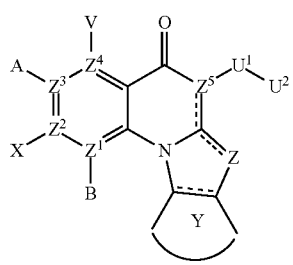

or a pharmaceutically acceptable salt or ester thereof;
wherein ----- indicates an optionally unsaturated bond;
each of B, X, A or V is absent if $Z^1$, $Z^2$, $Z^3$ and $Z^4$, respectively, is N; and
each of B, X, A and V is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$, when each of $Z^1$, $Z^2$, $Z^3$ and $Z^4$, respectively, is C;
Z is O, S, $CR^4{}_2$, $NR^4CR^4$, $CR^4NR^4$, $CR^4$, $NR^4$ or N;
each of $Z^1$, $Z^2$, $Z^3$ and $Z^4$ is independently C or N, provided any three N are non-adjacent;
$Z^5$ is C; or $Z^5$ may be N when Z is N;
Y is an optionally substituted 5-6 membered carbocyclic or heterocyclic ring;
$U^1$ is —C(=T)N(R)—, —C(=T)N(R)O—, —C(=T)-, —$SO_2N(R)$—, —$SO_2N(R)N(R^0)$—, —$SO_2$—, or —$SO_3$—, where T is O, S, or NH; or $U^1$ may be a bond when $Z^5$ is N or $U^2$ is H or —CN;
$U^2$ is H, —CN, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, V, A, X and B is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member;

with the proviso that when $Z^1$ is N, $Z^2$ and $Z^4$ are C, $Z^5$ is C, $U^1$ is —C(O)NH—, $U^2$ is -L-W, and L is an ethylene linker, one of V, A, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

In some embodiments, compounds of formula (I) are provided with the proviso that when each of $Z^1$, $Z^2$, $Z^4$ and $Z^5$ is C, $Z^3$ is C or N, $U^1$ is —C(O)NH—, $U^2$ is -L-W, and L is an ethylene linker, one of V, A, B, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

In another aspect, the invention provides a compound of Formula (II),

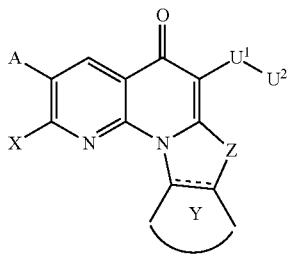

(II)

or a pharmaceutically acceptable salt or ester thereof;

wherein ----- indicates an optionally unsaturated bond;

each of A and X is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$;

Z is O, S, CR$^4{}_2$, NR$^4$CR$^4$, CR$^4$NR$^4$ or NR$^4$;

Y is an optionally substituted 5-6 membered carbocyclic or heterocyclic ring;

U$^1$ is —C(=T)N(R)—, —C(=T)N(R)O—, —C(=T)-, —SO$_2$N(R)—, —SO$_2$N(R)N(R$^0$)—, —SO$_2$—, or —SO$_3$—, where T is O, S, or NH; or U$^1$ may be a bond when U$^2$ is H or —CN;

U$^2$ is H, —CN, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or U$^2$ is —W, -L-W, -L-N(R)—W$^0$, A$^2$ or A$^3$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R$^4$ may be —W, -L-W or -L-N(R)—W$^0$;

each R and R$^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

W$^0$ is an optionally substituted 3-4 membered carbocyclic ring, or a C1-C6 alkyl group substituted with from 1 to 4 fluorine atoms;

provided one of U$^2$, A, and X is a secondary amine A$^2$ or a tertiary amine A$^3$, wherein the secondary amine A$^2$ is —NH—W$^0$, and the tertiary amine A$^3$ is a fully saturated and optionally substituted six-membered or seven-membered azacyclic ring optionally containing an additional heteroatom selected from N, O or S as a ring member, or the tertiary amine A$^3$ is a partially unsaturated or aromatic optionally substituted five-membered azacyclic ring optionally containing an additional heteroatom selected from N, O or S as a ring member;

with the proviso that when U$^1$ is —C(O)NH—, U$^2$ is -L-W, and L is an ethylene linker, one of A and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

In another aspect, the invention provides a compound of Formula (III),

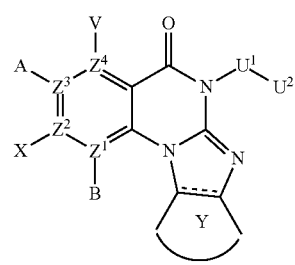

(III)

or a pharmaceutically acceptable salt or ester thereof;

wherein ----- indicates an optionally unsaturated bond; and

A, B, V, X, Z$^1$, Z$^2$, Z$^3$, Z$^4$, U$^1$, U$^2$ and Y are defined as for Formula (I).

In a further aspect, the invention provides a compound of Formula (IV),

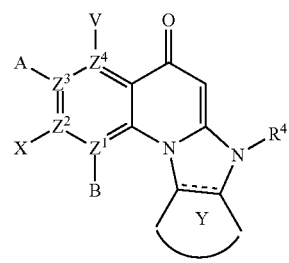

(IV)

or a pharmaceutically acceptable salt or ester thereof;

wherein ----- indicates an optionally unsaturated bond;

each of B, X, A or V is absent if Z$^1$, Z$^2$, Z$^3$ and Z$^4$, respectively, is N; and each of B, X, A and V is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$, when each of Z$^1$, Z$^2$, Z$^3$ and Z$^4$, respectively, is C;

each of Z$^1$, Z$^2$, Z$^3$ and Z$^4$ is independently C or N, provided any three N are non-adjacent;

Y is an optionally substituted 5-6 membered carbocyclic or heterocyclic ring;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

$R^4$ is —W, -L-W or -L-N(R)—$W^0$; and each R is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

In yet another aspect, the invention provides a compound of Formula (V),

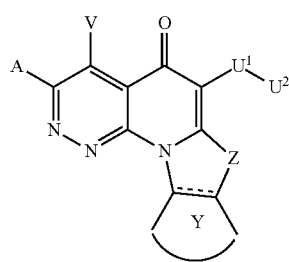

(V)

or a pharmaceutically acceptable salt or ester thereof; wherein:

----- indicates an optionally unsaturated bond;

A and V independently are H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;

Z is O, S, $CR^4_2$, $NR^4CR^4$, $CR^4NR^4$ or $NR^4$;

Y is an optionally substituted 5-6 membered carbocyclic or heterocyclic ring;

$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when $U^2$ is H or —CN;

$U^2$ is H, —CN, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W or -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, A, and V is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

In certain embodiments, compounds of Formula (V), one of $U^2$, A, and V is a secondary amine $A^2$ or a tertiary amine $A^3$, wherein the secondary amine $A^2$ is —NH—$W^0$, where $W^0$ is as defined for Formula (I), and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member. In certain embodiments, compounds of Formula (V) are provided with the proviso that when $U^1$ is —C(O)NH—, $U^2$ is -L-W, and L is an ethylene linker, one of A and V is an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

In another aspect, the invention includes a compound of Formula (VI),

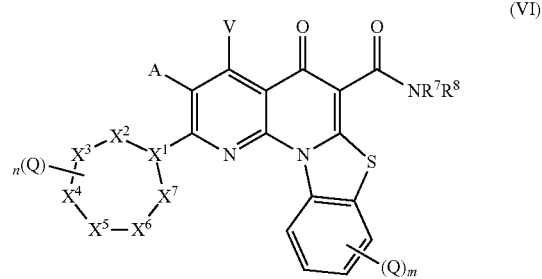

(VI)

or a pharmaceutically acceptable salt or ester thereof;
wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that: (i) zero, one or two of $X^2$, $X^3$, $X^4$, $X^5$, $X^6$ and $X^7$ are $NR^4$; (ii) when $X^1$ is N, both of $X^2$ and $X^7$ are not $NR^4$; (iii) when $X^1$ is N, $X^3$ and $X^6$ are not $NR^4$; and (iv) when $X^1$ is CH and two of $X^2$, $X^3$, $X^4$, $X^5$, $X^6$ and $X^7$ are $NR^4$, the two $NR^4$ are located at adjacent ring positions or are separated by two or more other ring positions;

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

In some embodiments of these compounds, $X^1$ is CH and two of $X^2$, $X^3$, $X^4$, $X^5$, $X^6$ and $X^7$ are $NR^4$. In some embodiments, $X^1$ is CH and one of $X^2$, $X^3$, $X^4$, $X^5$, $X^6$ and $X^7$ are $NR^4$. In other embodiments, $X^1$ is CH and none of $X^2$, $X^3$, $X^4$, $X^5$, $X^6$ and $X^7$ are $NR^4$. In yet other embodiments, $X^1$ is N and none of $X^2$, $X^3$, $X^4$, $X^5$, $X^6$ and $X^7$ are $NR^4$. In still other embodiments, $X^1$ is N and one of $X^4$ or $X^5$ is $NR^4$.

In another aspect, the invention provides a compound of Formula (VI'),

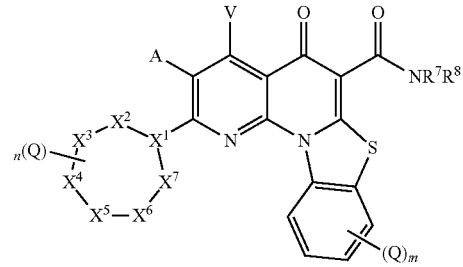

or a pharmaceutically acceptable salt or ester thereof;
wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that zero, one or two of $X^2$, $X^3$, $X^4$, $X^5$, $X^6$ and $X^7$ are $NR^4$;

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

In yet another aspect, the invention provides a compound of Formula (VII),

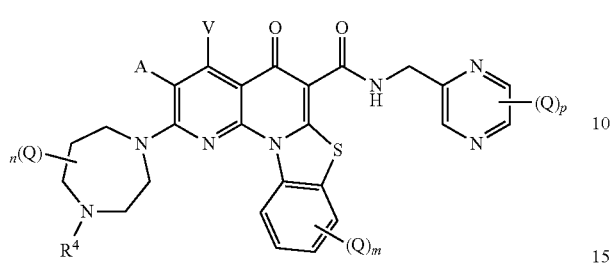

(VII)

or a pharmaceutically acceptable salt or ester thereof; wherein:

A and V independently are H, halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

each Q is independently halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R$^4$ may be —W, -L-W or -L-N(R)—W$^0$;

each R is independently H or C1-C6 alkyl;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W$^0$ is an optionally substituted 3-4 membered carbocyclic ring, or a C1-C6 alkyl group substituted with from 1 to 4 fluorine atoms.

In another, the invention provides a compound of Formula (VIII),

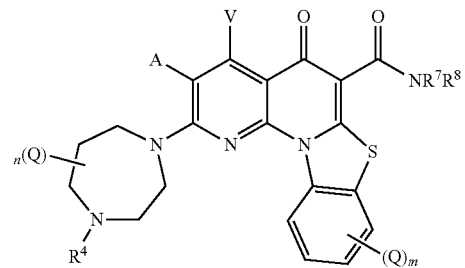

(VIII)

or a pharmaceutically acceptable salt or ester thereof; wherein:

A and V independently are H, halo, azido, —CN, —CF$_3$, —CONR$^1$R$^2$, —NR$^1$R$^2$, —SR$^2$, —OR$^2$, —R$^3$, —W, -L-W, —W$^0$, or -L-N(R)—W$^0$;

each Q is independently halo, azido, —CN, —CF$_3$, —CONR$^1$R$^2$, —SR$^2$, —OR$^2$, —R$^3$, —W, -L-W, —W$^0$, or -L-N(R)—W$^0$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R$^4$ may be —W, -L-W or -L-N(R)—W$^0$;

each R is independently H or C1-C6 alkyl;

R$^7$ is H and R$^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —NR$^7$R$^8$, R$^7$ and R$^8$ together with N may form an optionally substituted azacyclic ring, optionally containing an additional heteroatom selected from N, O and S as a ring member;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W$^0$ is an optionally substituted 3-4 membered carbocyclic ring, or a C1-C6 alkyl group substituted with from 1 to 4 fluorine atoms.

In a further aspect, the invention provides a pharmaceutical composition comprising a compound of Formula (I), Formula (II), Formula (III), Formula (IV), Formula (V), Formula (VI), Formula (VI'), Formula (VII), or Formula (VIII), as further described herein. In some embodiments, the pharmaceutical composition is suitable for oral administration. In other embodiments, the pharmaceutical composition is suitable for intravenous administration.

In a further aspect, the present invention provides a method for treating or ameliorating a cell proliferation disorder in a subject, said method comprising administering to a subject in need thereof a therapeutically effective amount of a compound of Formula (I), Formula (II), Formula (III), Formula (IV), Formula (V), Formula (VI), Formula (VI'), Formula (VII), or Formula (VIII), or a pharmaceutical composition thereof, as further described herein.

In some embodiments, the cell proliferative disorder is a tumor or cancer. In some embodiments, the subject is a human or an animal subject.

In another aspect, the invention provides a method for reducing or inhibiting cell proliferation, comprising contacting a system or a subject in need thereof with an effective amount of the compound of Formula (I), Formula (II), Formula (III), Formula (IV), Formula (V), Formula (VI), Formula (VI'), Formula (VII), or Formula (VIII), or a pharmaceutical composition thereof, thereby reducing or inhibiting cell proliferation.

In another aspect, the invention provides a method for reducing microbial titers and/or ameliorating a microbial infection, comprising contacting a system or a subject in need thereof with an effective amount of the compound of Formula (I), Formula (II), Formula (III), Formula (IV), Formula (V), Formula (VI), Formula (VI'), Formula (VII), or Formula (VIII), or a pharmaceutical composition thereof and optionally with an antimicrobial agent, thereby reducing microbial titers and/or ameliorating said microbial infection.

In some embodiments, the system is a cell or tissue, and the subject is a human or an animal subject. In some embodiments, the microbial titers and/or microbial infection are viral, bacterial or fungal titers.

In another aspect, the invention provides a method for inducing cell death and/or inducing apoptosis, comprising administering to a system or a subject in need thereof an effective amount of a compound of Formula (I), Formula (II), Formula (III), Formula (IV), Formula (V), Formula (VI), Formula (VI'), Formula (VII), or Formula (VIII), or a pharmaceutical composition thereof, and optionally with a procedure and/or a chemotherapeutic agent, thereby inducing cell death and/or inducing apoptosis.

In some embodiments, the system is a cell or tissue, and said subject is a human or an animal subject.

In compounds of Formula (I), each of B, X, A or V is absent if $Z^1$, $Z^2$, $Z^3$ and $Z^4$, respectively, is N; and each of B, X, A and V is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$ when each of $Z^1$, $Z^2$, $Z^3$ and $Z^4$, respectively, is C.

In compounds of Formula (I), each of $Z^1$, $Z^2$, $Z^3$ and $Z^4$ is independently C or N, provided any three N are non-adjacent. In preferred embodiments, at least one of $Z^1$, $Z^2$, $Z^3$ and $Z^4$ is N. In other preferred embodiments, at least two of $Z^1$, $Z^2$, $Z^3$ and $Z^4$ are N. In some embodiments of Formula (I), $Z^1$ is N and B is absent, or $Z^1$ is C and B is H or halogen. In certain embodiments, $Z^1$ is N and each of $Z^2$, $Z^3$ and $Z^4$ is C. In other embodiments, $Z^1$ and $Z^2$ are N, and $Z^3$ and $Z^4$ are C.

In compounds of Formula (I), Z is O, S, CR$^4{}_2$, NR$^4$CR$^4$, CR$^4$NR$^4$, CR$^4$, NR$^4$ or N. In frequent embodiments, Z is S or NR$^4$. In certain embodiments, Z is N when $Z^5$ is N. In some embodiments, the ring containing Z is a five-membered ring (e.g., when Z is O, S, CR$^4{}_2$, CR$^4$, NR$^4$ or N). In other embodiments where $Z^5$ is N, the ring containing Z is a six-membered ring (e.g., when Z is NR$^4$CR$^4$, or CR$^4$NR$^4$). In certain embodiments, Z is S.

In frequent embodiments of Formula (I), $Z^5$ is C. In certain embodiments, $Z^5$ may be N when Z is N.

Y in compounds of Formula (I) is an optionally substituted 5-6 membered carbocyclic or heterocyclic ring. In certain embodiments, Y is an optionally substituted phenyl, pyridyl or naphthyl ring system.

Examples of optional substituents when present on Y include one or more $C_{1-6}$ alkyl, $C_{1-6}$ heteroalkyl, $C_{6-12}$ arylalkyl, $C_{6-12}$ heteroarylalkyl, halo, —CN, —NO$_2$, azido, —CF$_3$, —OCF$_3$, or —OR', —SR', —NR'$_2$, —COOR', or —CONR'$_2$, where each R' is independently H or $C_{1-4}$ alkyl, or wherein the two R' groups on any NR'$_2$ may cyclize to form a 5-6 membered azacyclic ring. Y may also be optionally substituted by an optionally substituted carbocyclic or heterocyclic ring, which ring may be saturated, partially unsaturated, or aromatic.

In compounds of Formula (I), $U^1$ is —C(=X)N(R)—, —C(=X)N(R)O—, —C(=X)—, —SO$_2$N(R)—, —SO$_2$N(R)N(R)—, —SO$_2$—, or —SO$_3$—, where X is O, S, or NH, where each R is independently H or C1-C6 alkyl.

In frequent embodiments, $U^1$ is —C(O)N(R)—. In some such embodiments, R is H or $C_{1-4}$ alkyl. In specific embodiments, R is H or methyl. In certain embodiments, $U^1$ is —C(O)— or —SO$_2$N(R)—, where R is H or methyl. In other embodiments, $U^1$ may be a bond when $Z^5$ is N, or $U^1$ may be a bond when $U^2$ is H or —CN.

In compounds of Formula (I), $U^2$ is H, —CN, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-6 membered carbocyclic or heterocyclic ring; or $U^2$ is —W, -L-W, -L-N(R)—W$^0$, A$^2$ or A$^3$.

In compounds of Formula (I), in each —NR$^1$R$^2$, R$^1$ and R$^2$ together with N may form an optionally substituted azacyclic ring, optionally containing an additional heteroatom selected from N, O and S as a ring member.

In compounds of Formula (I), R$^1$ is H or C1-C6 alkyl, optionally substituted with one or more halogens, or =O. Often, R$^1$ is H or methyl.

R$^2$ in compounds of Formula (I) is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-6 membered carbocyclic or heterocyclic ring.

In compounds of Formula (I), R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, or an optionally substituted 3-6 membered carbocyclic or heterocyclic ring; and wherein the alkyl and alkenyl moieties, and their corresponding heteroforms, may be optionally substituted with =O.

In compounds of Formula (I), each R$^4$, where present, is independently H, or optionally substituted C1-C6 alkyl; or R$^4$ may be —W, -L-W or -L-N(R)—W$^0$;

L in compounds of Formula (I) is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl.

In compounds of Formula (I), W is an optionally substituted 4-7 membered saturated, partially unsaturated or aromatic azacyclic ring, optionally containing an additional heteroatom selected from N, O and S as a ring member, wherein the ring W may be connected through the bond labeled $R^4$, or through the linking group -L- or -L-N(R)— through any position on the azacyclic ring. In compounds of Formula (I), $W^0$ is an optionally substituted 3-4 membered carbocyclic ring, or a C1-C6 alkyl group substituted with from 1 to 4 fluorine atoms.

In certain embodiments, W contains at least one double bond. For example, W may be an optionally substituted imidazole, imidazoline, pyrrole, pyrroline, pyridine, dihydropyridine, tetrahydropyridine, pyrimidine, pyrazine, or pyridazine ring.

In other embodiments, W is an optionally substituted saturated azacyclic ring. For example, W may be an optionally substituted azetidine, pyrrolidine, piperidine, piperazine, morpholine, thiomorpholine, homopiperazine, homomorpholine, or homothiomorpholine ring.

In certain embodiments of Formula (I), $U^2$ is —W or -L-W, where W is an optionally substituted 4-7 membered azacyclic ring, optionally containing an additional heteroatom selected from N, O, and S as a ring member.

In some such embodiments, W is a fully saturated and optionally substituted six-membered or 7-membered azacyclic ring, optionally containing one additional heteroatom selected from N, O, and S as a ring member. In specific embodiments, W is an optionally substituted piperidine, piperazine, morpholine, thiomorpholine, or homopiperazine ring.

In other embodiments, W is an optionally substituted partially unsaturated or aromatic five-membered azacyclic ring, optionally containing one additional heteroatom selected from N, O and S as a ring member. In specific embodiments, W is an optionally substituted pyrrole, pyrroline, imidazole, imidazoline, pyrazole, pyrazoline, thiazole, thiazoline, oxazole, oxazoline, isoxazole, or isoxazoline ring.

In further embodiments, W is an optionally substituted aromatic six-membered azacyclic ring, optionally containing one or two additional N atoms as a ring member. In specific embodiments, W is an optionally pyridine, pyrimidine, pyrazine, pyridazine ring or triazine.

In other embodiments of Formula (I), $U^2$ is a cyclopropyl ring or is -L-N(R)—$W^0$, where L, R and $W^0$ are as defined above. In certain embodiments, L is a C1-C6 alkylene or heteroalkylene linker and R is H or methyl. In specific embodiments, $W^0$ is a cyclopropyl or cyclobutyl ring, or is a C1-C4 alkyl group substituted with 1 to 4 fluorine atoms.

In compounds of Formula (I), when $Z^1$ is N, $Z^2$ and $Z^4$ are C, $Z^5$ is C, $U^1$ is —C(O)NH—, $U^2$ is -L-W, and L is an ethylene linker, one of V, A, and X is independently an optionally substituted aryl or heteroaryl ring, or an optionally substituted 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl. In specific embodiments, the aryl or heteroaryl ring at V, A, or X is an optionally substituted phenyl, pyridinyl, pyrimidinyl, thiophenyl, oxazolyl, isoxazolyl or indolyl ring. In specific embodiments, the 7-membered azacyclic ring at V, A, or X is an optionally substituted homopiperazine ring.

In some embodiments, compounds of formula (I) are provided with the proviso that when each of $Z^1$, $Z^2$, $Z^4$ and $Z^5$ is C, $Z^3$ is C or N, $U^1$ is —C(O)NH—, $U^2$ is -L-W, and L is an ethylene linker, one of V, A, B, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

In compounds of Formula (I), at least one of $U^2$, V, A, X and B is a secondary amine $A^2$ or a tertiary amine $A^3$. The secondary amine $A^2$ is —NH—$W^0$, where $W^0$ is as defined above. The tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic five-membered azacyclic ring optionally containing an additional heteroatom selected from N, O or S as a ring member, and which may be optionally substituted.

For example, in certain embodiments, $A^3$ may be an optionally substituted piperidine, piperazine, homopiperazine, morpholine, thiomorpholine, homomorpholine, or homothiomorpholine ring. In other embodiments, $A^3$ may be an optionally substituted pyrrole, pyrroline, imidazole, imidazoline, pyrazole, pyrazoline, thiazole, thiazoline, oxazole, oxazoline, isoxazole, or isoxazoline ring.

In a preferred embodiment of Formula (I), $Z^1$ is N, B is absent, and each of $Z^2$-$Z^5$ is C.

In another preferred embodiment of Formula (I), $U^2$ comprises an optionally substituted 3-pyrroline ring.

In another preferred embodiment of Formula (I), $U^2$ comprises an optionally substituted imidazole ring.

In a further preferred embodiment of Formula (I), $U^2$ comprises a cyclopropyl ring.

In still other preferred embodiments of Formula (I), $U^2$ comprises an optionally substituted pyrazine ring.

In other preferred embodiments of Formula (I), X is a tertiary amine $A^3$.

In further preferred embodiments of Formula (I), A is H or fluoro.

In certain preferred embodiments, the compound of Formula (I) comprises two or more preferred features, sometimes three or more preferred features.

The same groups described herein for A, B, X, V, Z, $Z^1$, $Z^2$, $Z^3$, $Z^4$, $Z^5$, $U^1$, $U^2$ and Y in compounds of Formula (I) are also suitable for compounds of Formula (II), (III), (IV), (V), (VI), (VI'), (VII), or (VIII).

In compounds of Formula (II), each of A, X, $U^1$, $U^2$ and Y are defined as for Formula (I).

In certain embodiments of Formula (II), one of A or X is substituted with a secondary amine $A^2$ or a tertiary amine $A^3$, as defined herein. In preferred embodiments, one of A or X is a tertiary amine $A^3$. In particularly preferred embodiments, one of A or X is a tertiary amine $A^3$, wherein $A^3$ is selected from the group consisting of optionally substituted morpholine, thiomorpholine, pyrrolidine, piperazine, homopiperazine, homomorpholine, or homothiomorpholine.

In other embodiments of Formula (II), one of A or X is halogen. In some such embodiments, one of A or X is preferably fluoro or chloro.

In compounds of Formula (II), Z may be O, S, $CR^4_2$, or $NR^4$, where $R^4$ is defined as for Formula (I). In a certain embodiments, Z is S or $NR^4$, where $R^4$ is H, or a C1-C6 alkyl. In other embodiments, $R^4$ may be —W, -L-W or -L-N(R)$W^0$, where W, L, R and $W^0$ are as defined for Formula (I). In frequent embodiments, Z is S.

In certain embodiments of Formula (II), $U^1$ is —C(O)N(R)— or —$SO_2$N(R)—, where R is H or $C_{1-4}$ alkyl, preferably methyl. In some such embodiments, $U^2$ is cyclopropyl, or is be —W, -L-W, -L-N(R)$W^0$.

In frequent embodiments, $U^1$ is —C(O)N(R)— and $U^2$ is -L-W or -L-N(R)$W^0$, where L is a C1-C4 alkylene group, each R is independently H or methyl, and W and $W^0$ are as further defined herein. In other embodiments, $U^2$ is $A^2$ or $A^3$.

In a preferred embodiment of Formula (II), Z is S.

In a preferred embodiment of Formula (II), Y is an optionally substituted phenyl ring.

In another preferred embodiment of Formula (II), $U^2$ comprises an optionally substituted 3-pyrroline ring.

In another preferred embodiment of Formula (II), $U^2$ comprises an optionally substituted imidazole ring.

In a further preferred embodiment of Formula (II), $U^2$ comprises a cyclopropyl ring.

In still other preferred embodiments of Formula (II), $U^2$ comprises an optionally substituted pyrazine ring.

In other preferred embodiments of Formula (II), $U^2$ is -L-W or -L-N(R)$W^0$, wherein L is a C1-C4 alkylene group, each R is independently H or methyl, and W and $W^0$ are defined as further described herein. In particularly preferred embodiments, W is an optionally substituted five- or six-membered partially unsaturated or aromatic azacyclic ring, and $W^0$ is a cyclopropyl group. In specific embodiments, W is an optionally substituted five- or six-membered partially unsaturated or aromatic azacyclic ring selected from the group consisting of 3-pyrroline, imidazole, pyrazole, pyridine, pyrimidine, pyrazine, and pyridazine.

In other preferred embodiments of Formula (II), X is a tertiary amine $A^3$. In particularly preferred embodiments, X is a tertiary amine $A^3$, wherein $A^3$ is selected from the group consisting of optionally substituted morpholine, thiomorpholine, piperidine, piperazine, homopiperazine, homomorpholine, and homothiomorpholine. Sometimes $A^3$ is selected from the group consisting of optionally substituted imidazole, imidazoline, and pyrroline.

In further preferred embodiments of Formula (II), A is H or fluoro.

In certain particularly preferred embodiments, the compound of Formula (II) comprises two or more preferred features, sometimes three or more preferred features.

In compounds of Formula (III), each of A, B, V, X, $Z^1$, $Z^2$, $Z^3$, $Z^4$, $U^1$, $U^2$ and Y are defined as for Formula (I).

In certain embodiments of Formula (III), $U^1$ is a bond and $U^2$ is -L-W, where L and W are as defined for Formula (I). In preferred embodiments, L is an optionally substituted C1-C6 alkylene or heteroalkylene linker and W is a 5-6 membered saturated, unsaturated or aromatic azacyclic ring, optionally containing an additional heteroatom selected from N, O and S, which ring may be optionally substituted. In specific embodiments, W is an optionally substituted pyrrolidine, pyrroline, imidazole, imidazoline, piperidine, pyridine, piperazine, pyrimidine, pyridazine, morpholine or thiomorpholine ring.

In other embodiments of Formula (III), $U^1$ is a bond and $U^2$ is -L-N(R)—$W^0$, where L, R and $W^0$ are as defined for Formula (I). In preferred embodiments, L is an optionally substituted C1-C6 alkylene or heteroalkylene linker, and R is H or methyl. In some such embodiments, $W^0$ is a cyclopropyl or cyclobutyl ring. In further embodiments, $W^0$ is a C1-C4 alkyl group substituted with from 1 to 4 fluorine atoms.

In certain embodiments of Formula (III), $Z^1$ is N, and each of $Z^2$, $Z^3$ and $Z^4$ is C. In some such embodiments, at least one of A and X is a secondary amine $A^2$ or a tertiary amine $A^3$ and V is H.

In preferred embodiments of Formula (III), $Z^1$ is N, B is absent, and each of $Z^2$-$Z^4$ is C.

In another preferred embodiment of Formula (III), $U^1$ is a bond and $U^2$ is -L-W, wherein W is an optionally substituted pyrrolidine or pyrroline ring.

In another preferred embodiment of Formula (III), $U^1$ is a bond and $U^2$ is -LN(R)$W^0$, wherein $W^0$ is a cyclopropyl ring.

In another preferred embodiment of Formula (III), $U^1$ is a bond and $U^2$ is -LN(R)$W^0$, wherein $W^0$ is a C1-C6 alkyl substituted with from 1 to 4 fluorine atoms.

In another preferred embodiment of Formula (III), X is a tertiary amine $A^3$.

In a further preferred embodiment of Formula (III), A is H or fluoro.

In certain particularly preferred embodiments, the compound of Formula (III) comprises two or more preferred features, sometimes three or more preferred features.

In compounds of Formula (IV), $R^4$ is —W, -L-W or -L-N(R)—$W^0$, and each of A, B, V, X, $Z^1$, $Z^2$, $Z^3$, $Z^4$, Y, L, W, R and $W^0$ are defined as for Formula (I).

In some embodiments of Formula (IV), $Z^1$ is N, and each of $Z^2$, $Z^3$ and $Z^4$ is C. In some such embodiments, at least one of A and X is $A^2$ or $A^3$, and V is H or halo. In some embodiments, X is $A^3$, and each of A and V is independently H or halo.

In specific embodiments of Formula (IV), L is an optionally substituted C1-C6 alkylene or heteroalkylene linker. In specific embodiments, $R^4$ is -L-W, where W is an optionally substituted pyrrolidine, pyrroline, imidazole, imidazoline, piperidine, pyridine, piperazine, pyrimidine, pyridazine, morpholine or thiomorpholine ring.

In other embodiments, $R^4$ is -L-N(R)—$W^0$ and $W^0$ is a cyclopropyl or cyclobutyl ring or a C1-C4 alkyl group substituted with from 1 to 4 fluorine atoms.

In a preferred embodiment of Formula (IV), $Z^1$ is N, B is absent, and each of $Z^2$-$Z^4$ is C.

In another preferred embodiment of Formula (IV), $R^4$ is -L-W, wherein W is an optionally substituted pyrrolidine or pyrroline ring.

In another preferred embodiment of Formula (IV), $R^4$ is -LN(R)$W^0$, wherein $W^0$ is a cyclopropyl ring.

In another preferred embodiment of Formula (IV), $R^4$ is -LN(R)$W^0$, wherein $W^0$ is a C1-C6 alkyl substituted with from 1 to 4 fluorine atoms.

In other preferred embodiments of Formula (IV), Y is an optionally substituted phenyl ring.

In other preferred embodiments of Formula (IV), X is a tertiary amine $A^3$.

In further preferred embodiments of Formula (IV), A is H or fluoro.

In certain particularly preferred embodiments, the compound of Formula (IV) comprises two or more preferred features, sometimes three or more preferred features.

In certain embodiments of Formula (V), A is a secondary amine $A^2$, or a tertiary amine $A^3$, wherein the secondary amine $A^2$ is —NH—$W^0$, where $W^0$ is as defined for Formula (I), and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

In certain embodiments of Formula (V), $U^1$ is —CON(R)— and $U^2$ is cycloalkyl, —W, -L-W, or LN(R)$W^0$, wherein each R is independently H or C1-C6 alkyl, and W, L and $W^0$ are defined above.

In a preferred embodiment of Formula (V), $U^1$ is —CON(R)—, R is H or $C_{1-4}$ alkyl, preferably methyl; and $U^2$ is -L-W, where L is a C1-C4 alkylene linker and W is an optionally substituted 4-7 membered azacyclic ring, optionally containing an additional heteroatom selected from N, O and S as a ring member. In some such embodiments, W is an optionally substituted pyrrolidine, pyrroline, or imidazole ring.

In other preferred embodiments, $U^1$ is —CON(R)—, R is H or $C_{1-4}$ alkyl, preferably methyl, and $U^2$ is a C1-C6 alkyl of C1-C6 heteroalkyl group, optionally substituted by an optionally substituted carbocyclic or heterocyclic ring. In some such embodiments, the heterocyclic ring is an optionally substituted pyridine, pyrazine, pyrimidine, piperidine, pyrrolidine or imidazole ring.

In other preferred embodiments of Formula (V), $U^1$ is —C(O)— and $U^2$ is W, where W is defined as above.

In certain preferred embodiments of Formula (V), A is a tertiary amine $A^3$. In some such embodiments, A is an optionally substituted morpholine, thiomorpholine, piperazine or homopiperazine ring.

In a preferred embodiment of Formula (V), V is H or halo.

In another preferred embodiment of Formula (V), Z is S or N(Me).

In another preferred embodiment of Formula (V), Y is an optionally substituted phenyl ring.

In certain embodiments of Formula (V), when $U^1$ is —C(O)NH—, $U^2$ is -L-W, and L is an ethylene linker, one of A and V is an optionally substituted aryl, heteroaryl, or 7-membered azacyclic ring, optionally containing an additional heteroatom selected from N, O an S as a ring member, if W is pyrrolidin-1-yl, N-methyl-pyrrolidin-2-yl, piperidin-1-yl or morpholin-1-yl.

In certain particularly preferred embodiments, the compound of Formula (V) comprises two or more preferred features, sometimes three or more preferred features.

In some embodiments of Formula (VI), $X^1$ is CH or N, and $X^2, X^3, X^4, X^5, X^6$ and $X^7$ independently are $NR^4$, $CH_2$, CHQ or $C(Q)_2$, provided that zero, one or two of $X^2, X^3, X^4, X^5, X^6$ and $X^7$ are $NR^4$.

In some embodiments of Formula (VI), A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$. In frequent embodiments, A and V are independently H or halo.

In some embodiments of Formula (VI), each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$. It will be understood that each position optionally substituted by a group Q is substituted by hydrogen when m or n is 0. In preferred embodiments, each of m or n is 0 or 1.

In certain preferred embodiments of Formula (VI), $X^1$ is N, one or two of $X^3, X^4, X^5$ and $X^6$ independently is/are $NR^4$, and the remaining $X^2, X^3, X^4, X^5, X^6$ and $X^7$ independently are $CH_2$.

In certain preferred embodiments of Formula (VI), $X^1$ is N; one of $X^3, X^4, X^5$ and $X^6$ is $NR^4$; the remaining $X^3, X^4, X^5, X^6$ and $X^2$ and $X^7$ independently are $CH_2$.

In certain preferred embodiments, $X^1$ is N, and one of $X^4$ or $X^5$ is $NR^4$ and the other is $CH_2$, and $X^2, X^3$, and $X^6$ are $CH_2$.

In some embodiments of formula (VI), $R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring. In other embodiments, $R^7$ and $R^8$ together with N may form an optionally substituted azacyclic ring, optionally containing an additional heteroatom selected from N, O and S as a ring member.

In certain preferred embodiments of Formula (VI), $R^7$ is H and $R^8$ is selected from —$CH_2CH_2OCH_3$, —$CH_2CH_2OCH(CH_3)_2$, —$CH_2$-(pyridine), —$CH_2$-(methyl pyridine), —$CH_2$-(methyl pyrimidine), —$CH_2$-(methyl pyrimidine), —$CH_2$-(pyrazine), —$CH_2$-(methyl pyrazine), —$CH_2$-(imidazole); —$CH_2$—(N-methyl imidazole); —$CH_2$-(pyrrolidine); —$CH_2$—(N-methyl pyrrolidine); —$CH_2$-(thiazole); and $CH_2$—(N-methyl thiazole).

In some preferred embodiments of Formula (VI), $R^7$ and $R^8$ together with N in —$NR^7R^8$ form an optionally substituted morpholine, thiomorpholine, piperidine or piperazine ring.

In certain particularly preferred embodiments, the compound of Formula (VI) comprises two or more preferred features, sometimes three or more features.

The embodiments described herein for formula (VI) are also applicable to formula (VI').

In some embodiments of Formula (VII), A and V independently are H, halo, azido, —CN, —$CF_3$, —$CONR^1R^2$, —$NR^1R^2$, —$SR^2$, —$OR^2$, —$R^3$, —W, -L-W, $W^0$, or -L-N(R)—$W^0$, where $R^1$, $R^2$, —$R^3$, —W, -L, —$W^0$, and R are defined as above.

In certain embodiments of Formula (VII), A and V are independently H and halo, preferably fluoro. In some preferred embodiments, A and V are each H. In other preferred embodiments, A is fluoro and V is H.

In some embodiments of Formula (VII), each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$. It will be understood that each position optionally substituted by a group Q is substituted by hydrogen when m, n or p is 0.

In a preferred embodiment, each of m and n is 0 or 1.

In another preferred embodiment of Formula (VII), m and n are each 0.

In other preferred embodiments of Formula (VII), p is 0 or 1.

In a particularly preferred embodiment, m and n are 0, p is 1, and Q is C1-C4 alkyl, preferably methyl.

In a preferred embodiment of Formula (VII), $R^4$ is H, or C1-C4 alkyl or C3-C7 cycloalkyl. In a particularly preferred embodiment, $R^4$ is methyl. In another preferred embodiment, $R^4$ is H.

In certain particularly preferred embodiments, the compound of Formula (VII) comprises two or more preferred features, sometimes three or more preferred features.

In some embodiments of Formula (VIII), A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$ where $R^1$, $R^2$, —$R^3$, —W, -L, —$W^0$, and R are defined as above.

In certain embodiments, A and V are independently H and halo, preferably fluoro. In some preferred embodiments, A and V are each H. In other preferred embodiments, A is fluoro and V is H.

In some embodiments of Formula (VIII), each Q is independently halo, azido, —CN, —$CF_3$, —$CONR^1R^2$, —$NR^1R^2$, —$SR^2$, —$OR^2$, —$R^3$, —W, -L-W, —$W^0$, or L-N(R)—$W^0$. It will be understood that each position optionally substituted by a group Q is substituted by hydrogen when m, n or p is 0.

In a preferred embodiment, each of m and n is 0 or 1.

In another preferred embodiment of Formula (VIII), m and n are each 0.

In a preferred embodiment, m and n are 0.

In a preferred embodiment of Formula (VIII), $R^4$ is C1-C4 alkyl or C3-C7 cycloalkyl. In a particularly preferred embodiment, $R^4$ is methyl. In another preferred embodiment, $R^4$ is H.

In some embodiments of formula (VIII), $R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring. In some such embodiments, $R^8$ is a $C_{1-4}$ alkyl substituted with an optionally substituted aromatic heterocyclic ring. In certain preferred embodiments, $R^8$ is a $C_{1-4}$ alkyl substituted with an optionally substituted imidazole, pyridine, pyrimidine, pyridazine, or pyrazine ring. In other embodiments, $R^7$ and $R^8$ together with N may form an optionally substituted azacyclic ring, optionally containing an additional heteroatom selected from N, O and S as a ring member.

In some embodiments, $R^7$ is H and $R^8$ is a $C_{1-4}$ alkyl substituted with an optionally substituted aromatic heterocyclic ring. In some such embodiments, the optionally substituted aromatic heterocyclic ring is selected from pyridine, pyrimidine, pyrazine, imidazole, pyrrolidine, and thiazole.

In certain preferred embodiments of Formula (VIII), $R^7$ is H and $R^8$ is selected from —$CH_2CH_2OCH_3$, —$CH_2CH_2OCH(CH_3)_2$, —$CH_2$-(pyridine), —$CH_2$-(methyl pyridine), —$CH_2$-(methyl pyrimidine), —$CH_2$-(methyl pyrimidine), —$CH_2$-(pyrazine), —$CH_2$-(methyl pyrazine), —$CH_2$-(imidazole); —$CH_2$—(N-methyl imidazole); —$CH_2$-(pyrrolidine); —$CH_2$—(N-methyl pyrrolidine); —$CH_2$-(thiazole); and $CH_2$—(N-methyl thiazole).

In some preferred embodiments of Formula (VIII), $R^7$ and $R^8$ together with N in —$NR^7R^8$ form an optionally substituted morpholine or piperazine ring.

In certain particularly preferred embodiments, the compound of Formula (VIII) comprises two or more preferred features, sometimes three or more preferred features.

Preferred embodiments of the present invention include the compounds shown in Tables 1-8 and throughout the Examples.

In certain particularly preferred embodiments, compound has one of the following structures:

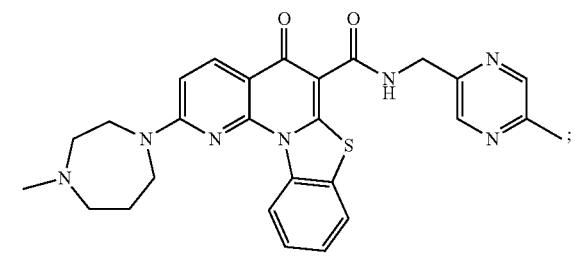

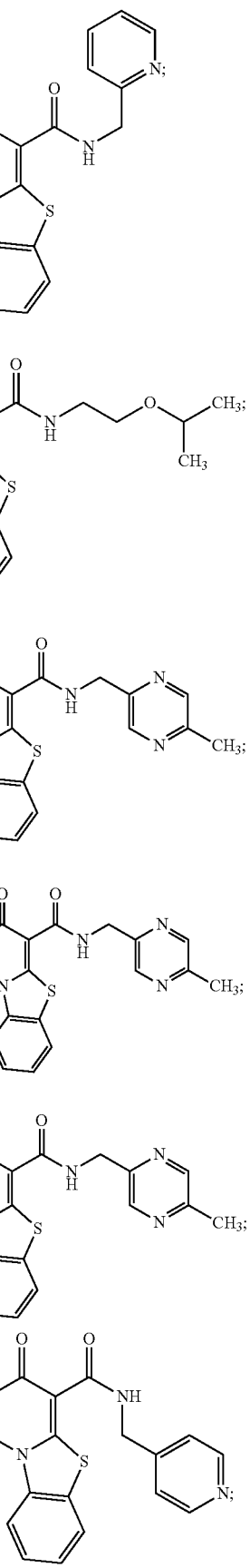

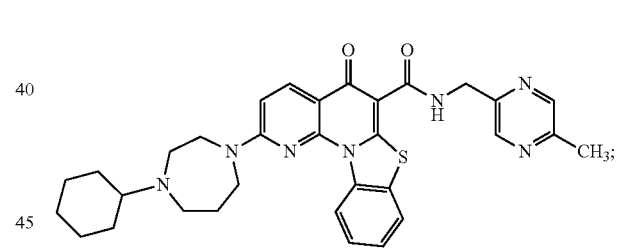

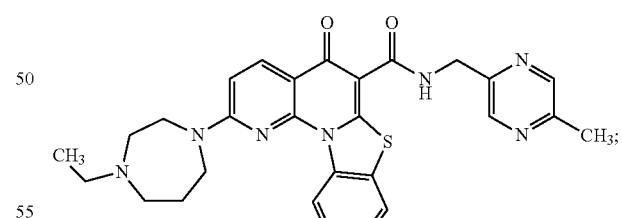

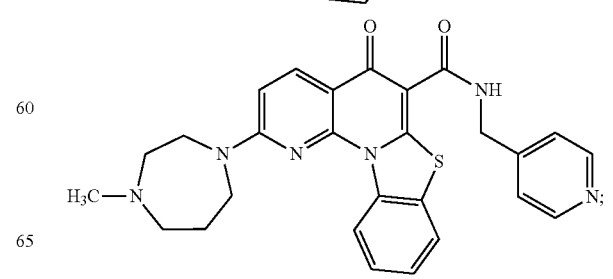

21
-continued
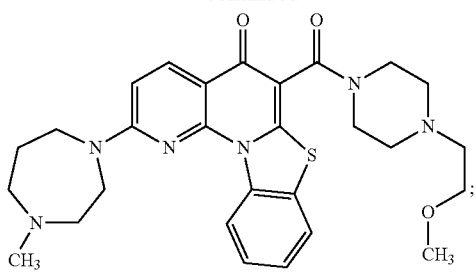
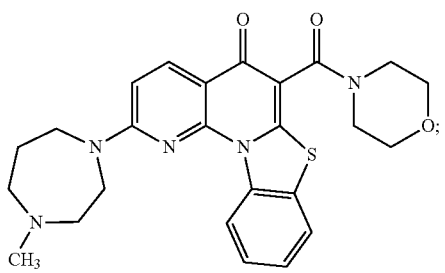
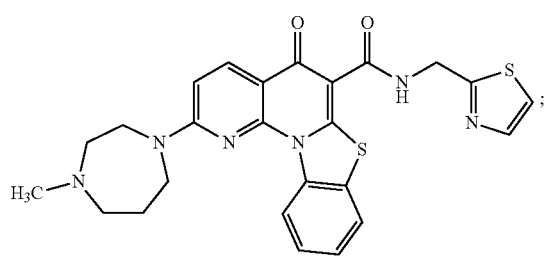
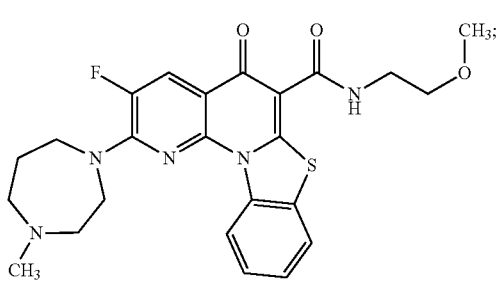
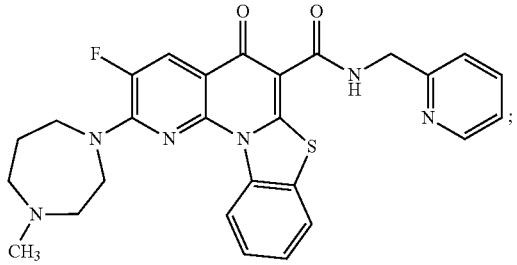
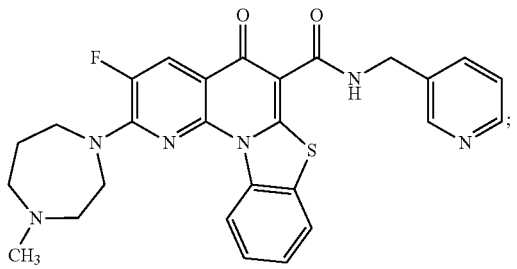
22
-continued
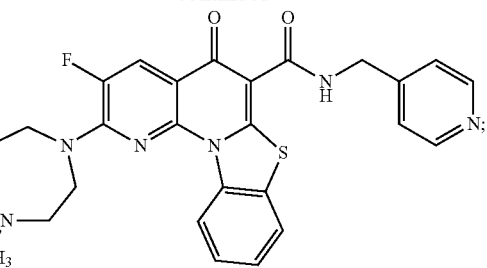
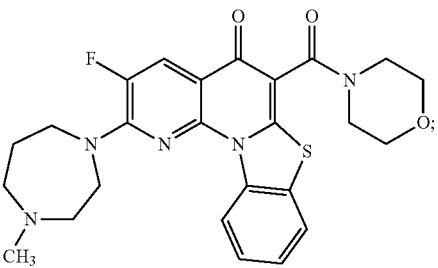
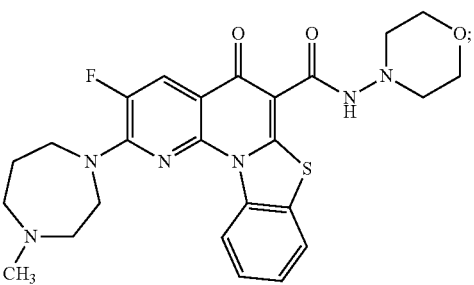
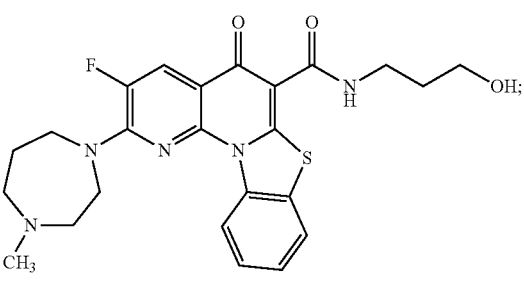
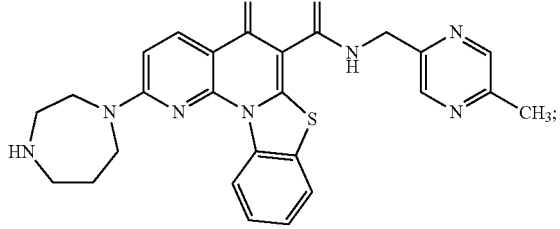
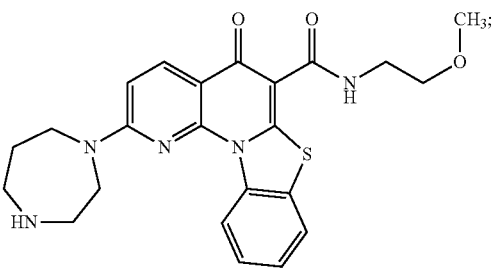

-continued

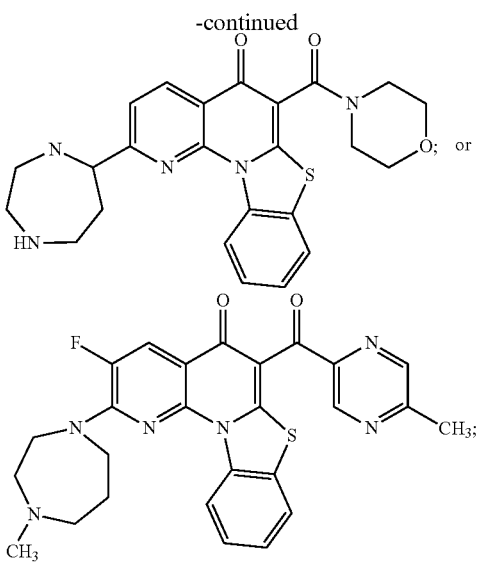

or a pharmaceutically acceptable salt or ester thereof.

The present invention provides pharmaceutical compositions comprising a compound having any one of the above Formula (I), (II), (III), (IV), (V), (VI), (VI'), (VII), or (VIII), and a pharmaceutically acceptable excipient. In one example, the composition comprises a compound having any one of the above formulae, polyethylene glycol, and propylene glycol in a buffer solution.

Compounds of the invention exert biological activity in assays described herein. For example, compounds of the invention can inhibit RNA biogenesis and can suppress tumor growth. Though not limiting the invention by any theory of its operation, it is believed that the compounds can function in part by interacting with quadruplex-forming regions of nucleic acids and modulating ribosomal RNA transcription. Compounds of the invention also may modulate the interaction of quadruplex-forming nucleic acids with nucleolin, a protein that is associated with apoptosis; thus modulation of the activity, localization or stability of nucleolin may also contribute to the ability of these compounds to induce apoptosis. The present invention also provides methods of preparing these compounds, and methods of using the same.

Accordingly, the present invention relates in part to methods for reducing cell proliferation and/or inducing cell death, comprising contacting a system with an effective amount of a compound having any one of the above formulae, or a pharmaceutical composition thereof and optionally in combination with a chemotherapeutic agent, thereby reducing cell proliferation and/or inducing cell death, such as apoptosis or apoptotic cell death, in said system. The system may be a cell or a tissue. In one embodiment, the system includes a pancreatic cell, such as a cell from a subject or a cultured cell (e.g., in vitro or ex vivo). In particular embodiments, the system includes a pancreatic cancer cell. In one embodiment, the system is a cell line such as PC3, HCT116, HT29, MIA Paca-2, HPAC, Hs700T, Panc10.05, Panc 02.13, PL45, SW 190, Hs 766T, CFPAC-1, PANC-1, MV-4-11, THP-1, and K-562.

The present invention also provides methods for treating or ameliorating a cell proliferative disorder, comprising administering to a subject in need thereof an effective amount of a compound of Formula (I), Formula (II), Formula (III), Formula (IV), Formula (V), Formula (VI), Formula (VI'), Formula (VII), or Formula (VIII), or a pharmaceutical composition thereof and optionally in combination with a chemotherapeutic agent, thereby treating or ameliorating said cell-proliferative disorder. For example, cell proliferation may be reduced, and/or cell death, such as apoptosis or apoptotic cell death, may be induced. The cell proliferative disorder may be a tumor or a cancer in a human or animal subject. In a particular embodiment, the cancer is pancreatic cancer, including non-endocrine and endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

The above methods for reducing cell proliferation and/or inducing cell death may also be practiced in combination with a procedure and/or a chemotherapeutic agent. Examples of procedures that may be used in combination with the methods of the present invention include but are not limited to radiotherapy and surgery. In certain embodiments, the compounds of the present invention are administered in combination with a chemotherapeutic agent, and used to reduce cell proliferation, induce cell death, and/or ameliorate a cell proliferative disorder.

The invention also provides methods for reducing or inhibiting cell proliferation, comprising contacting a system or a subject in need thereof with an effective amount of the compound of Formula (I), Formula (II), Formula (III), Formula (IV), Formula (V), Formula (VI), Formula (VI'), Formula (VII), or Formula (VIII), or a pharmaceutical composition thereof, thereby reducing or inhibiting cell proliferation.

Furthermore, the present invention provides methods for reducing microbial titers, comprising contacting a system with an effective amount of a compound of Formula (I), (II), (III), (IV), (V), (VI), (VI'), (VII), or (VIII), or a pharmaceutical composition thereof and optionally with an antimicrobial agent, thereby reducing microbial titers. The system may be a cell or a tissue. The present invention also provides methods for ameliorating a microbial infection, comprising administering to a subject in need thereof an effective amount of a compound having any one of the above formulae, or a pharmaceutical composition thereof and optionally with an antimicrobial agent, thereby ameliorating said microbial infection. The subject may be human or an animal. The microbial titers may be viral, bacterial or fungal titers.

The present invention also relates to methods for determining interaction selectivity between a compound having any one of the above formulae, and nucleic acids capable of forming a quadruplex structure, comprising: a) contacting a compound in the absence of a competitor molecule with three or more nucleic acids capable of forming a quadruplex structure, wherein each nucleic acid is not a telomere nucleic acid; b) measuring a direct interaction between the compound and said three or more nucleic acids; and c) determining interaction selectivity from a comparison of the interaction measurements. In one example, three or more nucleic acids comprise a nucleotide sequence located 5' of an oncogene nucleotide sequence. The oncogene may be MYC, HIF, VEGF, ABL, TGF, PDGFα, MYB, SPARC, HER, VAV, RET, H-RAS, EGF, SRC, BCL-1, BCL-2, DHFR, or HMGA. In determining interaction selectivity, the compound may be separately contacted with each of said three or more nucleic acids in a different vessel. Furthermore, the interaction selectivity may be determined from a comparison of $IC_{50}$ values.

The compounds of the present invention may or may not interact with regions of DNA that can form quadruplexes. In certain embodiments, the compounds of the present invention may bind and/or stabilize a propeller quadruplex. Examples of propeller quadruplexes include but are not limited to H-RAS, RET, BCL-1, DHFR, TGF-β, HIF-1α, VEGF, c-Myc, or PDGFα. In another embodiment, the compound may bind and/or stabilize a chair-eller or a basket quadruplex. For example, the compound may bind and/or stabilize BCL-2.

The present invention also provides methods for inducing cell death, such as apoptotic cell death (apoptosis), comprising administering to a system or a subject in need thereof an effective amount of a compound having any one of the above Formula (I), (II), (III), (IV), (V), (VI), (VI'), (VII), or (VIII), or a pharmaceutical composition thereof and optionally with a chemotherapeutic agent. The present invention also provides methods for treating or ameliorating a disorder mediated by oncogene overexpression, such as c-Myc overexpression, comprising administering to a system or a subject in need thereof an effective amount of a compound having any of the formulae, or a pharmaceutical composition thereof and optionally with a chemotherapeutic agent. The subject may be human or an animal, and system may be a cell or a tissue.

Compounds of the above formulae also may be capable of modulating the activities of various protein kinases, as they contain structural features that are known to bind to protein kinases, and are accordingly useful for the identification of protein kinase modulators using screening methods known in the art. Representative screening methods for certain kinases are provided herein. Accordingly, the invention provides a method for identifying a modulator of a protein kinase, which modulator sometimes is a potent modulator of one or more particular protein kinases. This method comprises screening a library of compounds described herein, which library contains at least 10 different compounds, each of which is of Formula (I), (II), (III), (IV), (V), (VI), (VI'), (VII) or (VIII), and often at least 100 of such compounds, for their ability to modulate the activity of a protein kinase.

Alternatively, the method comprises screening a set of protein kinases, such as at least three or at least ten protein kinases, with a compound of Formula (I), (II), (III), (IV), (V), (VI), (VI'), (VII), or (VIII), to determine a differential activity profile. These methods allow the user to identify a compound having a desired level of activity and/or selectivity as a protein kinase activity modulator, which compound may be used to initiate a drug development program. Thus in another embodiment, the invention provides a composition comprising an isolated protein kinase complexed with a compound of Formula (I), (II), (III), (IV), (V), (VI), (VI'), (VII), or (VIII). Such complexes are useful for the information they provide about the binding site of a modulating compound to the particular kinase, and as a research tool for analyzing the structure of the kinase. Such complexes are also useful because they may be more readily crystallized than the uncomplexed kinase, allowing crystallization and crystal structure determination where it would not be possible without the bound modulating compound.

Also provided herein is a method for identifying a molecule that modulates an interaction between a ribosomal nucleic acid and a protein that interacts with the nucleic acid, which comprises: (a) contacting a nucleic acid containing a human ribosomal nucleotide sequence and the protein with a test molecule having any of the structures disclosed above, where the nucleic acid is capable of binding to the protein, and (b) detecting the amount of the nucleic acid bound or not bound to the protein, whereby the test molecule is identified as a molecule that modulates the interaction when a different amount of the nucleic acid binds to the protein in the presence of the test molecule than in the absence of the test molecule.

In some embodiments, the protein is selected from the group consisting of Nucleolin, Fibrillarin, RecQ, QPN1 and functional fragments of the foregoing.

In some embodiments, provided is a method for identifying a molecule that causes nucleolin displacement, which comprises (a) contacting a nucleic acid containing a human ribosomal nucleotide sequence and a nucleolin protein with a test molecule of Formula (I), (II), (III), (IV), (V), (VI), (VI'), (VII), or (VIII), where the nucleic acid is capable of binding to the nucleolin protein, and (b) detecting the amount of the nucleic acid bound or not bound to the nucleolin protein, whereby the test molecule is identified as a molecule that causes nucleolin displacement when less of the nucleic acid binds to the nucleolin protein in the presence of the test molecule than in the absence of the test molecule. In some embodiments, the nucleolin protein is in association with a detectable label, and the nucleolin protein sometimes is in association with a solid phase. The nucleic acid sometimes is in association with a detectable label, and the nucleic acid may be in association with a solid phase in certain embodiments. The nucleic acid may be DNA, RNA or an analog thereof, and may comprise a nucleotide sequence described above in specific embodiments. Provided also is a composition comprising a nucleic acid having a ribosomal nucleotide sequence provided herein, or substantially identical sequence thereof, and/or a protein that binds to the nucleotide sequence (e.g., Nucleolin, Fibrillarin, RecQ, QPN1 and functional fragments of the foregoing), and a compound of Formula (I), (II), (III), (IV), (V), (VI), (VI'), (VII), or (VIII).

Also provided is a method for identifying a molecule that binds to a nucleic acid containing a human ribosomal nucleotide sequence, which comprises: (a) contacting a nucleic acid containing a human ribosomal nucleotide sequence described herein, a compound that binds to the nucleic acid and a test molecule of Formula (I), (II), (III), (IV), (V), (VI), (VI'), (VII), or (VIII), and (b) detecting the amount of the compound bound or not bound to the nucleic acid, whereby the test molecule is identified as a molecule that binds to the nucleic acid when less of the compound binds to the nucleic acid in the presence of the test molecule than in the absence of the test molecule. The compound sometimes is in association with a detectable label, and at times is radiolabeled. The nucleic acid may be in association with a solid phase in certain embodiments. The nucleic acid may be DNA, RNA or an analog thereof, and may comprise a nucleotide sequence described above in specific embodiments. The nucleic acid may form a quadruplex, such as an intramolecular quadruplex, in certain embodiments.

Also provided herein is a method for identifying a modulator of nucleic acid synthesis, which comprises contacting a template nucleic acid, a primer oligonucleotide having a nucleotide sequence complementary to a template nucleic acid nucleotide sequence, extension nucleotides, a polymerase and a test molecule of Formula (I), (II), (III), (IV), (V), (VI), (VI'), (VII), or (VIII), under conditions that allow the primer oligonucleotide to hybridize to the template nucleic acid, wherein the template nucleic acid comprises a human ribosomal nucleotide sequence, and detecting the presence, absence or amount of an elongated primer product synthesized by extension of the primer nucleic acid, whereby the test molecule is identified as a modulator of nucleic acid synthesis when less of the elongated primer product is synthesized in the presence of the test molecule than in the absence of the test molecule.

In certain embodiments, the method is directed to identifying a modulator of RNA synthesis, and in certain embodiments, identifying a modulator of nucleolar RNA synthesis.

The template nucleic acid sometimes is DNA and at times is RNA, and the template can include by way of example any one or more of the ribosomal nucleotide sequences described herein. The polymerase sometimes is a DNA polymerase and at times is a RNA polymerase. In certain embodiments, cells are contacted with a test compound of Formula (I), (II), (III), (IV), (V), (VI), (VI'), (VII), or (VIII) and RNA levels are detected in the cells, whereby a test compound that reduces the amount of RNA compared to cells not treated with the test compound is identified as a molecule that modulates RNA synthesis. In the latter embodiments, total RNA levels may be assessed, and in some embodiments, the total amount of newly synthesized RNA may be assessed, such as by incorporation and detection of a detectable nucleotide in the RNA (e.g., radioactively labeled nucleotide (e.g., tritiated nucleotide)), for example.

In a specific assay embodiment, provided herein is a method for identifying a molecule that modulates ribosomal RNA (rRNA) synthesis, which comprises: contacting cells with a test molecule of Formula (I), (II), (III), (IV), (V), (VI), (VI'), (VII), or (VIII), contacting a ribosomal nucleotide sequence with one or more primers that amplify a portion thereof and a labeled probe that hybridizes to the amplification product, and detecting the amount of the amplification product by hybridization of the labeled probe, whereby a test molecule that reduces or increases the amount of amplification product is identified as a molecule that modulates rRNA synthesis. The labeled probe in some embodiments is added after the primers are added and the rRNA is amplified, and in certain embodiments, the labeled probe and the primers are added at the same time. The portion of ribosomal nucleotide sequence amplified sometimes is at the 5' end of rDNA.

In certain embodiments, the invention provides a library of compounds, which library comprises at least 10 compounds of Formula (I), (II), (III), (IV), (V), (VI), (VI'), (VII), or (VIII). The library preferably contains at least 100 such compounds. This library can be used to identify compounds having one or more of the activities described herein, or a specific combination of such activities using methods known in the art. The method is particularly useful for identifying molecules having a threshold level of biological activity, including but not limited to (a) binding to quadruplex nucleic acid or inhibiting formation of quadruplex nucleic acid (rDNA or rRNA), (b) activity against a specific protein kinase or set of protein kinases and (c) activity as a modulator of binding of a nucleic acid to a protein, such as nucleolin, for example.

BRIEF DESCRIPTION OF THE FIGURES

FIG. 1 shows a comparison of cassette and single AUC values for oral administration of RBI compounds.

DEFINITIONS

The present invention may be understood more readily by reference to the following detailed description of the preferred embodiments of the invention and the Examples included herein. It is to be understood that the terminology used herein is for the purpose of describing specific embodiments only and is not intended to be limiting.

Unless defined otherwise, all technical and scientific terms used herein have the same meaning as is commonly understood by one of ordinary skill in the art to which this invention belongs.

As used herein, "a" or "an" means "at least one" or "one or more."

As used herein, "about" means that the numerical value is approximate and small variations would not significantly affect the practice of the invention. Where a numerical limitation is used, unless indicated otherwise by the context, "about" means the numerical value can vary by ±10% and remain within the scope of the invention.

As used herein, the term "alkyl" refers to a carbon-containing compound, and encompasses compounds containing one or more heteroatoms. The term "alkyl" also encompasses alkyl moieties substituted with one or more substituent groups. "Alkyl" groups may be linear, branched or cyclic. In some cases, cyclic alkyl groups are referred to herein as "cycloalkyl". "Heteroalkyl" refers to a compound in which at least one carbon atom of the alkyl backbone has been replaced by a heteroatom, typically N, O, or S. "Alkenyl" and "alkynyl" moieties refer to alkyl moieties containing at least one double bond or triple bond, respectively.

Optional substituents when present on an alkyl, alkenyl or alkynyl moiety, or a heteroform of one of these, include but are not limited to OH, $C_{1-6}$ alkoxy, optionally substituted amino, amido, CN, carboxy, halo, =O, aryl, optionally substituted heterocyclic or carbocyclic rings, or inorganic substituents.

As used herein, the term "carbocycle" refers to a cyclic compound containing only carbon atoms in the ring, whereas a "heterocycle" refers to a cyclic compound comprising a heteroatom as a ring member. The carbocyclic and heterocyclic structures encompass compounds having monocyclic, bicyclic or multiple ring systems, and may be saturated, partially unsaturated or aromatic. Carbocyclic and heterocyclic rings may be optionally substituted with substituent groups suitable for their structure.

As used herein, the term "azacyclic" or "azacyclic ring" refers to a saturated, partially unsaturated, or aromatic 3-7 membered monocyclic ring or an 8-12 membered fused bicyclic ring system containing at least one nitrogen atom. Such azacyclic rings may optionally contain from 1-2 additional heteroatoms selected from N, O, and S as ring members, and may be optionally substituted to the extent such substitution makes chemical sense.

As used herein, the term "aryl" refers to a polyunsaturated, typically aromatic hydrocarbon substituent, whereas a "heteroaryl" or "heteroaromatic" refer to an aromatic ring containing a heteroatom as a ring member. The aryl and heteroaryl structures encompass compounds having monocyclic, bicyclic or multiple ring systems, and may be optionally substituted.

As used herein, the term "heteroatom" refers to any atom that is not carbon or hydrogen, such as nitrogen, oxygen or sulfur.

"Heteroform" as used herein refers to a group wherein one or more carbon atoms of a hydrocarbyl moiety have been replaced with a heteroatom, typically N, O, or S. For example, heteroaryl is the heteroform of aryl, and heteroalkyl is the heteroform of alkyl.

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

Illustrative examples of azacyclic rings include but are not limited to optionally substituted aziridine, azetidine, imidazole, imidazoline, pyrrole, pyrroline, pyrrolidine, pyrazole, pyrazoline, oxazole, oxazoline, isoxazole, isoxazoline, thiazole, thiazoline, pyridine, dihydropyridine, tetrahydropyridine, piperidine, piperazine, pyrimidine, pyridazine, pyrazine, morpholine, thiomorpholine, homopiperazine, homomorpholine, homothiomorpholine, benzimidazole, and indole rings.

Preferred substituents when present on an azacyclic or heterocyclic ring include halo, =O, acyl, aroyl, carbamoyl, or an optionally substituted carbocyclic or heterocyclic ring; or optionally substituted $C_{1-6}$ alkyl, $C_{2-6}$ alkenyl, $C_{2-6}$ alkynyl, or heteroforms of these; or —$OR^5$, —$NR^5R^6$, —$COOR^5$, or —$C(O)NR^5R^6$, where each of $R^5$ and $R^6$ is independently H, or C1-C6 alkyl, aryl, or arylalkyl, or a heteroform of one of these; and wherein in each —$NR^5R^6$, $R^5$ and $R^6$ together with N may form an optionally substituted 5-6 membered ring, optionally containing one additional heteroatom selected from N, O and S as a ring member.

Particularly preferred substituents when present on an aromatic azacyclic ring include one or more halo or optionally substituted $C_{1-6}$ alkyl groups, wherein said optional substituents are selected from the group consisting of halo, hydroxy, and oxo (=O).

Preferred substituents when present on an aryl or heteroaryl ring include optionally substituted $C_{1-6}$ alkyl, $C_{2-6}$ alkenyl, $C_{2-6}$ alkynyl; halo, —CN, —$CF_3$, —$OCF_3$, $NO_2$; or —$OR^5$, —$NR^5R^6$, —$COOR^5$, or —$C(O)NR^5R^6$, —$SO_2NR^5R^6$, —$NC(O)R^5$, or —$NSO_2R^5$, where each of $R^5$ and $R^6$ is independently H, or C1-C6 alkyl, aryl, or arylalkyl, or a heteroform of one of these; and wherein in each —$NR^5R^6$, $R^5$ and $R^6$ together with N may form an optionally substituted 5-7 membered ring, optionally containing one additional heteroatom selected from N, O and S as a ring member.

As used herein, the term "inorganic substituent" refers to substituents that do not contain carbon or contain carbon bound to elements other than hydrogen (e.g., elemental carbon, carbon monoxide, carbon dioxide, and carbonate). Examples of inorganic substituents include but are not limited to nitro, halogen, sulfonyls, sulfinyls, phosphates, etc.

The terms "treat," "treatment" and "therapeutic effect" as used herein refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "chemotherapeutic agent" refers to a therapeutic agent that may be used for treating or ameliorating a cell proliferative disorder such as tumors or cancer. Examples of chemotherapeutic agents include but are not limited to an antineoplastic agent, an alkylating agent, a plant alkaloid, an antimicrobial agent, a sulfonamide, an antiviral agent, a platinum agent, and other anticancer agents known in the art. Particular examples of chemotherapeutic agents include but are not limited to cisplatin, carboplatin, busulphan, methotrexate, daunorubicin, doxorubicin, cyclophosphamide, mephalan, vincristine, vinblastine, chlorambucil, paclitaxel, gemcitabine, and others known in the art. (See e.g., Goodman & Gilman's, *The Pharmacological Basis of Therapeutics* (9th Ed) (Goodman, et al., eds.) (McGraw-Hill) (1996); and 1999 *Physician's Desk Reference* (1998)).

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

As used herein, "subject" refers to a human or animal subject. In certain preferred embodiments, the subject is human.

DESCRIPTION OF THE INVENTION

The present invention relates to compounds having Formula (I), (II), (III), (IV), (V), (VI), and (VII), and pharmaceutically acceptable salts, esters, and prodrugs thereof. The invention provides orally active quinolone analogs which may inhibit cell proliferation and/or induce cell apoptosis. The present invention also provides methods of preparing such orally active quinolone analogs, and methods of treating cell proliferation disorders by administering the same.

The compounds of the present invention may or may not interact with regions of DNA that can form quadruplexes.

The compounds of present invention having Formulae (I), (II), (III), (IV) are reproduced below:

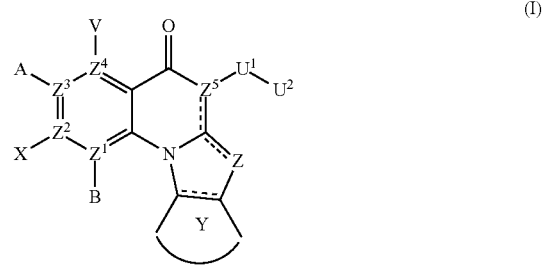

(I)

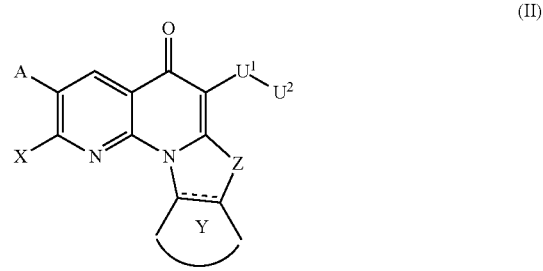

(II)

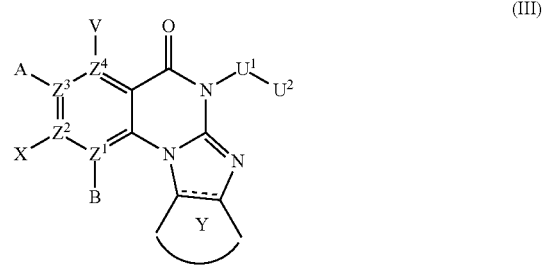

(III)

-continued

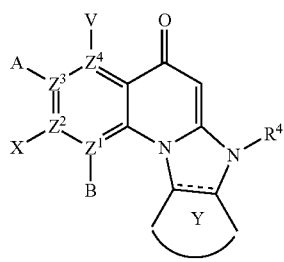
(IV)

wherein A, B, V, X, Z, $Z^1$, $Z^2$, $Z^3$, $Z^4$, $Z^5$, $U^1$, $U^2$, Y and $R^4$ are defined as further described herein.

The compounds of present invention having Formulae (V), (VI), (VI'), (VII) and (VIII) are reproduced below:

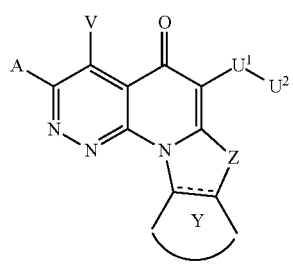
(V)

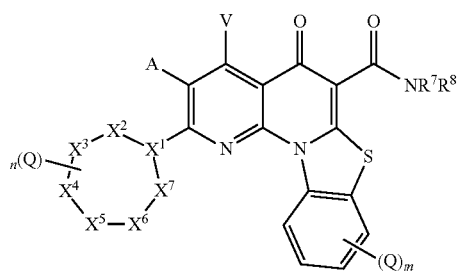
(VI)/(VI')

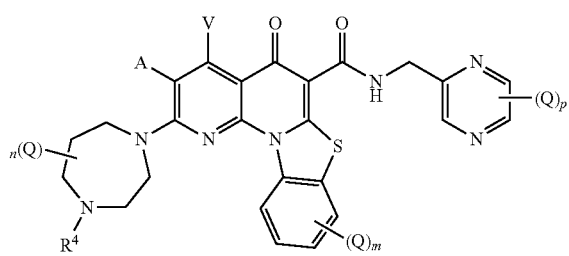
(VII)

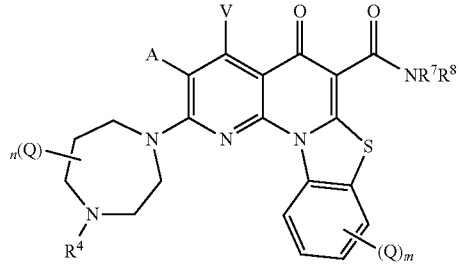
(VIII)

wherein A, V, Y, Z, $U^1$, $U^2$, $X^1$, $X^2$, $X^3$, $X^4$, $X^5$, $X^6$, $X^7$, $R^4$, $R^7$, $R^8$, Q, m, n and p are defined as further described herein.

The compounds of the present invention may be chiral. As used herein, a chiral compound is a compound that is different from its mirror image, and has an enantiomer. Furthermore, the compounds may be racemic, or an isolated enantiomer or stereoisomer. Methods of synthesizing chiral compounds and resolving a racemic mixture of enantiomers are well known to those skilled in the art. See, e.g., March, "*Advanced Organic Chemistry*," John Wiley and Sons, Inc., New York, (1985), which is incorporated herein by reference.

The compounds of the present invention may be tested using screening assays such as those described herein.

The compounds described herein may interact with regions of nucleic acids that can form quadruplexes. Because regions of DNA that can form quadruplexes are regulators of biological processes such as oncogene transcription, modulators of quadruplex biological activity can be utilized as cancer therapeutics. Molecules that interact with regions of DNA that can form quadruplexes can exert a therapeutic effect on certain cell proliferative disorders and related conditions. Particularly, abnormally increased oncogene expression can cause cell proliferative disorders, and quadruplex structures typically down-regulate oncogene expression. Examples of oncogenes include but are not limited to MYC, HIF, VEGF, ABL, TGF, PDGFA, MYB, SPARC, HUMTEL, HER, VAV, RET, H-RAS, EGF, SRC, BCL1, BCL2, DHFR, HMGA, and other oncogenes known to one of skill in the art. Furthermore, the compounds described herein may induce cell death (e.g., apoptosis) and not interact with regions of DNA that can form quadruplexes.

Molecules that bind to regions of DNA that can form quadruplexes can exert a biological effect according to different mechanisms, which include for example, stabilizing a native quadruplex structure, inhibiting conversion of a native quadruplex to duplex DNA by blocking strand cleavage, and stabilizing a native quadruplex structure having a quadruplex-destabilizing nucleotide substitution and other sequence specific interactions. Thus, compounds that bind to regions of DNA that can form quadruplexes described herein may be administered to cells, tissues, or organisms for the purpose of down-regulating oncogene transcription and thereby treating cell proliferative disorders.

Determining whether the biological activity of native DNA that can form quadruplexes is modulated in a cell, tissue, or organism can be accomplished by monitoring quadruplex biological activity. Quadruplex forming regions of DNA biological activity may be monitored in cells, tissues, or organisms, for example, by detecting a decrease or increase of gene transcription in response to contacting the quadruplex forming DNA with a molecule. Transcription can be detected by directly observing RNA transcripts or observing polypeptides translated by transcripts, which are methods well known in the art.

Molecules that interact with quadruplex forming DNA and quadruplex forming nucleic acids can be utilized to treat many cell proliferative disorders. Cell proliferative disorders include, for example, colorectal cancers and hematopoietic neoplastic disorders (i.e., diseases involving hyperplastic/neoplastic cells of hematopoietic origin such as those arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (Vaickus, Crit. Rev. in *Oncol./Hemotol.* 11:267-297 (1991)). Lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, lymph node, colon, prostate, brain, head and neck, skin, liver, kidney, and heart. Compounds that interact with regions of DNA that may form quadruplexes also can be utilized to target cancer related processes and conditions, such as increased angiogenesis, by inhibiting angiogenesis in a subject.

The present invention provides a method for reducing cell proliferation or for treating or alleviating cell proliferative disorders, comprising contacting a system having a native DNA capable of forming a quadruplex region with a compound having any one of the above formulae. The system may be a group of cells or one or more tissues. In one embodiment, the system is a subject in need of a treatment of a cell proliferative disorder (e.g., a mammal such as a mouse, rat, monkey, or human). The present invention also provides a method for treating colorectal cancer by administering a compound that interacts with a c-MYC quadruplex forming region to a subject in need thereof, thereby reducing the colorectal cancer cell proliferation. Furthermore, the present invention provides a method for inhibiting angiogenesis and optionally treating a cancer associated with angiogenesis, comprising administering a compound that interacts with a vascular endothelial growth factor (VEGF) quadruplex forming region to a subject in need thereof, thereby reducing angiogenesis and optionally treating a cancer associated with angiogenesis.

Compounds that interact with quadruplex forming regions of DNA can also be used to reduce a microbial infection, such as a viral infection. Retroviruses offer a wealth of potential targets for G-quadruplex targeted therapeutics. G-quadruplex structures have been implicated as functional elements in at least two secondary structures formed by either viral RNA or DNA in HIV, the dimer linker structure (DLS) and the central DNA flap (CDF). Additionally, DNA aptamers which are able to adopt either inter- or intramolecular quadruplex structures are able to inhibit viral replication. In one example, DNA aptamers are able to inhibit viral replication by targeting the envelope glycoprotein (putatively). In another example, DNA aptamers inhibit viral replication by targeting the HIV-integrase respectively, suggesting the involvement of native quadruplex structures in interaction with the integrase enzyme.

Dimer linker structures, which are common to all retroviruses, serve to bind two copies of the viral genome together by a non-covalent interaction between the two 5' ends of the two viral RNA sequences. The genomic dimer is stably associated with the gag protein in the mature virus particle. In the case of HIV, the origin of this non-covalent binding may be traced to a 98 base-pair sequence containing several runs of at least two consecutive guanines (e.g., the 3' for the formation of RNA dimers in vitro). An observed cation (potassium) dependence for the formation and stability of the dimer in vitro, in addition to the failure of an antisense sequence to effectively dimerize, has revealed the most likely binding structure to be an intermolecular G-quadruplex.

Prior to integration into the host genome, reverse transcribed viral DNA forms a pre-integration complex (PIC) with at least two major viral proteins, integrase and reverse transcriptase, which is subsequently transported into the nucleus. The Central DNA Flap (CDF) refers to 99-base length single-stranded tail of the + strand, occurring near the center of the viral duplex DNA, which is known to a play a role in the nuclear import of the PIC. Oligonucleotide mimics of the CDF have been shown to form intermolecular G-quadruplex structures in cell-free systems.

Thus, compounds that recognize quadruplex forming regions can be used to stabilize the dimer linker structure and thus prevent de-coupling of the two RNA strands. Also, by binding to the quadruplex structure formed by the CDF, protein recognition and/or binding events for nuclear transport of the PIC may be disrupted. In either case, a substantial advantage can exist over other anti-viral therapeutics. Current Highly Active Anti-Retroviral Therapeutic (HAART) regimes rely on the use of combinations of drugs targeted towards the HIV protease and HIV integrase. The requirement for multi-drug regimes is to minimize the emergence of resistance, which will usually develop rapidly when agents are used in isolation. The source of such rapid resistance is the infidelity of the reverse transcriptase enzyme which makes a mutation approximately once in every 10,000 base pairs. An advantage of targeting viral quadruplex structures over protein targets, is that the development of resistance is slow or is impossible. A point mutation of the target quadruplex can compromise the integrity of the quadruplex structure and lead to a non-functional copy of the virus. A single therapeutic agent based on this concept may replace the multiple drug regimes currently employed, with the concomitant benefits of reduced costs and the elimination of harmful drug/drug interactions.

The present invention provides a method for reducing a microbial titer in a system, comprising contacting a system having a native DNA quadruplex forming region with a compound having any one of the above formulae. The system may be one or more cells or tissues. Examples of microbial titers include but are not limited to viral, bacterial or fungal titers. In a particular embodiment, the system is a subject in need of a treatment for a viral infection (e.g., a mammal such as a mouse, rat, monkey, or human). Examples of viral infections include infections by a hepatitis virus (e.g., hepatitis B or C), human immunodeficiency virus (HIV), rhinovirus, herpeszoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Barr virus, and respiratory syncytial virus. The present invention also provides a method for treating HIV infection by administering a compound having any one of the above formulae to a subject in need thereof, thereby reducing the HIV infection.

Identifying Compounds that can Bind to Quadruplex Forming Regions of DNA

Compounds described herein may bind to quadruplex forming regions of DNA where a biological activity of this region, often expressed as a "signal," produced in a system containing the compound is different than the signal produced in a system not containing the compound. While background signals may be assessed each time a new molecule is probed by the assay, detecting the background signal is not required each time a new molecule is assayed.

In addition to determining whether a test molecule or test nucleic acid gives rise to a different signal, the affinity of the interaction between the nucleic acid and the compound may be quantified. $IC_{50}$, Kd, or Ki threshold values may be compared to the measured $IC_{50}$ or Kd values for each interaction, and thereby identify a test molecule as a quadruplex interacting molecule or a test nucleic acid as a quadruplex forming nucleic acid. For example, $IC_{50}$ or Kd threshold values of 10

μM or less, 1 μM or less, and 100 nM or less are often utilized. In another example, threshold values of 10 nM or less, 1 nM or less, 100 pM or less, and 10 pM or less may be utilized to identify quadruplex interacting molecules and quadruplex forming nucleic acids.

Many assays are available for identifying compounds that have affinity for quadruplex forming regions of DNA. In some of these assays, the biological activity is the quadruplex nucleic acid binding to a compound and binding is measured as a signal. In other assays, the biological activity is a polymerase arresting function of a quadruplex and the degree of arrest is measured as a decrease in a signal. In certain assays, the biological activity is transcription and transcription levels can be quantified as a signal. In another assay, the biological activity is cell death and the number of cells undergoing cell death is quantified. Another assay monitors proliferation rates of cancer cells. Examples of assays are fluorescence binding assays, gel mobility shift assays (see, e.g., Jin & Pike, *Mol. Endocrinol.* (1996) 10:196-205), polymerase arrest assays, transcription reporter assays, cancer cell proliferation assays, and apoptosis assays (see, e.g., Amersham Biosciences (Piscataway, N.J.)), and embodiments of such assays are described hereafter in Example 8. Also, topoisomerase assays can be utilized to determine whether the quadruplex interacting molecules have a topoisomerase pathway activity (see, e.g., TopoGEN, Inc. (Columbus, Ohio)).

Formulation of Compounds

As used herein, the term "pharmaceutically acceptable salt or ester thereof" includes but are not limited to carboxylate salts, amino acid addition salts, and esters of the compounds, as well as the zwitterionic forms thereof, which are known to those skilled in the art as suitable for use with humans and animals. (See, e.g., Gerge, S. M., et al., "Pharmaceutical Salts," *J. Pharm. Sci.* (1977) 66:1-19, which is incorporated herein by reference.)

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art. For example, pharmaceutically acceptable salts may be obtained by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids also are made.

A compound may be formulated as a pharmaceutical composition and administered to a mammalian host in need of such treatment. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703, 055 (Felgner, et al.) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required.

In a particular example, the pharmaceutical composition comprises about 2% w/w of a compound having formula (I), about 4% mannitol, and about 0.5% sucrose. In particular examples, the formulation has a pH of about 3.5. For injectable formulations, water may be added to the final weight.

The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

A useful compound dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938,949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range of circulating concentrations for which the $ED_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e., the concentration of the test compound which achieves a half-maximal inhibition of symptoms) as determined in in vitro assays, as such information often is used to more accurately determine useful doses in humans. Levels in plasma may be measured, for example, by high performance liquid chromatography.

Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., *Current Opinion in Biotechnology* (1996) 7:89-94 and in Shea, *Trends in Polymer Science* (1994) 2:166-173). Such "imprinted" affinity matrixes are amenable to ligand-binding assays, whereby the immobilized monoclonal antibody component is replaced by an appropriately imprinted matrix (see, e.g., Vlatakis, et al., *Nature* (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual $IC_{50}$. An example of such a "biosensor" is discussed in Kriz, et al., *Analytical Chemistry* (1995) 67:2142-2144.

In some embodiments, the compounds and compositions provided demonstrate oral bioavailability in a mouse or human subject. In particular embodiments, the present invention provides compositions comprising the compound of Formula (I), (II), (III), (IV), (V), (VI), (VI'), (VII), or (VIII) that are at least 15% orally bioavailable in a mouse or a human subject. In other embodiments, the compositions are at least 20%, 30%, 40% or 50% orally bioavailable in a mouse or a human subject. In a preferred embodiment, the subject is human. Without wishing to be bound by theory, it is believed that oral bioavailability demonstrated by compounds of the present invention may be due at least in part of the protonation state of the basic moiety present in the group represented as $A^2$, $A^3$, —W, -L-W, or -L-N(R)—$W^0$.

Exemplary compounds of the present invention may be selected such that the conjugate acid of the basic moiety present in the group represented as $A^2$, $A^3$, —W, -L-W, or -L-N(R)—$W^0$ has a pKa of between about 7 and 9, such that the group is about 50% protonated at a pH range of from about 7.0 to about 9.0. In some embodiments, the 7-membered $X^1$-$X^7$ ring in formula (VI) or (VI'), or the homopiperazine ring in formula (VII) and (VIII), may serve as the basic moiety, as described above.

The present invention further provides pharmaceutical compositions in unit dosage form, comprising a therapeutically effective amount of at least one compound of Formula (I), Formula (II), Formula (III), Formula (IV), Formula (V), Formula (VI), Formula (VI'), Formula (VII) or Formula (VIII).

In specific embodiments, the invention provides a pharmaceutical composition in unit dosage form, comprising a compound of Formula (I), Formula (II), Formula (III), Formula (IV), Formula (V), Formula (VI), Formula (VI'), Formula (VII) or Formula (VIII), wherein a single oral administration of the dosage form to a subject provides an AUC (8 hr) of at least 1000 ng/mL*hr, preferably greater than 2000 ng/mL*hr, more preferably greater than 10,000 ng/mL*hr.

Bioavailability (F) is a measurement of the extent to which an administered dose of a drug reaches the systemic circulation or the intended site of action. Bioavailability depends on both the rate of absorption and the extent to which the drug is eliminated or metabolized prior to reaching the systemic circulation. For example, an orally administered drug passes through the liver before reaching the systemic circulation, and may be subject to first pass metabolism by the liver or biliary excretion.

For certain therapeutic indications, oral dosing is the preferred route of administration, owing to its safety, convenience and economic advantages. The development of highly orally bioavailable compounds is frequently an important consideration in the development of bioactive molecules as therapeutic agents.

Poor oral bioavailability can result in variable exposure to active drug, and may lead to either lack of efficacy or overexposure to a particular agent. For example, polymorphic variability in drug-metabolizing enzymes, such as cytochrome P450's or methyltransferases, or co-administration with drugs that inhibit such enzymes, may reduce the first pass clearance and increase drug exposure to undesired or toxic levels.

Absorption, which describes the rate and extent to which a drug leaves its site of administration, is influenced by a number of variables including physicochemical properties of the drug that affect transport across membranes and the dosage form selected. For orally administered compounds, absorption predominantly occurs in the gastrointestinal (GI) tract, and is influenced by factors including the available surface area for absorption, extent of blood flow, physical state of the drug, and the local concentration of the drug at the site of absorption. In particular, aqueous solubility will influence both the rate and site of absorption. Low solubility drugs often show poor bioavailability or irregular absorption, with the extent of absorption affected by factors such as dose level, fed state of the patient, and dosage form. In solid dosage forms, the rate of dissolution may be the limiting factor in determining absorption.

Drug solubility is affected by the pH gradient in the GI tract. For example, basic drugs which are soluble in the low pH environment of the stomach (pH ~1.2) may become less soluble when the drug reaches the higher pH environment of the small intestine (pH 5 to 7, typically about 6.5), depending on the pKa of the drug. While the nonionized form of a drug will be more rapidly absorbed than the ionized form at a particular location in the GI tract, the overall rate of absorption from the intestine is greater than from the stomach, regardless of the ionization state, because of the larger available surface area. (See e.g., Goodman & Gilman's, *The Pharmacological Basis of Therapeutics* (9th Ed.) (Goodman, et al., eds.) (McGraw-Hill) (1996).

Many drugs are comprised of weak acids or weak bases, which are present in solution as an equilibrium between their ionized (i.e., charged) and nonionized forms. The extent of ionization is determined by the pKa of the drug as well as the pH of the solution. The pH influences the rate of dissociation of both weak acids and weak bases. Weak acids dissociate, becoming ionized, in an alkaline environment, whereas weak bases become ionized in an acidic environment.

The percent of ionization may be calculated using Eq. 1 for HA acids and Eq. 2 for $BH^+$ acids:

$$\% \text{ ionization} = 100/(1+10^{(pKa-pH)}) \qquad \text{(Eq. 1)}$$

$$\% \text{ ionization} = 100/(1+10^{(pH-pKa)}) \qquad \text{(Eq. 2)}$$

When the pH equals the pKa, the compound will be 50% ionized; i.e., the ratio of ionized to nonionized drug will be 50:50. In the Henderson-Hasselbalch equation, pKa=pH when the log [conjugate base]/[acid]=1. An increase in one pH unit from the pKa (i.e., an increase in alkalinity of the solution) causes a decrease in the percent ionization of a $BH^+$ acid to only 9.1%, and causes an HA acid to become 90.9% in the ionized conjugate base form. An increase of two pH units essentially shifts a $BH^+$ acid to the non-ionic conjugate base form (0.99%), while the HA acid becomes nearly completely ionized (99%). The opposite is seen when the solution is made more acidic relative to the drug's pKa value. (See e.g., Block, in *Textbook of Organic Medicinal and Pharmaceutical Chemistry* (10th Ed.) (Delgado & Remers, eds.) (Lippincott-Raven) (1998).

In one aspect, an orally active compound of composition of the present invention is selected such that the compounds are about 50% ionized at a pH ranging from about 7 to about 9. Such compounds may demonstrate optimal oral bioavailability and efficacy.

In certain embodiments, preferred groups for $A^2$, $A^3$, —W, -L-W and -L-N(R)$W^0$ are those which exhibit a dissociation constant, pKa, in aqueous solutions of such a magnitude that at least a portion of the amine is ionized at physiological pH values, e.g., at pH-values between about 4 and about 9. Amines which exhibit a pKa of between about 6 and about 10, preferably between about 7 to about 9, may be especially well suited.

Pharmacokinetics

Based upon the amount of a compound in samples taken at different time points, pharmacokinetic parameters can be determined. The types of pharmacokinetic parameters and the methodology for determining the parameters can be appropriately selected by the person of ordinary skill in the art. Examples of pharmacokinetic parameters that can be assessed include, but are not limited to, maximum (peak) plasma drug concentration (Cmax) (typically expressed in ng/ml); the time at which maximum plasma drug concentration occurs (peak time; Tmax); and the area under the fluid (e.g., plasma) concentration-time curve (AUC). The person of ordinary skill in the art is capable of calculating such parameters (e.g., Mei et al., *AAPS Journal* (2006) 8(3) article 58 (http address www.aapsj.org)).

Oral bioavailability can be assessed by measuring "area under the curve" (AUC) or $C_{max}$, both parameters well known in the art. AUC is determined by plotting the serum or plasma concentration of drug along the ordinate (Y-axis) against time along the abscissa (X-axis). Generally, the values for AUC represent a number of values taken from all the subjects in a test population and are therefore mean values averaged over the entire test population.

$AUC_{0-8}$ (ng·hr/ml) is the area under the plasma concentration versus time curve from time zero to 8 hours, and can be computed using the linear trapezoidal rule according to Gibaldi, M. and Perrier, D. *Pharmacokinetics*, Second Edition, Marcel Dekker, Inc., New York (1982). $AUC_{0-inf}$ is the area under the plasma concentration versus time curve, extrapolated from time zero to infinity (expressed in ng·hr/ml).

Other pharmacokinetic parameters may be determined. For example, $T_{1/2}$ is the terminal half life (expressed in hr); $Vd_{ss}$ is the volume of distribution at steady state (expressed in L/kg); and $Cl_s$ is the systemic clearance (expressed in L/hr/kg).

Dosages

A useful compound dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938,949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range of circulating concentrations for which the $ED_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e., the concentration of the test compound which achieves a half-maximal inhibition of symptoms) as determined in in vitro assays, as such information often is used to more accurately determine useful doses in humans. Levels in plasma may be measured, for example, by high performance liquid chromatography.

Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., *Current Opinion in Biotechnology* (1996) 7:89-94 and in Shea, *Trends in Polymer Science* (1994) 2:166-173).

Such "imprinted" affinity matrixes are amenable to ligand-binding assays, whereby the immobilized monoclonal antibody component is replaced by an appropriately imprinted matrix (see, e.g., Vlatakis, et al., *Nature* (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual $IC_{50}$. An example of such a "biosensor" is discussed in Kriz, et al., *Analytical Chemistry* (1995) 67:2142-2144.

Exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The following examples are offered to illustrate but not to limit the invention.

Example 1

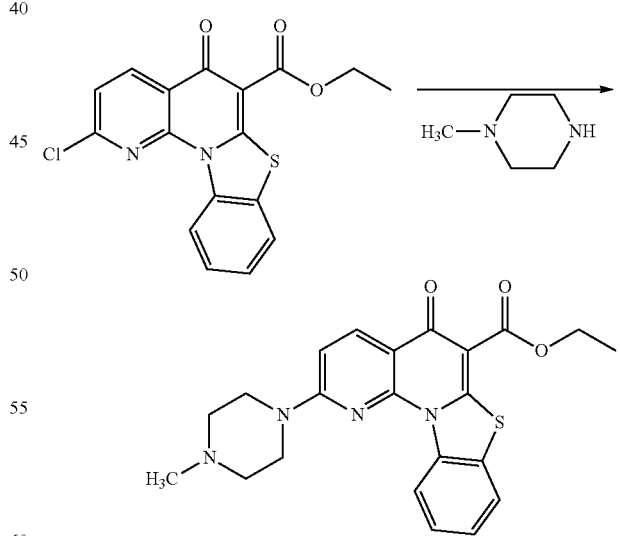

To a slurry of the chloroester (5.00 g, 13.94 mmol) in ACN (50 mL) was added N-methylpiperazine (3.10 mL, 27.95 mmol) and the mixture was heated at reflux over night. The reaction was cooled to rt and the precipitate was collected by filtration to yield desired product as a tan solid (4.7 g, 80%).
$^1$H NMR (CDCl$_3$) δ: 9.47 (d, 1H), 8.62 (d, 1H), 7.74 (dd, 1H), 7.51 (m, 1H), 7.43 (m, 1H), 6.89 (d, 1H), 4.50 (q, 2H), 3.85 (t, 4H), 2.62 (t, 4H), 2.40 (s, 3H), 1.49 (t, 3H). LCMS (ES): m/z 423 [M+1]+.

Example 2

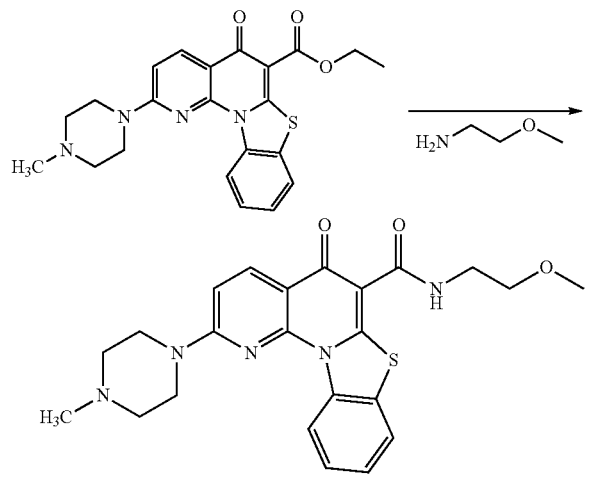

To a solution of ester (150 mg, 0.34 mmol) and 2-methoxyethylamine (0.50 mL, 5.80 mmol) in DCM (10 mL) was added AlCl$_3$ (150 mg, 1.12 mmol). The reaction mixture was stirred at rt over night. The reaction was diluted with DCM (100 mL) and 6N NaOH (25 mL) and stirred for 10 min. The layers were separated and the organic layer was washed with H$_2$O (2×50 mL), brine (50 mL), and dried over Na$_2$SO$_4$. The solvent was removed under reduced pressure and the resulting solid was triturated in ACN to give the desired product as a white solid. LCMS (ES): m/z 470 [M+1]+.

Example 3

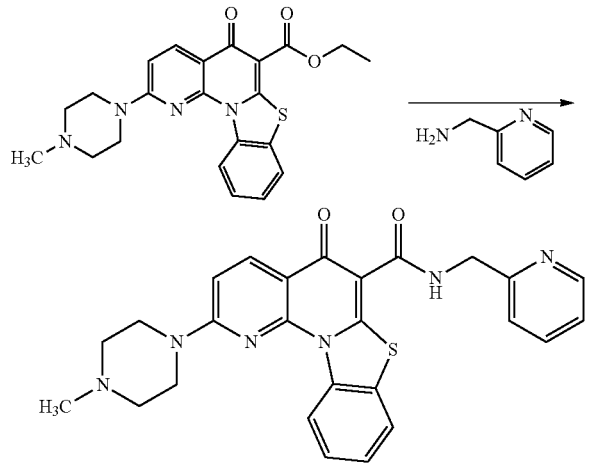

To a solution of ester (1.45 g, 3.44 mmol), pyridin-2-ylmethanamine (1.00 mL, 9.78 mmol), and DBU (1.50 mL, 10.03 mmol) in DCM (40 mL) was added AlCl$_3$ (475 mg, 7.31 mmol). The reaction mixture was stirred at rt over night. The reaction was diluted with DCM (400 mL) and 1N NaOH (200 mL) and stirred for 10 min. The layers were separated and the organic layer was washed with H$_2$O (2×100 mL), brine (100 mL), and dried over Na$_2$SO$_4$. The solvent was removed under reduced pressure and the resulting solid was triturated in ACN to give the desired product as a white solid (1.07 g, 64%). $^1$H NMR (CDCl$_3$) δ: 11.24 (t, 1H), 9.50 (d, 1H), 8.62 (m, 2H), 7.77 (dd, 1H), 7.65 (m, 1H), 7.53 (m, 1H), 7.49 (m, 2H), 6.93 (d, 1H), 4.89 (d, 2H), 3.88 (t, 4H), 2.63 (t, 4H), 2.41 (s, 3H). LCMS (ES): m/z 485 [M+1]+.

Example 4

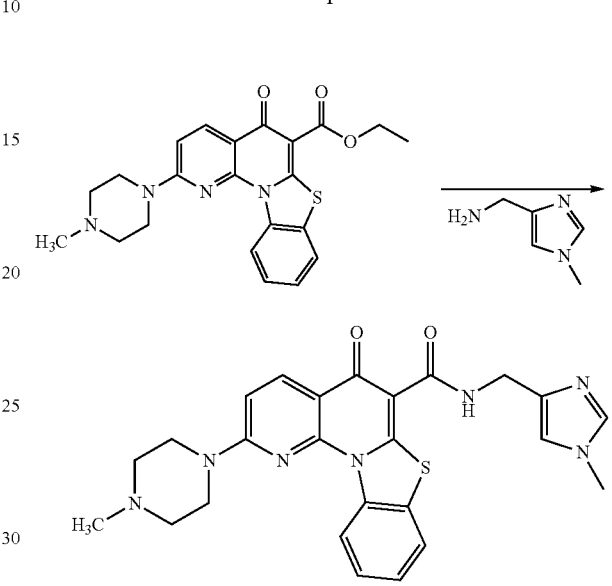

To a solution of ester (150 mg, 0.34 mmol), (1-methyl-1H-imidazol-4-yl)methanamine (0.15 mL, 1.35 mmol), and DBU (2.00 mL, 1.33 mmol) in DCM (10 mL) was added AlCl$_3$ (130 mg, 0.97 mmol). The reaction mixture was stirred at rt over night. The reaction was diluted with DCM (100 mL) and 6N NaOH (25 mL) and stirred for 10 min. The layers were separated and the organic layer was washed with H$_2$O (2×50 mL), brine (50 mL), and dried over Na$_2$SO$_4$. The solvent was removed under reduced pressure and the reaction crude was purified on silica prep TLC (10% MeOH/DCM) to yield the desired product. LCMS (ES): m/z 506 [M+1]+.

Example 5

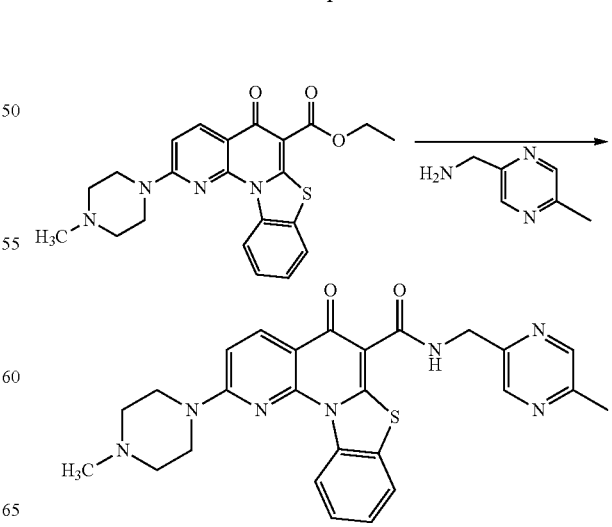

To a solution of ester (72 m g, 0.17 mmol), (5-methylpyrazin-2-yl)methanamine (0.10 mL, 0.81 mmol), and DBU (0.20 mL, 1.34 mmol) in DCM (10 mL) was added AlCl₃ (80 mg, 0.60 mmol). The reaction mixture was stirred at rt for 30 min. The reaction was diluted with DCM (100 mL) and 3N NaOH (25 mL) and stirred for 10 min. The layers were separated and the organic layer was washed with H₂O (2×50 mL), brine (50 mL), and dried over Na₂SO₄. The solvent was removed under reduced pressure and the resulting solid was triturated in ACN to give the desired product as a white solid (60 mg, 71%). LCMS (ES): m/z 500 [M+1]⁺.

Example 6

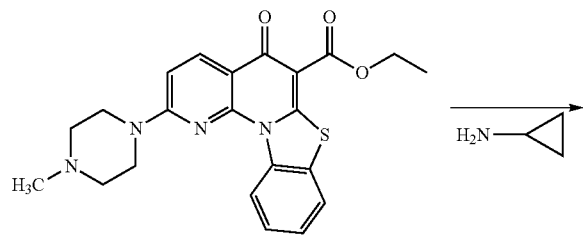

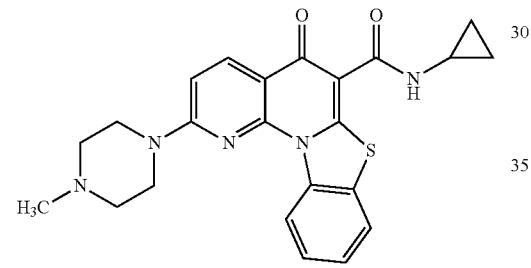

To a solution of ester (100 mg, 0.238 mmol) and cyclopropylamine (37.7 mg, 0.66 mmol) in DCM (10 mL) was added DBU (0.35 mL) and AlCl₃ (130 mg). The reaction mixture was stirred at rt for 2 hrs. The reaction was diluted with DCM (30 mL) and 6N NaOH (10 mL) and stirred for 10 min. The layers were separated and the organic layer was washed with H₂O (2×10 mL), brine (20 mL), and dried over Na₂SO₄. The solvent was removed under reduced pressure and the resulting solid was triturated in ethyl acetate to give the desired product as a white solid. LCMS (ES): m/z 431 [M+1]⁺

Example 7

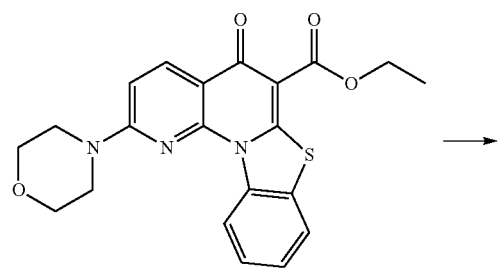

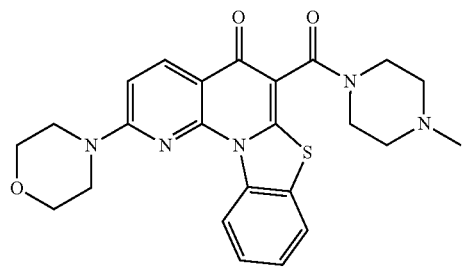

To a slurry of the morpholino ester (1.0 g, 2.44 mmol) in methylene chloride (20 mL) was added 1-methyl-piperazine (370 mg, 3.66 mmol) and aluminum chloride (487 mg, 3.66 mmol) and the mixture was allowed to stir at room temperature for 2 hours. The solvent was removed in vacuo and 1N HCl (10 mL) was added followed by 2 mL of a saturated solution of tartaric acid and the mixture was stirred for 30 minutes, until homogeneous and diluted with 50 mL water. The resulting mixture was extracted 3×20 mL ethyl acetate (discarded) and then basified with 1N NaOH. The resulting solid was collected by filtration, dried and triturated with acetonitrile (20 mL). Filtration afforded the final compound as a white solid (1.184 g, slightly damp with acetonitrile). LCMS (ES): m/z 464[M+1]⁺.

Example 8

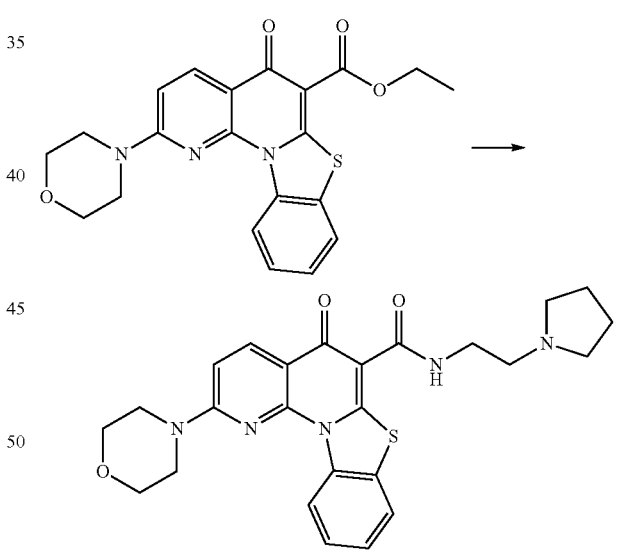

To a slurry of the morpholino ester (1.0 g, 2.44 mmol) in methylene chloride (20 mL) was added 1-2,aminoethylpyrrolidine (418 mg, 3.66 mmol) and aluminum chloride (487 mg, 3.66 mmol) and the mixture was allowed to stir at room temperature for 2 hours. The solvent was removed in vacuo and 1N HCl (10 mL) was added followed by 2 mL of a saturated solution of tartaric acid and the mixture was stirred for 30 minutes, until homogeneous and diluted with 50 mL water. The resulting mixture was extracted 3×20 mL ethyl acetate (discarded) and then basified with 1N NaOH. The resulting solid was collected by filtration, dried and triturated with acetonitrile (20 mL). Filtration afforded the final compound as a white solid (900 mg, 77%). LCMS (ES): m/z 478[M+1]⁺.

Example 9

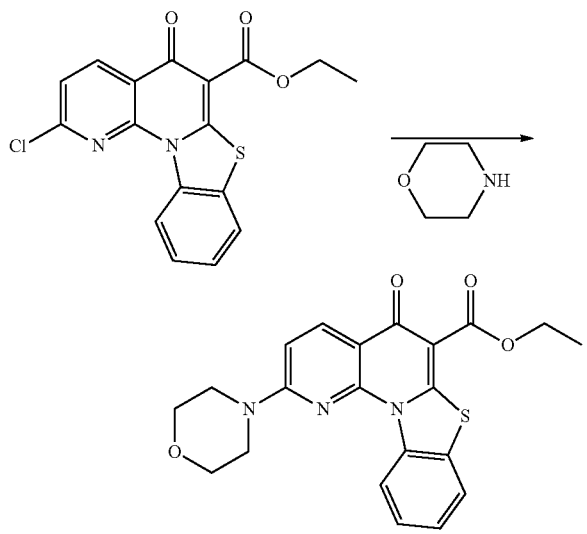

To a slurry of the chloroester (15.00 g, 41.81 mmol) in ACN (150 mL) was added morpholine (7.5 mL, 85.74 mmol) and the mixture was heated at reflux over night. The reaction was cooled to rt and the precipitate was collected by filtration. The solid was then dissolved in CHCl₃ (600 mL) and passed through a pad of CELITE™. The solvent was removed under reduced pressure and the resulting solid was triturated in ACN to give the desired product as an off-white solid (14.00 g, 82%). ¹H NMR (CDCl₃) δ: 9.36 (d, 1H), 8.60 (d, 1H), 7.70 (dd, 1H), 7.47 (m, 1H), 7.37 (m, 1H), 6.84 (d, 1H), 4.51 (q, 2H), 3.92 (t, 4H), 3.77 (t, 4H), 1.49 (t, 3H). LCMS (ES): m/z 410 [M+1]⁺.

Example 10

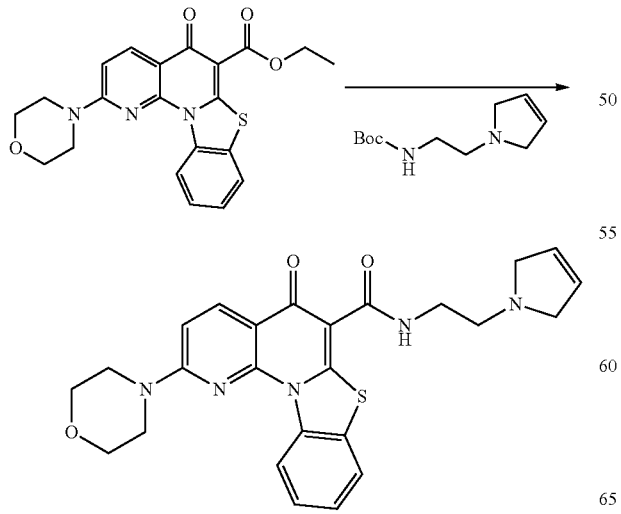

To a solution of t-butyl 2-(2,5-dihydro-1H-pyrrol-1-yl)ethylcarbamate (160 mg, 0.75 mmol) in DCM (1 mL) was added HCl (2.0 mL, 4 M in dioxane). The reaction mixture was stirred at rt for 2 h. The solvent was removed under reduced pressure and redissolved in DCM (10 mL) and DBU (0.56 mL, 3.74 mmol). The ester (150 mg, 0.37 mmol) was added to the reaction followed by AlCl₃ (150 mg, 1.12 mmol) and it was stirred for 1 h at rt. The reaction was diluted with DCM (100 mL) and 3N NaOH (50 mL) and stirred for 10 min. The layers were separated and the organic layer was washed with H₂O (2×50 mL), brine (50 mL), and dried over Na₂SO₄. The solvent was removed under reduced pressure and the reaction crude was purified on silica gel column (0-10% MeOH/DCM) to yield the desired product as a white solid (130 mg, 75%). ¹H NMR (CDCl₃) δ: 10.60 (t, 1H), 9.44 (d, 1H), 8.62 (d, 1H), 7.75 (dd, 1H), 7.48 (m, 1H), 7.44 (m, 1H), 6.91 (d, 1H), 5.78 (s, 2H), 3.94 (t, 4H), 3.81 (t, 4H), 3.66 (q, 2H), 3.63 (s, 4H), 2.96 (t, 2H). LCMS (ES): m/z 476 [M+1]⁺.

Example 11

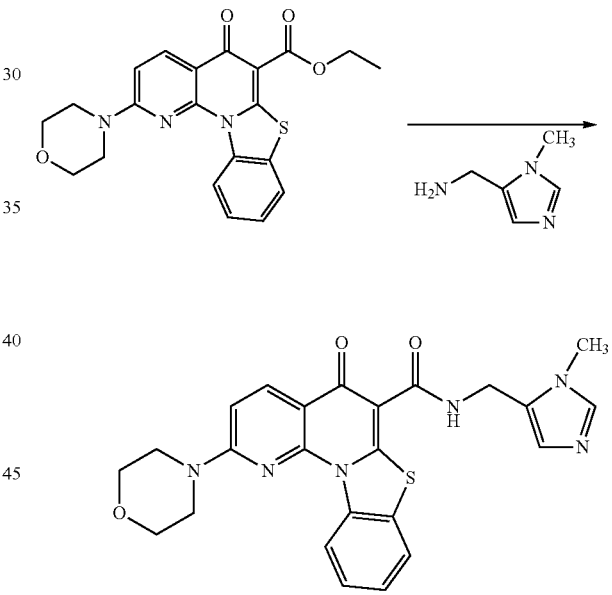

To a solution of ester (150 mg, 0.37 mmol), (1-methyl-1H-imidazol-5-yl)methanamine (0.15 mL, 1.35 mmol) and DBU (0.20 mL, 1.34 mmol) in DCM (10 mL) was added AlCl₃ (150 mg, 1.12 mmol). The reaction mixture was stirred at rt for 1 h, more DBU (0.30 mL, 2.01 mmol) was added and stirred for additional 30 min. The reaction was diluted with DCM (150 mL) and 6N NaOH (25 mL) and stirred for 10 min. The layers were separated and the organic layer was washed with H₂O (2×50 mL), brine (50 mL), and dried over Na₂SO₄. The solvent was removed under reduced pressure and the reaction crude was purified on silica prep TLC (10% MeOH/DCM) to yield the desired product (100 mg, 58%). LCMS (ES): m/z 475 [M+1]⁺.

Example 12

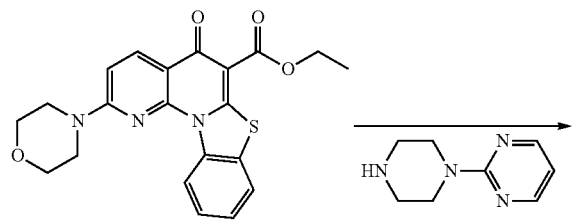

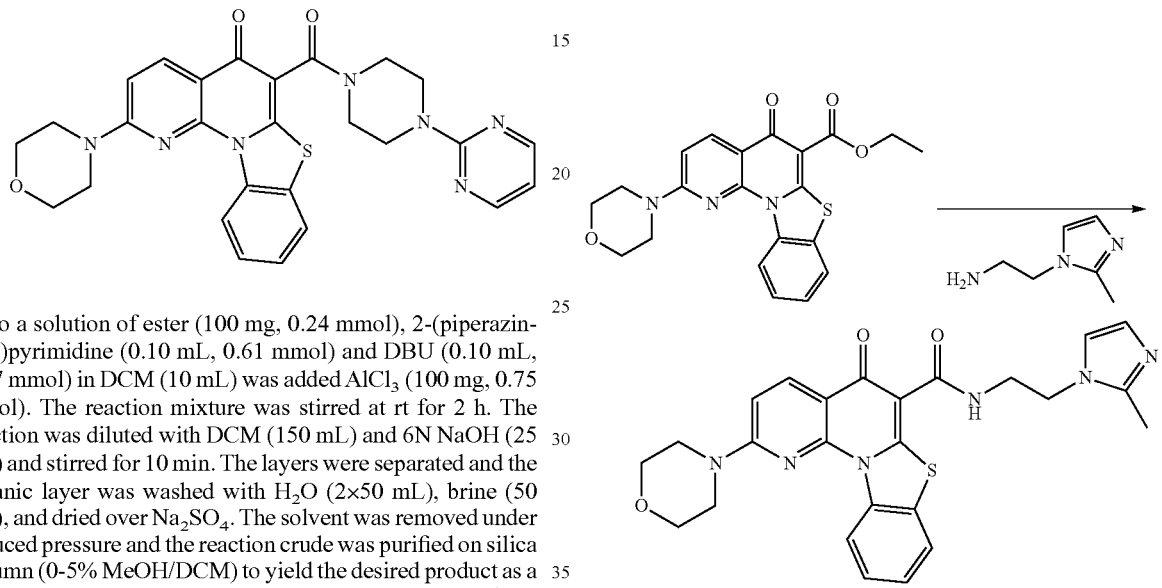

To a solution of ester (100 mg, 0.24 mmol), 2-(piperazin-1-yl)pyrimidine (0.10 mL, 0.61 mmol) and DBU (0.10 mL, 0.67 mmol) in DCM (10 mL) was added AlCl$_3$ (100 mg, 0.75 mmol). The reaction mixture was stirred at rt for 2 h. The reaction was diluted with DCM (150 mL) and 6N NaOH (25 mL) and stirred for 10 min. The layers were separated and the organic layer was washed with H$_2$O (2×50 mL), brine (50 mL), and dried over Na$_2$SO$_4$. The solvent was removed under reduced pressure and the reaction crude was purified on silica column (0-5% MeOH/DCM) to yield the desired product as a white solid (80 mg, 63%). LCMS (ES): m/z 528 [M+1]$^+$.

Example 13

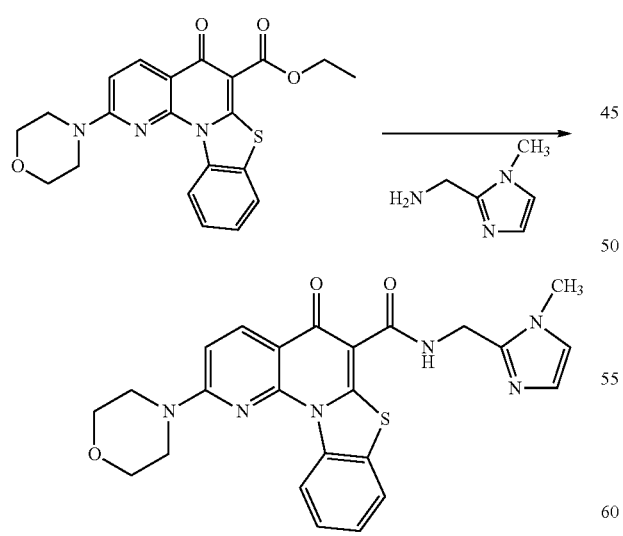

To a solution of ester (750 mg, 1.83 mmol), (1-methyl-1H-imidazol-2-yl)methanamine (0.50 mL, 4.50 mmol) and DBU (0.80 mL, 5.35 mmol) in DCM (50 mL) was added AlCl$_3$ (750 mg, 5.62 mmol). The reaction mixture was stirred at rt for 3 h. The reaction was diluted with DCM (200 mL) and 3N NaOH (100 mL) and stirred for 10 min. The layers were separated and the organic layer was washed with H$_2$O (2×100 mL), brine (100 mL), and dried over Na$_2$SO$_4$. The solvent was removed under reduced pressure and the reaction crude was purified on silica column (0-5% MeOH/DCM) to yield the desired product as a white solid (275 mg, 32%). $^1$H NMR (CDCl$_3$) δ: 11.0 (t, 1H), 9.45 (d, 1H), 8.61 (d, 1H), 7.76 (dd, 1H), 7.50 (m, 1H), 7.45 (m, 1H), 6.99 (d, 1H), 6.90 (d, 1H), 6.83 (d, 1H), 4.82 (d, 2H), 3.93 (t, 4H), 3.81 (t, 4H), 3.70 (s, 3H). LCMS (ES): m/z 475 [M+1]$^+$.

Example 14

To a solution of ester (500 mg, 1.22 mmol), 2-(2-methyl-1H-imidazol-1-yl)ethanamine (325 mg, 2.60 mmol) and DBU (1.00 mL, 6.69 mmol) in DCM (18 mL) was added AlCl$_3$ (350 mg, 2.62 mmol). The reaction mixture was stirred at rt over night. The reaction was diluted with DCM (200 mL) and 3N NaOH (50 mL) and stirred for 10 min. The layers were separated and the organic layer was washed with H$_2$O (2×50 mL), brine (50 mL), and dried over Na$_2$SO$_4$. The solvent was removed under reduced pressure and the resulting solid was triturated in ACN to give the desired product as an off-white solid (360 mg, 60%). $^1$H NMR (CDCl$_3$) δ: 10.77 (t, 1H), 9.47 (d, 1H), 8.60 (d, 1H), 7.78 (dd, 1H), 7.53 (m, 1H), 7.44 (m, 1H), 6.93 (m, 3H), 4.15 (t, 2H), 3.94 (t, 4H), 3.83 (t, 4H), 3.79 (q, 2H), 2.42 (s, 3H). LCMS (ES): m/z 489 [M+1]$^+$.

Example 15

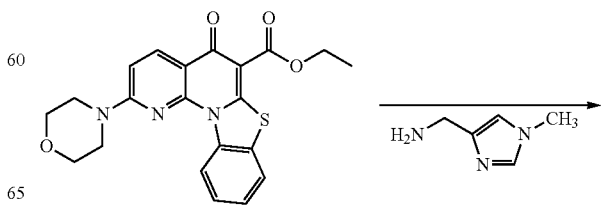

-continued

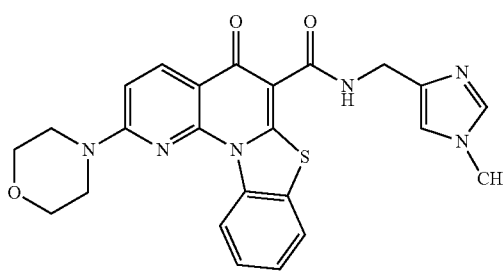

To a solution of ester (105 mg, 0.26 mmol), (1-methyl-1H-imidazol-4-yl)methanamine (0.10 mL, 0.90 mmol) and DBU (0.10 mL, 0.71 mmol) in DCM (10 mL) was added AlCl₃ (75 mg, 0.56 mmol). The reaction mixture was stirred at rt over night. The reaction was diluted with DCM (100 mL), 6N NaOH (50 mL), and saturated sodium potassium tartrate (50 mL) and stirred for 10 min. The layers were separated and the organic layer was washed with H₂O (2×50 mL), brine (50 mL), and dried over Na₂SO₄. The solvent was removed under reduced pressure and the reaction crude was purified on silica prep TLC (5% MeOH/DCM) to yield the desired product as a white solid (40 mg, 33%). LCMS (ES): m/z 475 [M+1]⁺.

Example 16

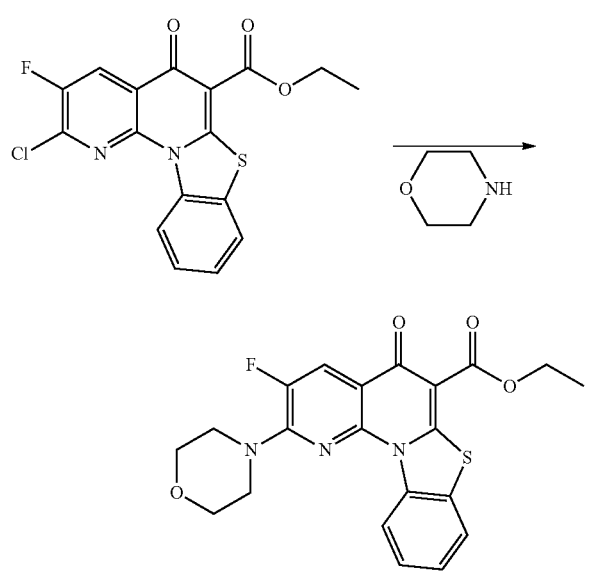

To a slurry of the chloroester (6.08 g, 16.14 mmol) in ACN (100 mL) was added morpholine (2.8 mL, 32.01 mmol) and the mixture was heated at reflux for 3 h. The reaction was cooled to rt and the precipitate was collected by filtration. The solid was then dissolved in CHCl₃ (200 mL) and passed through a pad of CELITE™. The solvent was removed under reduced pressure and the resulting solid was triturated in ACN to give the desired product as a white solid (5.00 g, 73%). ¹H NMR (CDCl₃) δ: 9.37 (d, 1H), 8.29 (d, 1H), 7.72 (dd, 1H), 7.47 (m, 1H), 7.42 (m, 1H), 4.50 (q, 2H), 3.94 (t, 4H), 3.81 (t, 4H), 1.48 (t, 3H). LCMS (ES): m/z 428 [M+1]⁺.

Example 17

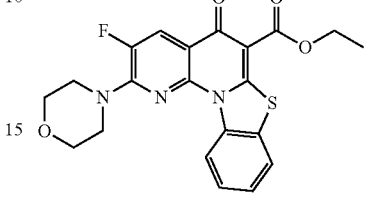

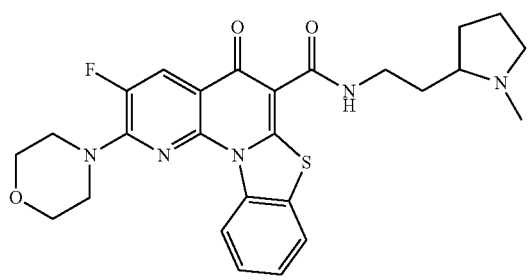

To a solution of ester (700 mg, 1.64 mmol) and 2-(1-methylpyrrolidin-2-yl)ethanamine (0.70 mL, 4.83 mmol) in DCM (25 mL) was added AlCl₃ (645 mg, 4.84 mmol). The reaction mixture was stirred at rt for 1 h. The reaction was diluted with DCM (150 mL), 6N NaOH (50 mL), and saturated sodium potassium tartrate (50 mL) and stirred for 10 min. The layers were separated and the organic layer was washed with H₂O (2×50 mL), brine (50 mL), and dried over Na₂SO₄. The solvent was removed under reduced pressure and the resulting solid was triturated in Et₂O/EtOAc (1:1) to give the desired product as a white solid (690 mg, 83%). ¹H NMR (CDCl₃) δ: 10.45 (t, 1H), 9.41 (d, 1H), 8.29 (d, 1H), 7.76 (dd, 1H), 7.50 (m, 1H), 7.49 (m, 1H), 3.96 (t, 4H), 3.85 (t, 4H), 3.55 (m, 2H), 3.06 (m, 1H), 2.34 (s, 3H), 2.17 (m, 1H), 2.08 (m, 3H), 1.80 (m, 2H), 1.56 (m, 2H). LCMS (ES): m/z 510 [M+1]⁺.

Example 18

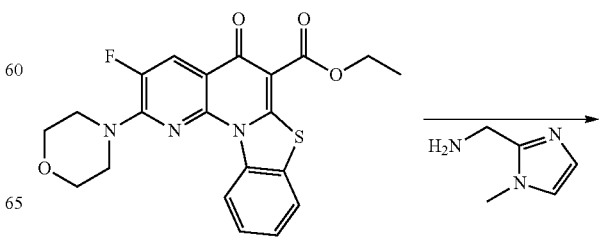

3.95 (t, 4H), 3.88 (m, 2H), 3.82 (t, 4H), 3.48 (m, 2H), 2.54 (m, 2H), 2.44 (m, 2H), 2.32 (s, 3H). LCMS (ES): m/z 482 [M+1]+.

Example 20

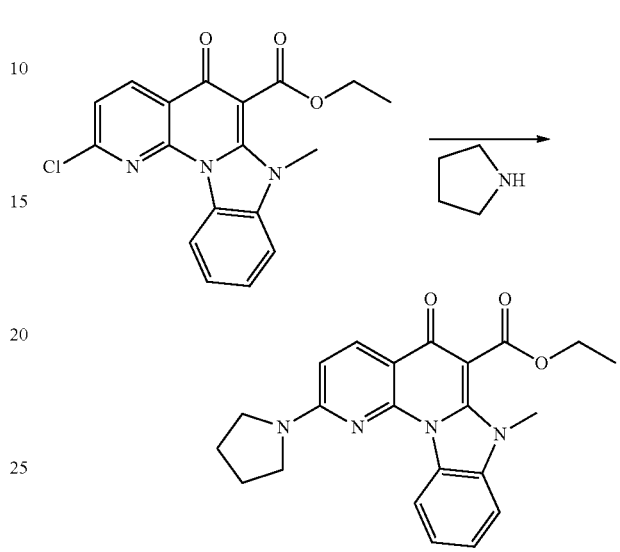

A slurry of chloroester (800 mg, 2.25 mmol), and pyrrolidine (0.40 mL, 4.79 mmol) in DMF (5.0 mL) was heated at 65° C. for 15 min in microwave. The reaction was diluted with EtOAc (50 mL) and the resulting precipitate was collected by filtration to yield the desired product. LCMS (ES): m/z 391 [M+1]+

Example 21

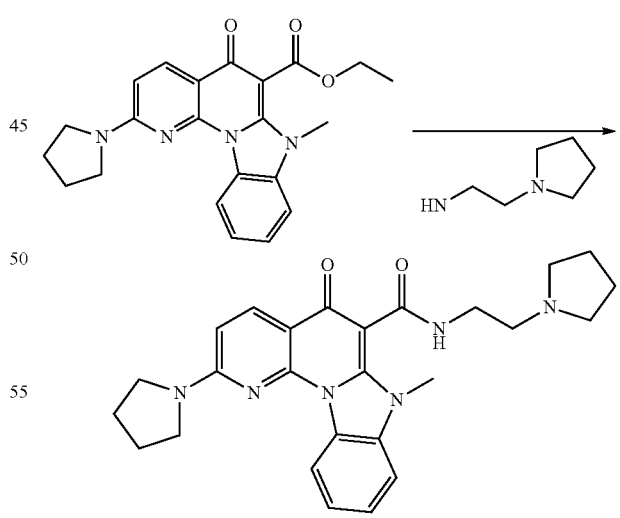

To a solution of ester (675 mg, 1.73 mmol), 2-(pyrrolidin-1-yl)ethanamine (0.65 mL, 5.13 mmol), and DBU (0.75 mL, 5.02 mmol) in DCM (30 mL) was added AlCl₃ (680 mg, 5.10 mmol). The reaction mixture was stirred at rt for 1.5 h. The reaction was diluted with DCM (100 mL), 6N NaOH (50 mL), and saturated sodium potassium tartrate (50 mL) and

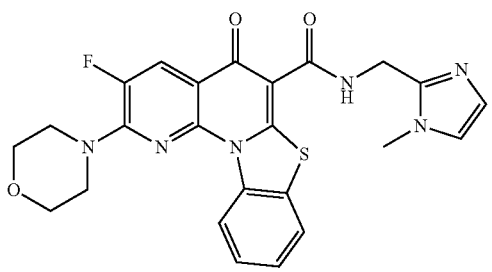

To a solution of ester (515 mg, 1.20 mmol) and C-(1-methyl-1H-imidazol-2-yl)-methylamine (199.5, 1.79 mmol) in DCM (40 mL) was added DBU (0.98 mL) and AlCl₃ (352.3 mg). The reaction mixture was stirred at rt over night. The reaction was diluted with DCM (100 mL) and 6N NaOH (25 mL) and stirred for 10 min. The layers were separated and the organic layer was washed with H₂O (2×50 mL), brine (50 mL), and dried over Na₂SO₄. The solvent was removed under reduced pressure and the resulting solid was triturated in ethyl acetate to give the desired product as a white solid. LCMS (ES): m/z 493 [M+1]+

Example 19

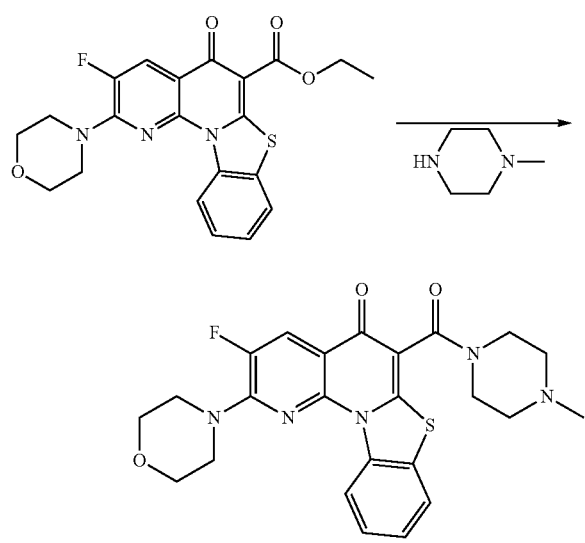

To a solution of ester (300 mg, 0.70 mmol) and 1-methylpiperazine (0.25 mL, 2.25 mmol) in DCM (15 mL) was added AlCl₃ (305 mg, 2.29 mmol). The reaction mixture was stirred at rt for 1 h. The reaction was diluted with DCM (100 mL), 6N NaOH (50 mL), and saturated sodium potassium tartrate (50 mL) and stirred for 10 min. The layers were separated and the organic layer was washed with H₂O (2×50 mL), brine (50 mL), and dried over Na₂SO₄. The solvent was removed under reduced pressure and the resulting solid was triturated in Et₂O/EtOAc (1:1) to give the desired product as a white solid (280 mg, 83%). ¹H NMR (CDCl₃) δ: 9.37 (d, 1H), 8.29 (d, 1H), 7.65 (dd, 1H), 7.48 (m, 1H), 7.40 (m, 1H), stirred for 15 min. The layers were separated and the organic layer was washed with H₂O (2×100 mL), brine (100 mL), and dried over Na₂SO₄. The solvent was removed under reduced pressure and the reaction crude was purified on silica gel column (5% MeOH/2% TEA/DCM) to give the desired product as a white solid (538 mg, 68%). ¹H NMR (CDCl₃) δ: 9.91 (t, 1H), 8.90 (d, 1H), 8.45 (d, 1H), 7.37 (m, 3H), 6.52 (d, 1H), 4.00-3.40 (br s, 4H), 3.81 (s, 3H), 3.65 (q, 2H), 2.79 (t, 2H), 2.63 (m, 4H), 2.14 (m, 4H), 1.81 (m, 4H). LCMS (ES): m/z 459 [M+1]⁺.

Example 22

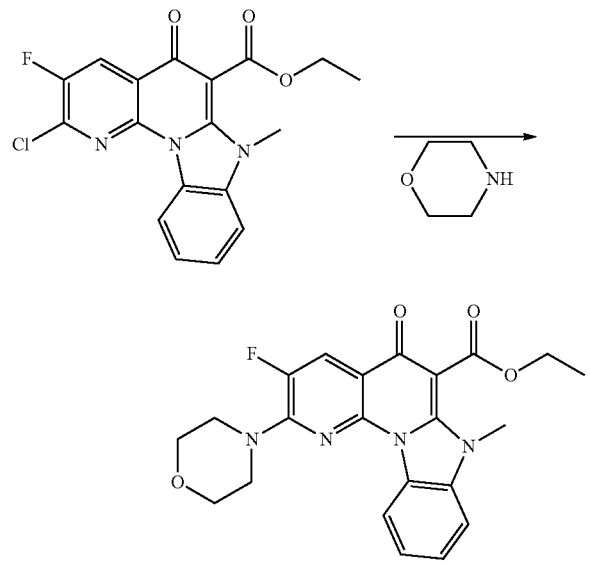

The chloroester (1.0 eq, 250 mg, 2.67 mmol) was reacted with morpholine (0.29 ml) in NMP (1 ml) under microwave heating at 100° C. for 5 min. The solid that formed upon cooling was filtered and washed with NMP. The material was sonicated in hot AcOEt and filtered after cooling. Product 2 was isolated as a white solid (173 mg, 62% yield). LCMS (ES): 95% pure, m/z 425 [M+1]⁺.

Example 23

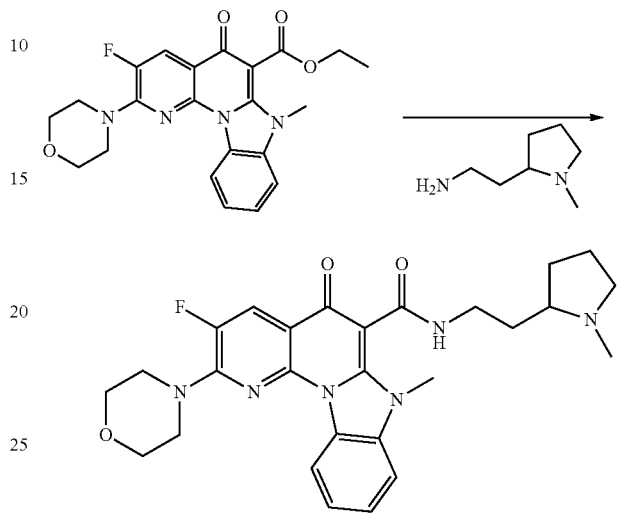

Ester (1.0 eq, 312 mg, 0.73 mmol) and 2-(1-methylpyrrolidin-2-yl)ethanamine (2.0 eq, 0.21 ml, 1.45 mmol) were mixed with DBU (4.0 eq, 0.44 ml, 2.94 mmol) in CH₂Cl₂ (5 ml). Aluminum chloride was added (2.0 eq, 196 mg, 1.47 mmol) and the reaction was stirred at 45° C. for 5 hours. The solvent was removed in vacuo and the solid treated with a saturated aqueous solution of tartaric acid for one hour. After addition of water, the pH was adjusted to 12-14 by adding NaOH. The product was extracted with CH₂Cl₂ (4×). The combined extracts were washed with water and brine, dried over Na₂SO₄ and the solvent removed in vacuo. The residue was triturated in a mixture of AcOEt and hexanes, filtered and dried to afford desired compound as an off-white solid (318 mg, 85% yield). LCMS (ES): 95% pure, m/z 507 [M+1]⁺.

The following compounds in Table 1 were prepared by the same method, using the appropriate amines and quinolone ethyl esters.

TABLE 1

| Structure | MW | LCMS (ES) m/z [M + 1]⁺ |
|---|---|---|
| 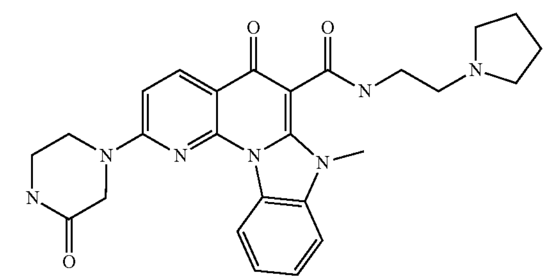 [SMILES: Cn1c2ccccc2n2c3nc(N4CCNC(=O)C4)ccc3c(=O)c(C(=O)NCCN3CCCC3)c12] | 487.55 | 488 |

TABLE 1-continued

| Structure | MW | LCMS (ES) m/z [M + 1]+ |
|---|---|---|
| 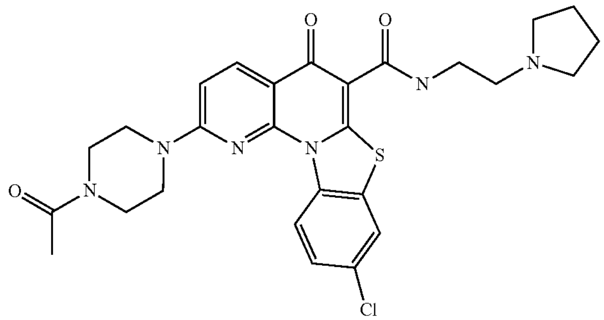 [SMILES: CC(=O)N1CCN(c2ccc3c(=O)c(C(=O)NCCN4CCCC4)c4sc5cc(Cl)ccc5n4c3n2)CC1] | 553.08 | 553 |
| 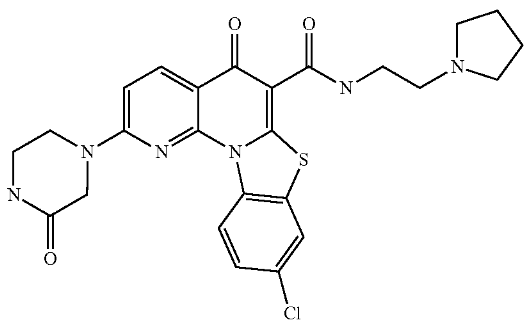 [SMILES: O=C1CN(c2ccc3c(=O)c(C(=O)NCCN4CCCC4)c4sc5cc(Cl)ccc5n4c3n2)CCN1] | 525.02 | 525 |
| 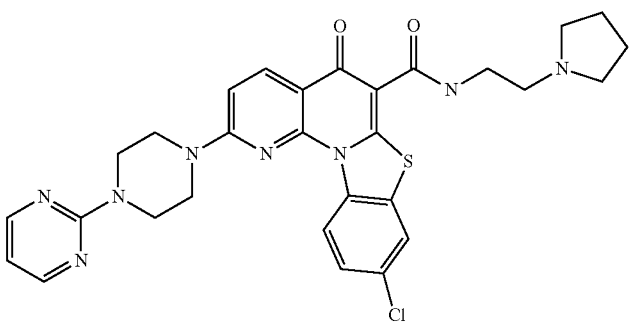 [SMILES: O=C(NCCN1CCCC1)c1c(=O)c2ccc(N3CCN(c4ncccn4)CC3)nc2n2c1sc1cc(Cl)ccc12] | 589.19 | 589 |
| 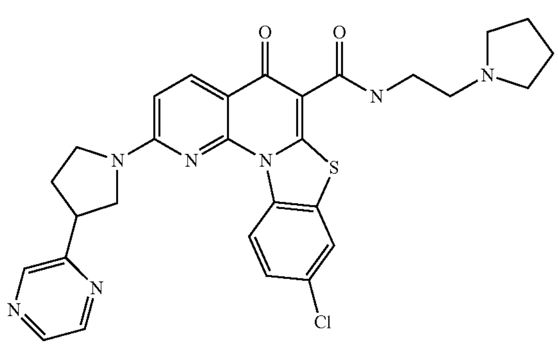 [SMILES: O=C(NCCN1CCCC1)c1c(=O)c2ccc(N3CCC(c4cnccn4)C3)nc2n2c1sc1cc(Cl)ccc12] | 574.10 | 574 |

TABLE 1-continued

| Structure | MW | LCMS (ES) m/z [M + 1]+ |
|---|---|---|
| 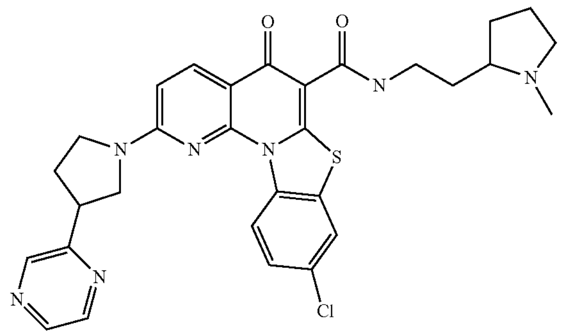 [SMILES: CN1CCCC1CCNC(=O)c1c(=O)c2ccc(N3CCC(c4cnccn4)C3)nc2n2c1sc1cc(Cl)ccc12] | 588.12 | 588 |
| 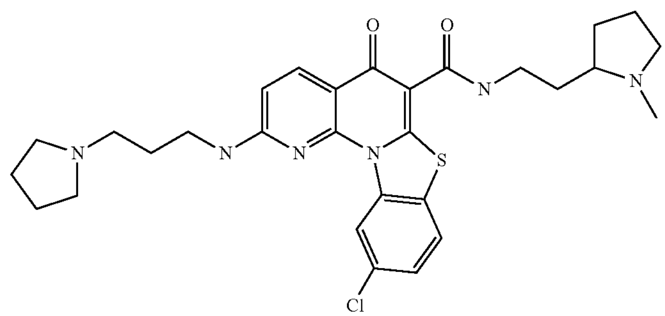 [SMILES: CN1CCCC1CCNC(=O)c1c(=O)c2ccc(NCCCN3CCCC3)nc2n2c1sc1ccc(Cl)cc12] | 567.15 | 567 |
| 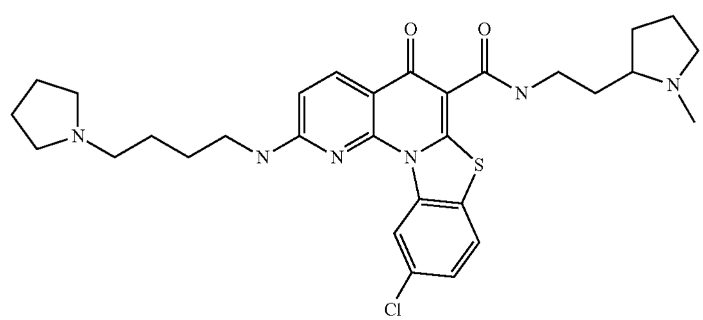 [SMILES: CN1CCCC1CCNC(=O)c1c(=O)c2ccc(NCCCCN3CCCC3)nc2n2c1sc1ccc(Cl)cc12] | 581.17 | 581 |
| 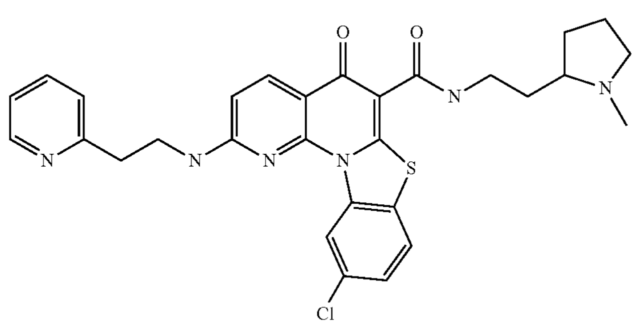 [SMILES: CN1CCCC1CCNC(=O)c1c(=O)c2ccc(NCCc3ccccn3)nc2n2c1sc1ccc(Cl)cc12] | 561.10 | 561 |

TABLE 1-continued

| Structure | MW | LCMS (ES) m/z [M + 1]+ |
|---|---|---|
| 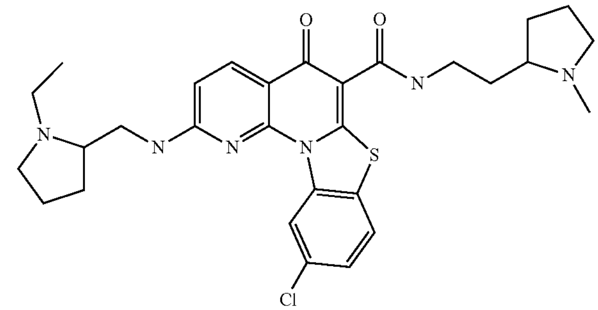 [SMILES: CCN1CCCC1CNc1ccc2c(=O)c(C(=O)NCCC3CCCN3C)c3sc4ccc(Cl)cc4n3c2n1] | 567.15 | 567 |
| 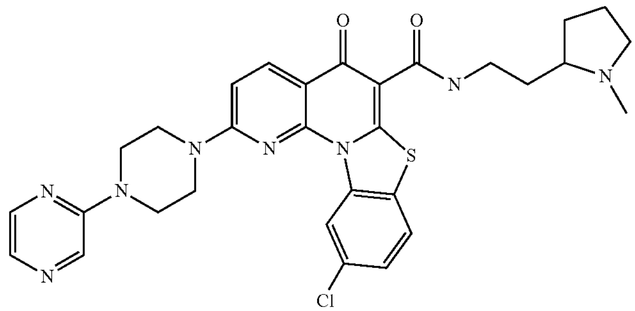 [SMILES: CN1CCCC1CCNC(=O)c1c(=O)c2ccc(N3CCN(c4cnccn4)CC3)nc2n2c1sc1ccc(Cl)cc12] | 603.14 | 603 |
| 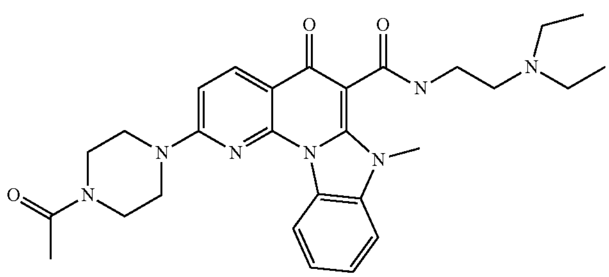 [SMILES: CCN(CC)CCNC(=O)c1c(=O)c2ccc(N3CCN(C(C)=O)CC3)nc2n2c3ccccc3n(C)c12] | 517.62 | 518 |
| 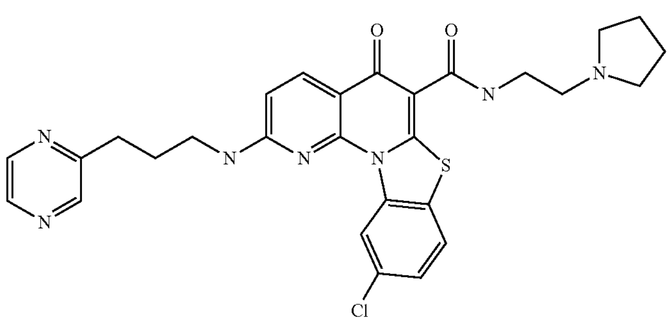 [SMILES: O=C(NCCN1CCCC1)c1c(=O)c2ccc(NCCCc3cnccn3)nc2n2c1sc1ccc(Cl)cc12] | 562.09 | 562 |
| 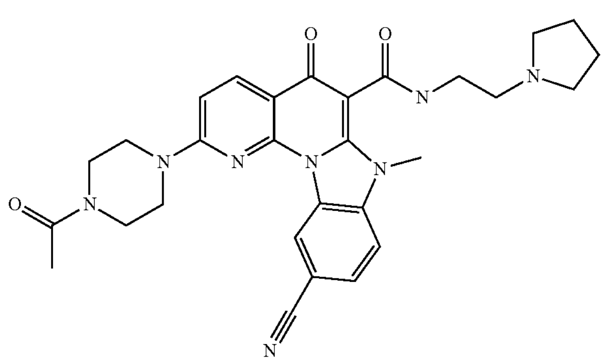 [SMILES: CC(=O)N1CCN(c2ccc3c(=O)c(C(=O)NCCN4CCCC4)c4n(C)c5ccc(C#N)cc5n4c3n2)CC1] | 540.62 | 541 |

TABLE 1-continued
| Structure | MW | LCMS (ES) m/z [M + 1]+ |
|---|---|---|
| 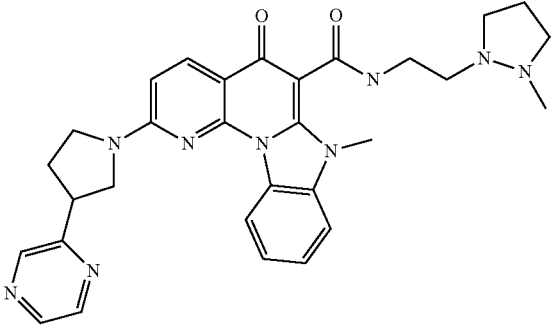 [SMILES: CN1CCCN1CCNC(=O)c1c(=O)c2ccc(N3CCC(c4cnccn4)C3)nc2n2c3ccccc3n(C)c12] | 550.65 | 551 |
| 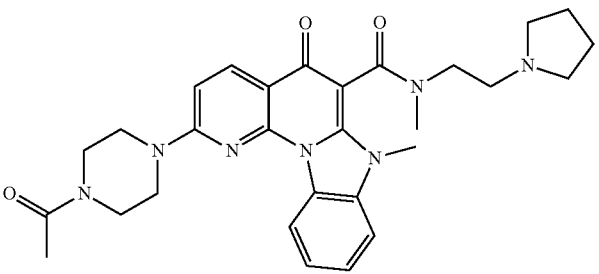 [SMILES: CC(=O)N1CCN(c2ccc3c(=O)c(C(=O)N(C)CCN4CCCC4)c4n(C)c5ccccc5n4c3n2)CC1] | 529.63 | 530 |
| 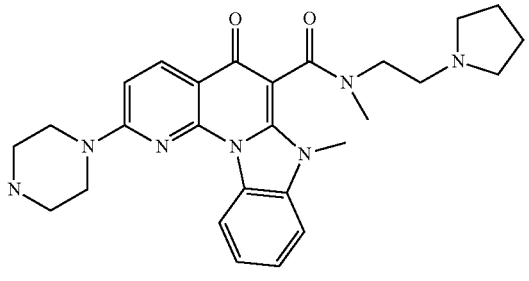 [SMILES: CN(CCN1CCCC1)C(=O)c1c(=O)c2ccc(N3CCNCC3)nc2n2c3ccccc3n(C)c12] | 487.60 | 488 |
| 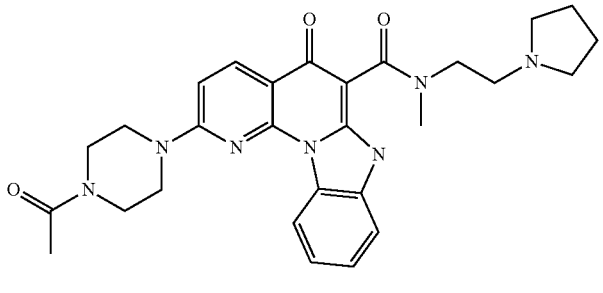 [SMILES: CC(=O)N1CCN(c2ccc3c(=O)c(C(=O)N(C)CCN4CCCC4)c4[nH]c5ccccc5n4c3n2)CC1] | 515.61 | 516 |
| 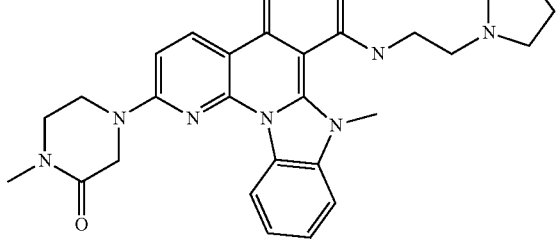 | 501.58 | 502 |

TABLE 1-continued

| Structure | MW | LCMS (ES) m/z [M + 1]+ |
|---|---|---|
| 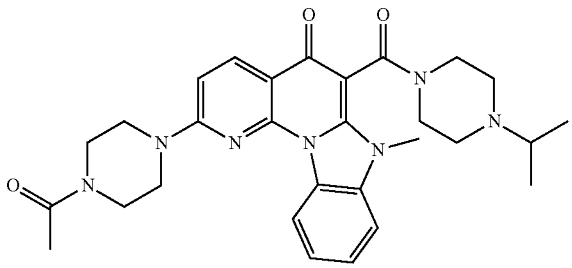 [SMILES: CC(=O)N1CCN(c2ccc3c(=O)c(C(=O)N4CCN(C(C)C)CC4)c4n(C)c5ccccc5n4c3n2)CC1] | 529.63 | 530 |
| 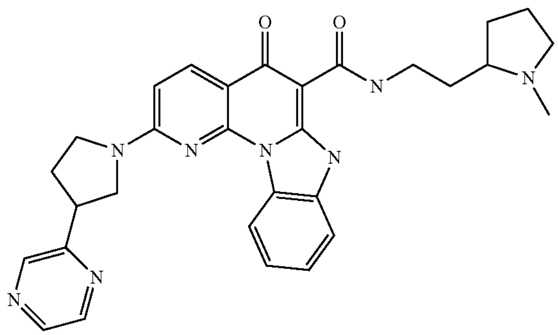 [SMILES: CN1CCCC1CCNC(=O)c1c(=O)c2ccc(N3CCC(c4cnccn4)C3)nc2n2c1[nH]c1ccccc12] | 536.63 | 537 |
| 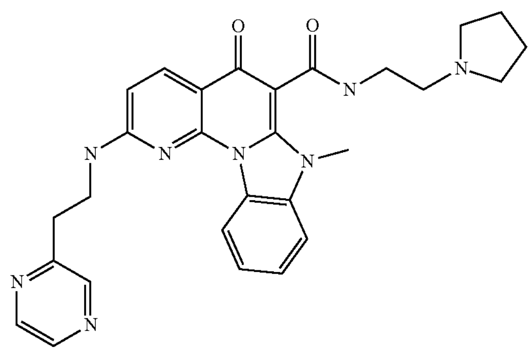 [SMILES: Cn1c2ccccc2n2c3nc(NCCc4cnccn4)ccc3c(=O)c(C(=O)NCCN3CCCC3)c12] | 510.59 | 511 |
| 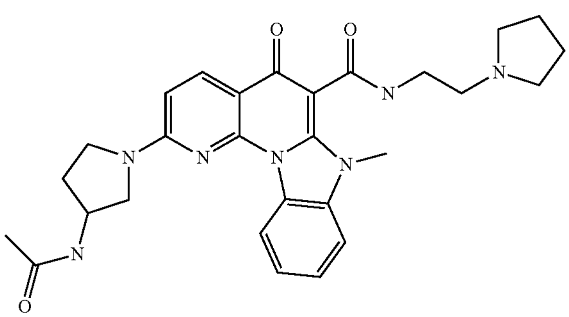 [SMILES: CC(=O)NC1CCN(c2ccc3c(=O)c(C(=O)NCCN4CCCC4)c4n(C)c5ccccc5n4c3n2)C1] | 515.61 | 516 |
| 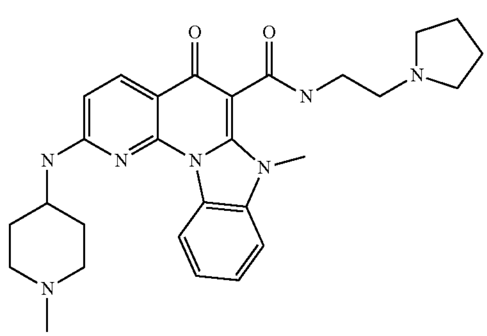 [SMILES: CN1CCC(Nc2ccc3c(=O)c(C(=O)NCCN4CCCC4)c4n(C)c5ccccc5n4c3n2)CC1] | 501.62 | 502 |

TABLE 1-continued

| Structure | MW | LCMS (ES) m/z [M + 1]+ |
|---|---|---|
| 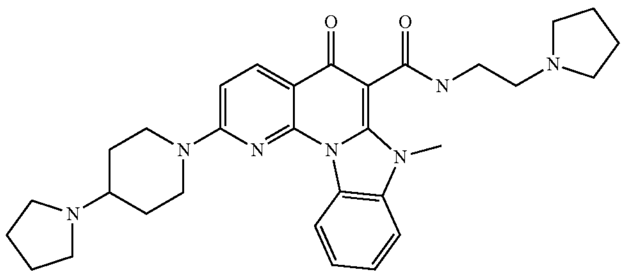 [SMILES: Cn1c2ccccc2n2c3nc(N4CCC(N5CCCC5)CC4)ccc3c(=O)c(C(=O)NCCN3CCCC3)c12] | 541.69 | 542 |
| 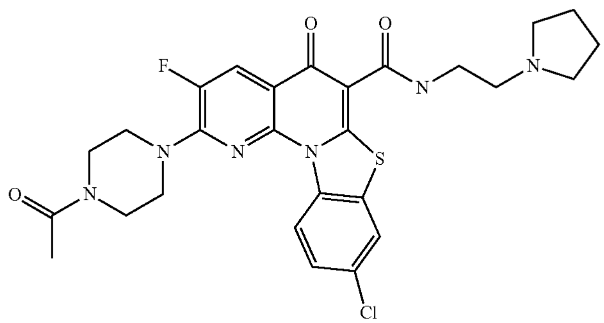 [SMILES: CC(=O)N1CCN(c2nc3c(cc2F)c(=O)c(C(=O)NCCN2CCCC2)c2sc4cc(Cl)ccc4n23)CC1] | 571.07 | 571 |
| 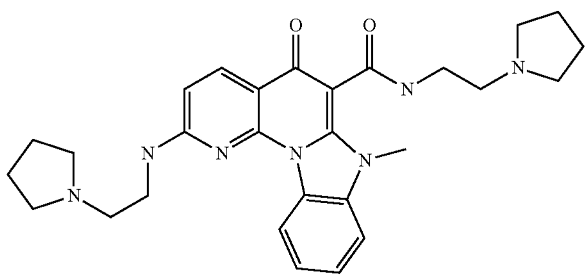 [SMILES: Cn1c2ccccc2n2c3nc(NCCN4CCCC4)ccc3c(=O)c(C(=O)NCCN3CCCC3)c12] | 501.62 | 502 |
| 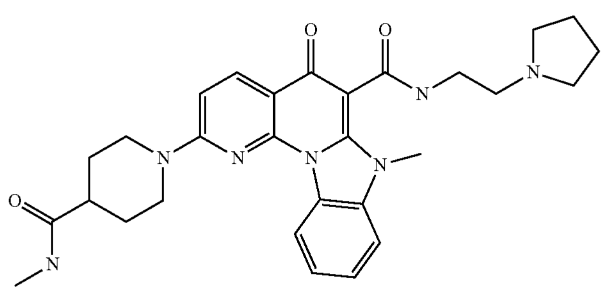 | 529.63 | 530 |
| 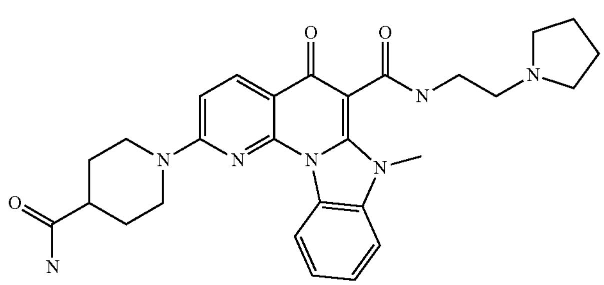 [SMILES: Cn1c2ccccc2n2c3nc(N4CCC(C(N)=O)CC4)ccc3c(=O)c(C(=O)NCCN3CCCC3)c12] | 515.61 | 516 |

TABLE 1-continued
| Structure | MW | LCMS (ES) m/z [M + 1]+ |
|---|---|---|
| 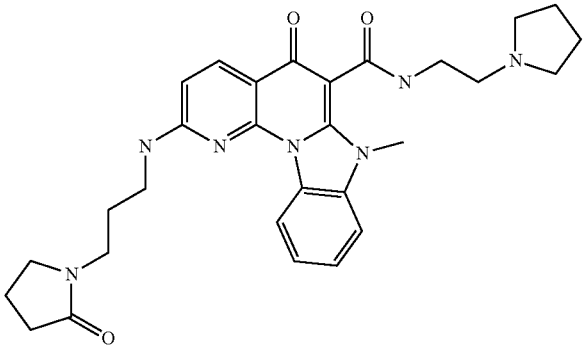 [SMILES: Cn1c2ccccc2n2c3nc(NCCCN4CCCC4=O)ccc3c(=O)c(C(=O)NCCN3CCCC3)c12] | 529.63 | 530 |
| 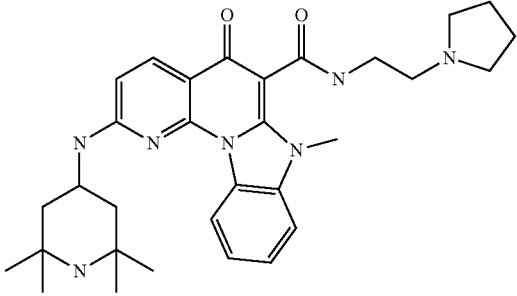 [SMILES: Cn1c2ccccc2n2c3nc(NC4CC(C)(C)NC(C)(C)C4)ccc3c(=O)c(C(=O)NCCN3CCCC3)c12] | 543.70 | 544 |
| 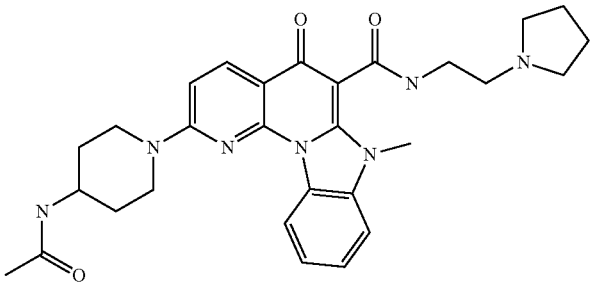 [SMILES: CC(=O)NC1CCN(c2ccc3c(=O)c(C(=O)NCCN4CCCC4)c4n(C)c5ccccc5n4c3n2)CC1] | 529.63 | 530 |
| 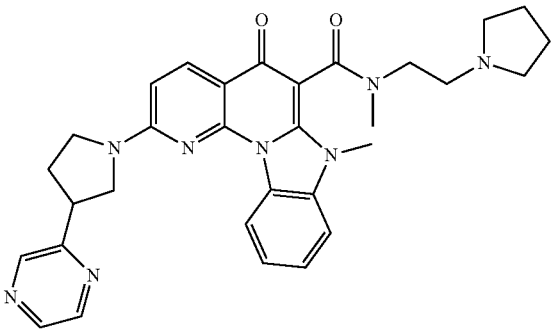 [SMILES: CN(CCN1CCCC1)C(=O)c1c(=O)c2ccc(N3CCC(c4cnccn4)C3)nc2n2c3ccccc3n(C)c12] | 550.65 | 551 |
| 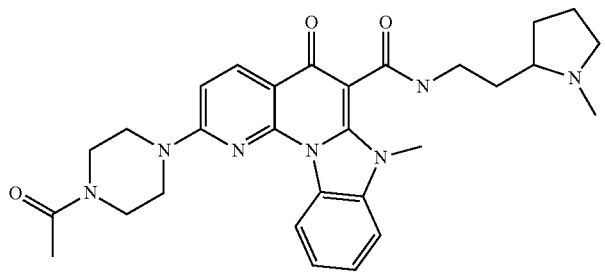 [SMILES: CC(=O)N1CCN(c2ccc3c(=O)c(C(=O)NCCC4CCCN4C)c4n(C)c5ccccc5n4c3n2)CC1] | 529.63 | 530 |

TABLE 1-continued
| Structure | MW | LCMS (ES) m/z [M + 1]+ |
|---|---|---|
| 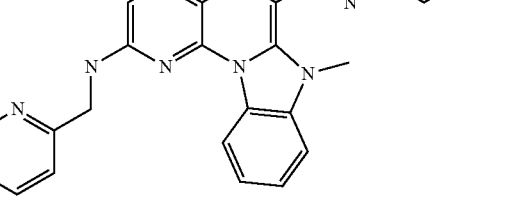 | 495.58 | 496 |
| 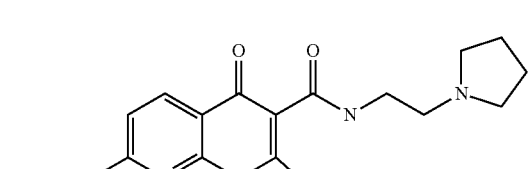 | 494.59 | 495 |
| 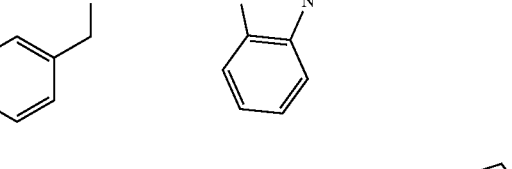 | 524.61 | 525 |
| 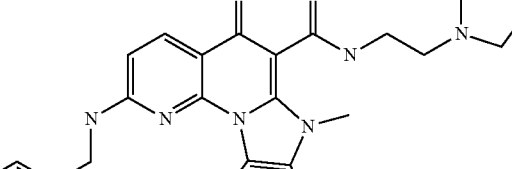 | 496.56 | 497 |
| 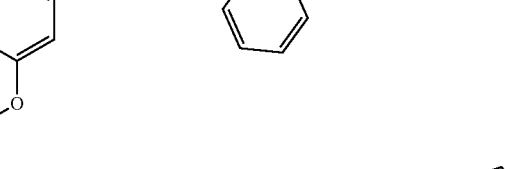 | 501.60 | 502 |

TABLE 1-continued
| Structure | MW | LCMS (ES) m/z [M + 1]+ |
|---|---|---|
| 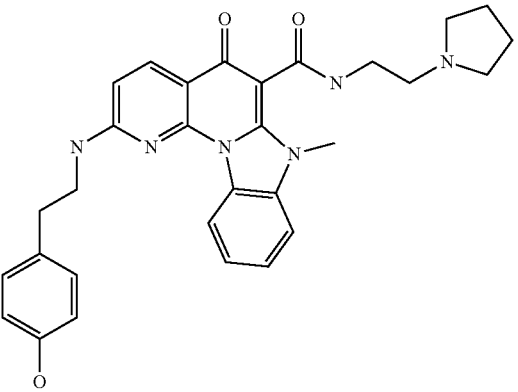 [SMILES: Cn1c2ccccc2n2c3nc(NCCc4ccc(O)cc4)ccc3c(=O)c(C(=O)NCCN3CCCC3)c12] | 524.61 | 525 |
| 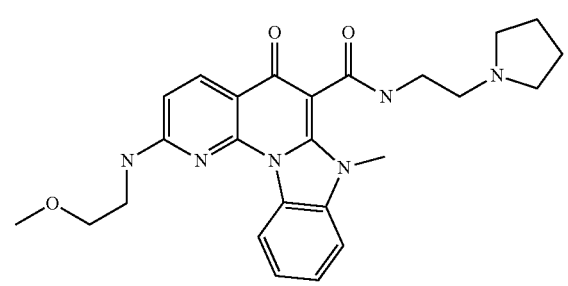 [SMILES: COCCNc1ccc2c(=O)c(C(=O)NCCN3CCCC3)c3n(C)c4ccccc4n3c2n1] | 462.54 | 463 |
| 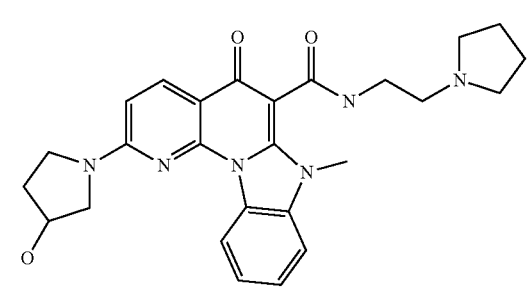 [SMILES: Cn1c2ccccc2n2c3nc(N4CCC(O)C4)ccc3c(=O)c(C(=O)NCCN3CCCC3)c12] | 474.55 | 475 |
| 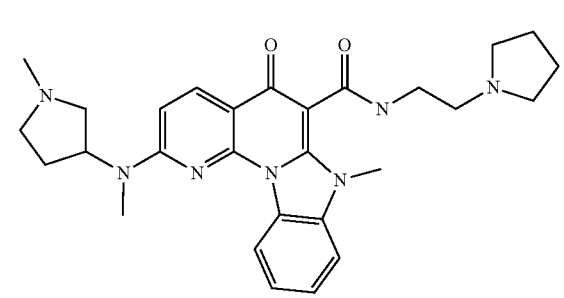 [SMILES: CN1CCC(N(C)c2ccc3c(=O)c(C(=O)NCCN4CCCC4)c4n(C)c5ccccc5n4c3n2)C1] | 501.62 | 502 |
| 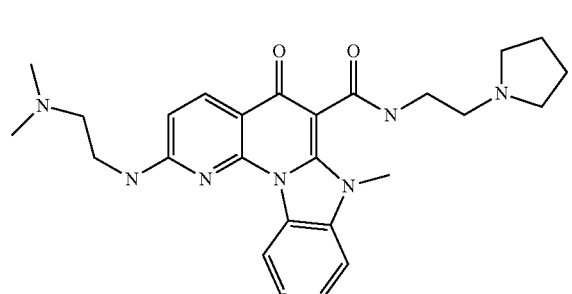 | 475.59 | 476 |

TABLE 1-continued

| Structure | MW | LCMS (ES) m/z [M + 1]+ |
|---|---|---|
| 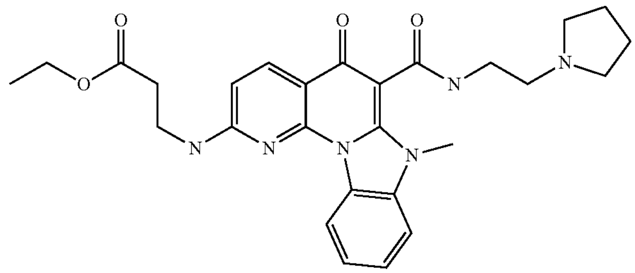 [SMILES: CCOC(=O)CCNc1ccc2c(=O)c(C(=O)NCCN3CCCC3)c3n(C)c4ccccc4n3c2n1] | 504.58 | 505 |
| 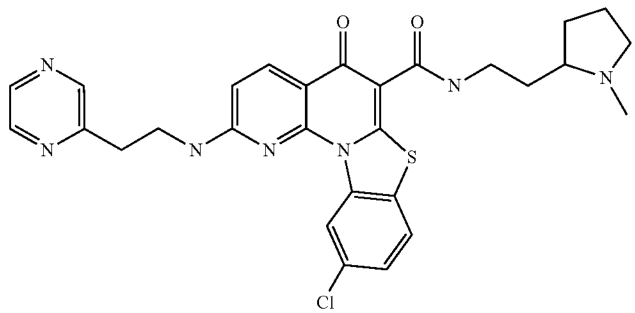 [SMILES: CN1CCCC1CCNC(=O)c1c(=O)c2ccc(NCCc3cnccn3)nc2n2c1sc1ccc(Cl)cc12] | 562.09 | 562 |
| 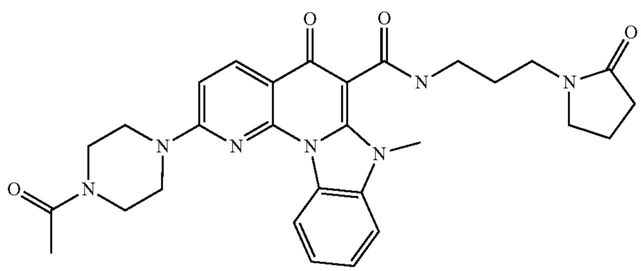 [SMILES: CC(=O)N1CCN(c2ccc3c(=O)c(C(=O)NCCCN4CCCC4=O)c4n(C)c5ccccc5n4c3n2)CC1] | 543.62 | 544 |
| 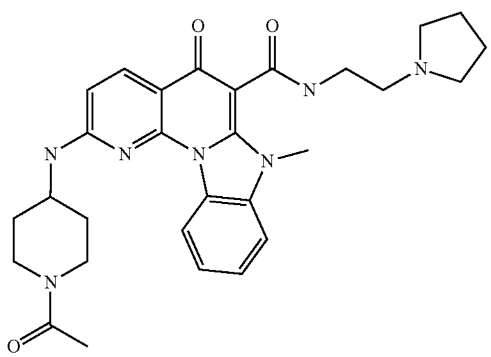 [SMILES: CC(=O)N1CCC(Nc2ccc3c(=O)c(C(=O)NCCN4CCCC4)c4n(C)c5ccccc5n4c3n2)CC1] | 529.63 | 530 |
| 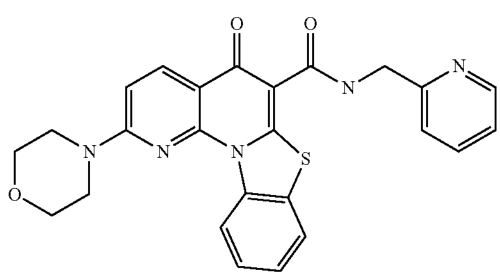 [SMILES: O=C(NCc1ccccn1)c1c(=O)c2ccc(N3CCOCC3)nc2n2c1sc1ccccc12] | 471.53 | 472 |

TABLE 1-continued

| Structure | MW | LCMS (ES) m/z [M + 1]+ |
|---|---|---|
| 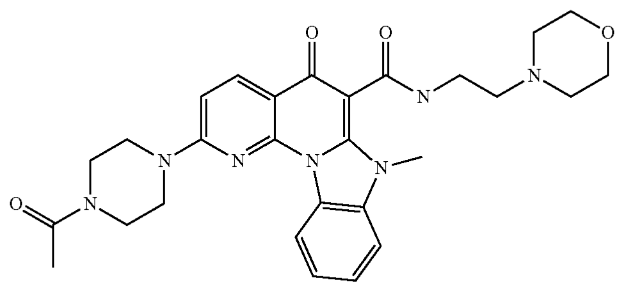 [SMILES: CC(=O)N1CCN(c2ccc3c(=O)c(C(=O)NCCN4CCOCC4)c4n(C)c5ccccc5n4c3n2)CC1] | 531.61 | 532 |
| 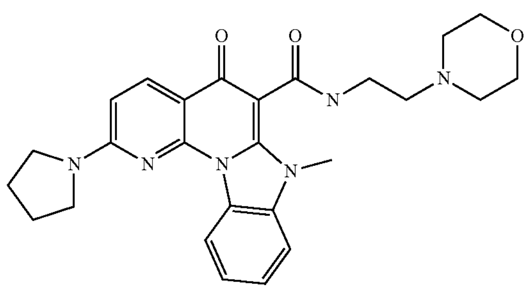 [SMILES: Cn1c2ccccc2n2c3nc(N4CCCC4)ccc3c(=O)c(C(=O)NCCN3CCOCC3)c12] | 474.55 | 475 |
| 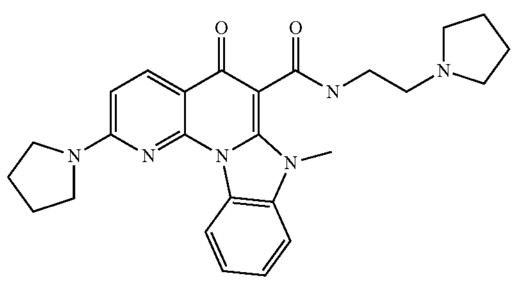 [SMILES: Cn1c2ccccc2n2c3nc(N4CCCC4)ccc3c(=O)c(C(=O)NCCN3CCCC3)c12] | 458.56 | 459 |
| 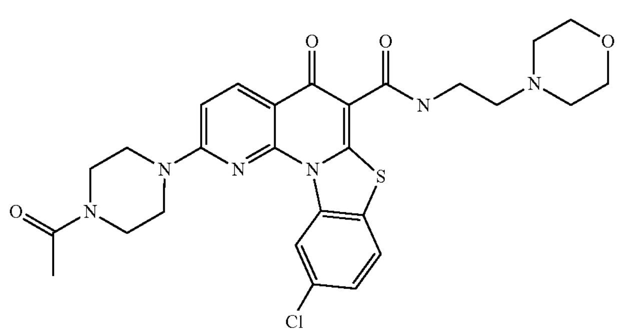 [SMILES: CC(=O)N1CCN(c2ccc3c(=O)c(C(=O)NCCN4CCOCC4)c4sc5ccc(Cl)cc5n4c3n2)CC1] | 569.07 | 569 |
| 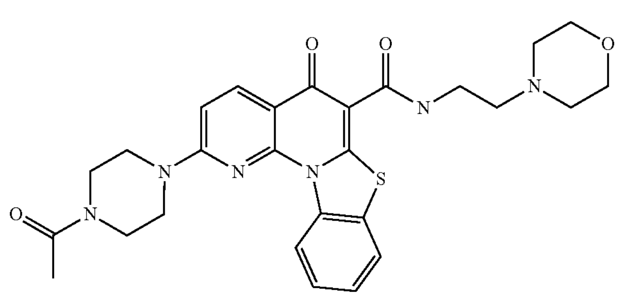 [SMILES: CC(=O)N1CCN(c2ccc3c(=O)c(C(=O)NCCN4CCOCC4)c4sc5ccccc5n4c3n2)CC1] | 534.63 | 535 |

TABLE 1-continued
| Structure | MW | LCMS (ES) m/z [M + 1]+ |
|---|---|---|
| 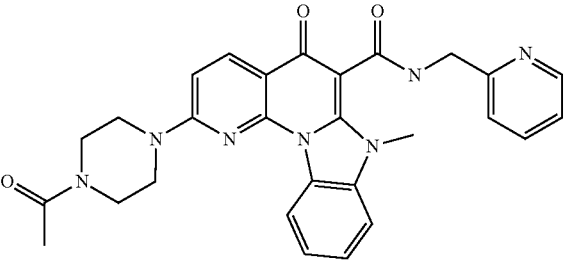 [SMILES: CC(=O)N1CCN(c2ccc3c(=O)c(C(=O)NCc4ccccn4)c4n(C)c5ccccc5n4c3n2)CC1] | 509.56 | 510 |
| 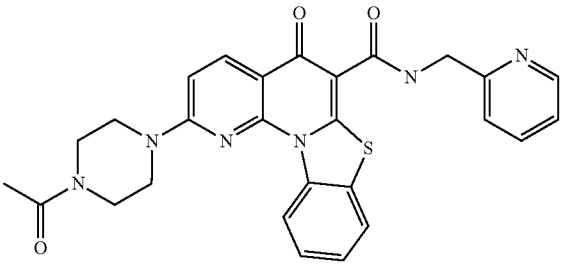 [SMILES: CC(=O)N1CCN(c2ccc3c(=O)c(C(=O)NCc4ccccn4)c4sc5ccccc5n4c3n2)CC1] | 512.58 | 513 |
| 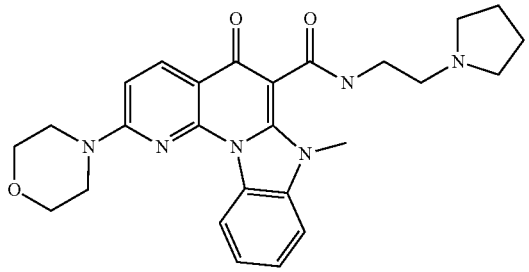 [SMILES: Cn1c2ccccc2n2c3nc(N4CCOCC4)ccc3c(=O)c(C(=O)NCCN3CCCC3)c12] | 474.55 | 475 |
| 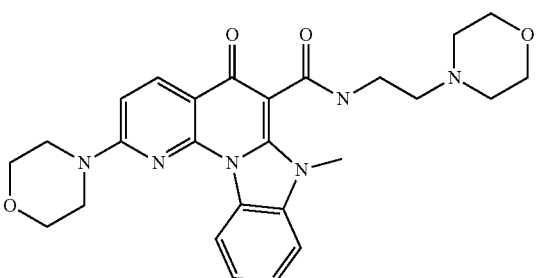 | 490.55 | 491 |
| 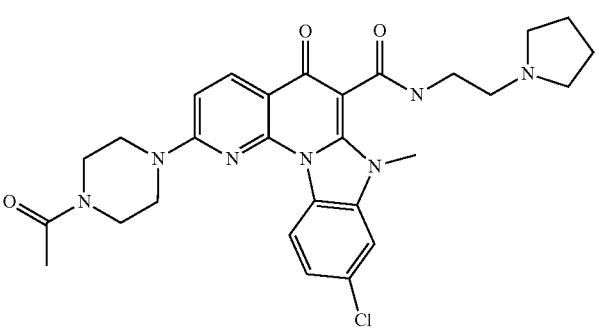 [SMILES: CC(=O)N1CCN(c2ccc3c(=O)c(C(=O)NCCN4CCCC4)c4n(C)c5cc(Cl)ccc5n4c3n2)CC1] | 550.05 | 550 |

TABLE 1-continued
| Structure | MW | LCMS (ES) m/z [M + 1]+ |
|---|---|---|
| 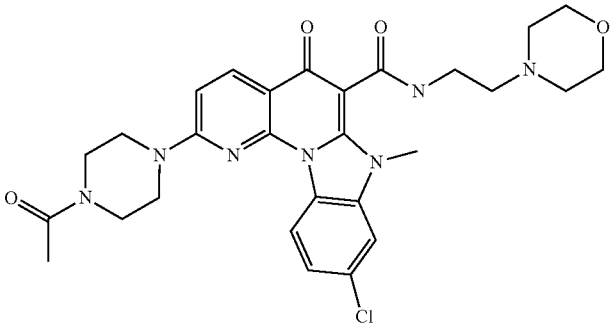 [SMILES: CC(=O)N1CCN(c2ccc3c(=O)c(C(=O)NCCN4CCOCC4)c4n(C)c5cc(Cl)ccc5n4c3n2)CC1] | 566.05 | 566 |
| 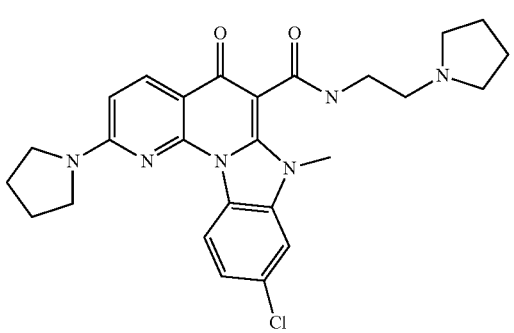 [SMILES: Cn1c2cc(Cl)ccc2n2c3nc(N4CCCC4)ccc3c(=O)c(C(=O)NCCN3CCCC3)c12] | 493.00 | 493 |
| 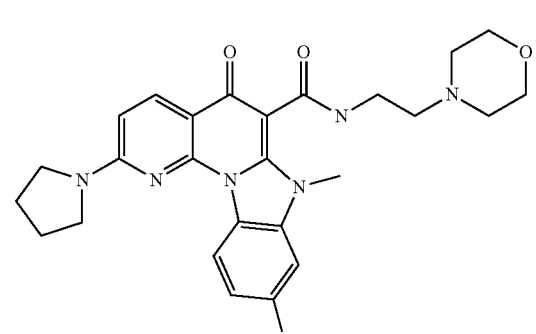 | 509.00 | 509 |
| 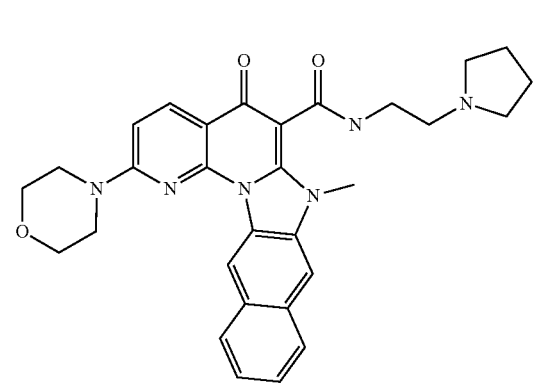 [SMILES: Cn1c2cc3ccccc3cc2n2c3nc(N4CCOCC4)ccc3c(=O)c(C(=O)NCCN3CCCC3)c12] | 524.61 | 525 |

TABLE 1-continued
| Structure | MW | LCMS (ES) m/z [M + 1]+ |
|---|---|---|
| 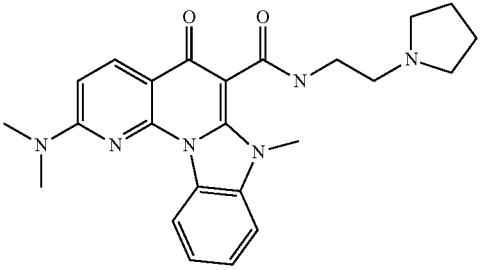 [SMILES: CN(C)c1ccc2c(=O)c(C(=O)NCCN3CCCC3)c3n(C)c4ccccc4n3c2n1] | 432.52 | 433 |
| 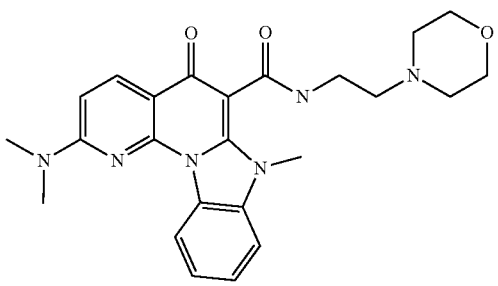 [SMILES: CN(C)c1ccc2c(=O)c(C(=O)NCCN3CCOCC3)c3n(C)c4ccccc4n3c2n1] | 448.52 | 449 |
| 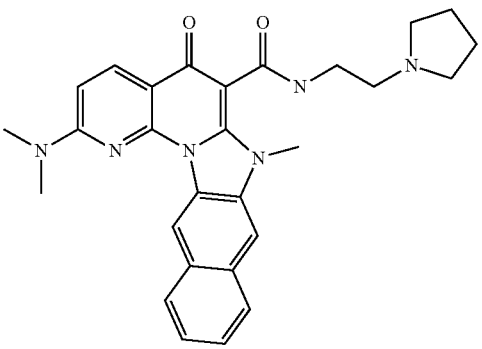 [SMILES: CN(C)c1ccc2c(=O)c(C(=O)NCCN3CCCC3)c3n(C)c4cc5ccccc5cc4n3c2n1] | 482.58 | 483 |
| 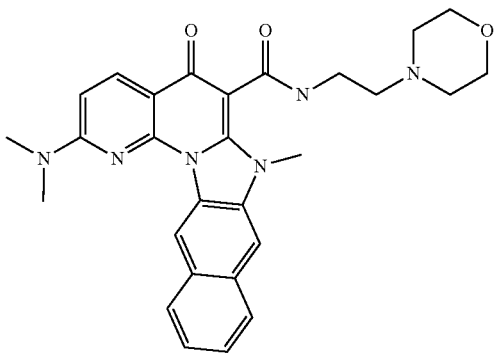 [SMILES: CN(C)c1ccc2c(=O)c(C(=O)NCCN3CCOCC3)c3n(C)c4cc5ccccc5cc4n3c2n1] | 498.58 | 499 |

TABLE 1-continued

| Structure | MW | LCMS (ES) m/z [M + 1]+ |
|---|---|---|
| 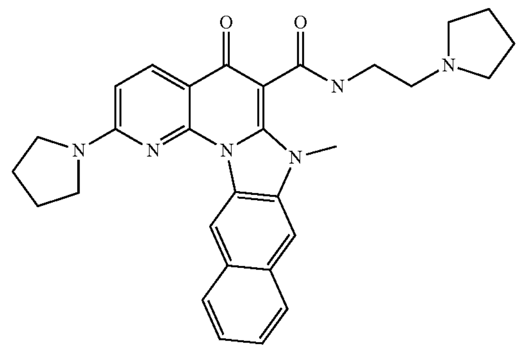 [SMILES: Cn1c2cc3ccccc3cc2n2c3nc(N4CCCC4)ccc3c(=O)c(C(=O)NCCN3CCCC3)c12] | 508.61 | 509 |
| 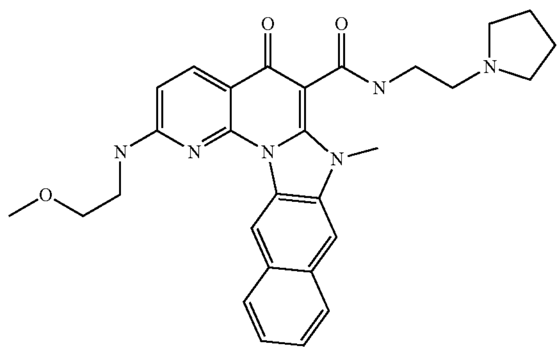 [SMILES: COCCNc1ccc2c(=O)c(C(=O)NCCN3CCCC3)c3n(C)c4cc5ccccc5cc4n3c2n1] | 512.60 | 513 |
| 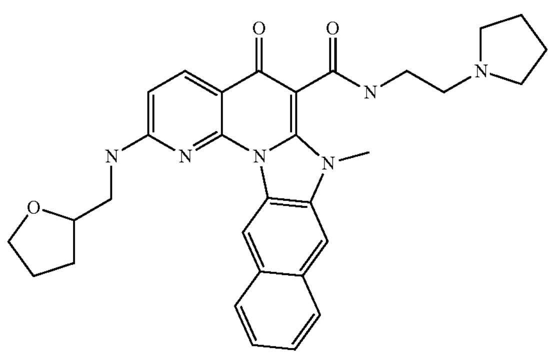 [SMILES: Cn1c2cc3ccccc3cc2n2c3nc(NCC4CCCO4)ccc3c(=O)c(C(=O)NCCN3CCCC3)c12] | 538.64 | 539 |
| 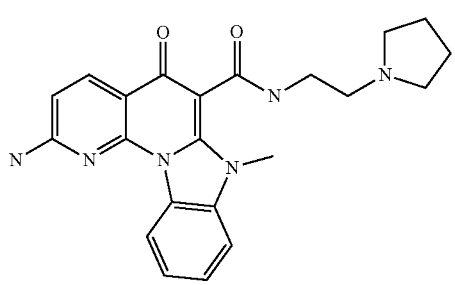 [SMILES: Cn1c2ccccc2n2c3nc(N)ccc3c(=O)c(C(=O)NCCN3CCCC3)c12] | 404.46 | 405 |

TABLE 1-continued

| Structure | MW | LCMS (ES) m/z [M + 1]+ |
|---|---|---|
| | 488.58 | 489 |
| | 488.58 | 489 |
| 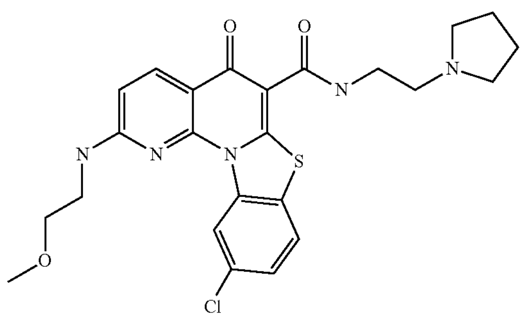 [SMILES: COCCNc1ccc2c(=O)c(C(=O)NCCN3CCCC3)c3sc4ccc(Cl)cc4n3c2n1] | 500.01 | 500 |
| 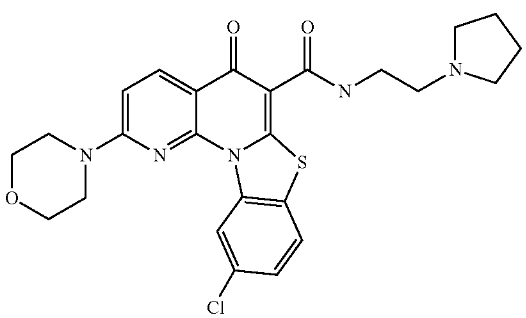 [SMILES: O=C(NCCN1CCCC1)c1c(=O)c2ccc(N3CCOCC3)nc2n2c1sc1ccc(Cl)cc12] | 512.02 | 512 |
| 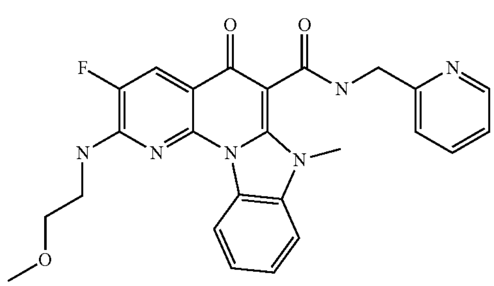 [SMILES: COCCNc1nc2c(cc1F)c(=O)c(C(=O)NCc1ccccn1)c1n(C)c3ccccc3n21] | 474.79 | 475 |

TABLE 1-continued

| Structure | MW | LCMS (ES) m/z [M + 1]+ |
|---|---|---|
| 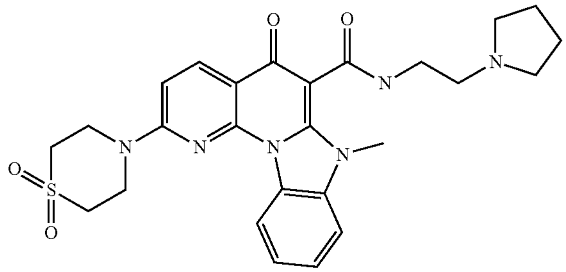 [SMILES: Cn1c2ccccc2n2c3nc(N4CCS(=O)(=O)CC4)ccc3c(=O)c(C(=O)NCCN3CCCC3)c12] | 522.62 | 523 |
| 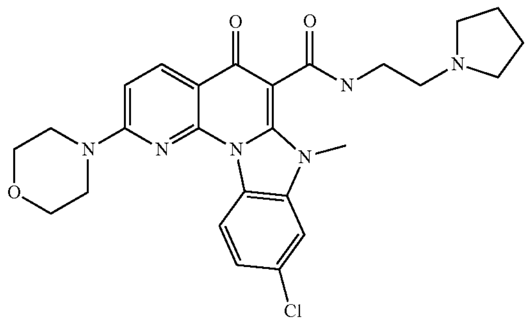 [SMILES: Cn1c2cc(Cl)ccc2n2c3nc(N4CCOCC4)ccc3c(=O)c(C(=O)NCCN3CCCC3)c12] | 509.00 | 509 |
| 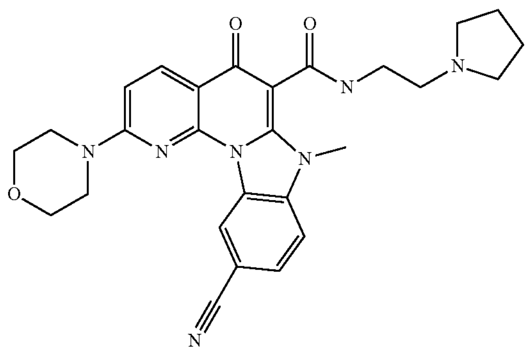 [SMILES: Cn1c2ccc(C#N)cc2n2c3nc(N4CCOCC4)ccc3c(=O)c(C(=O)NCCN3CCCC3)c12] | 499.56 | 500 |
| 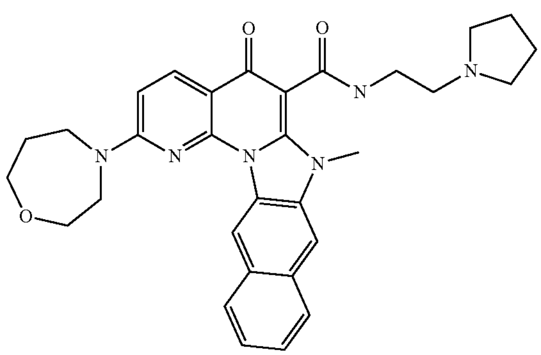 [SMILES: Cn1c2cc3ccccc3cc2n2c3nc(N4CCCOCC4)ccc3c(=O)c(C(=O)NCCN3CCCC3)c12] | 538.64 | 539 |
| 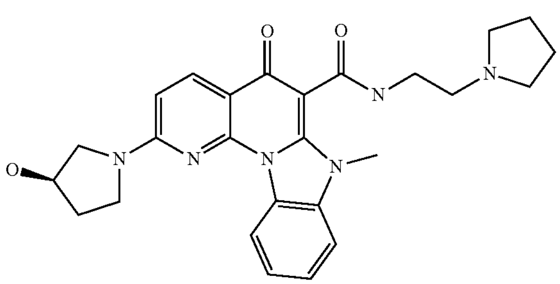 [SMILES: Cn1c2ccccc2n2c3nc(N4CC[C@@H](O)C4)ccc3c(=O)c(C(=O)NCCN3CCCC3)c12] | 474.55 | 475 |

TABLE 1-continued
| Structure | MW | LCMS (ES) m/z [M + 1]+ |
|---|---|---|
| 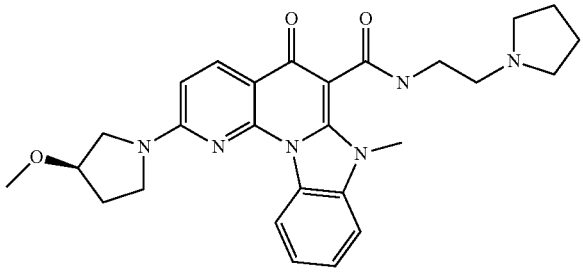 [SMILES: CO[C@@H]1CCN(c2ccc3c(=O)c(C(=O)NCCN4CCCC4)c4n(C)c5ccccc5n4c3n2)C1] | 488.58 | 489 |
| 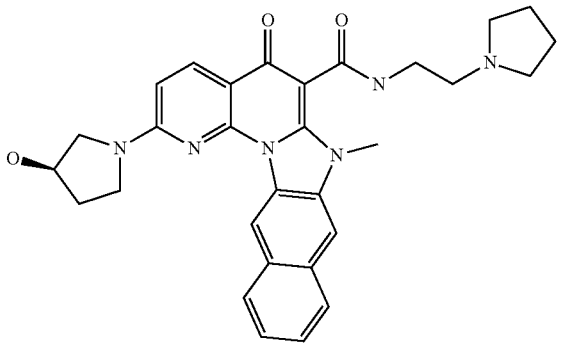 [SMILES: Cn1c2cc3ccccc3cc2n2c3nc(N4CC[C@@H](O)C4)ccc3c(=O)c(C(=O)NCCN3CCCC3)c12] | 524.61 | 525 |
| 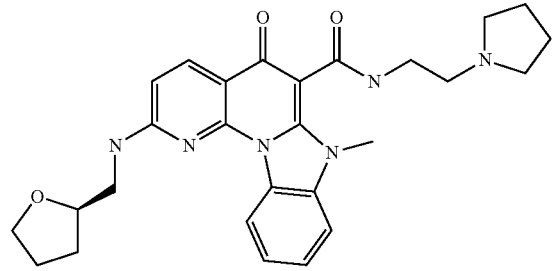 [SMILES: Cn1c2ccccc2n2c3nc(NC[C@H]4CCCO4)ccc3c(=O)c(C(=O)NCCN3CCCC3)c12] | 488.58 | 489 |
| 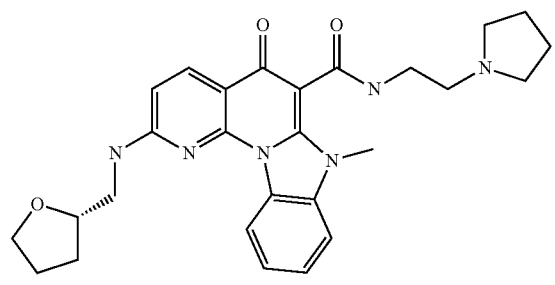 [SMILES: Cn1c2ccccc2n2c3nc(NC[C@@H]4CCCO4)ccc3c(=O)c(C(=O)NCCN3CCCC3)c12] | 488.58 | 489 |
| 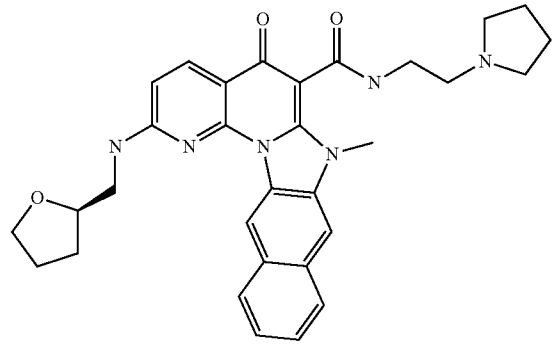 [SMILES: Cn1c2cc3ccccc3cc2n2c3nc(NC[C@H]4CCCO4)ccc3c(=O)c(C(=O)NCCN3CCCC3)c12] | 538.64 | 539 |

TABLE 1-continued
| Structure | MW | LCMS (ES) m/z [M + 1]+ |
|---|---|---|
| 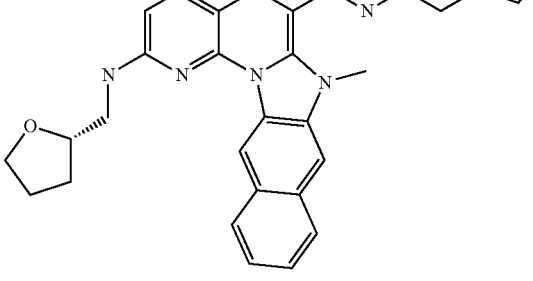 | 538.64 | 539 |
| 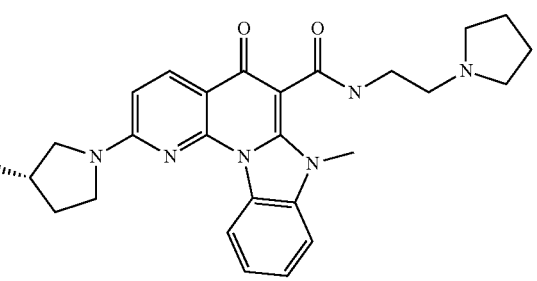 | 474.55 | 475 |
| 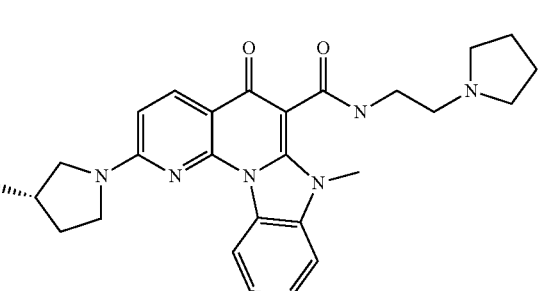 | 488.58 | 489 |
| 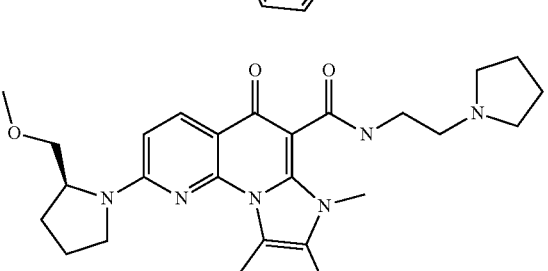 | 502.61 | 503 |
| 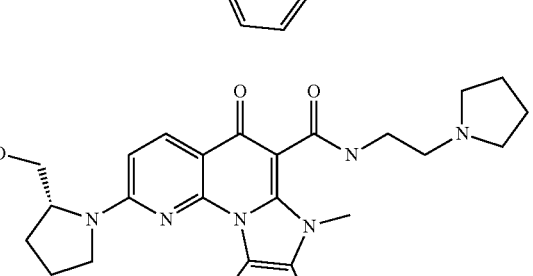 | 502.61 | 503 |

TABLE 1-continued

| Structure | MW | LCMS (ES) m/z [M + 1]+ |
|---|---|---|
| | 552.67 | 553 |
| 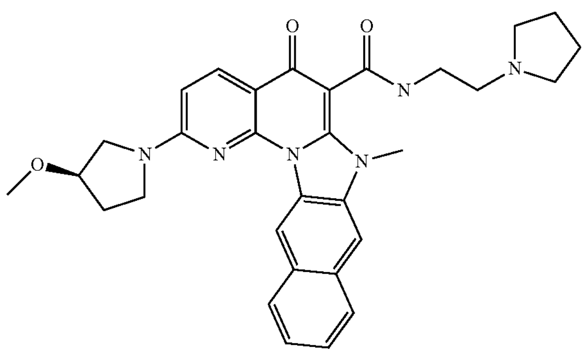 [SMILES: CO[C@@H]1CCN(c2ccc3c(=O)c(C(=O)NCCN4CCCC4)c4n(C)c5cc6ccccc6cc5n4c3n2)C1] | 538.64 | 539 |
| | 552.67 | 553 |
| 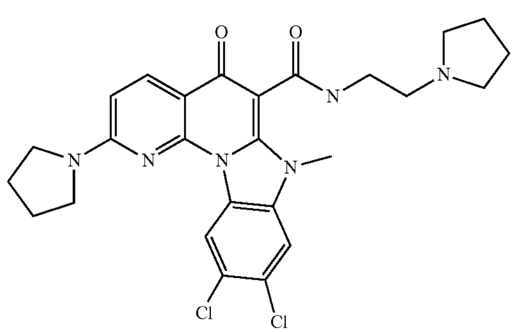 [SMILES: Cn1c2cc(Cl)c(Cl)cc2n2c3nc(N4CCCC4)ccc3c(=O)c(C(=O)NCCN3CCCC3)c12] | 527.45 | 527 |

TABLE 1-continued
| Structure | MW | LCMS (ES) m/z [M + 1]+ |
|---|---|---|
| 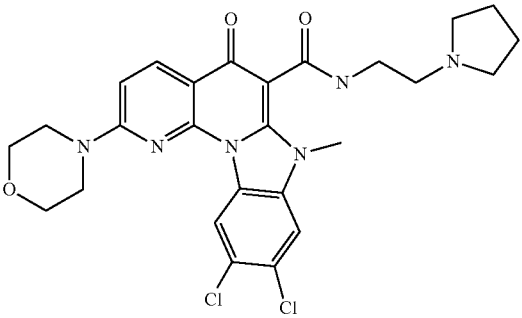 [SMILES: Cn1c2cc(Cl)c(Cl)cc2n2c3nc(N4CCOCC4)ccc3c(=O)c(C(=O)NCCN3CCCC3)c12] | 543.44 | 543 |
| 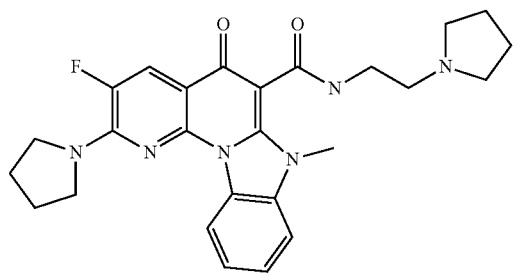 [SMILES: Cn1c2ccccc2n2c3nc(N4CCCC4)c(F)cc3c(=O)c(C(=O)NCCN3CCCC3)c12] | 476.55 | 477 |
| 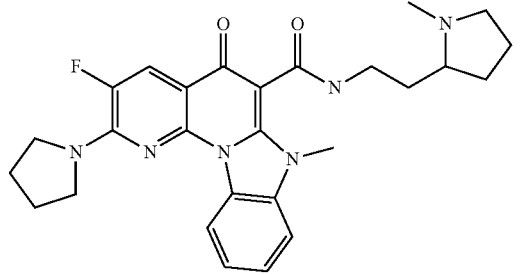 [SMILES: CN1CCCC1CCNC(=O)c1c(=O)c2cc(F)c(N3CCCC3)nc2n2c3ccccc3n(C)c12] | 490.57 | 491 |
| 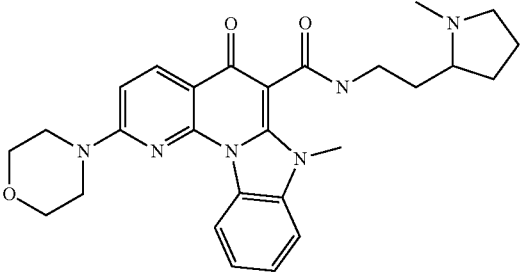 [SMILES: CN1CCCC1CCNC(=O)c1c(=O)c2ccc(N3CCOCC3)nc2n2c3ccccc3n(C)c12] | 488.58 | 489 |
| 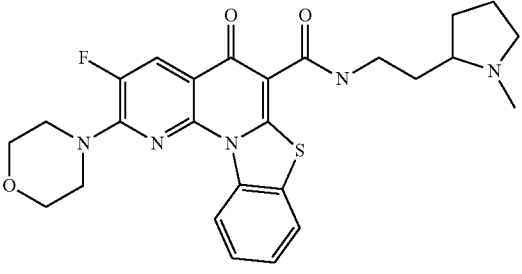 [SMILES: CN1CCCC1CCNC(=O)c1c(=O)c2cc(F)c(N3CCOCC3)nc2n2c1sc1ccccc12] | 509.60 | 510 |

TABLE 1-continued

| Structure | MW | LCMS (ES) m/z [M + 1]+ |
|---|---|---|
| 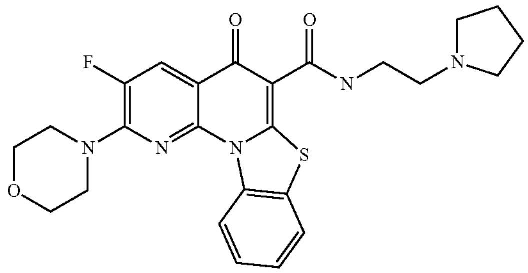 [SMILES: O=C(NCCN1CCCC1)c1c(=O)c2cc(F)c(N3CCOCC3)nc2n2c1sc1ccccc12] | 495.57 | 496 |
| 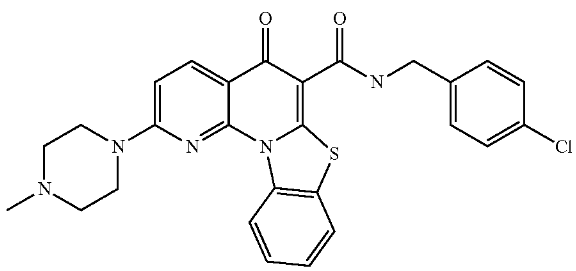 [SMILES: CN1CCN(c2ccc3c(=O)c(C(=O)NCc4ccc(Cl)cc4)c4sc5ccccc5n4c3n2)CC1] | 518.03 | 518 |
| 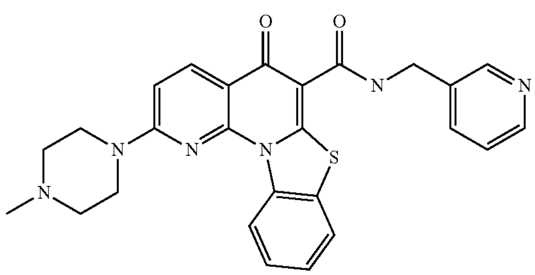 [SMILES: CN1CCN(c2ccc3c(=O)c(C(=O)NCc4cccnc4)c4sc5ccccc5n4c3n2)CC1] | 484.57 | 485 |
| | 471.53 | 472 |
| | 471.53 | 471.53 |

TABLE 1-continued

| Structure | MW | LCMS (ES) m/z [M + 1]+ |
|---|---|---|
| 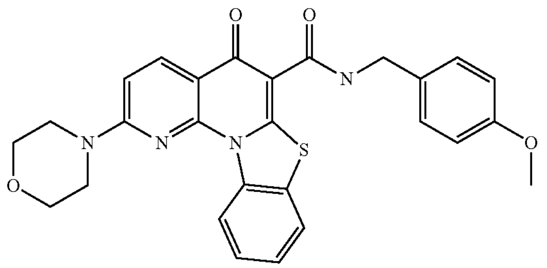 [SMILES: COc1ccc(CNC(=O)c2c(=O)c3ccc(N4CCOCC4)nc3n3c2sc2ccccc23)cc1] | 500.57 | 501 |
| 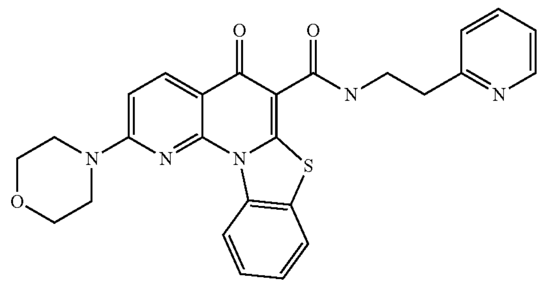 [SMILES: O=C(NCCc1ccccn1)c1c(=O)c2ccc(N3CCOCC3)nc2n2c1sc1ccccc12] | 485.56 | 486 |
| 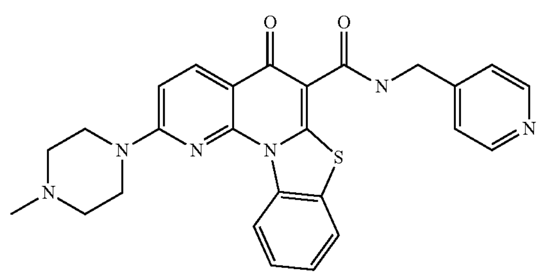 [SMILES: CN1CCN(c2ccc3c(=O)c(C(=O)NCc4ccncc4)c4sc5ccccc5n4c3n2)CC1] | 484.57 | 485 |
| | 513.61 | 514 |
| | 513.61 | 514 |

TABLE 1-continued

| Structure | MW | LCMS (ES) m/z [M + 1]+ |
|---|---|---|
| 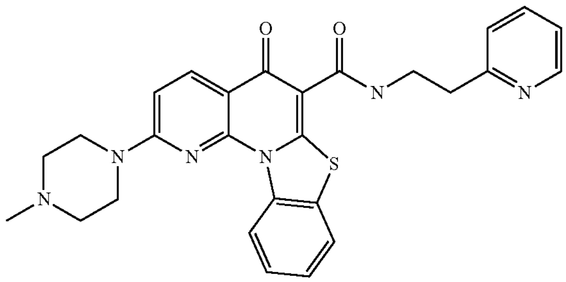 [SMILES: CN1CCN(c2ccc3c(=O)c(C(=O)NCCc4ccccn4)c4sc5ccccc5n4c3n2)CC1] | 498.60 | 499 |
| 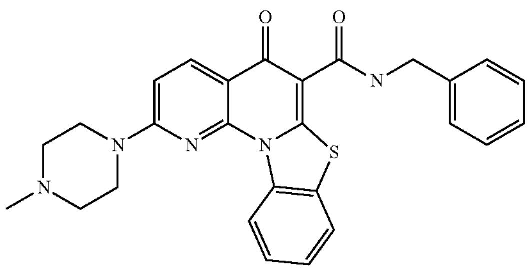 [SMILES: CN1CCN(c2ccc3c(=O)c(C(=O)NCc4ccccc4)c4sc5ccccc5n4c3n2)CC1] | 483.58 | 484 |
| 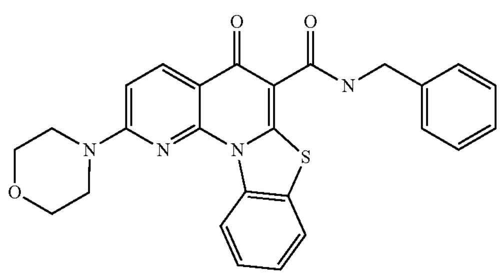 [SMILES: O=C(NCc1ccccc1)c1c(=O)c2ccc(N3CCOCC3)nc2n2c1sc1ccccc12] | 470.54 | 471 |
| 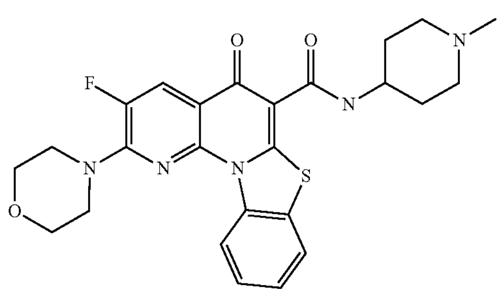 [SMILES: CN1CCC(NC(=O)c2c(=O)c3cc(F)c(N4CCOCC4)nc3n3c2sc2ccccc23)CC1] | 495.57 | 496 |
| 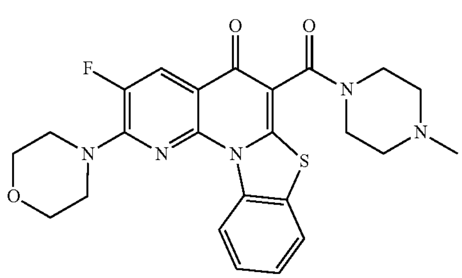 [SMILES: CN1CCN(C(=O)c2c(=O)c3cc(F)c(N4CCOCC4)nc3n3c2sc2ccccc23)CC1] | 481.54 | 482 |

TABLE 1-continued

| Structure | MW | LCMS (ES) m/z [M + 1]+ |
|---|---|---|
| | 509.60 | 510 |
| 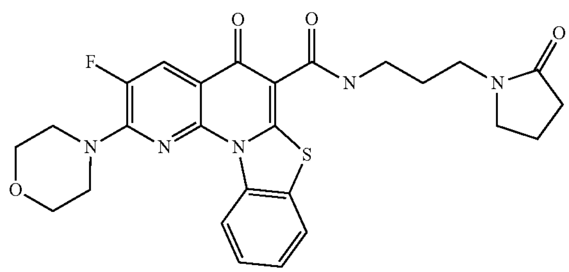 [SMILES: O=C(NCCCN1CCCC1=O)c1c(=O)c2cc(F)c(N3CCOCC3)nc2n2c1sc1ccccc12] | 523.58 | 524 |
| | 509.60 | 510 |
| 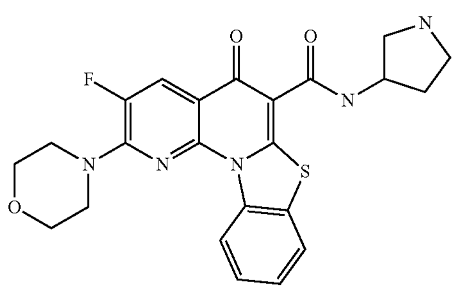 [SMILES: O=C(NC1CCNC1)c1c(=O)c2cc(F)c(N3CCOCC3)nc2n2c1sc1ccccc12] | 467.52 | 468 |
| 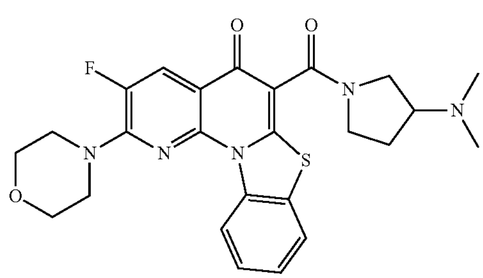 [SMILES: CN(C)C1CCN(C(=O)c2c(=O)c3cc(F)c(N4CCOCC4)nc3n3c2sc2ccccc23)C1] | 495.57 | 496 |

TABLE 1-continued

| Structure | MW | LCMS (ES) m/z [M + 1]+ |
|---|---|---|
| | 506.57 | 507 |
| | 506.57 | 507 |
| | 509.60 | 510 |
| | 509.60 | 510 |
| 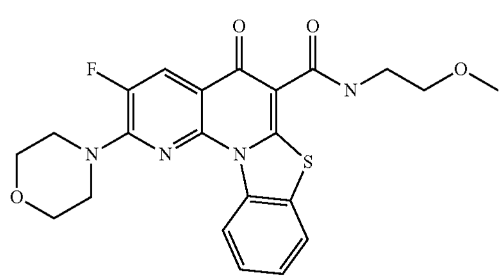 [SMILES: COCCNC(=O)c1c(=O)c2cc(F)c(N3CCOCC3)nc2n2c1sc1ccccc12] | 456.49 | 457 |

TABLE 1-continued
| Structure | MW | LCMS (ES) m/z [M + 1]+ |
|---|---|---|
| 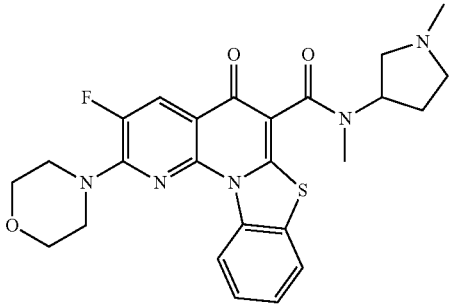 [SMILES: CN1CCC(N(C)C(=O)c2c(=O)c3cc(F)c(N4CCOCC4)nc3n3c2sc2ccccc23)C1] | 495.57 | 496 |
| 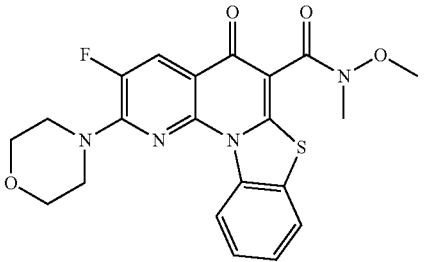 [SMILES: CON(C)C(=O)c1c(=O)c2cc(F)c(N3CCOCC3)nc2n2c1sc1ccccc12] | 442.46 | 443 |
| 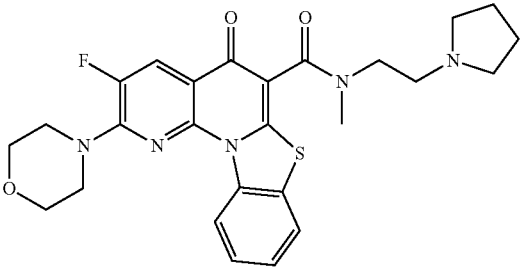 [SMILES: CN(CCN1CCCC1)C(=O)c1c(=O)c2cc(F)c(N3CCOCC3)nc2n2c1sc1ccccc12] | 509.60 | 510 |
| 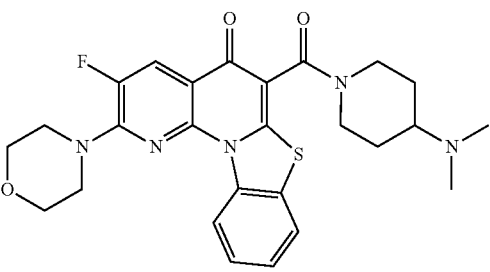 [SMILES: CN(C)C1CCN(C(=O)c2c(=O)c3cc(F)c(N4CCOCC4)nc3n3c2sc2ccccc23)CC1] | 509.60 | 510 |
| 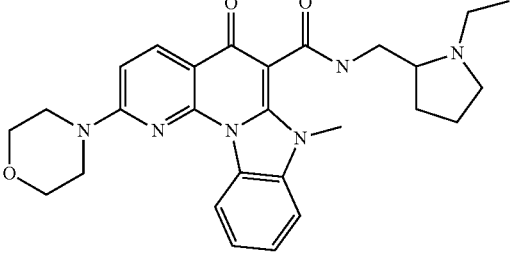 | 488.58 | 489 |

TABLE 1-continued

| Structure | MW | LCMS (ES) m/z [M + 1]+ |
|---|---|---|
| 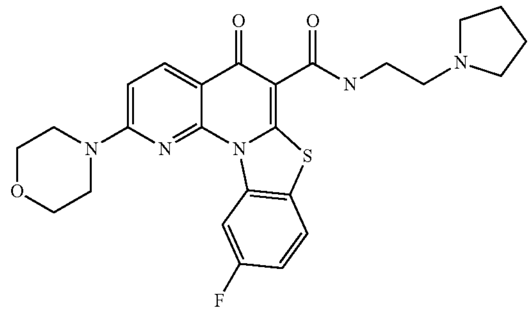 [SMILES: O=C(NCCN1CCCC1)c1c(=O)c2ccc(N3CCOCC3)nc2n2c1sc1ccc(F)cc12] | 495.57 | 496 |
| | 509.60 | 510 |
| | 509.60 | 510 |
| 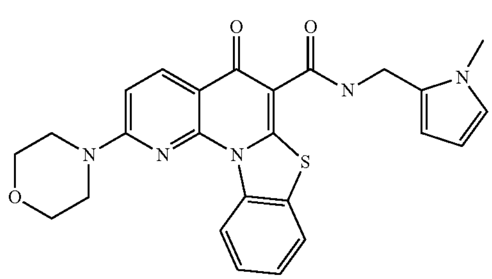 [SMILES: Cn1cccc1CNC(=O)c1c(=O)c2ccc(N3CCOCC3)nc2n2c1sc1ccccc12] | 473.55 | 474 |
| 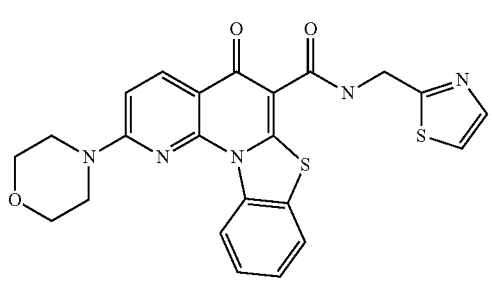 [SMILES: O=C(NCc1nccs1)c1c(=O)c2ccc(N3CCOCC3)nc2n2c1sc1ccccc12] | 477.56 | 478 |

TABLE 1-continued

| Structure | MW | LCMS (ES) m/z [M + 1]+ |
|---|---|---|
| 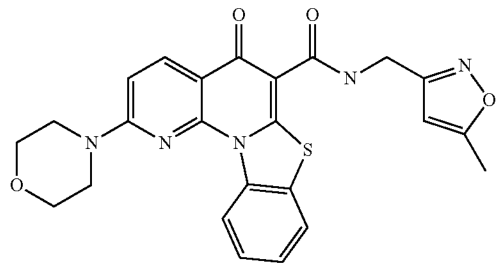 [SMILES: Cc1cc(CNC(=O)c2c(=O)c3ccc(N4CCOCC4)nc3n3c2sc2ccccc23)no1] | 475.52 | 476 |
| | 486.55 | 487 |
| | 474.53 | 475 |
| | 474.53 | 475 |
| | 486.55 | 487 |

TABLE 1-continued

| Structure | MW | LCMS (ES) m/z [M + 1]+ |
|---|---|---|
| 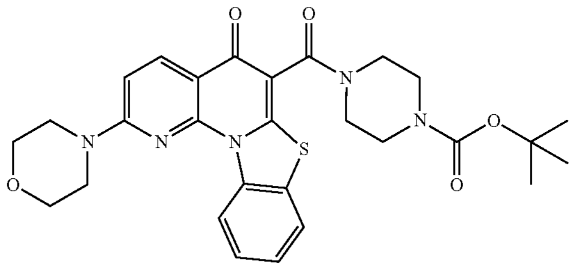 [SMILES: CC(C)(C)OC(=O)N1CCN(C(=O)c2c(=O)c3ccc(N4CCOCC4)nc3n3c2sc2ccccc23)CC1] | 549.64 | 550 |
| 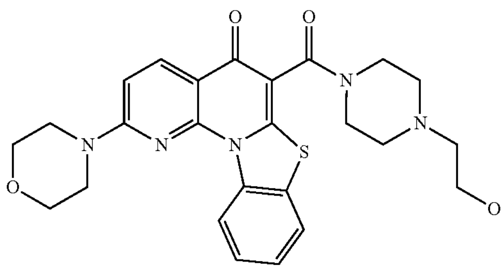 [SMILES: O=C(c1c(=O)c2ccc(N3CCOCC3)nc2n2c1sc1ccccc12)N1CCN(CCO)CC1] | 493.58 | 494 |
| | 507.60 | 508 |
| 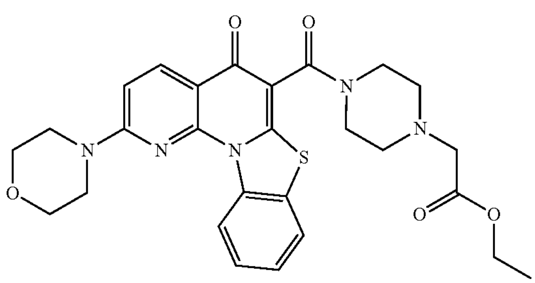 [SMILES: CCOC(=O)CN1CCN(C(=O)c2c(=O)c3ccc(N4CCOCC4)nc3n3c2sc2ccccc23)CC1] | 535.61 | 536 |
| | 507.60 | 508 |

TABLE 1-continued

| Structure | MW | LCMS (ES) m/z [M + 1]+ |
|---|---|---|
| 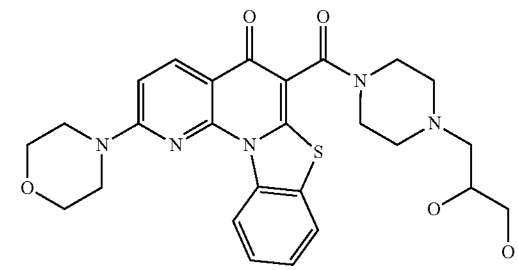 [SMILES: O=C(c1c(=O)c2ccc(N3CCOCC3)nc2n2c1sc1ccccc12)N1CCN(CC(O)CO)CC1] | 523.60 | 524 |
| 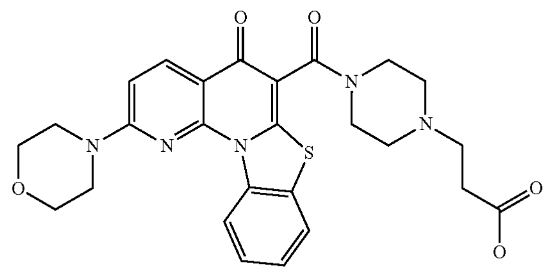 [SMILES: O=C(O)CCN1CCN(C(=O)c2c(=O)c3ccc(N4CCOCC4)nc3n3c2sc2ccccc23)CC1] | 521.59 | 522 |
| | 527.60 | 528 |
| 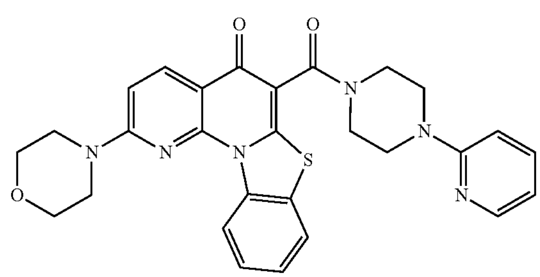 [SMILES: O=C(c1c(=O)c2ccc(N3CCOCC3)nc2n2c1sc1ccccc12)N1CCN(c2ccccn2)CC1] | 526.61 | 527 |
| | 527.60 | 528 |

TABLE 1-continued

| Structure | MW | LCMS (ES) m/z [M + 1]+ |
|---|---|---|
| 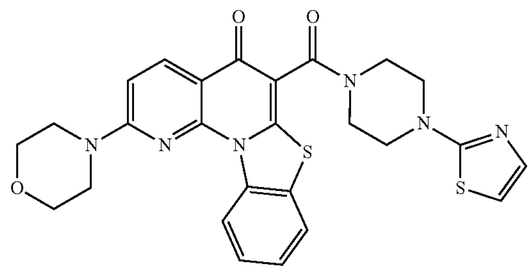 [SMILES: O=C(c1c(=O)c2ccc(N3CCOCC3)nc2n2c1sc1ccccc12)N1CCN(c2nccs2)CC1] | 532.64 | 533 |
| 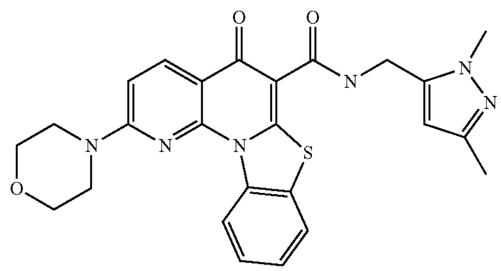 [SMILES: Cc1cc(CNC(=O)c2c(=O)c3ccc(N4CCOCC4)nc3n3c2sc2ccccc23)n(C)n1] | 488.56 | 489 |
| 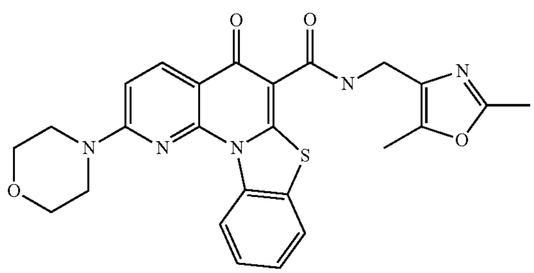 [SMILES: Cc1nc(CNC(=O)c2c(=O)c3ccc(N4CCOCC4)nc3n3c2sc2ccccc23)c(C)o1] | 489.55 | 490 |
| 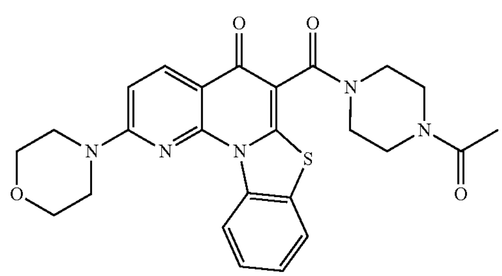 [SMILES: CC(=O)N1CCN(C(=O)c2c(=O)c3ccc(N4CCOCC4)nc3n3c2sc2ccccc23)CC1] | 491.56 | 492 |
| 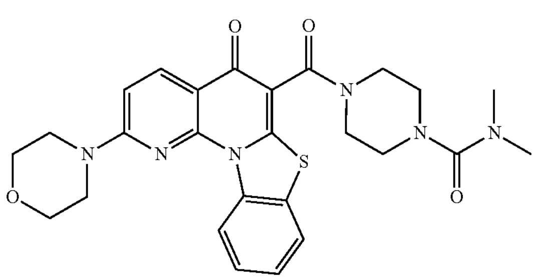 [SMILES: CN(C)C(=O)N1CCN(C(=O)c2c(=O)c3ccc(N4CCOCC4)nc3n3c2sc2ccccc23)CC1] | 520.60 | 521 |

TABLE 1-continued

| Structure | MW | LCMS (ES) m/z [M + 1]+ |
|---|---|---|
| 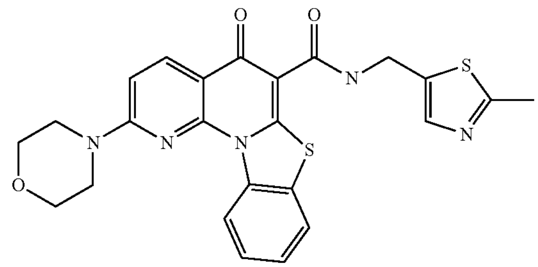 [SMILES: Cc1ncc(CNC(=O)c2c(=O)c3ccc(N4CCOCC4)nc3n3c2sc2ccccc23)s1] | 491.59 | 492 |
| | 488.56 | 489 |
| 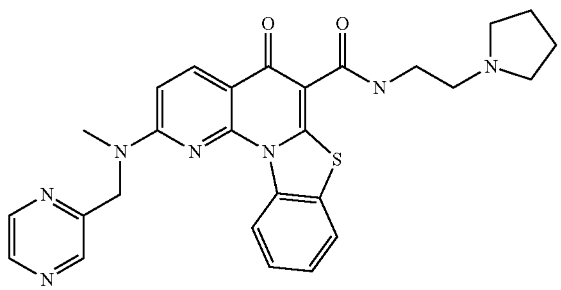 [SMILES: CN(Cc1cnccn1)c1ccc2c(=O)c(C(=O)NCCN3CCCC3)c3sc4ccccc4n3c2n1] | 513.61 | 514 |
| 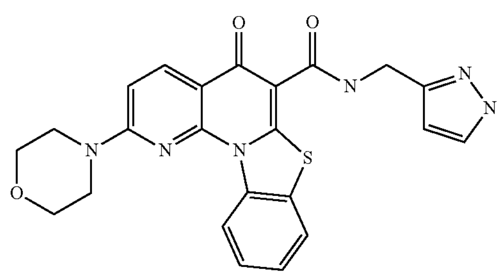 [SMILES: O=C(NCc1cc[nH]n1)c1c(=O)c2ccc(N3CCOCC3)nc2n2c1sc1ccccc12] | 460.51 | 461 |
| | 488.56 | 489 |

TABLE 1-continued

| Structure | MW | LCMS (ES) m/z [M + 1]+ |
|---|---|---|
| 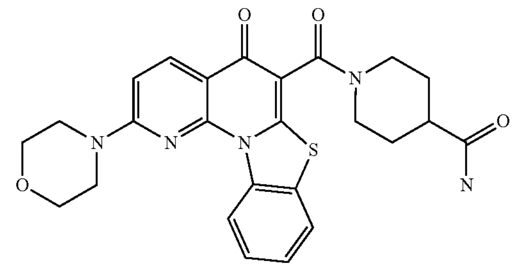 [SMILES: NC(=O)C1CCN(C(=O)c2c(=O)c3ccc(N4CCOCC4)nc3n3c2sc2ccccc23)CC1] | 491.56 | 492 |
| | 474.53 | 475 |
| | 474.53 | 475 |
| 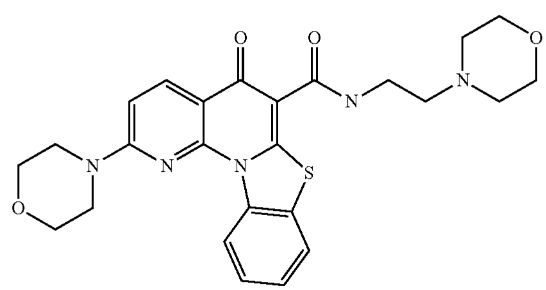 [SMILES: O=C(NCCN1CCOCC1)c1c(=O)c2ccc(N3CCOCC3)nc2n2c1sc1ccccc12] | 493.58 | 494 |
| 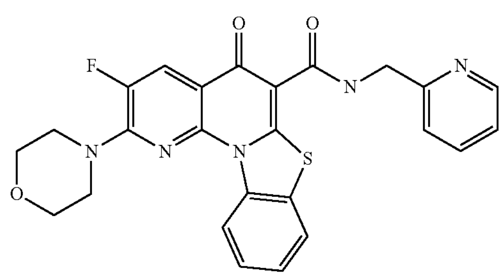 [SMILES: O=C(NCc1ccccn1)c1c(=O)c2cc(F)c(N3CCOCC3)nc2n2c1sc1ccccc12] | 489.52 | 490 |

TABLE 1-continued
| Structure | MW | LCMS (ES) m/z [M + 1]+ |
|---|---|---|
| 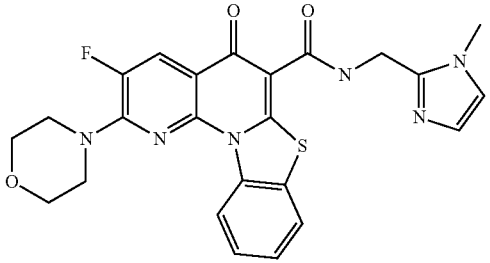 [SMILES: Cn1ccnc1CNC(=O)c1c(=O)c2cc(F)c(N3CCOCC3)nc2n2c1sc1ccccc12] | 492.53 | 493 |
| 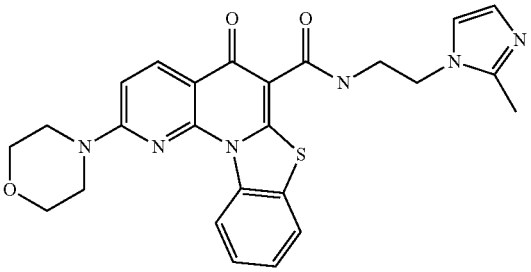 [SMILES: Cc1nccn1CCNC(=O)c1c(=O)c2ccc(N3CCOCC3)nc2n2c1sc1ccccc12] | 488.56 | 489 |
| 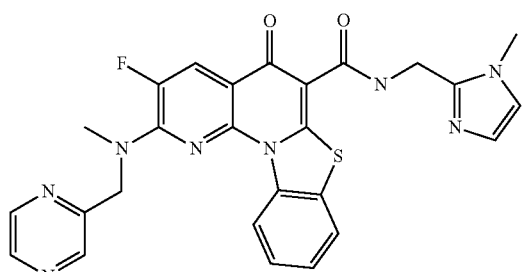 | 528.56 | 529 |
| 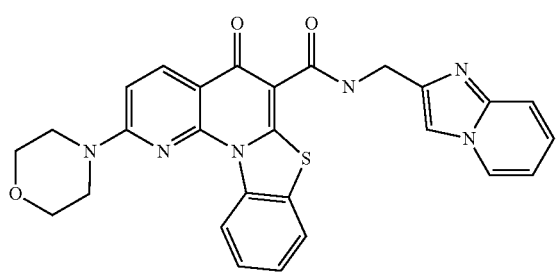 [SMILES: O=C(NCc1cn2ccccc2n1)c1c(=O)c2ccc(N3CCOCC3)nc2n2c1sc1ccccc12] | 510.57 | 511 |
| 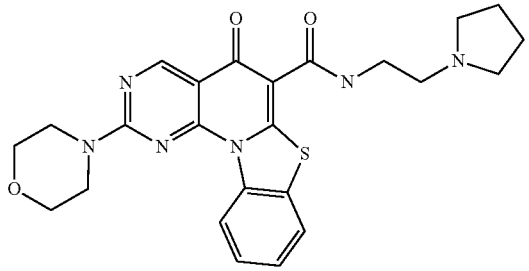 [SMILES: O=C(NCCN1CCCC1)c1c(=O)c2cnc(N3CCOCC3)nc2n2c1sc1ccccc12] | 478.57 | 479 |

TABLE 1-continued

| Structure | MW | LCMS (ES) m/z [M + 1]+ |
|---|---|---|
| 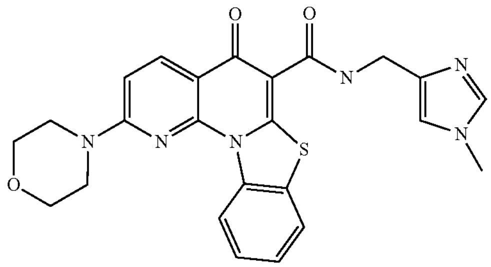 | 474.53 | 475 |
| 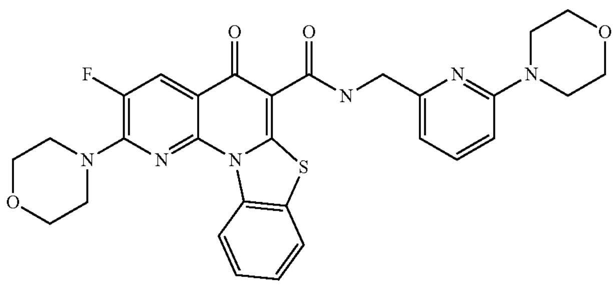 [SMILES: O=C(NCc1cccc(N2CCOCC2)n1)c1c(=O)c2cc(F)c(N3CCOCC3)nc2n2c1sc1ccccc12] | 574.63 | 575 |
| 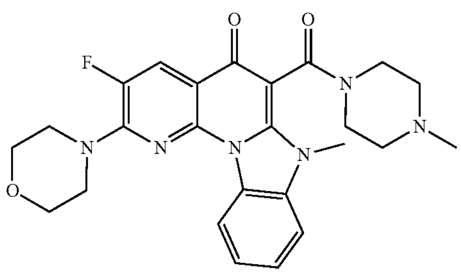 [SMILES: CN1CCN(C(=O)c2c(=O)c3cc(F)c(N4CCOCC4)nc3n3c4ccccc4n(C)c23)CC1] | 478.52 | 479 |
| 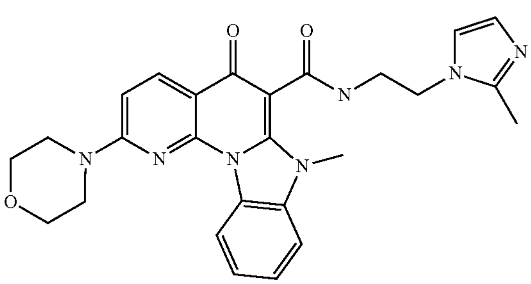 [SMILES: Cc1nccn1CCNC(=O)c1c(=O)c2ccc(N3CCOCC3)nc2n2c3ccccc3n(C)c12] | 485.54 | 486 |
| 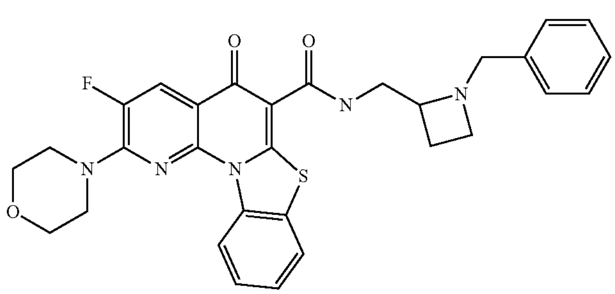 [SMILES: O=C(NCC1CCN1Cc1ccccc1)c1c(=O)c2cc(F)c(N3CCOCC3)nc2n2c1sc1ccccc12] | 557.64 | 558 |

TABLE 1-continued

| Structure | MW | LCMS (ES) m/z [M + 1]+ |
|---|---|---|
| 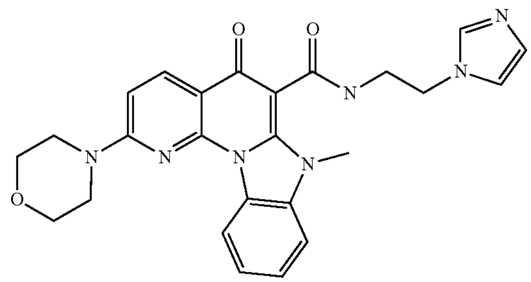 [SMILES: Cn1c2ccccc2n2c3nc(N4CCOCC4)ccc3c(=O)c(C(=O)NCCn3ccnc3)c12] | 471.51 | 472 |
| 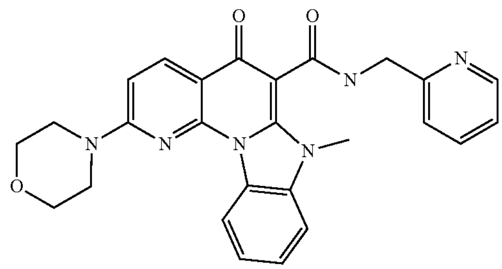 [SMILES: Cn1c2ccccc2n2c3nc(N4CCOCC4)ccc3c(=O)c(C(=O)NCc3ccccn3)c12] | 468.51 | 469 |
| 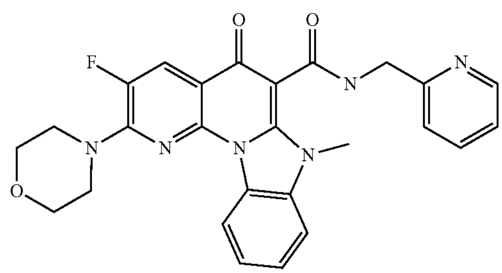 [SMILES: Cn1c2ccccc2n2c3nc(N4CCOCC4)c(F)cc3c(=O)c(C(=O)NCc3ccccn3)c12] | 486.50 | 487 |
| 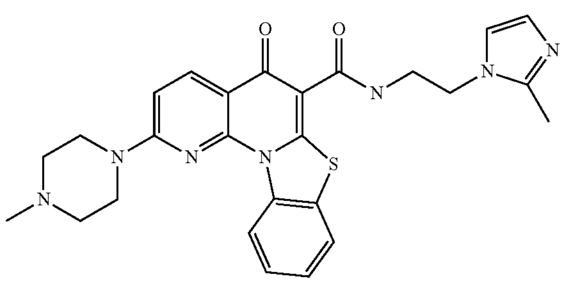 [SMILES: Cc1nccn1CCNC(=O)c1c(=O)c2ccc(N3CCN(C)CC3)nc2n2c1sc1ccccc12] | 501.60 | 502 |
| 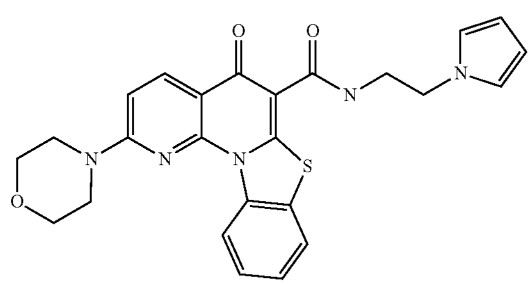 [SMILES: O=C(NCCn1cccc1)c1c(=O)c2ccc(N3CCOCC3)nc2n2c1sc1ccccc12] | 473.55 | 474 |

TABLE 1-continued

| Structure | MW | LCMS (ES) m/z [M + 1]+ |
|---|---|---|
| 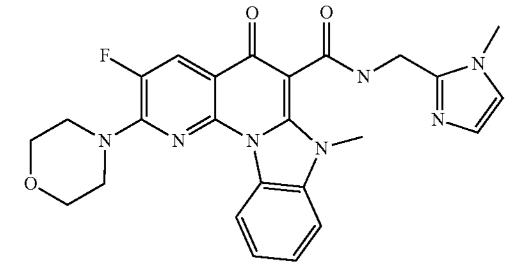 [SMILES: Cn1ccnc1CNC(=O)c1c(=O)c2cc(F)c(N3CCOCC3)nc2n2c3ccccc3n(C)c12] | 489.50 | 490 |
| 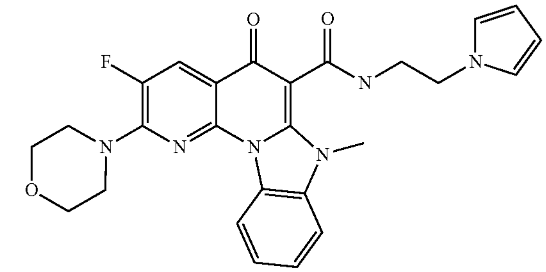 [SMILES: Cn1c2ccccc2n2c3nc(N4CCOCC4)c(F)cc3c(=O)c(C(=O)NCCn3cccc3)c12] | 488.51 | 489 |
| 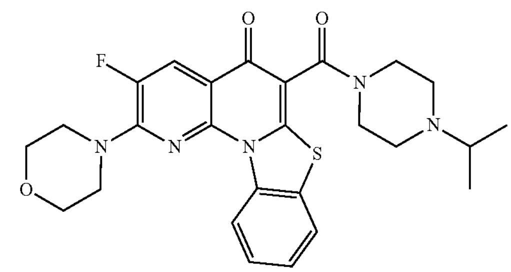 [SMILES: CC(C)N1CCN(C(=O)c2c(=O)c3cc(F)c(N4CCOCC4)nc3n3c2sc2ccccc23)CC1] | 509.60 | 510 |
| 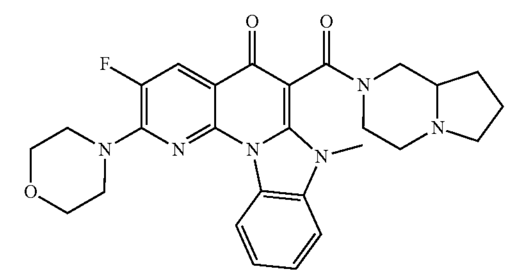 [SMILES: Cn1c2ccccc2n2c3nc(N4CCOCC4)c(F)cc3c(=O)c(C(=O)N3CCN4CCCC4C3)c12] | 504.56 | 505 |
| 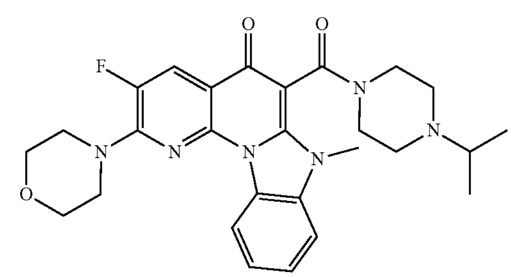 [SMILES: CC(C)N1CCN(C(=O)c2c(=O)c3cc(F)c(N4CCOCC4)nc3n3c4ccccc4n(C)c23)CC1] | 506.57 | 507 |

TABLE 1-continued

| Structure | MW | LCMS (ES) m/z [M + 1]+ |
|---|---|---|
| 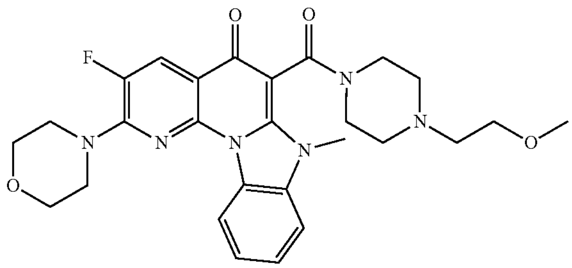 [SMILES: COCCN1CCN(C(=O)c2c(=O)c3cc(F)c(N4CCOCC4)nc3n3c4ccccc4n(C)c23)CC1] | 522.57 | 523 |
| 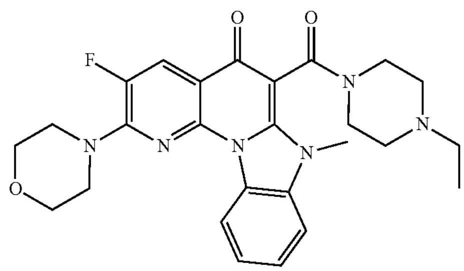 [SMILES: CCN1CCN(C(=O)c2c(=O)c3cc(F)c(N4CCOCC4)nc3n3c4ccccc4n(C)c23)CC1] | 492.55 | 493 |
| 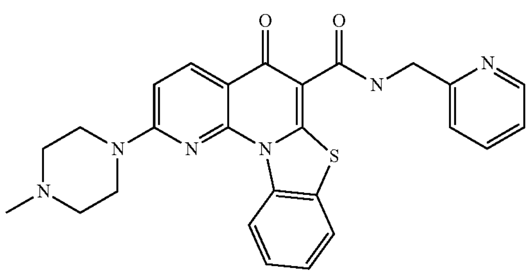 [SMILES: CN1CCN(c2ccc3c(=O)c(C(=O)NCc4ccccn4)c4sc5ccccc5n4c3n2)CC1] | 484.57 | 485 |
| 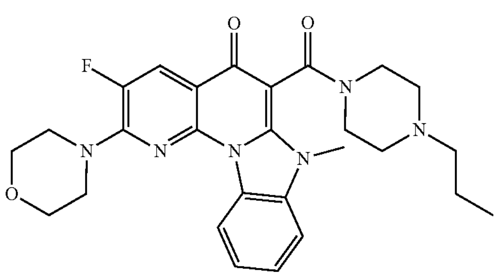 [SMILES: CCCN1CCN(C(=O)c2c(=O)c3cc(F)c(N4CCOCC4)nc3n3c4ccccc4n(C)c23)CC1] | 506.57 | 507 |
| 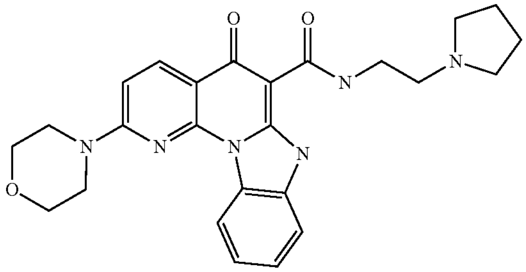 [SMILES: O=C(NCCN1CCCC1)c1c(=O)c2ccc(N3CCOCC3)nc2n2c1[nH]c1ccccc12] | 460.53 | 461 |

TABLE 1-continued

| Structure | MW | LCMS (ES) m/z [M + 1]+ |
|---|---|---|
| 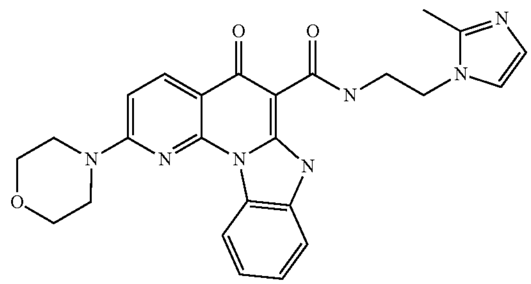 [SMILES: Cc1nccn1CCNC(=O)c1c(=O)c2ccc(N3CCOCC3)nc2n2c1[nH]c1ccccc12] | 471.51 | 472 |
| 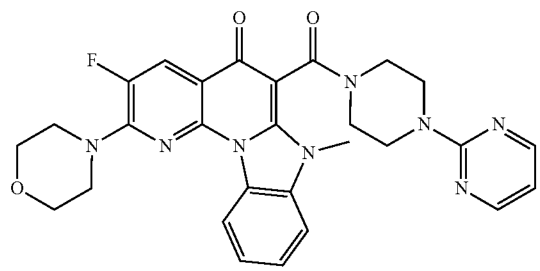 [SMILES: Cn1c2ccccc2n2c3nc(N4CCOCC4)c(F)cc3c(=O)c(C(=O)N3CCN(c4ncccn4)CC3)c12] | 542.56 | 543 |
| 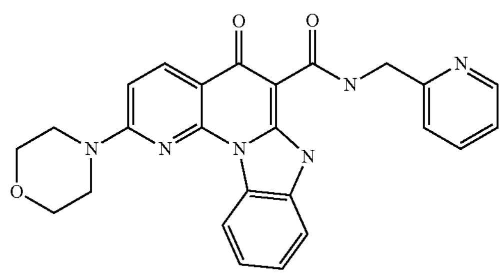 [SMILES: O=C(NCc1ccccn1)c1c(=O)c2ccc(N3CCOCC3)nc2n2c1[nH]c1ccccc12] | 454.58 | 455 |
| 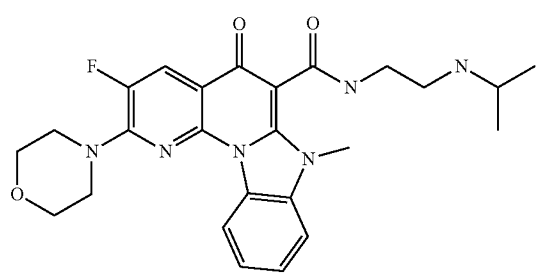 [SMILES: CC(C)NCCNC(=O)c1c(=O)c2cc(F)c(N3CCOCC3)nc2n2c3ccccc3n(C)c12] | 480.53 | 481 |
| 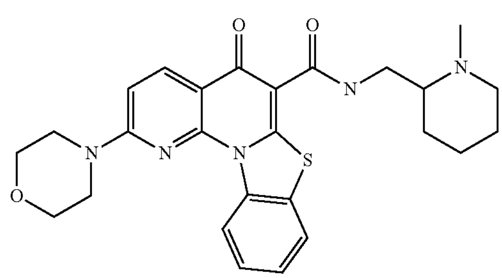 [SMILES: CN1CCCCC1CNC(=O)c1c(=O)c2ccc(N3CCOCC3)nc2n2c1sc1ccccc12] | 491.61 | 492 |

TABLE 1-continued

| Structure | MW | LCMS (ES) m/z [M + 1]+ |
|---|---|---|
| | 495.57 | 496 |
| | 495.57 | 496 |
| 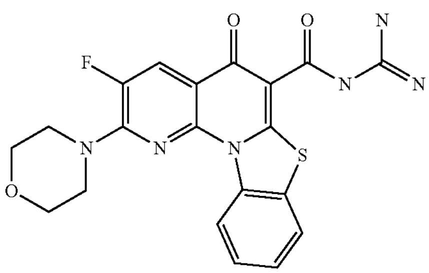 [SMILES: N=C(N)NC(=O)c1c(=O)c2cc(F)c(N3CCOCC3)nc2n2c1sc1ccccc12] | 440.45 | 441 |
| 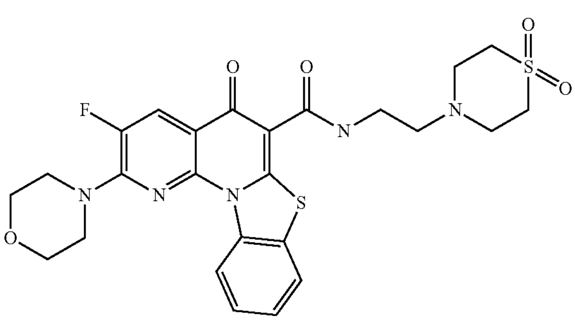 [SMILES: O=C(NCCN1CCS(=O)(=O)CC1)c1c(=O)c2cc(F)c(N3CCOCC3)nc2n2c1sc1ccccc12] | 559.63 | 560 |
| 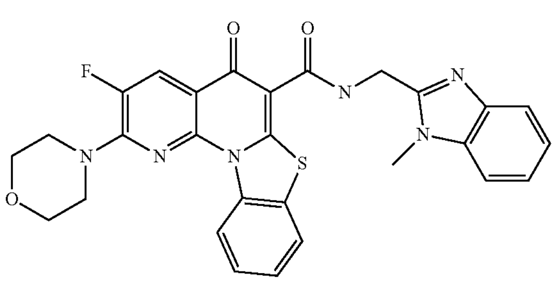 [SMILES: Cn1c(CNC(=O)c2c(=O)c3cc(F)c(N4CCOCC4)nc3n3c2sc2ccccc23)nc2ccccc21] | 542.58 | 543 |

TABLE 1-continued

| Structure | MW | LCMS (ES) m/z [M + 1]+ |
|---|---|---|
| 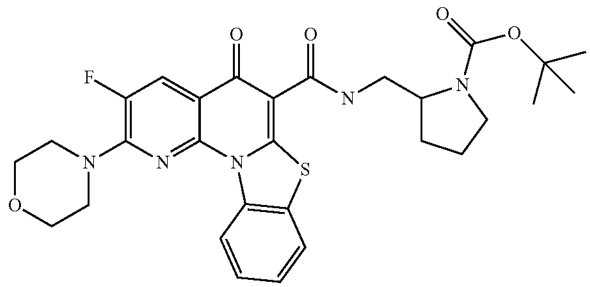 [SMILES: CC(C)(C)OC(=O)N1CCCC1CNC(=O)c1c(=O)c2cc(F)c(N3CCOCC3)nc2n2c1sc1ccccc12] | 581.66 | 582 |
| 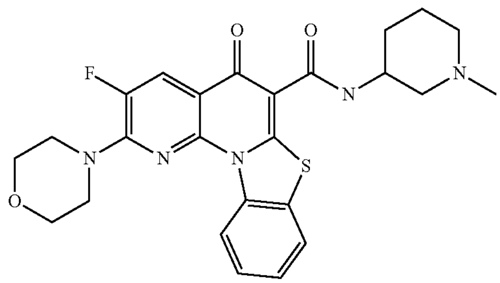 [SMILES: CN1CCCC(NC(=O)c2c(=O)c3cc(F)c(N4CCOCC4)nc3n3c2sc2ccccc23)C1] | 495.55 | 496 |
| 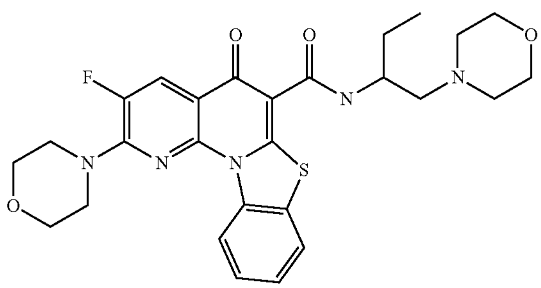 [SMILES: CCC(CN1CCOCC1)NC(=O)c1c(=O)c2cc(F)c(N3CCOCC3)nc2n2c1sc1ccccc12] | 539.62 | 540 |
| 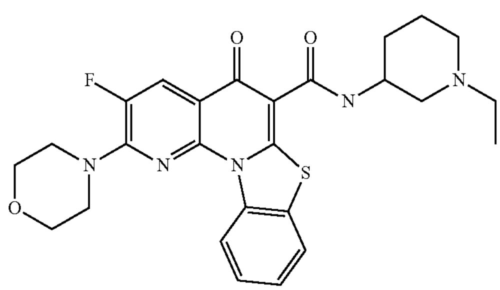 [SMILES: CCN1CCCC(NC(=O)c2c(=O)c3cc(F)c(N4CCOCC4)nc3n3c2sc2ccccc23)C1] | 509.60 | 510 |
| 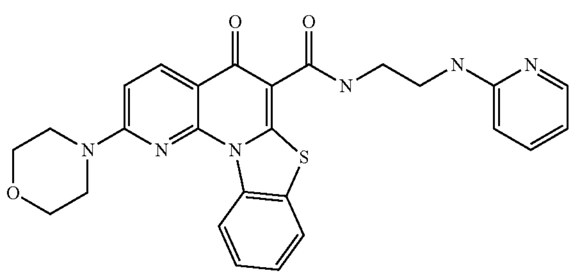 [SMILES: O=C(NCCNc1ccccn1)c1c(=O)c2ccc(N3CCOCC3)nc2n2c1sc1ccccc12] | 500.57 | 501 |

TABLE 1-continued

| Structure | MW | LCMS (ES) m/z [M + 1]+ |
|---|---|---|
| 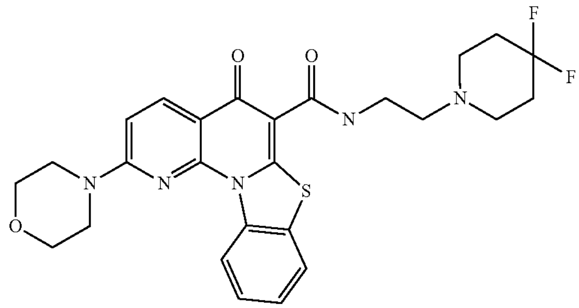 [SMILES: O=C(NCCN1CCC(F)(F)CC1)c1c(=O)c2ccc(N3CCOCC3)nc2n2c1sc1ccccc12] | 527.59 | 528 |
| 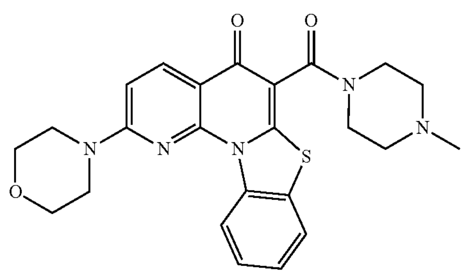 [SMILES: CN1CCN(C(=O)c2c(=O)c3ccc(N4CCOCC4)nc3n3c2sc2ccccc23)CC1] | 463.55 | 464 |
| 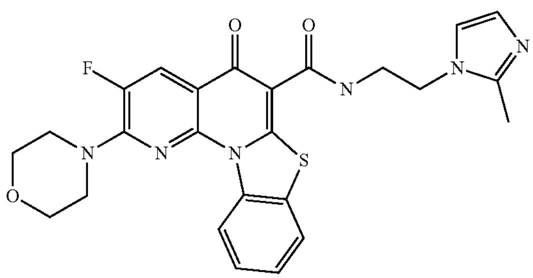 [SMILES: Cc1nccn1CCNC(=O)c1c(=O)c2cc(F)c(N3CCOCC3)nc2n2c1sc1ccccc12] | 506.55 | 507 |
| 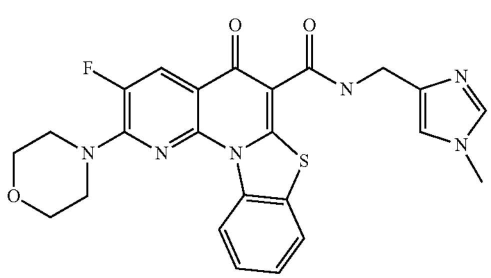 [SMILES: Cn1cnc(CNC(=O)c2c(=O)c3cc(F)c(N4CCOCC4)nc3n3c2sc2ccccc23)c1] | 492.53 | 493 |
| 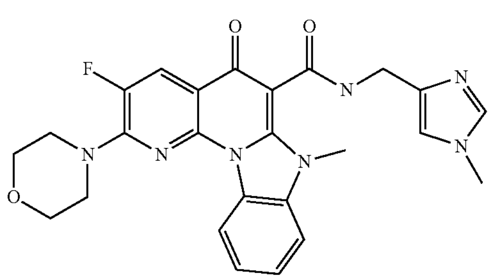 [SMILES: Cn1cnc(CNC(=O)c2c(=O)c3cc(F)c(N4CCOCC4)nc3n3c4ccccc4n(C)c23)c1] | 489.50 | 490 |

TABLE 1-continued

| Structure | MW | LCMS (ES) m/z [M + 1]+ |
|---|---|---|
| 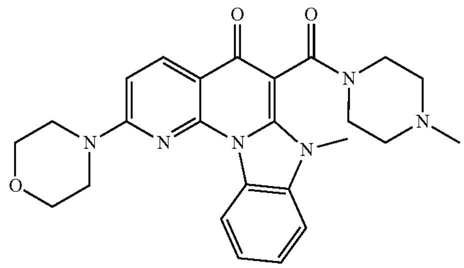 [SMILES: CN1CCN(C(=O)c2c(=O)c3ccc(N4CCOCC4)nc3n3c4ccccc4n(C)c23)CC1] | 460.53 | 461 |
| 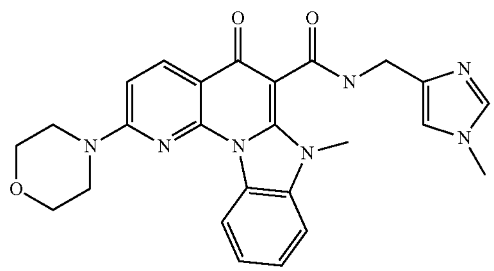 [SMILES: Cn1cnc(CNC(=O)c2c(=O)c3ccc(N4CCOCC4)nc3n3c4ccccc4n(C)c23)c1] | 471.51 | 472 |
| | 512.63 | 513 |
| | 512.63 | 513 |
| 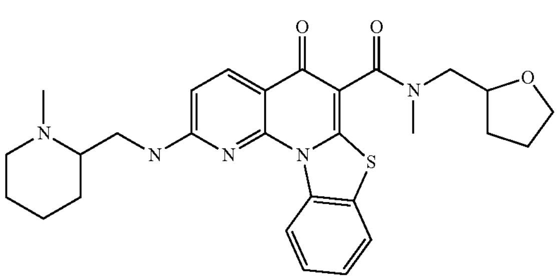 [SMILES: CN(CC1CCCO1)C(=O)c1c(=O)c2ccc(NCC3CCCCN3C)nc2n2c1sc1ccccc12] | 519.66 | 520 |

TABLE 1-continued

| Structure | MW | LCMS (ES) m/z [M + 1]+ |
|---|---|---|
| 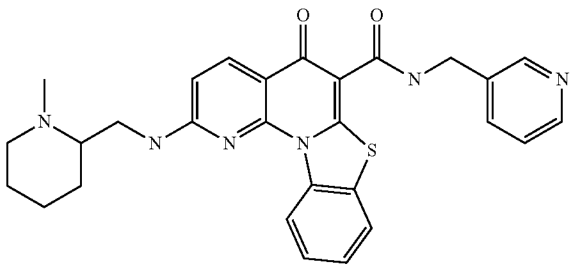 [SMILES: CN1CCCCC1CNc1ccc2c(=O)c(C(=O)NCc3cccnc3)c3sc4ccccc4n3c2n1] | 512.63 | 513 |
| | 502.56 | 503 |
| 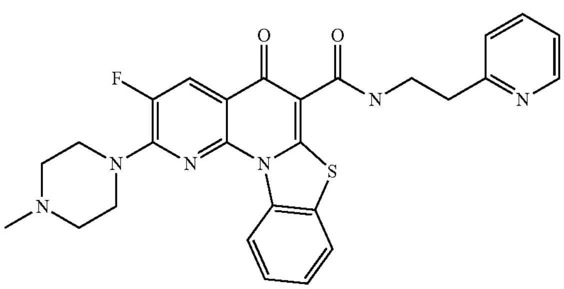 [SMILES: CN1CCN(c2nc3c(cc2F)c(=O)c(C(=O)NCCc2ccccn2)c2sc4ccccc4n23)CC1] | 516.59 | 517 |
| | 502.56 | 503 |
| | 502.56 | 503 |

TABLE 1-continued
| Structure | MW | LCMS (ES) m/z [M + 1]+ |
|---|---|---|
| 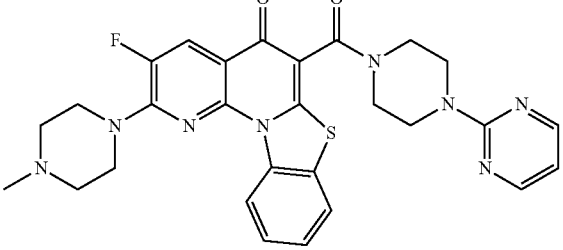 | 558.63 | 559 |
| 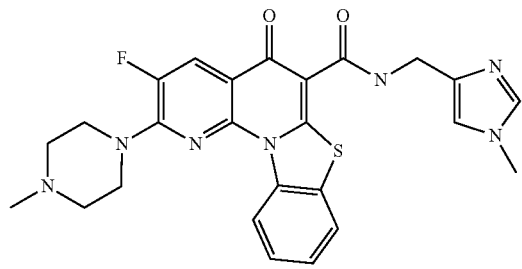 [SMILES: CN1CCN(c2nc3c(cc2F)c(=O)c(C(=O)NCc2cn(C)cn2)c2sc4ccccc4n23)CC1] | 505.57 | 506 |
| 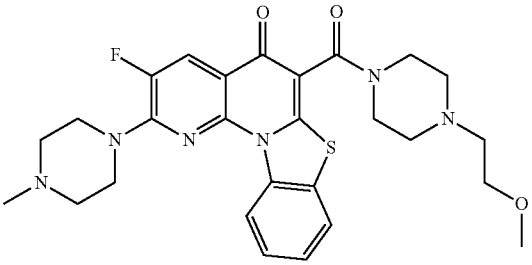 | 538.64 | 539 |
| 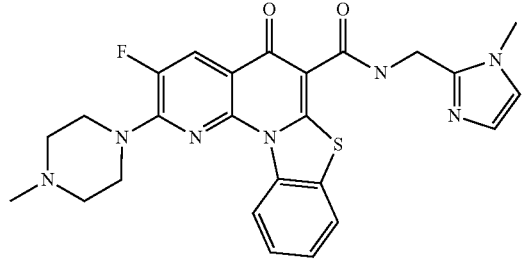 [SMILES: CN1CCN(c2nc3c(cc2F)c(=O)c(C(=O)NCc2nccn2C)c2sc4ccccc4n23)CC1] | 505.57 | 506 |
| 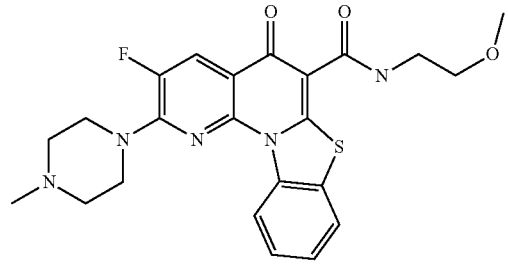 | 469.53 | 470 |

TABLE 1-continued
| Structure | MW | LCMS (ES) m/z [M + 1]+ |
|---|---|---|
| 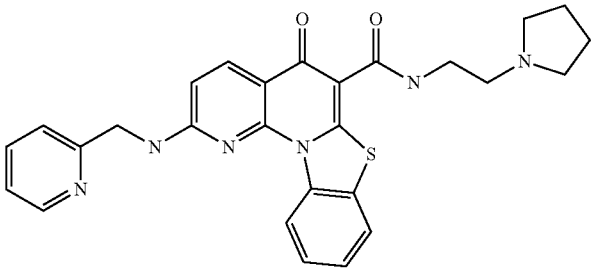 [SMILES: O=C(NCCN1CCCC1)c1c(=O)c2ccc(NCc3ccccn3)nc2n2c1sc1ccccc12] | 498.60 | 499 |
| 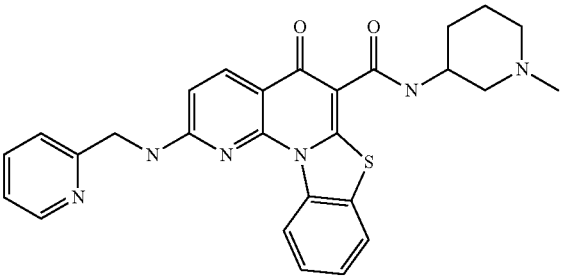 [SMILES: CN1CCCC(NC(=O)c2c(=O)c3ccc(NCc4ccccn4)nc3n3c2sc2ccccc23)C1] | 498.60 | 499 |
| 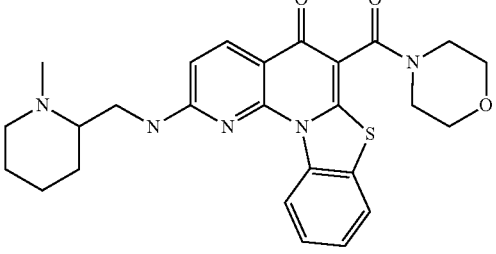 | 491.61 | 492 |
| 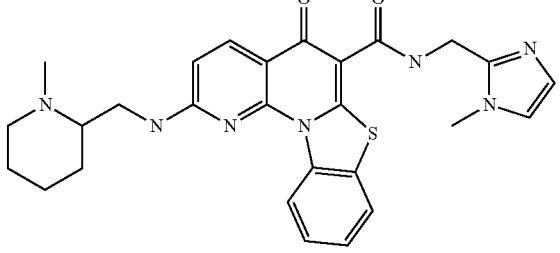 | 515.63 | 516 |
| 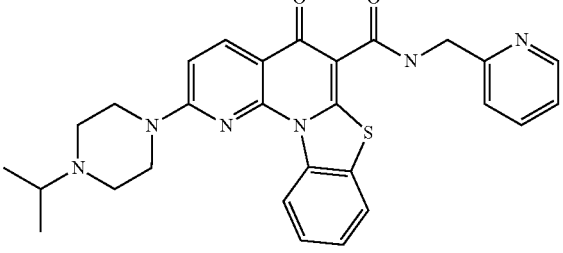 | 512.63 | 513 |

TABLE 1-continued

| Structure | MW | LCMS (ES) m/z [M + 1]+ |
|---|---|---|
| | 512.63 | 513 |
| | 512.63 | 513 |
| 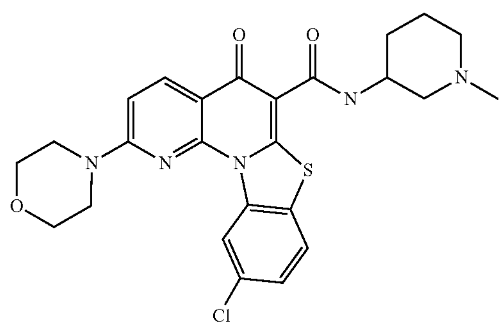 [SMILES: CN1CCCC(NC(=O)c2c(=O)c3ccc(N4CCOCC4)nc3n3c2sc2ccc(Cl)cc23)C1] | 512.02 | 512 |
| 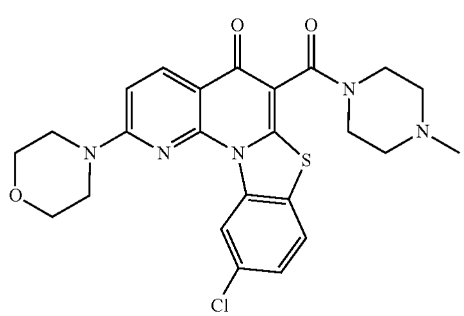 [SMILES: CN1CCN(C(=O)c2c(=O)c3ccc(N4CCOCC4)nc3n3c2sc2ccc(Cl)cc23)CC1] | 498.00 | 498 |
| 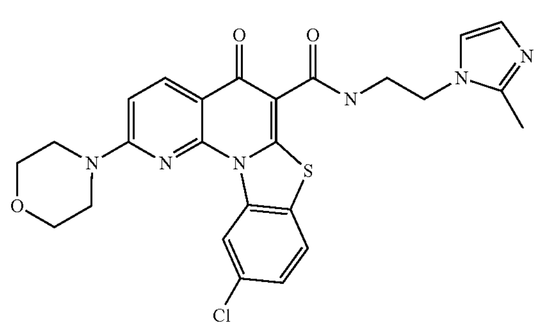 [SMILES: Cc1nccn1CCNC(=O)c1c(=O)c2ccc(N3CCOCC3)nc2n2c1sc1ccc(Cl)cc12] | 523.01 | 523 |

TABLE 1-continued
| Structure | MW | LCMS (ES) m/z [M + 1]+ |
|---|---|---|
| 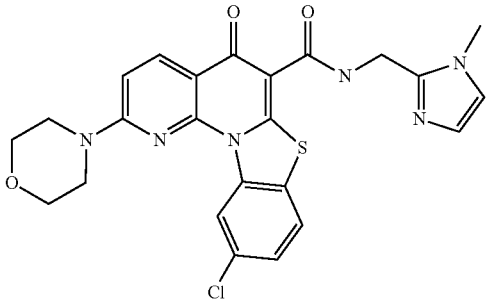 [SMILES: Cn1ccnc1CNC(=O)c1c(=O)c2ccc(N3CCOCC3)nc2n2c1sc1ccc(Cl)cc12] | 508.98 | 509 |
| 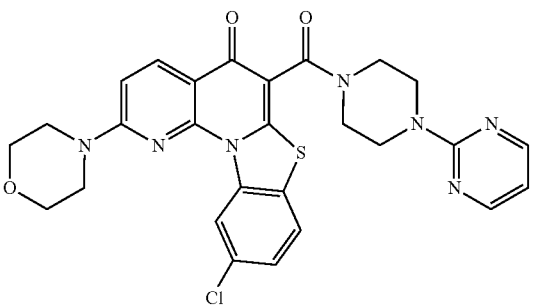 [SMILES: O=C(c1c(=O)c2ccc(N3CCOCC3)nc2n2c1sc1ccc(Cl)cc12)N1CCN(c2ncccn2)CC1] | 562.04 | 563 |
| 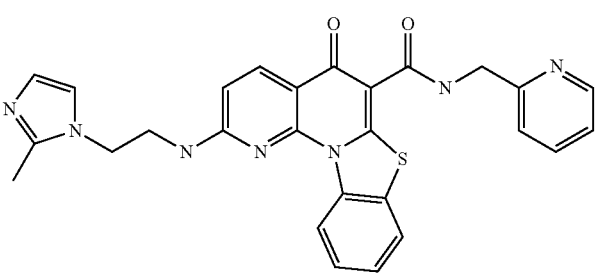 [SMILES: Cc1nccn1CCNc1ccc2c(=O)c(C(=O)NCc3ccccn3)c3sc4ccccc4n3c2n1] | 509.58 | 510 |
| 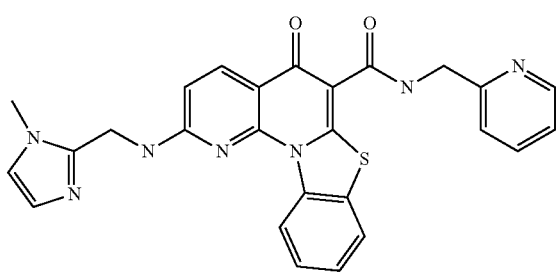 [SMILES: Cn1ccnc1CNc1ccc2c(=O)c(C(=O)NCc3ccccn3)c3sc4ccccc4n3c2n1] | 495.56 | 496 |
| 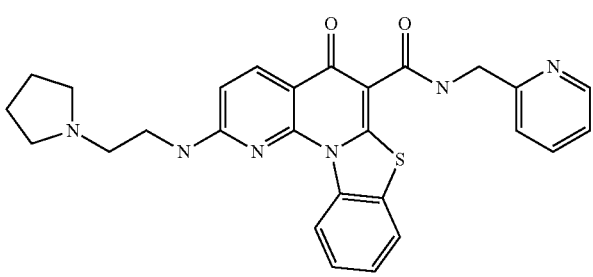 [SMILES: O=C(NCc1ccccn1)c1c(=O)c2ccc(NCCN3CCCC3)nc2n2c1sc1ccccc12] | 498.60 | 499 |

TABLE 1-continued

| Structure | MW | LCMS (ES) m/z [M + 1]+ |
|---|---|---|
| 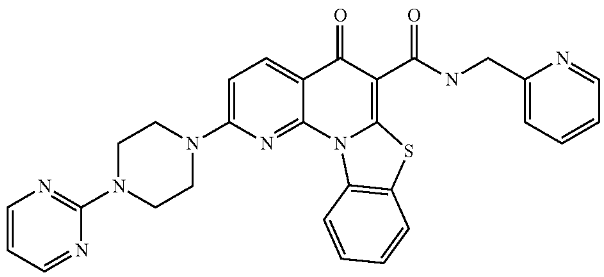 [SMILES: O=C(NCc1ccccn1)c1c(=O)c2ccc(N3CCN(c4ncccn4)CC3)nc2n2c1sc1ccccc12] | 548.62 | 549 |
| 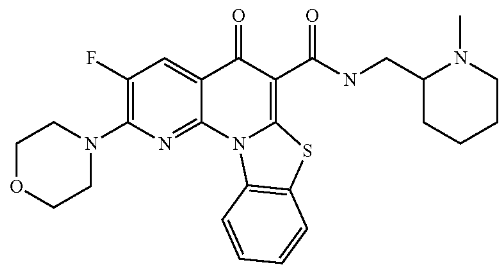 [SMILES: CN1CCCCC1CNC(=O)c1c(=O)c2cc(F)c(N3CCOCC3)nc2n2c1sc1ccccc12] | 509.60 | 510 |
| 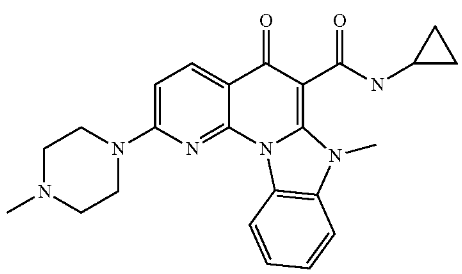 [SMILES: CN1CCN(c2ccc3c(=O)c(C(=O)NC4CC4)c4n(C)c5ccccc5n4c3n2)CC1] | 430.50 | 431 |
| 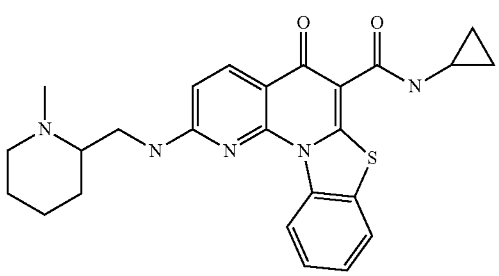 [SMILES: CN1CCCCC1CNc1ccc2c(=O)c(C(=O)NC3CC3)c3sc4ccccc4n3c2n1] | 461.58 | 462 |
| 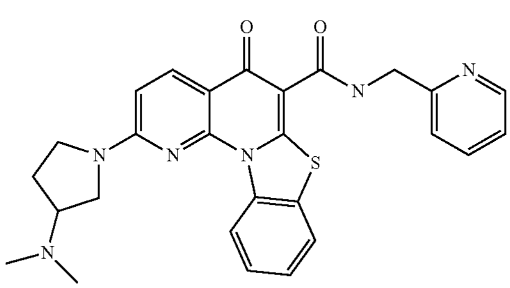 [SMILES: CN(C)C1CCN(c2ccc3c(=O)c(C(=O)NCc4ccccn4)c4sc5ccccc5n4c3n2)C1] | 498.60 | 499 |

TABLE 1-continued
| Structure | MW | LCMS (ES) m/z [M + 1]+ |
|---|---|---|
| 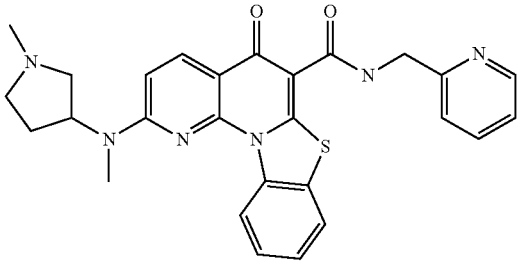 [SMILES: CN1CCC(N(C)c2ccc3c(=O)c(C(=O)NCc4ccccn4)c4sc5ccccc5n4c3n2)C1] | 498.60 | 499 |
| 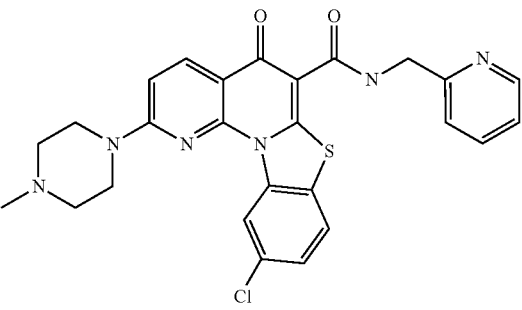 [SMILES: CN1CCN(c2ccc3c(=O)c(C(=O)NCc4ccccn4)c4sc5ccc(Cl)cc5n4c3n2)CC1] | 519.02 | 519 |
| 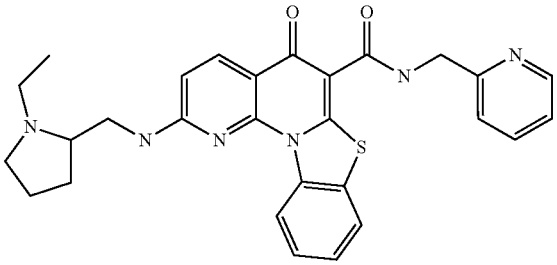 [SMILES: CCN1CCCC1CNc1ccc2c(=O)c(C(=O)NCc3ccccn3)c3sc4ccccc4n3c2n1] | 512.63 | 513 |
| 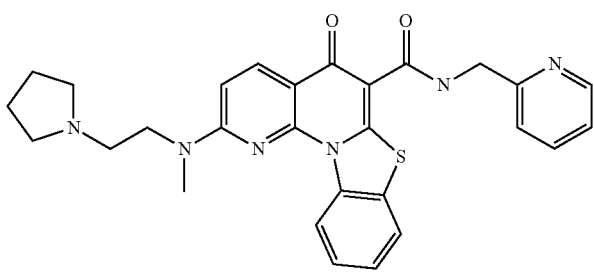 | 512.63 | 513 |
| 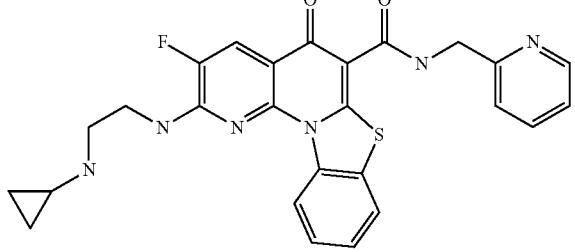 | 502.56 | 503 |

TABLE 1-continued

| Structure | MW | LCMS (ES) m/z [M + 1]+ |
|---|---|---|
| 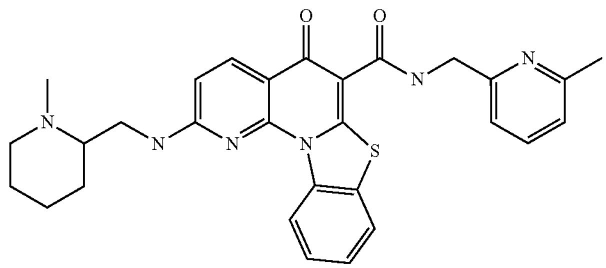 [SMILES: Cc1cccc(CNC(=O)c2c(=O)c3ccc(NCC4CCCCN4C)nc3n3c2sc2ccccc23)n1] | 526.65 | 527 |
| 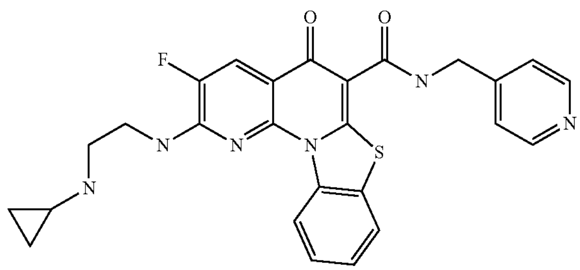 [SMILES: O=C(NCc1ccncc1)c1c(=O)c2cc(F)c(NCCNC3CC3)nc2n2c1sc1ccccc12] | 502.56 | 503 |
| 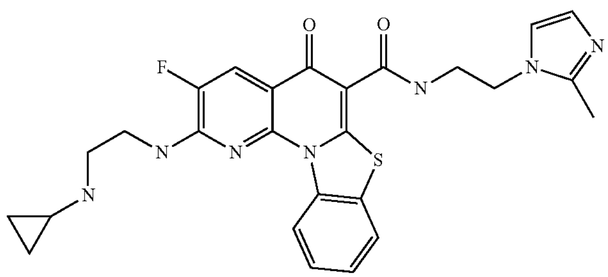 [SMILES: Cc1nccn1CCNC(=O)c1c(=O)c2cc(F)c(NCCNC3CC3)nc2n2c1sc1ccccc12] | 519.59 | 520 |
| | 514.57 | 515 |
| | 514.57 | 515 |

TABLE 1-continued

| Structure | MW | LCMS (ES) m/z [M + 1]+ |
|---|---|---|
| 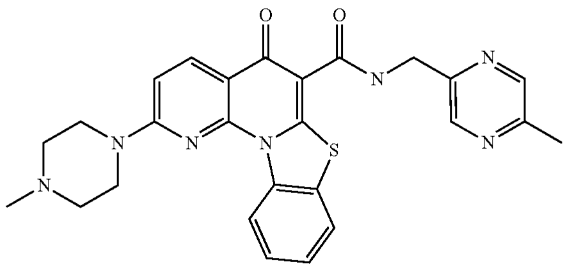 | 499.59 | 500 |
| 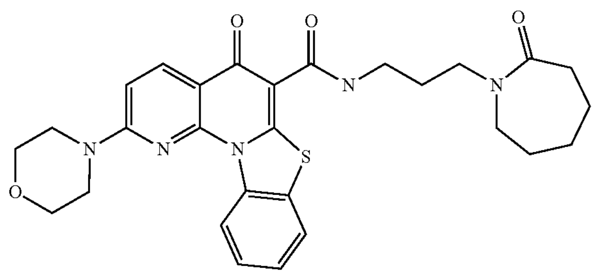 [SMILES: O=C(NCCCN1CCCCCC1=O)c1c(=O)c2ccc(N3CCOCC3)nc2n2c1sc1ccccc12] | 533.64 | 534 |
| 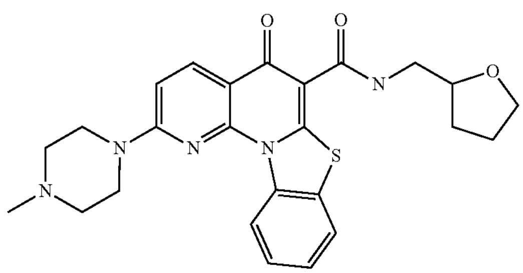 [SMILES: CN1CCN(c2ccc3c(=O)c(C(=O)NCC4CCCO4)c4sc5ccccc5n4c3n2)CC1] | 477.58 | 478 |
| | 498.60 | 499 |
| | 498.60 | 499 |

TABLE 1-continued

| Structure | MW | LCMS (ES) m/z [M + 1]+ |
|---|---|---|
| | 484.57 | 485 |
| | 484.57 | 485 |
| 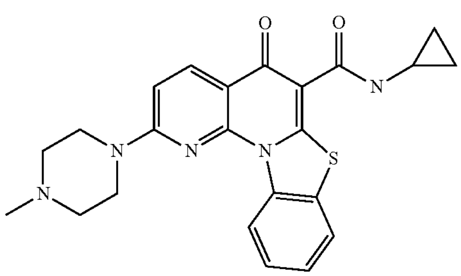 [SMILES: CN1CCN(c2ccc3c(=O)c(C(=O)NC4CC4)c4sc5ccccc5n4c3n2)CC1] | 433.53 | 434 |
| | 499.6 | 500 |
| | 499.6 | 500 |

TABLE 1-continued

| Structure | MW | LCMS (ES) m/z [M + 1]+ |
|---|---|---|
| 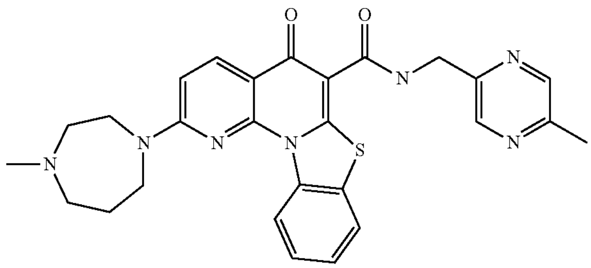 | 513.62 | 514 |
| 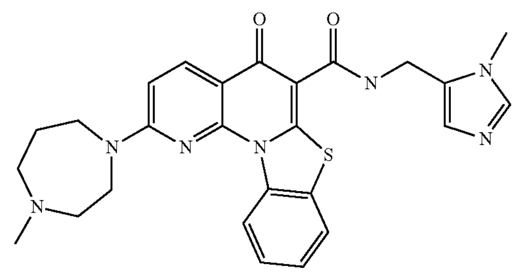 [SMILES: CN1CCCN(c2ccc3c(=O)c(C(=O)NCc4cncn4C)c4sc5ccccc5n4c3n2)CC1] | 501.61 | 502 |

Example 24

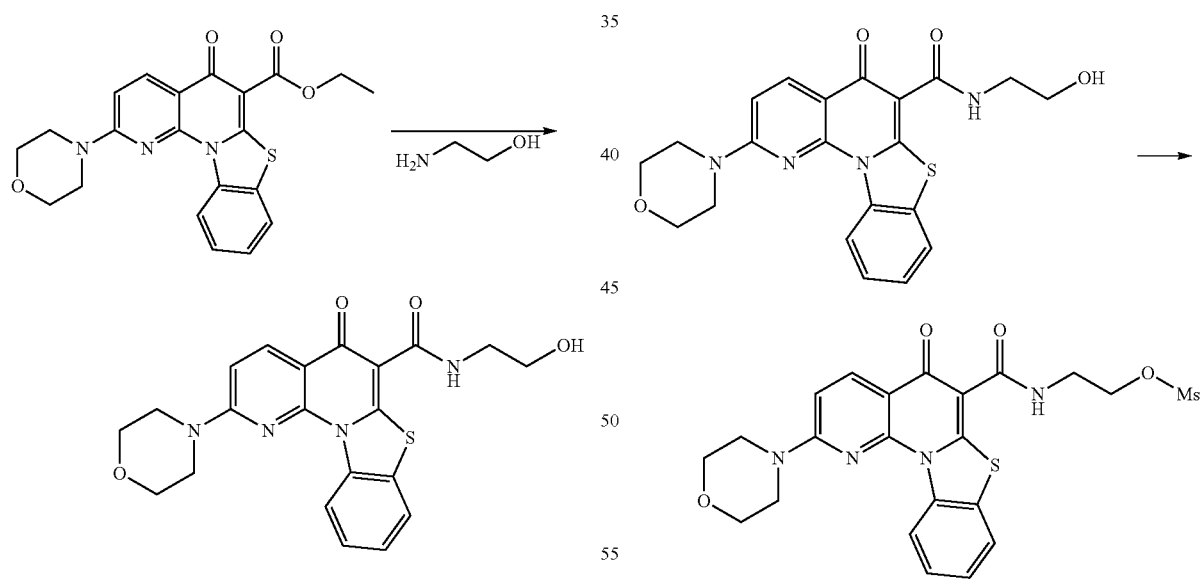

Example 25

A solution of ester (6.53 g, 15.97 mmol) in ethanolamine (30 mL) was stirred at 150° C. over night. The reaction was diluted with H$_2$O (100 mL) and the resulting precipitate was collected by filtration. The solid was washed with H$_2$O (2×) and ACN (2×) to yield the desired product as a white solid (5.75 g, 85%). $^1$H NMR (DMSO-d$^6$) δ: 10.57 (t, 1H), 9.32 (d, 1H), 8.36 (d, 1H), 7.99 (dd, 1H), 7.55 (m, 1H), 7.48 (m, 1H), 7.18 (d, 1H), 4.85 (t, 1H), 3.82 (t, 4H), 3.75 (t, 4H), 3.56 (q, 2H), 3.43 (q, 2H). LCMS (ES): m/z 425 [M+1]+.

To a solution of alcohol (500 mg, 1.18 mmol) and TEA (0.50 mL, 3.58 mmol) in DCM (30 mL) was added MsCl (0.20 mL, 2.58 mmol). The reaction mixture was stirred at rt for 1 h and then diluted with DCM (100 mL) and saturated NH$_4$Cl (50 mL). The layers were separated and the organic layer was washed with H$_2$O (100 mL), brine (50 mL), and dried over Na$_2$SO$_4$. The solvent was removed under reduced pressure and the reaction crude was triturated in ACN to yield the desired product as a pale yellow solid (400 mg, 68%). The material was used as is without further purification. LCMS (ES): m/z 503 [M+1]+.

Example 26

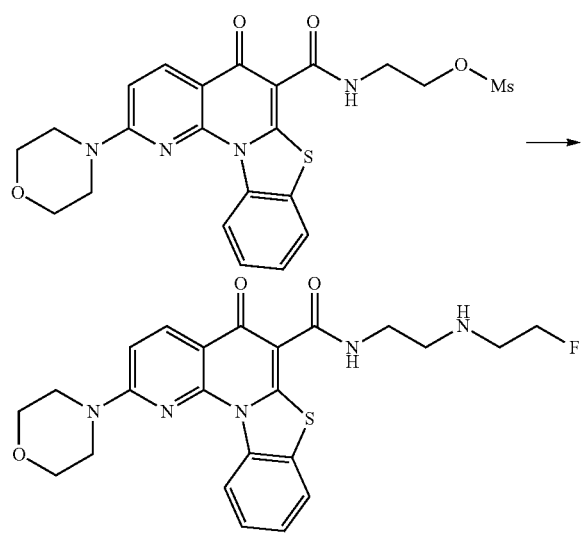

A solution of mesylate (90 mg, 0.18 mmol), 2-fluoroethanamine (40 mg, 0.40 mmol), and TEA (0.05 mL) in NMP (1.5 mL) was heated at 130° C. for 20 min in microwave. The reaction was diluted with ACN (5 mL) and the resulting precipitate was collected by filtration. The reaction crude was purified on silica gel TLC (10% MeOH/DCM) to yield the desired product. LCMS (ES): m/z 470 [M+1]+.

Example 27

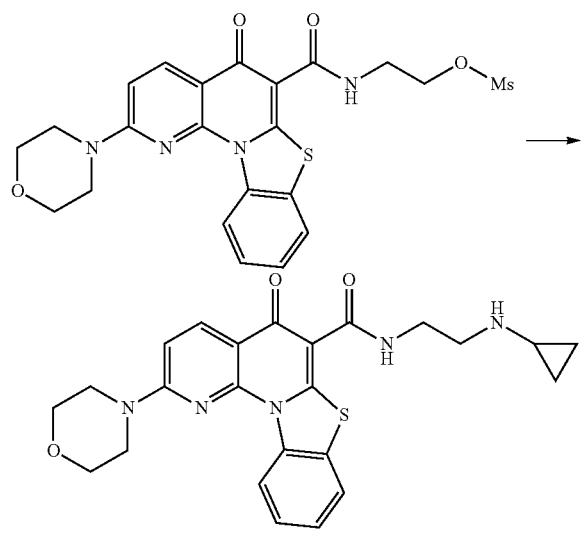

A solution of mesylate (50 mg, 0.10 mmol), cyclopropylamine (0.10 mL, 1.75 mmol), HCl (1N, 0.05 mL) and TEA (0.05 mL) in NMP (1.5 mL) was heated at 130° C. for 20 min in microwave. The reaction crude was purified on reverse phase HPLC to yield the desired product. $^1$H NMR (CDCl$_3$) δ: 10.64 (t, 1H), 9.45 (d, 1H), 8.63 (d, 1H), 7.77 (dd, 1H), 7.50 (m, 1H), 7.42 (m, 1H), 6.92 (d, 1H), 3.94 (t, 4H), 3.82 (t, 4H), 3.66 (q, 2H), 3.01 (t, 2H), 2.00 (m, 1H), 0.43 (m, 4H). LCMS (ES): m/z 464 [M+1]+

Example 28

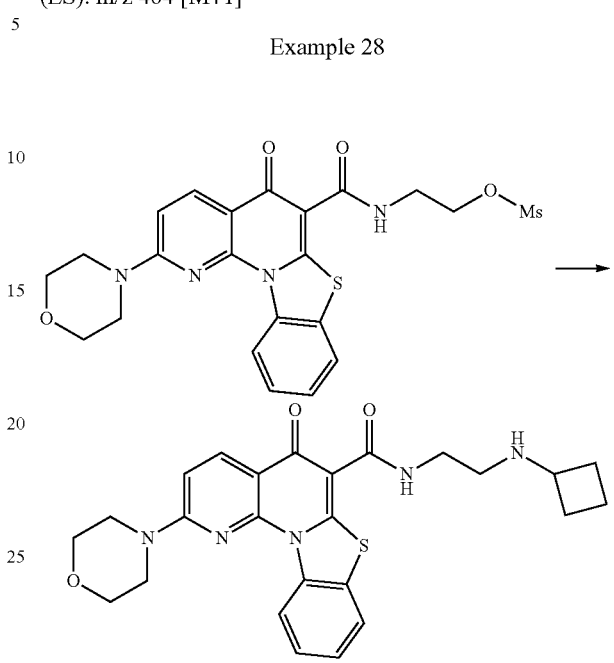

A solution of mesylate (100 mg, 0.20 mmol), cyclobutylamine (0.10 mL, 1.41 mmol), HCl (1N, 0.05 mL) and TEA (0.05 mL) in ACN (2.0 mL) was heated at 120° C. for 15 min in microwave. The resulting precipitate was collected by filtration and purified on silica gel TLC (15% MeOH/DCM) to yield the desired product (65 mg, 98%). LCMS (ES): m/z 478 [M+1]+.

Example 29

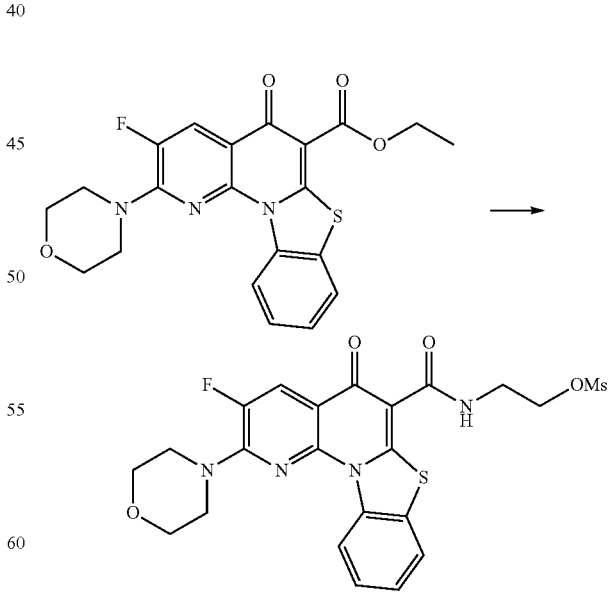

The ester (0.5 g, 1.16 mmole) and ethanol amine (0.7 mL, 11.63 mmole) in 3 mL NMP were heated a 160° C. for 20 min (microwave). Solid formed was filtered, washed several times with MeOH and air dried under vacuum. The alcohol was obtained as off white solid and used in the next step without further purification. To the alcohol (0.204 g, 0.46 mmole) and triethyl amine in DCM (10 mL) was added MsCl at room temperature. The mixture was stirred for 30 min at room temperature. Dichloromethane (100 mL) was added and the resulting solution was washed with saturated solution of sodium bicarbonate (2×100 mL), brine (100 mL), dried with sodium sulfate and concentrated under vacuum to the mesylate as a yellow solid.

Example 30

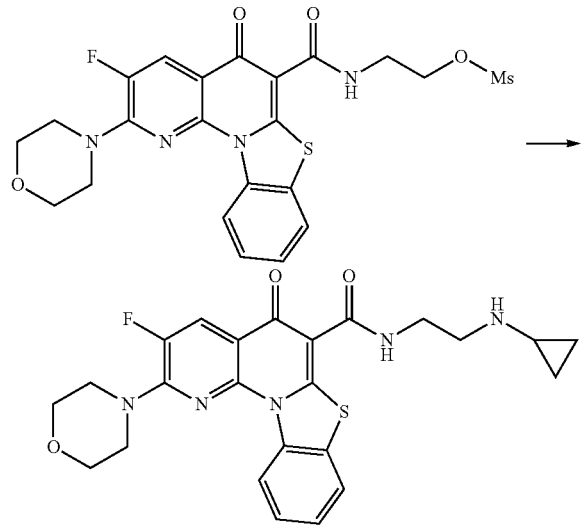

A solution of mesylate (50 mg) and cyclopropylamine (0.2 mL) in ACN (1 mL) was heated at 100° C. for 20 min (microwave). The solvent was removed under vacuum and compound was triturated with ethyl acetate to give a white solid. LCMS (ES): m/z 482 [M+1]$^+$ Example 31

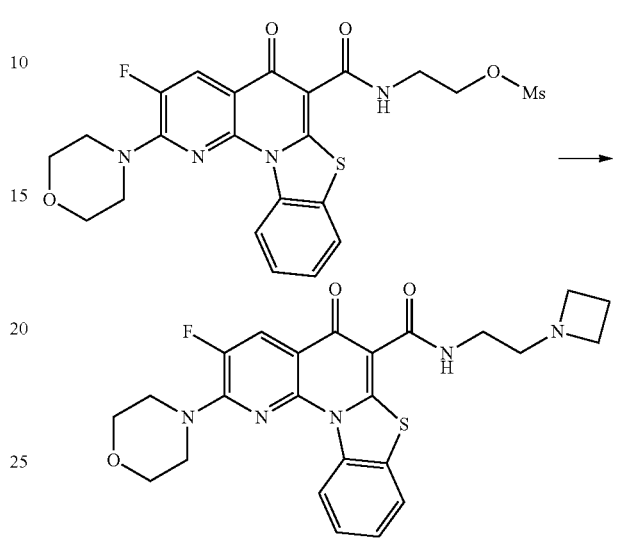

A solution of mesylate (54 mg) and cyclobutylamine hydrochloride (0.2 g) and TEA (0.2 mL) in ACN (1 mL) was heated at 90° C. for 1 h (microwave). The solvent was removed under vacuum and the residue was purified by silica gel TLC (10% MeOH/DCM) to give a white solid. LCMS (ES): m/z 482 [M+1]$^+$ The following analogues in Table 2 were prepared by the same method, using the appropriate amines and mesylate.

TABLE 2

| Structure | MW | LCMS (ES) m/z [M + 1]$^+$ |
|---|---|---|
| 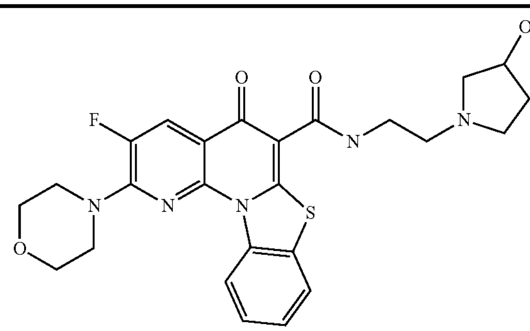 | 511.58 | 512 |
| 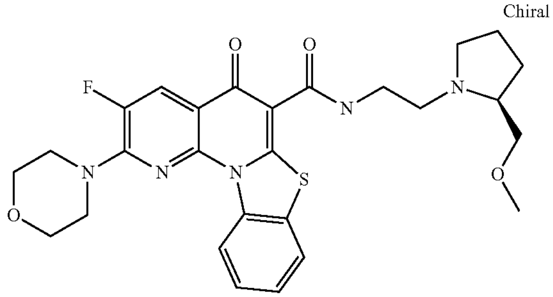 [SMILES: COC[C@@H]1CCCN1CCNC(=O)c1c(=O)c2cc(F)c(N3CCOCC3)nc2n2c1sc1ccccc12] | 539.62 | 540 |

TABLE 2-continued

| Structure | MW | LCMS (ES) m/z [M + 1]+ |
|---|---|---|
| Chiral | 525.60 | 526 |
|  | 525.60 | 526 |
| 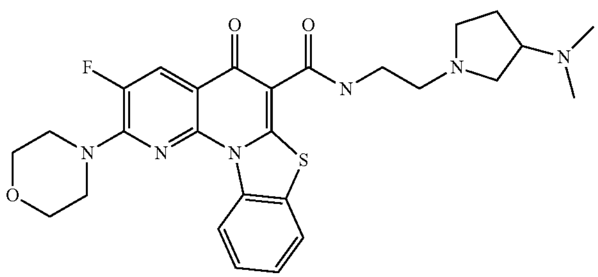 [SMILES: CN(C)C1CCN(CCNC(=O)c2c(=O)c3cc(F)c(N4CCOCC4)nc3n3c2sc2ccccc23)C1] | 538.64 | 539 |
| 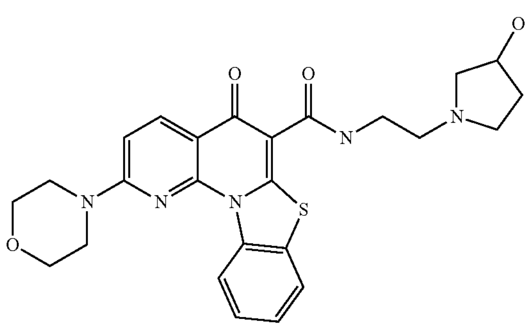 [SMILES: O=C(NCCN1CCC(O)C1)c1c(=O)c2ccc(N3CCOCC3)nc2n2c1sc1ccccc12] | 493.58 | 494 |
| 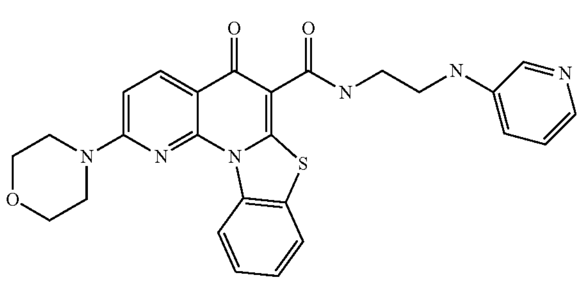 [SMILES: O=C(NCCNc1cccnc1)c1c(=O)c2ccc(N3CCOCC3)nc2n2c1sc1ccccc12] | 500.57 | 501 |

TABLE 2-continued

| Structure | MW | LCMS (ES) m/z [M + 1]+ |
|---|---|---|
| 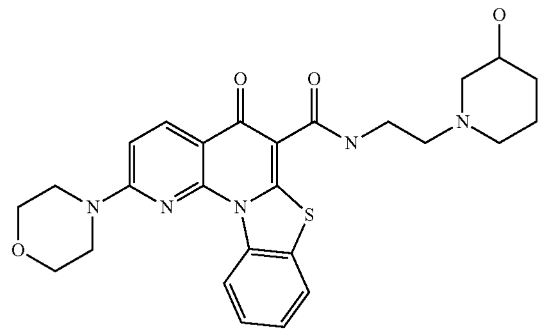 [SMILES: O=C(NCCN1CCCC(O)C1)c1c(=O)c2ccc(N3CCOCC3)nc2n2c1sc1ccccc12] | 507.60 | 508 |
| 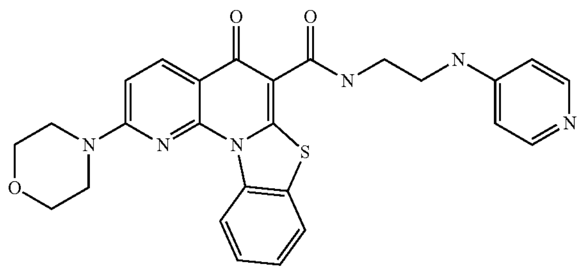 [SMILES: O=C(NCCNc1ccncc1)c1c(=O)c2ccc(N3CCOCC3)nc2n2c1sc1ccccc12] | 500.57 | 501 |
| 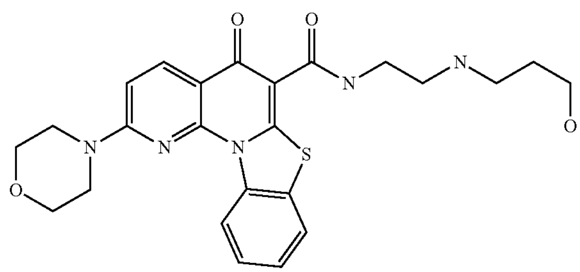 [SMILES: O=C(NCCNCCCO)c1c(=O)c2ccc(N3CCOCC3)nc2n2c1sc1ccccc12] | 481.57 | 482 |
| 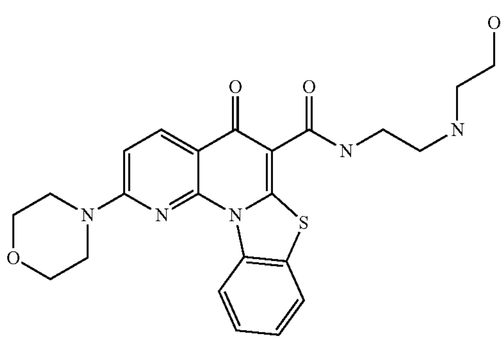 [SMILES: O=C(NCCNCCO)c1c(=O)c2ccc(N3CCOCC3)nc2n2c1sc1ccccc12] | 467.54 | 468 |
| 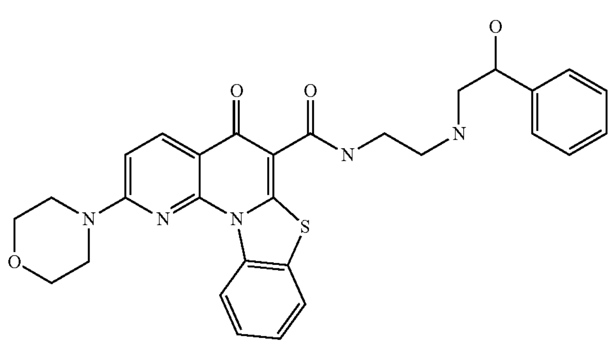 [SMILES: O=C(NCCNCC(O)c1ccccc1)c1c(=O)c2ccc(N3CCOCC3)nc2n2c1sc1ccccc12] | 543.64 | 544 |

TABLE 2-continued
| Structure | MW | LCMS (ES) m/z [M + 1]+ |
|---|---|---|
| 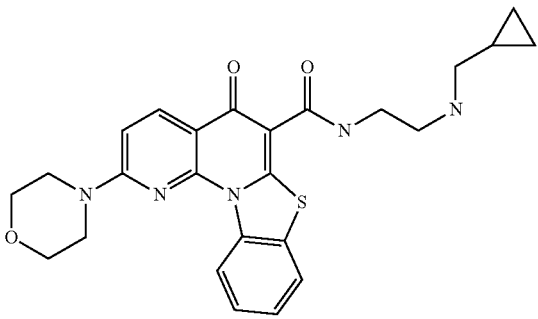 [SMILES: O=C(NCCNCC1CC1)c1c(=O)c2ccc(N3CCOCC3)nc2n2c1sc1ccccc12] | 477.58 | 478 |
| 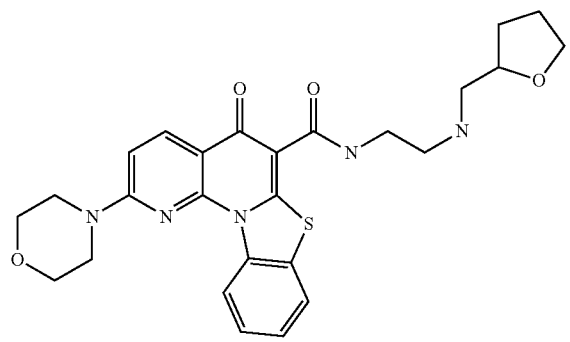 [SMILES: O=C(NCCNCC1CCCO1)c1c(=O)c2ccc(N3CCOCC3)nc2n2c1sc1ccccc12] | 507.60 | 508 |
| 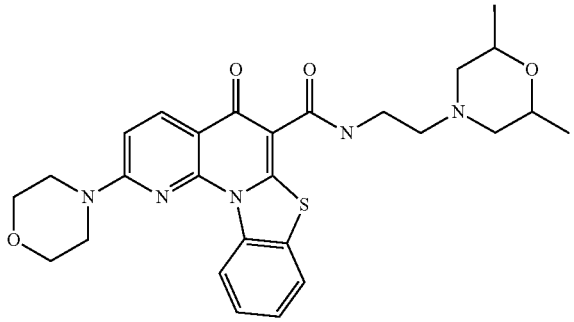 [SMILES: CC1CN(CCNC(=O)c2c(=O)c3ccc(N4CCOCC4)nc3n3c2sc2ccccc23)CC(C)O1] | 521.63 | 522 |
| 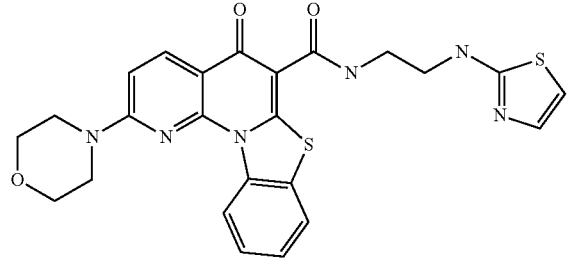 [SMILES: O=C(NCCNc1nccs1)c1c(=O)c2ccc(N3CCOCC3)nc2n2c1sc1ccccc12] | 506.60 | 507 |
| 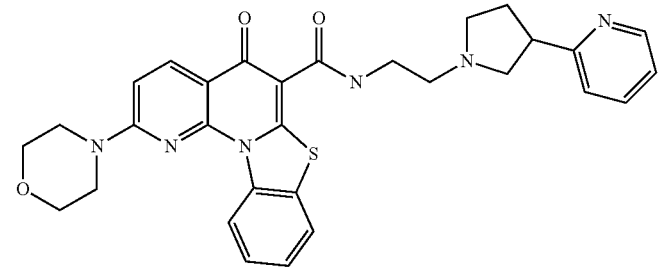 [SMILES: O=C(NCCN1CCC(c2ccccn2)C1)c1c(=O)c2ccc(N3CCOCC3)nc2n2c1sc1ccccc12] | 554.66 | 555 |

TABLE 2-continued

| Structure | MW | LCMS (ES) m/z [M + 1]+ |
|---|---|---|
| 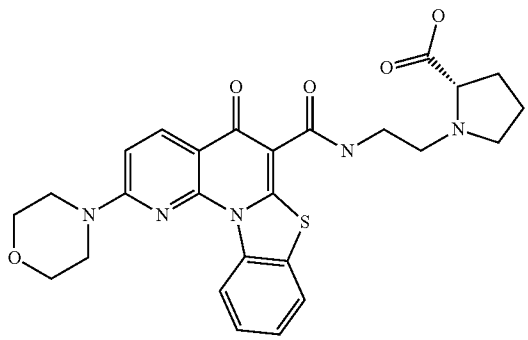 [SMILES: O=C(NCCN1CCC[C@H]1C(=O)O)c1c(=O)c2ccc(N3CCOCC3)nc2n2c1sc1ccccc12] | 521.59 | 522 |
| 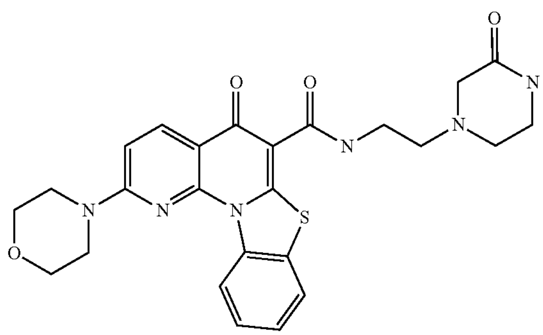 [SMILES: O=C1CN(CCNC(=O)c2c(=O)c3ccc(N4CCOCC4)nc3n3c2sc2ccccc23)CCN1] | 506.58 | 507 |
| 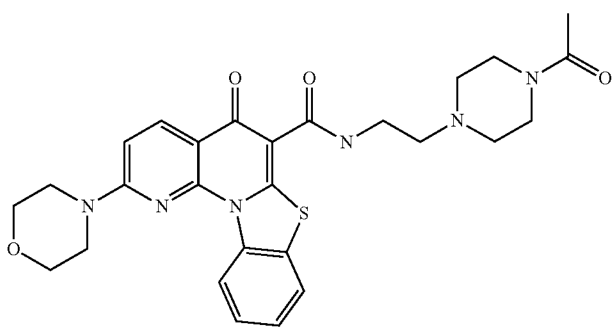 [SMILES: CC(=O)N1CCN(CCNC(=O)c2c(=O)c3ccc(N4CCOCC4)nc3n3c2sc2ccccc23)CC1] | 534.63 | 535 |
| 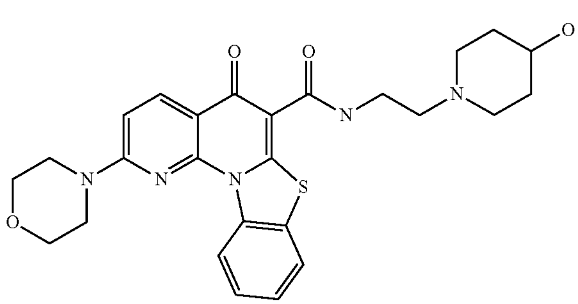 [SMILES: O=C(NCCN1CCC(O)CC1)c1c(=O)c2ccc(N3CCOCC3)nc2n2c1sc1ccccc12] | 507.60 | 508 |

TABLE 2-continued

| Structure | MW | LCMS (ES) m/z [M + 1]+ |
|---|---|---|
| | 534.63 | 535 |
| | 534.63 | 535 |
| 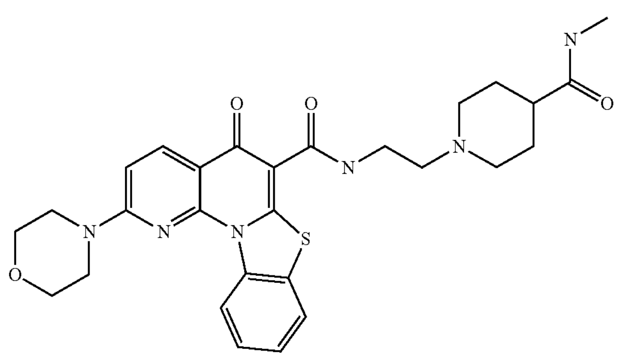 [SMILES: CNC(=O)C1CCN(CCNC(=O)c2c(=O)c3ccc(N4CCOCC4)nc3n3c2sc2ccccc23)CC1] | 548.66 | 549 |
| 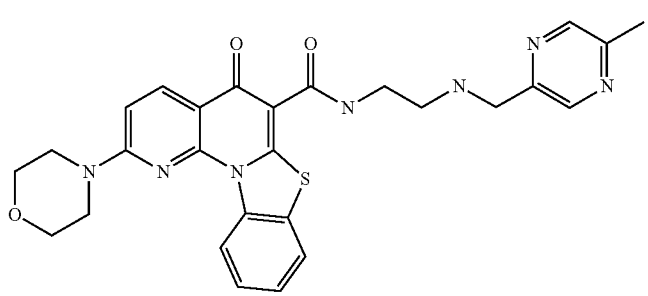 [SMILES: Cc1cnc(CNCCNC(=O)c2c(=O)c3ccc(N4CCOCC4)nc3n3c2sc2ccccc23)cn1] | 529.61 | 530 |

TABLE 2-continued

| Structure | MW | LCMS (ES) m/z [M + 1]+ |
|---|---|---|
| 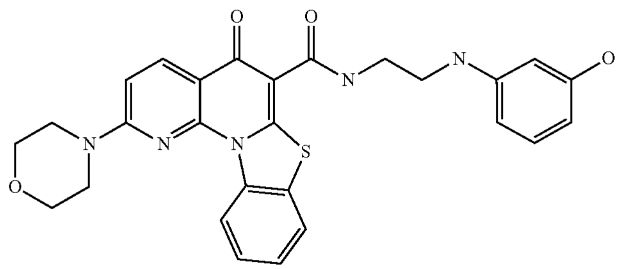 [SMILES: O=C(NCCNc1cccc(O)c1)c1c(=O)c2ccc(N3CCOCC3)nc2n2c1sc1ccccc12] | 515.58 | 516 |
| 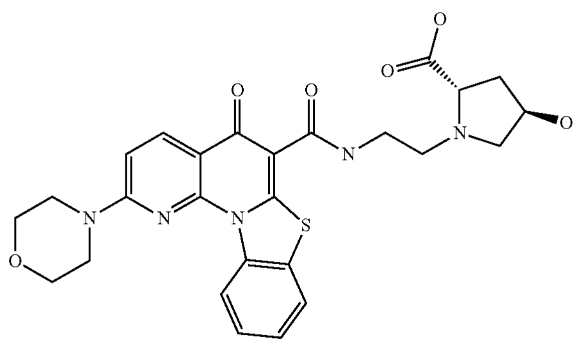 [SMILES: O=C(NCCN1C[C@H](O)C[C@H]1C(=O)O)c1c(=O)c2ccc(N3CCOCC3)nc2n2c1sc1ccccc12] | 537.59 | 538 |
| 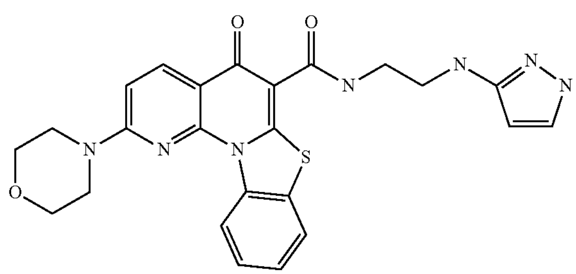 [SMILES: O=C(NCCNc1cc[nH]n1)c1c(=O)c2ccc(N3CCOCC3)nc2n2c1sc1ccccc12] | 489.55 | 490 |
| 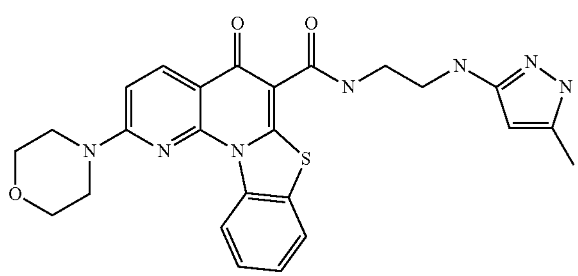 [SMILES: Cc1cc(NCCNC(=O)c2c(=O)c3ccc(N4CCOCC4)nc3n3c2sc2ccccc23)n[nH]1] | 503.58 | 504 |
| 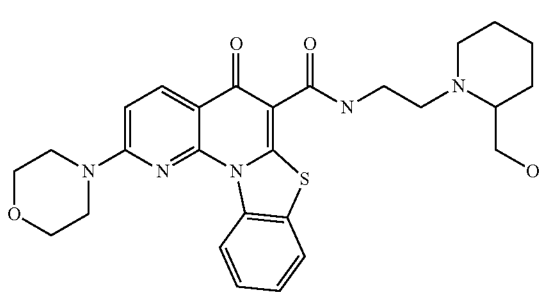 [SMILES: O=C(NCCN1CCCCC1CO)c1c(=O)c2ccc(N3CCOCC3)nc2n2c1sc1ccccc12] | 521.63 | 522 |

TABLE 2-continued

| Structure | MW | LCMS (ES) m/z [M + 1]+ |
|---|---|---|
| | 520.63 | 521 |
| | 520.63 | 521 |
| | 550.61 | 551 |
| | 550.61 | 551 |
| 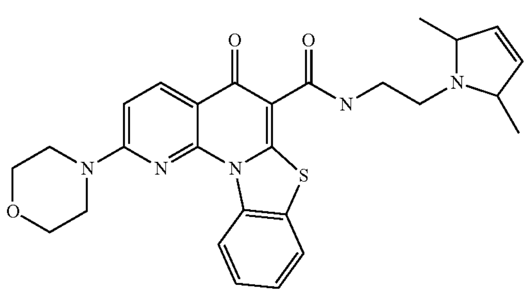 [SMILES: CC1C=CC(C)N1CCNC(=O)c1c(=O)c2ccc(N3CCOCC3)nc2n2c1sc1ccccc12] | 503.62 | 504 |

TABLE 2-continued
| Structure | MW | LCMS (ES) m/z [M + 1]+ |
|---|---|---|
| 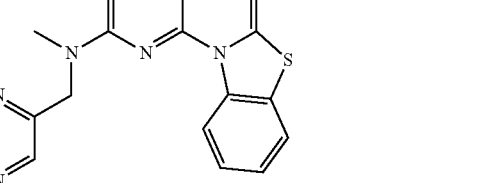 | 511.60 | 512 |
| 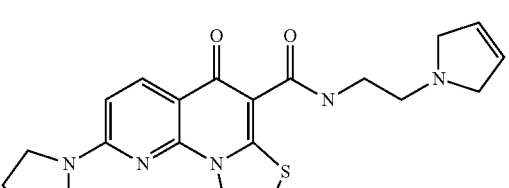 | 537.64 | 538 |
| 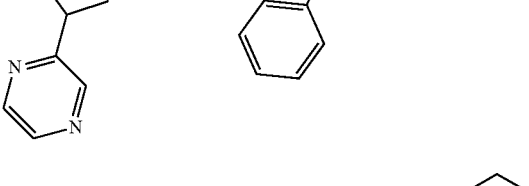 | 489.59 | 490 |
| 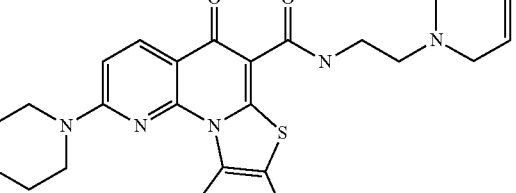 | 545.58 | 546 |
| 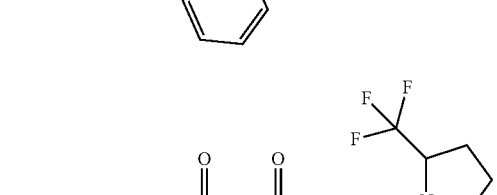 | 513.56 | 514 |

TABLE 2-continued

| Structure | MW | LCMS (ES) m/z [M + 1]+ |
|---|---|---|
| 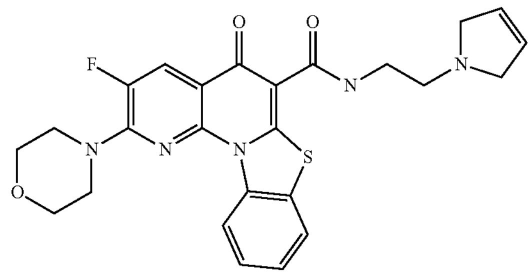 [SMILES: O=C(NCCN1CC=CC1)c1c(=O)c2cc(F)c(N3CCOCC3)nc2n2c1sc1ccccc12] | 493.55 | 494 |
| | 495.57 | 496 |
| | 495.57 | 496 |
| | 513.56 | 514 |
| | 513.56 | 514 |

TABLE 2-continued

| Structure | MW | LCMS (ES) m/z [M + 1]+ |
|---|---|---|
| 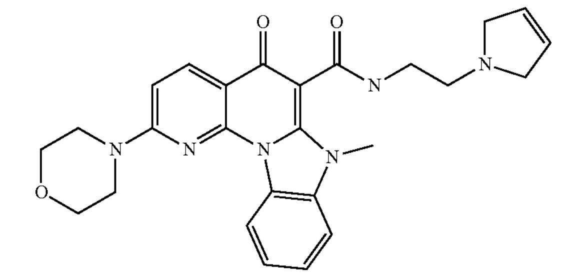 [SMILES: Cn1c2ccccc2n2c3nc(N4CCOCC4)ccc3c(=O)c(C(=O)NCCN3CC=CC3)c12] | 472.54 | 473 |
| 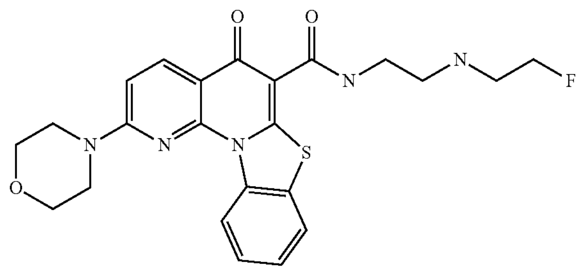 [SMILES: O=C(NCCNCCF)c1c(=O)c2ccc(N3CCOCC3)nc2n2c1sc1ccccc12] | 469.53 | 470 |
| 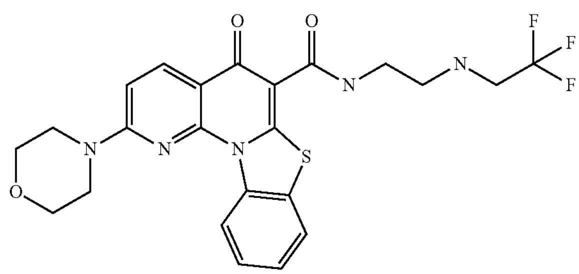 [SMILES: O=C(NCCNCC(F)(F)F)c1c(=O)c2ccc(N3CCOCC3)nc2n2c1sc1ccccc12] | 505.51 | 506 |
| 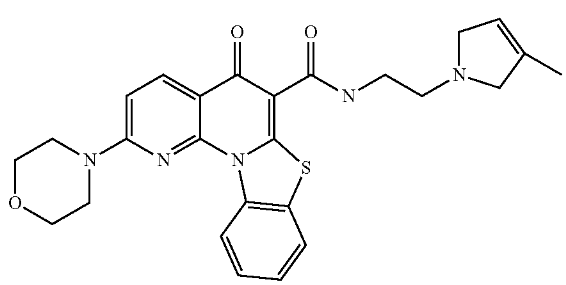 [SMILES: CC1=CCN(CCNC(=O)c2c(=O)c3ccc(N4CCOCC4)nc3n3c2sc2ccccc23)C1] | 489.59 | 490 |
| 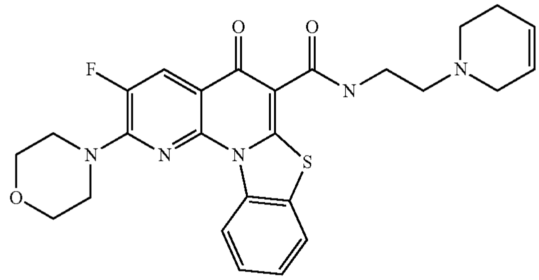 [SMILES: O=C(NCCN1CC=CCC1)c1c(=O)c2cc(F)c(N3CCOCC3)nc2n2c1sc1ccccc12] | 507.58 | 508 |

TABLE 2-continued

| Structure | MW | LCMS (ES) m/z [M + 1]+ |
|---|---|---|
| | 507.58 | 508 |
| 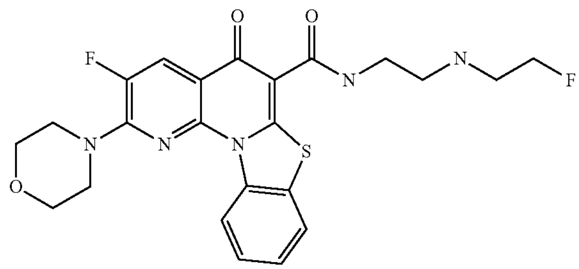 [SMILES: O=C(NCCNCCF)c1c(=O)c2cc(F)c(N3CCOCC3)nc2n2c1sc1ccccc12] | 487.52 | 488 |
| | 507.58 | 508 |
| | 507.60 | 508 |
| | 507.60 | 508 |

TABLE 2-continued
| Structure | MW | LCMS (ES) m/z [M + 1]+ |
|---|---|---|
| 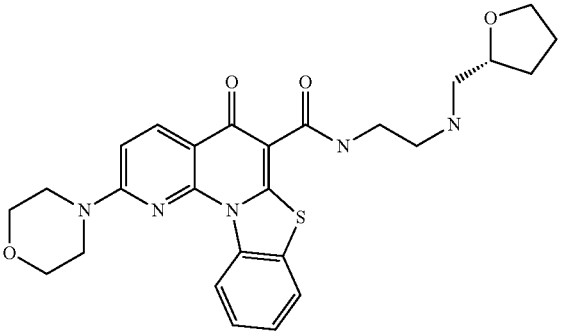 [SMILES: O=C(NCCNC[C@H]1CCCO1)c1c(=O)c2ccc(N3CCOCC3)nc2n2c1sc1ccccc12] | 507.60 | 508 |
| 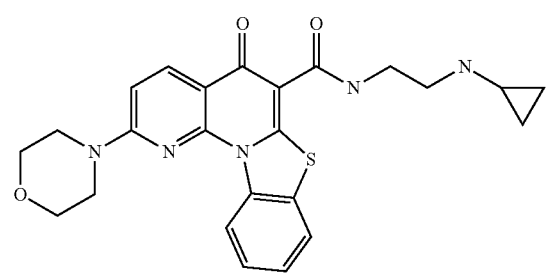 [SMILES: O=C(NCCNC1CC1)c1c(=O)c2ccc(N3CCOCC3)nc2n2c1sc1ccccc12] | 463.55 | 464 |
| 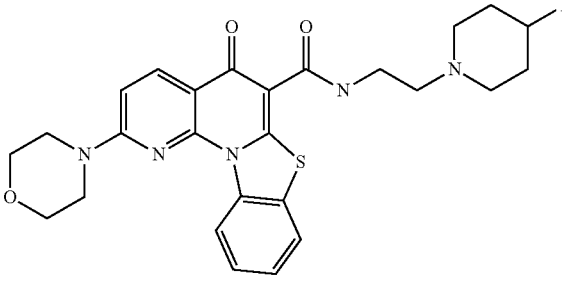 | 509.60 | 510 |
| 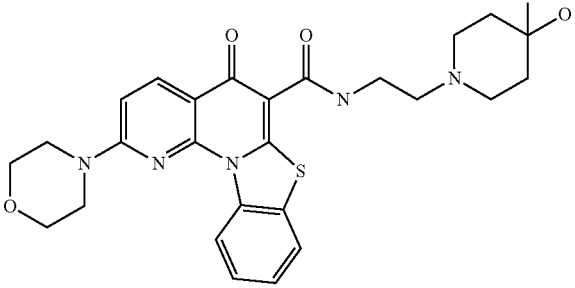 | 523.60 | 524 |
| 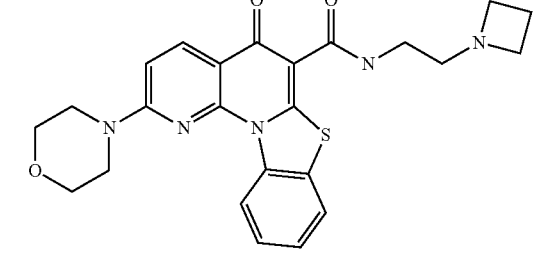 | 463.55 | 464 |

TABLE 2-continued

| Structure | MW | LCMS (ES) m/z [M + 1]+ |
|---|---|---|
| 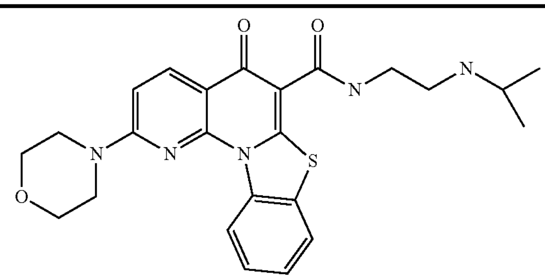 | 465.57 | 466 |
| 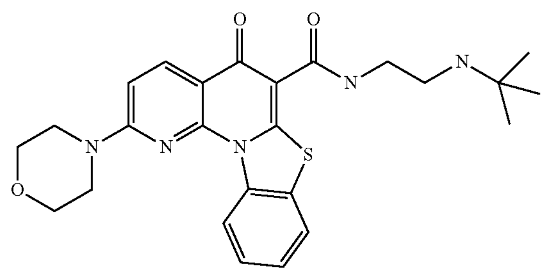 [SMILES: CC(C)(C)NCCNC(=O)c1c(=O)c2ccc(N3CCOCC3)nc2n2c1sc1ccccc12] | 479.59 | 480 |
| 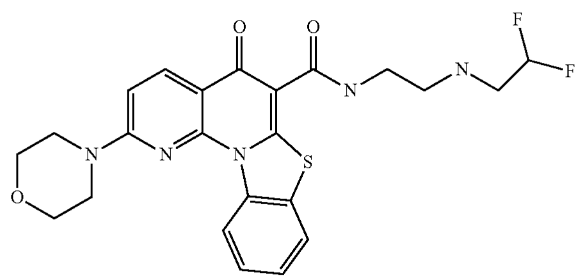 [SMILES: O=C(NCCNCC(F)F)c1c(=O)c2ccc(N3CCOCC3)nc2n2c1sc1ccccc12] | 487.52 | 488 |
| 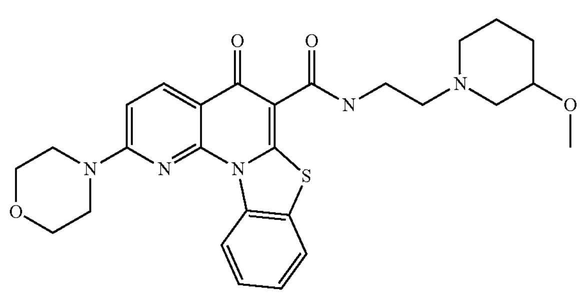 [SMILES: COC1CCCN(CCNC(=O)c2c(=O)c3ccc(N4CCOCC4)nc3n3c2sc2ccccc23)C1] | 521.63 | 522 |
| 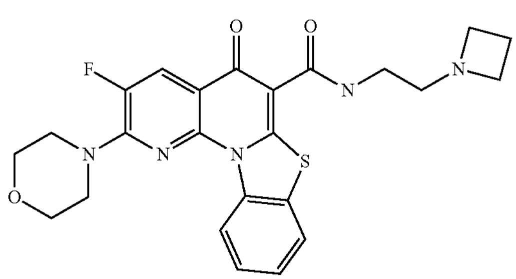 [SMILES: O=C(NCCN1CCC1)c1c(=O)c2cc(F)c(N3CCOCC3)nc2n2c1sc1ccccc12] | 481.54 | 482 |

TABLE 2-continued

| Structure | MW | LCMS (ES) m/z [M + 1]+ |
|---|---|---|
| 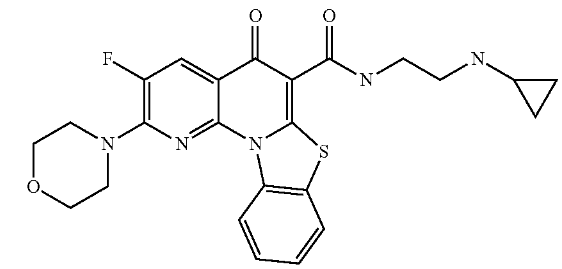 [SMILES: O=C(NCCNC1CC1)c1c(=O)c2cc(F)c(N3CCOCC3)nc2n2c1sc1ccccc12] | 481.54 | 482 |
| 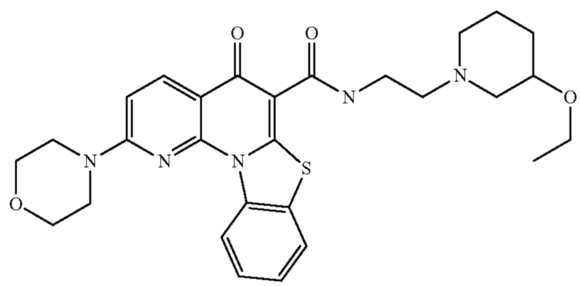 [SMILES: CCOC1CCCN(CCNC(=O)c2c(=O)c3ccc(N4CCOCC4)nc3n3c2sc2ccccc23)C1] | 535.66 | 536 |
| 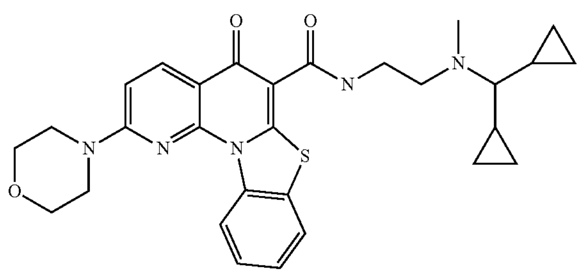 [SMILES: CN(CCNC(=O)c1c(=O)c2ccc(N3CCOCC3)nc2n2c1sc1ccccc12)C(C1CC1)C1CC1] | 531.67 | 532 |
| 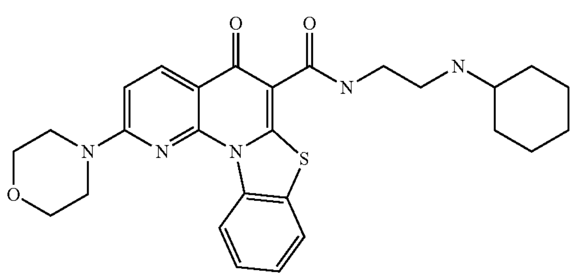 [SMILES: O=C(NCCNC1CCCCC1)c1c(=O)c2ccc(N3CCOCC3)nc2n2c1sc1ccccc12] | 505.63 | 506 |
| 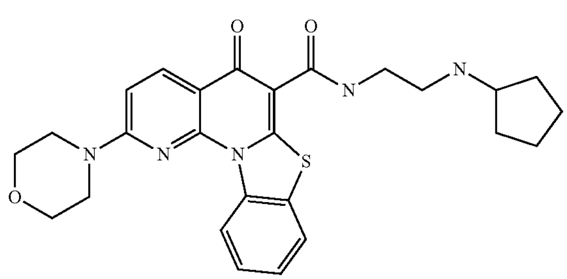 [SMILES: O=C(NCCNC1CCCC1)c1c(=O)c2ccc(N3CCOCC3)nc2n2c1sc1ccccc12] | 491.61 | 492 |

TABLE 2-continued

| Structure | MW | LCMS (ES) m/z [M + 1]+ |
|---|---|---|
| 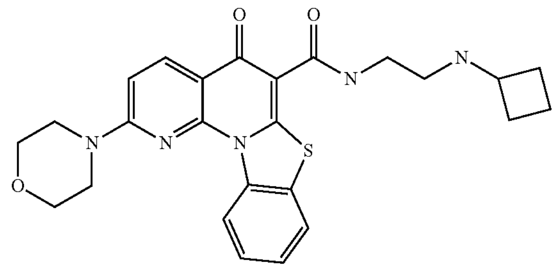 [SMILES: O=C(NCCNC1CCC1)c1c(=O)c2ccc(N3CCOCC3)nc2n2c1sc1ccccc12] | 477.58 | 478 |
| 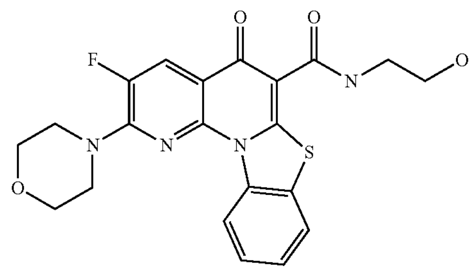 [SMILES: O=C(NCCO)c1c(=O)c2cc(F)c(N3CCOCC3)nc2n2c1sc1ccccc12] | 442.46 | 443 |
| 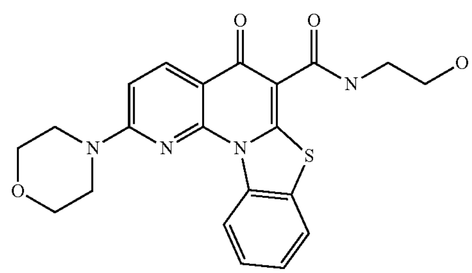 [SMILES: O=C(NCCO)c1c(=O)c2ccc(N3CCOCC3)nc2n2c1sc1ccccc12] | 424.47 | 425 |
| 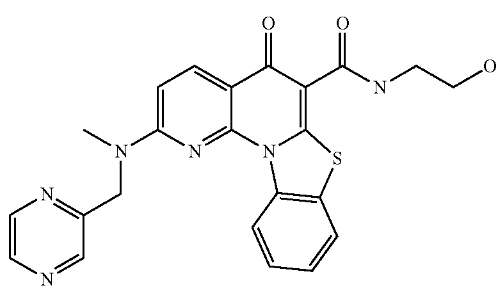 [SMILES: CN(Cc1cnccn1)c1ccc2c(=O)c(C(=O)NCCO)c3sc4ccccc4n3c2n1] | 460.51 | 461 |
| 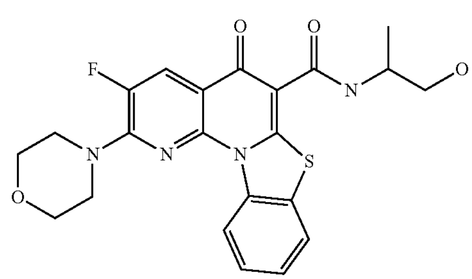 [SMILES: CC(CO)NC(=O)c1c(=O)c2cc(F)c(N3CCOCC3)nc2n2c1sc1ccccc12] | 456.49 | 457 |

TABLE 2-continued

| Structure | MW | LCMS (ES) m/z [M + 1]+ |
|---|---|---|
| 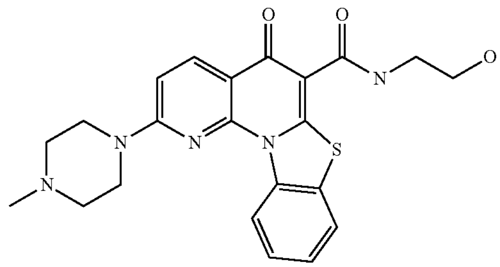 [SMILES: CN1CCN(c2ccc3c(=O)c(C(=O)NCCO)c4sc5ccccc5n4c3n2)CC1] | 437.51 | 438 |
| 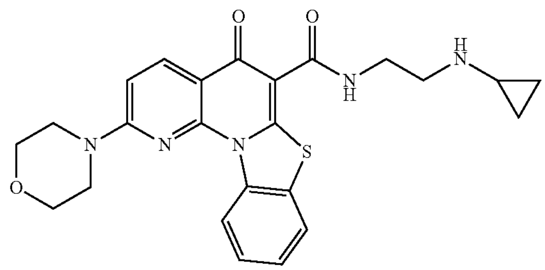 [SMILES: O=C(NCCNC1CC1)c1c(=O)c2ccc(N3CCOCC3)nc2n2c1sc1ccccc12] | 463.58 | 464 |

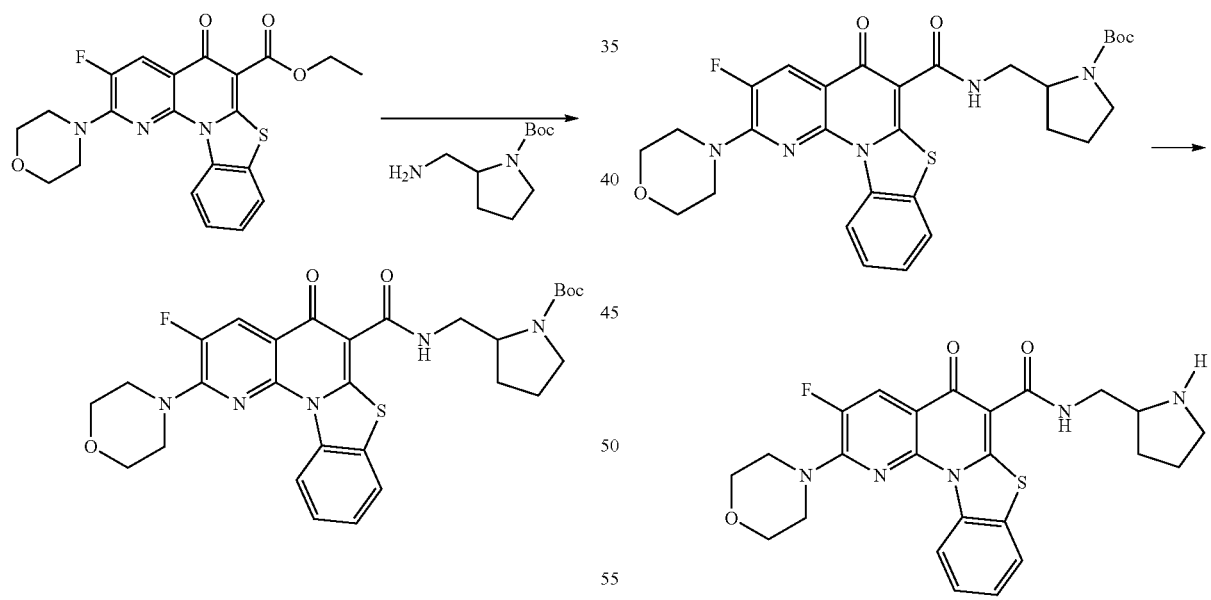

Example 32

Example 33

To a solution of ester (1.00 g, 2.34 mmol), (1-methylpyrrolidin-2-yl)methanamine (1.20 g, 5.99 mmol) and DBU (1.80 mL, 12.06 mmol) in DCM (40 mL) was added AlCl₃ (650 mg, 4.87 mmol). The reaction mixture was stirred at rt over night. The reaction was diluted with DCM (150 mL) and 1N NaOH (50 mL) and stirred for 15 min. The layers were separated and the organic layer was washed with H₂O (2×100 mL), brine (100 mL), and dried over Na₂SO₄. The solvent was removed under reduced pressure and the resulting solid was triturated in ACN to give the desired product as a white solid. LCMS (ES): m/z 582 [M+1]⁺.

To a solution of Boc-amine (321 mg, 0.55 mmol) in DCM (3.0 mL) was added HCl (3.0 mL, 4 M in dioxane) and stirred at rt for 1 h. The reaction was diluted with DCM (150 mL) and 6N NaOH (50 mL) and stirred for 10 min. The layers were separated and the organic layer was washed with brine (50 mL), and dried over Na₂SO₄. The solvent was removed under reduced pressure to yield the desired product as a white solid (250 mg, 94%). ¹H NMR (CDCl₃) δ: 10.63 (t, 1H), 9.44 (d, 1H), 8.33 (d, 1H), 7.77 (dd, 1H), 7.53 (m, 1H), 7.44 (m, 1H), 3.91 (t, 4H), 3.86 (t, 4H), 3.61 (m, 1H), 3.43 (m, 2H), 3.03 (m, 1H), 2.94 (m, 1H), 1.97 (m, 1H), 1.85 (m, 1H), 1.75 (m, 1H), 1.52 (m, 1H). LCMS (ES): m/z 482 [M+1]$^+$.

Example 34

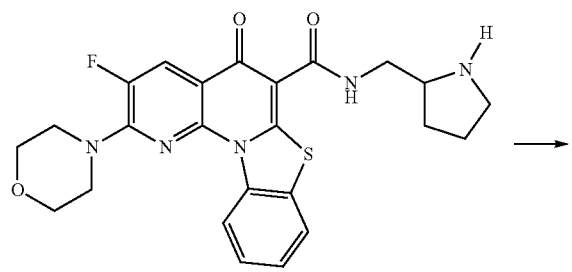

To a solution of amine (40 mg, 0.08 mmol) in DCM (5.0 mL) and TEA (0.05 mL) was added iodomethane (0.05 mL) and stirred at rt for 10 min. The solvent was removed under reduced pressure and the resulting solid was triturated in ACN. The reaction crude was purified on silica gel TLC (10% MeOH/DCM) to yield the desired product as a white solid. LCMS (ES): m/z 496 [M+1]$^+$.

The following analogues in Table 3 were prepared by the same method, using the appropriate aminoquinolones and alkyl halide, acyl halide or anhydride.

TABLE 3

| Structure | MW | LCMS (ES) m/z [M + 1]$^+$ |
|---|---|---|
| 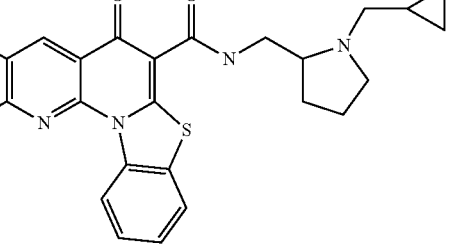 | 535.63 | 536 |
| 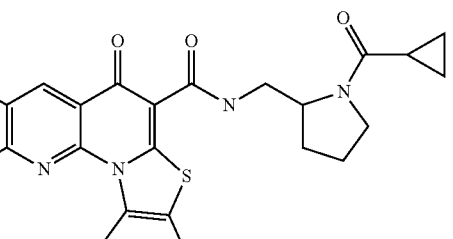 | 549.62 | 550 |
| 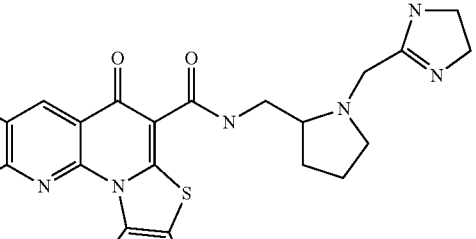 | 563.65 | 564 |

TABLE 3-continued

| Structure | MW | LCMS (ES) m/z [M + 1]+ |
|---|---|---|
| 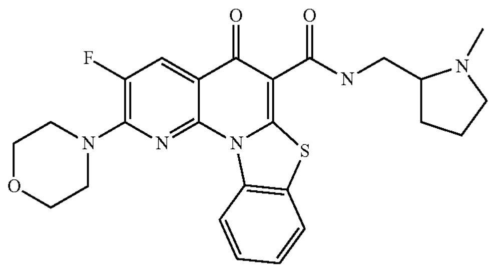 [SMILES: CN1CCCC1CNC(=O)c1c(=O)c2cc(F)c(N3CCOCC3)nc2n2c1sc1ccccc12] | 495.57 | 496 |
| 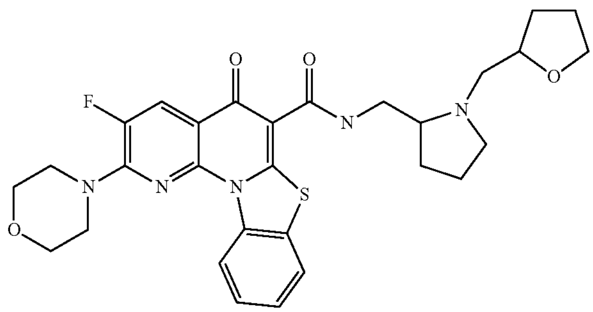 [SMILES: O=C(NCC1CCCN1CC1CCCO1)c1c(=O)c2cc(F)c(N3CCOCC3)nc2n2c1sc1ccccc12] | 565.66 | 566 |
| 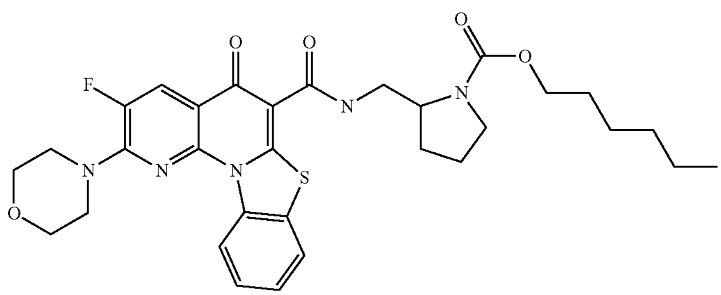 [SMILES: CCCCCCOC(=O)N1CCCC1CNC(=O)c1c(=O)c2cc(F)c(N3CCOCC3)nc2n2c1sc1ccccc12] | 609.71 | 610 |
| 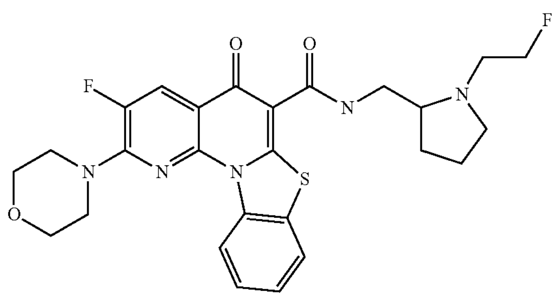 [SMILES: O=C(NCC1CCCN1CCF)c1c(=O)c2cc(F)c(N3CCOCC3)nc2n2c1sc1ccccc12] | 527.59 | 528 |
| 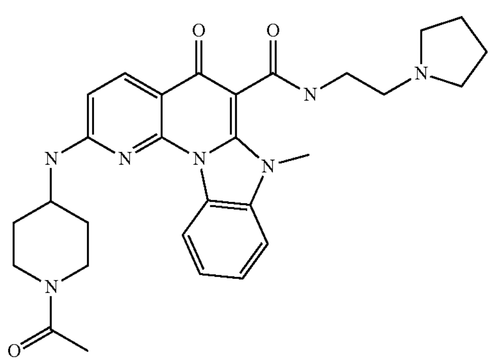 [SMILES: CC(=O)N1CCC(Nc2ccc3c(=O)c(C(=O)NCCN4CCCC4)c4n(C)c5ccccc5n4c3n2)CC1] | 529.63 | 530 |

TABLE 3-continued

| Structure | MW | LCMS (ES) m/z [M + 1]+ |
|---|---|---|
| 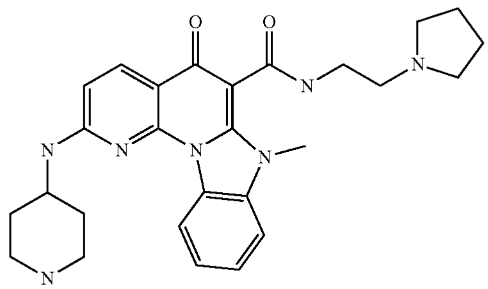 [SMILES: Cn1c2ccccc2n2c3nc(NC4CCNCC4)ccc3c(=O)c(C(=O)NCCN3CCCC3)c12] | 487.60 | 488 |
| 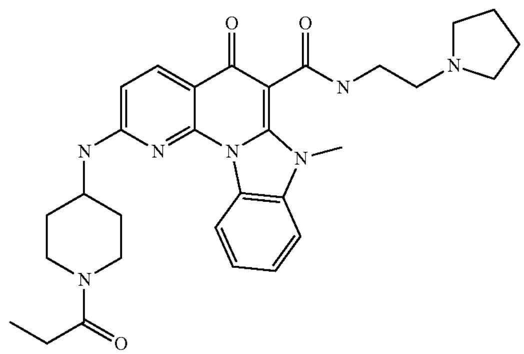 [SMILES: CCC(=O)N1CCC(Nc2ccc3c(=O)c(C(=O)NCCN4CCCC4)c4n(C)c5ccccc5n4c3n2)CC1] | 543.66 | 544 |
| 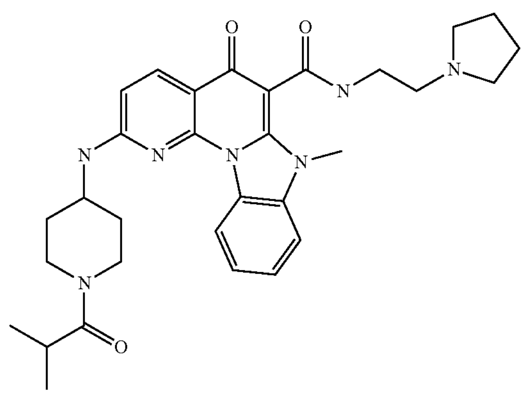 [SMILES: CC(C)C(=O)N1CCC(Nc2ccc3c(=O)c(C(=O)NCCN4CCCC4)c4n(C)c5ccccc5n4c3n2)CC1] | 557.69 | 558 |
| 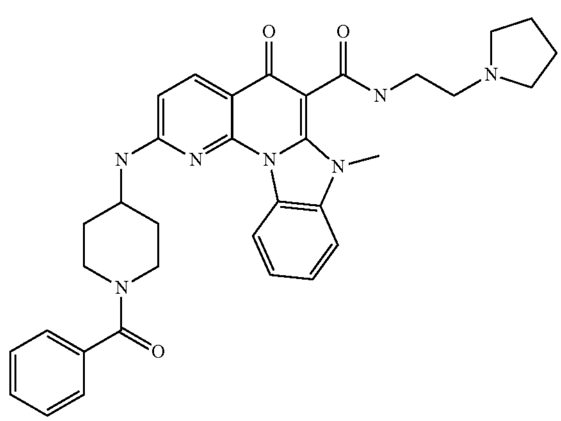 [SMILES: Cn1c2ccccc2n2c3nc(NC4CCN(C(=O)c5ccccc5)CC4)ccc3c(=O)c(C(=O)NCCN3CCCC3)c12] | 591.70 | 592 |

TABLE 3-continued

| Structure | MW | LCMS (ES) m/z [M + 1]+ |
|---|---|---|
| 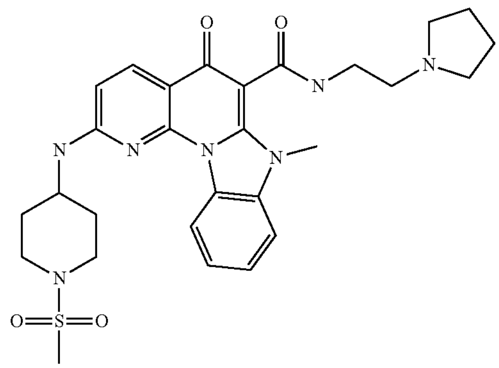 [SMILES: Cn1c2ccccc2n2c3nc(NC4CCN(S(C)(=O)=O)CC4)ccc3c(=O)c(C(=O)NCCN3CCCC3)c12] | 565.69 | 566 |
| | 641.78 | 642 |
| | 641.78 | 642 |
| 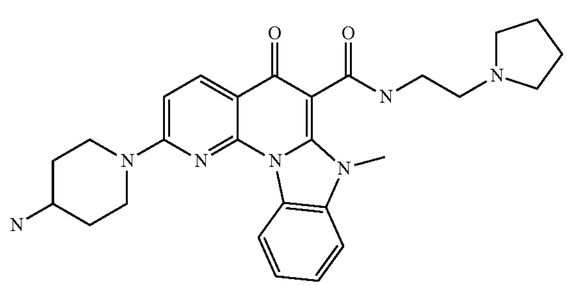 [SMILES: Cn1c2ccccc2n2c3nc(N4CCC(N)CC4)ccc3c(=O)c(C(=O)NCCN3CCCC3)c12] | 487.60 | 488 |

TABLE 3-continued

| Structure | MW | LCMS (ES) m/z [M + 1]+ |
|---|---|---|
| 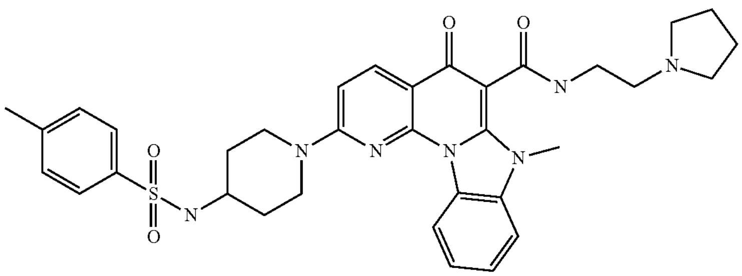 [SMILES: Cc1ccc(S(=O)(=O)NC2CCN(c3ccc4c(=O)c(C(=O)NCCN5CCCC5)c5n(C)c6ccccc6n5c4n3)CC2)cc1] | 641.78 | 642 |
| 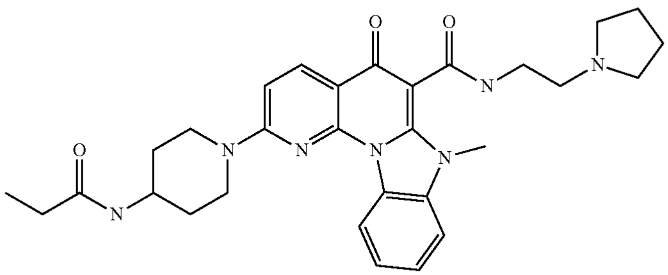 [SMILES: CCC(=O)NC1CCN(c2ccc3c(=O)c(C(=O)NCCN4CCCC4)c4n(C)c5ccccc5n4c3n2)CC1] | 543.66 | 544 |
| 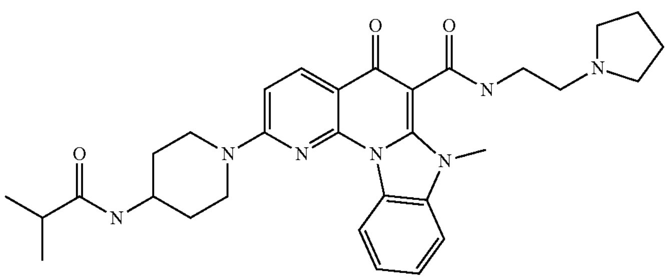 [SMILES: CC(C)C(=O)NC1CCN(c2ccc3c(=O)c(C(=O)NCCN4CCCC4)c4n(C)c5ccccc5n4c3n2)CC1] | 557.69 | 558 |
| 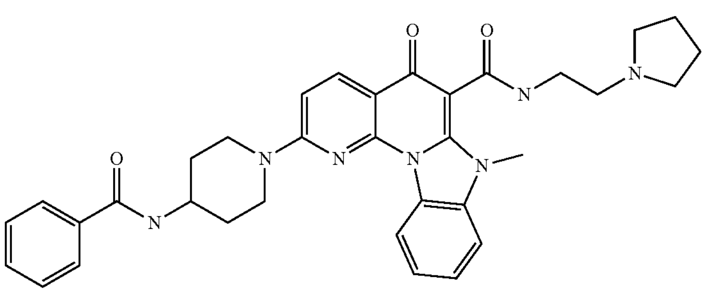 [SMILES: Cn1c2ccccc2n2c3nc(N4CCC(NC(=O)c5ccccc5)CC4)ccc3c(=O)c(C(=O)NCCN3CCCC3)c12] | 591.70 | 592 |
| 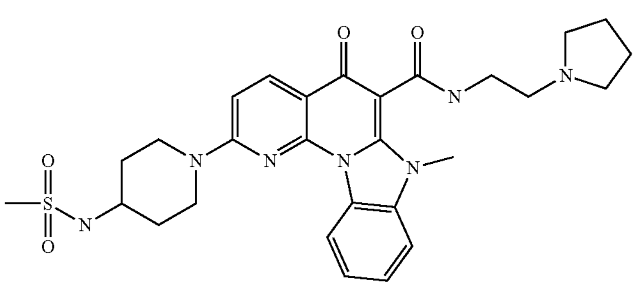 [SMILES: Cn1c2ccccc2n2c3nc(N4CCC(NS(C)(=O)=O)CC4)ccc3c(=O)c(C(=O)NCCN3CCCC3)c12] | 565.69 | 566 |

TABLE 3-continued

| Structure | MW | LCMS (ES) m/z [M + 1]+ |
|---|---|---|
| 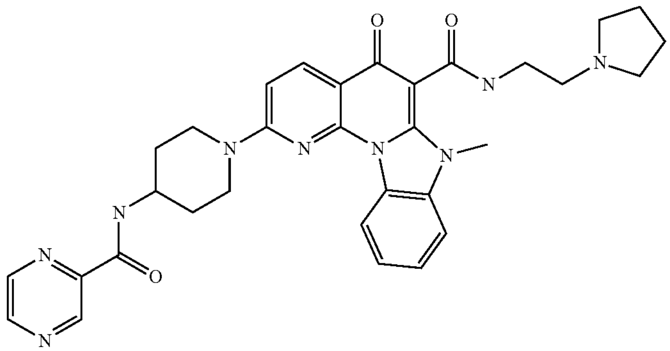 [SMILES: Cn1c2ccccc2n2c3nc(N4CCC(NC(=O)c5cnccn5)CC4)ccc3c(=O)c(C(=O)NCCN3CCCC3)c12] | 593.68 | 594 |
| 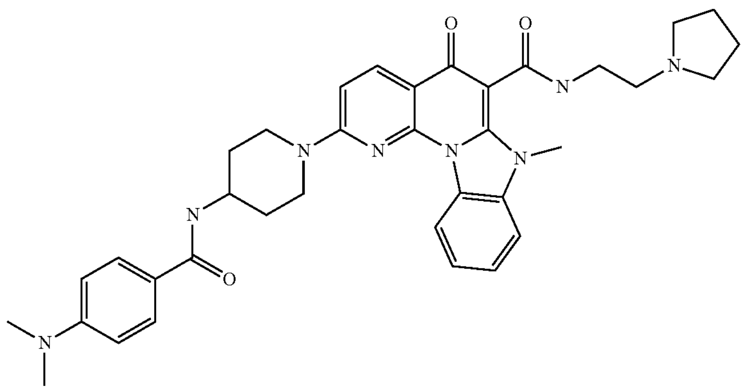 [SMILES: CN(C)c1ccc(C(=O)NC2CCN(c3ccc4c(=O)c(C(=O)NCCN5CCCC5)c5n(C)c6ccccc6n5c4n3)CC2)cc1] | 634.77 | 635 |
| 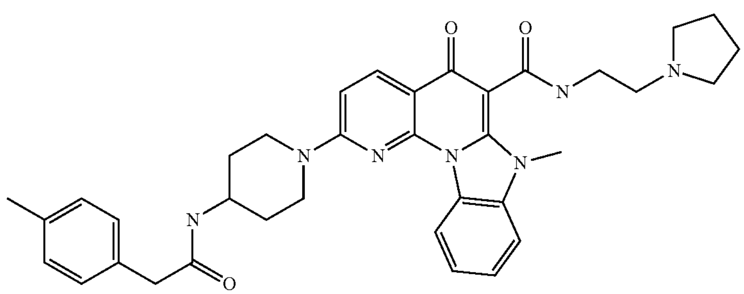 [SMILES: Cc1ccc(CC(=O)NC2CCN(c3ccc4c(=O)c(C(=O)NCCN5CCCC5)c5n(C)c6ccccc6n5c4n3)CC2)cc1] | 619.76 | 620 |
| 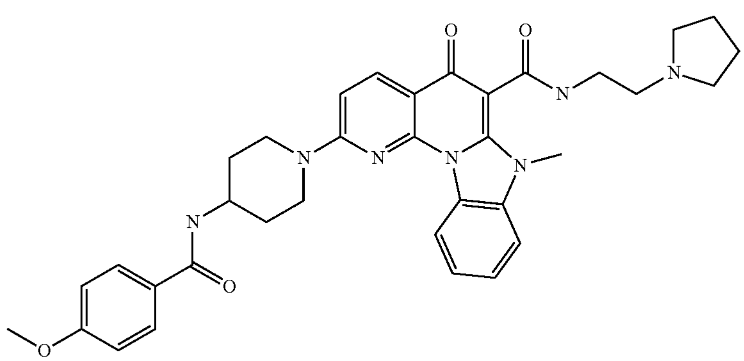 [SMILES: COc1ccc(C(=O)NC2CCN(c3ccc4c(=O)c(C(=O)NCCN5CCCC5)c5n(C)c6ccccc6n5c4n3)CC2)cc1] | 621.73 | 622 |

TABLE 3-continued
| Structure | MW | LCMS (ES) m/z [M + 1]+ |
|---|---|---|
| 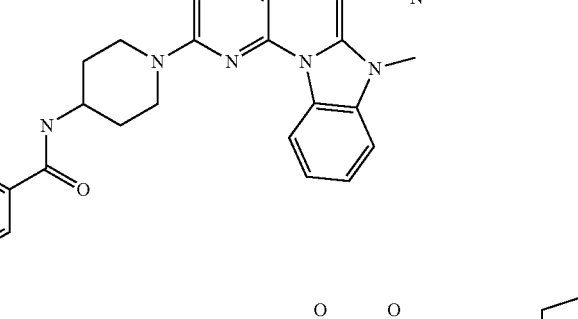 | 608.69 | 609 |
| 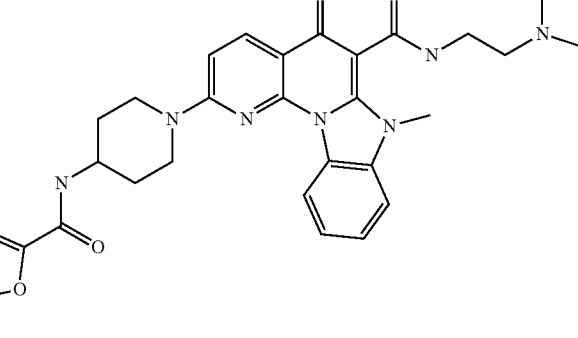 | 631.72 | 632 |
| 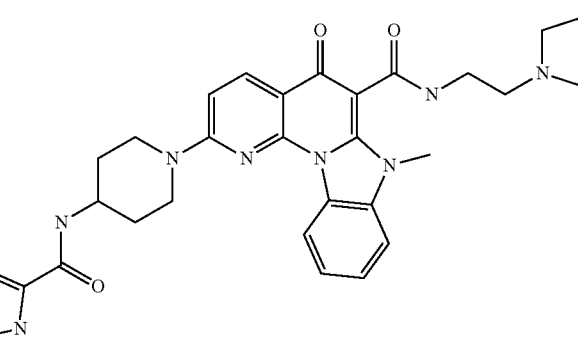 | 630.74 | 631 |
| 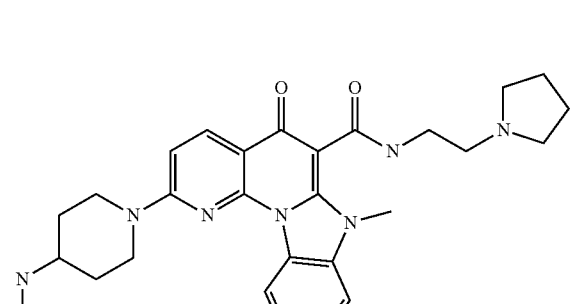 | 644.77 | 645 |

TABLE 3-continued

| Structure | MW | LCMS (ES) m/z [M + 1]+ |
|---|---|---|
| 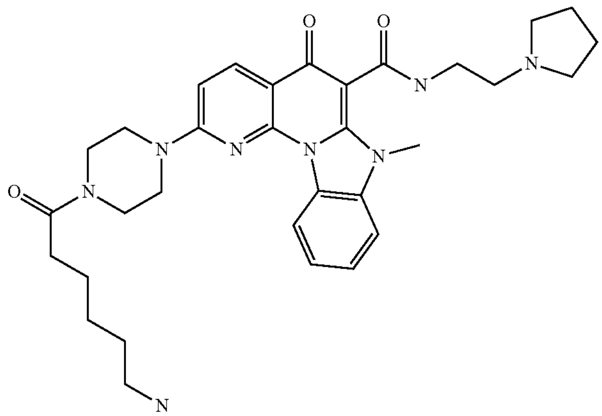 [SMILES: Cn1c2ccccc2n2c3nc(N4CCN(C(=O)CCCCCN)CC4)ccc3c(=O)c(C(=O)NCCN3CCCC3)c12] | 586.73 | 587 |
| 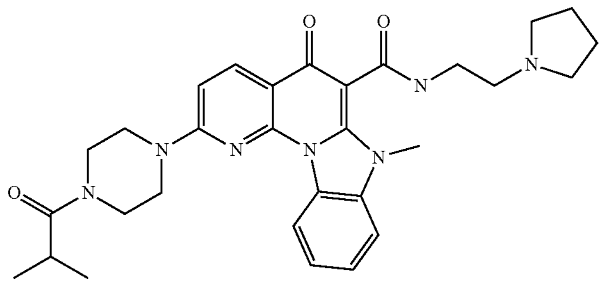 [SMILES: CC(C)C(=O)N1CCN(c2ccc3c(=O)c(C(=O)NCCN4CCCC4)c4n(C)c5ccccc5n4c3n2)CC1] | 543.66 | 544 |
| 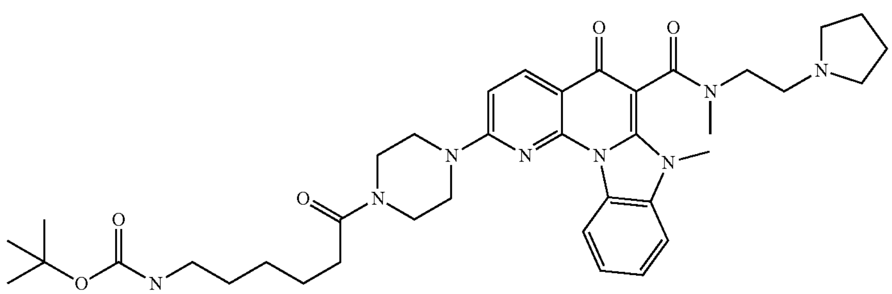 [SMILES: CN(CCN1CCCC1)C(=O)c1c(=O)c2ccc(N3CCN(C(=O)CCCCCNC(=O)OC(C)(C)C)CC3)nc2n2c3ccccc3n(C)c12] | 700.87 | 701 |
| 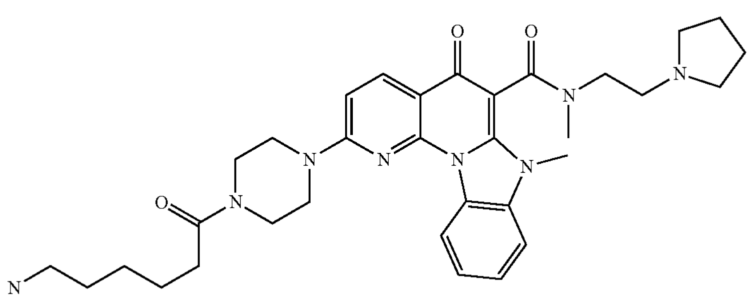 [SMILES: CN(CCN1CCCC1)C(=O)c1c(=O)c2ccc(N3CCN(C(=O)CCCCCN)CC3)nc2n2c3ccccc3n(C)c12] | 600.75 | 601 |

TABLE 3-continued

| Structure | MW | LCMS (ES) m/z [M + 1]+ |
|---|---|---|
| 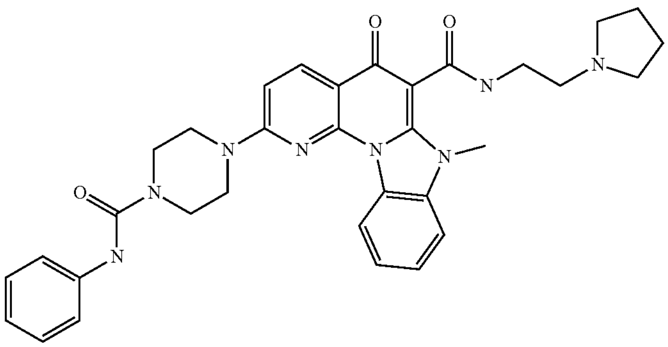 [SMILES: Cn1c2ccccc2n2c3nc(N4CCN(C(=O)Nc5ccccc5)CC4)ccc3c(=O)c(C(=O)NCCN3CCCC3)c12] | 592.69 | 593 |
| 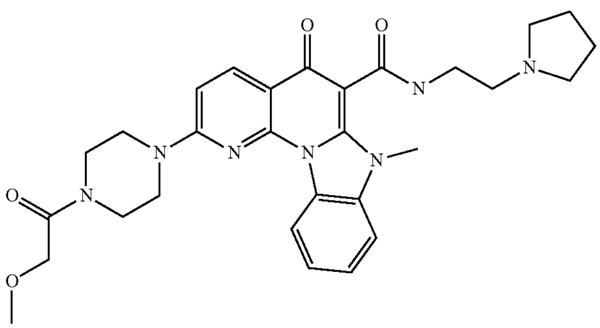 [SMILES: COCC(=O)N1CCN(c2ccc3c(=O)c(C(=O)NCCN4CCCC4)c4n(C)c5ccccc5n4c3n2)CC1] | 545.63 | 546 |
| 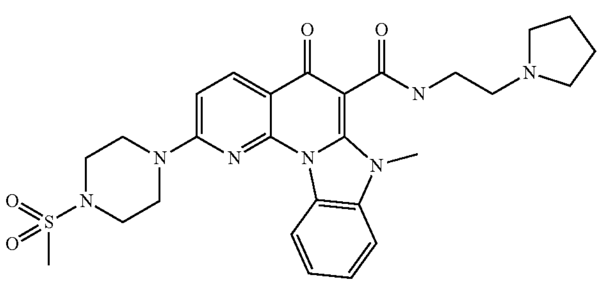 [SMILES: Cn1c2ccccc2n2c3nc(N4CCN(S(C)(=O)=O)CC4)ccc3c(=O)c(C(=O)NCCN3CCCC3)c12] | 551.66 | 552 |
| 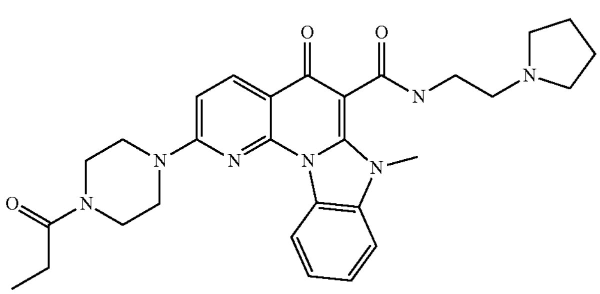 [SMILES: CCC(=O)N1CCN(c2ccc3c(=O)c(C(=O)NCCN4CCCC4)c4n(C)c5ccccc5n4c3n2)CC1] | 529.63 | 530 |

TABLE 3-continued

| Structure | MW | LCMS (ES) m/z [M + 1]+ |
|---|---|---|
| 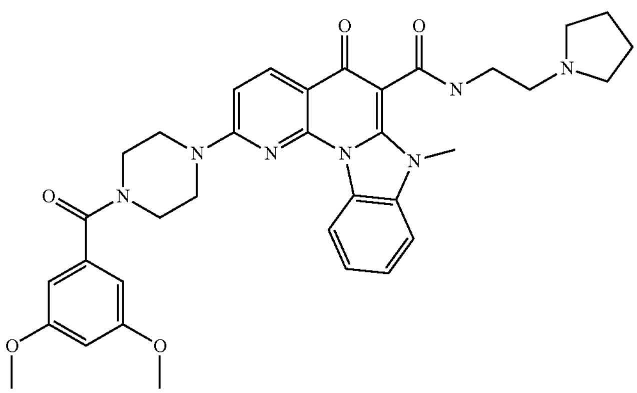 [SMILES: COc1cc(OC)cc(C(=O)N2CCN(c3ccc4c(=O)c(C(=O)NCCN5CCCC5)c5n(C)c6ccccc6n5c4n3)CC2)c1] | 637.73 | 638 |
| 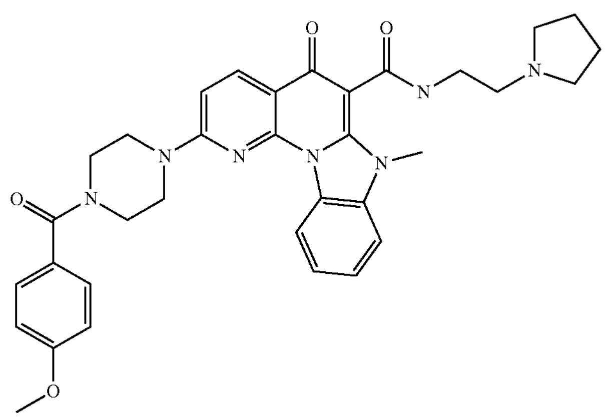 [SMILES: COc1ccc(C(=O)N2CCN(c3ccc4c(=O)c(C(=O)NCCN5CCCC5)c5n(C)c6ccccc6n5c4n3)CC2)cc1] | 607.70 | 608 |
| 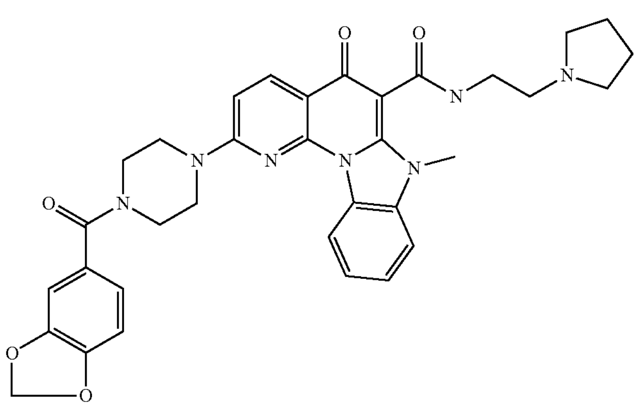 [SMILES: Cn1c2ccccc2n2c3nc(N4CCN(C(=O)c5ccc6c(c5)OCO6)CC4)ccc3c(=O)c(C(=O)NCCN3CCCC3)c12] | 621.69 | 622 |

TABLE 3-continued

| Structure | MW | LCMS (ES) m/z [M + 1]+ |
|---|---|---|
| 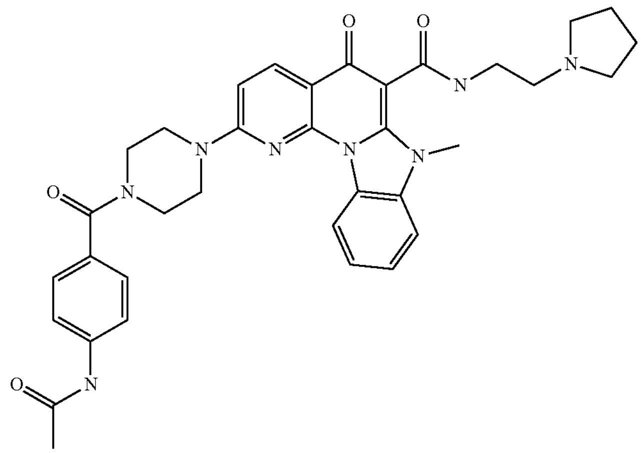 [SMILES: CC(=O)Nc1ccc(C(=O)N2CCN(c3ccc4c(=O)c(C(=O)NCCN5CCCC5)c5n(C)c6ccccc6n5c4n3)CC2)cc1] | 634.73 | 635 |
| 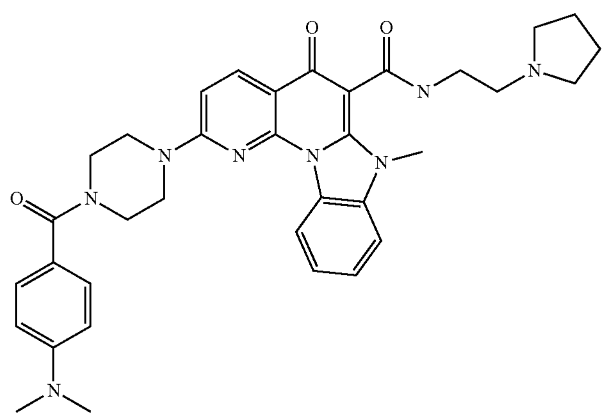 [SMILES: CN(C)c1ccc(C(=O)N2CCN(c3ccc4c(=O)c(C(=O)NCCN5CCCC5)c5n(C)c6ccccc6n5c4n3)CC2)cc1] | 620.74 | 621 |
| 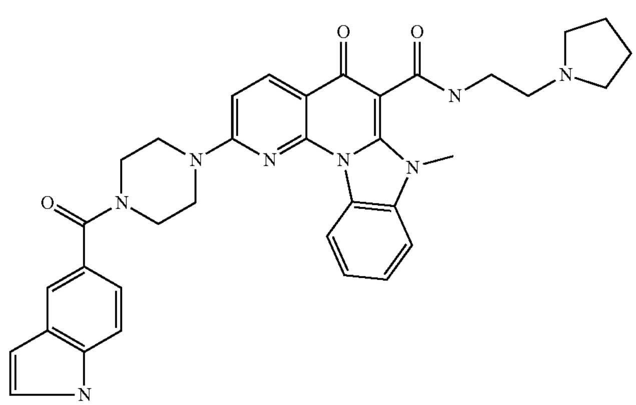 [SMILES: Cn1c2ccccc2n2c3nc(N4CCN(C(=O)c5ccc6[nH]ccc6c5)CC4)ccc3c(=O)c(C(=O)NCCN3CCCC3)c12] | 616.71 | 617 |

TABLE 3-continued

| Structure | MW | LCMS (ES) m/z [M + 1]+ |
|---|---|---|
| 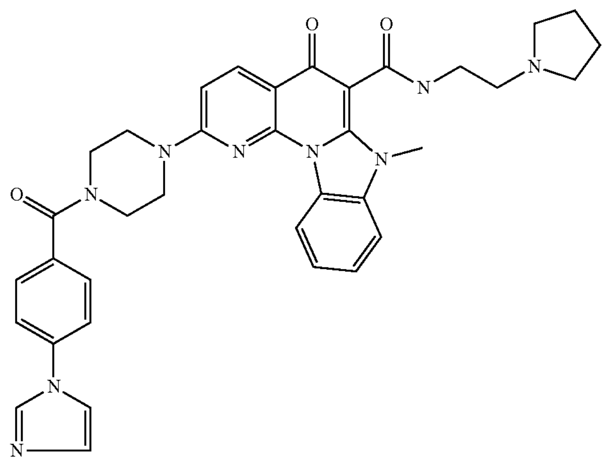 [SMILES: Cn1c2ccccc2n2c3nc(N4CCN(C(=O)c5ccc(-n6ccnc6)cc5)CC4)ccc3c(=O)c(C(=O)NCCN3CCCC3)c12] | 643.74 | 644 |
| 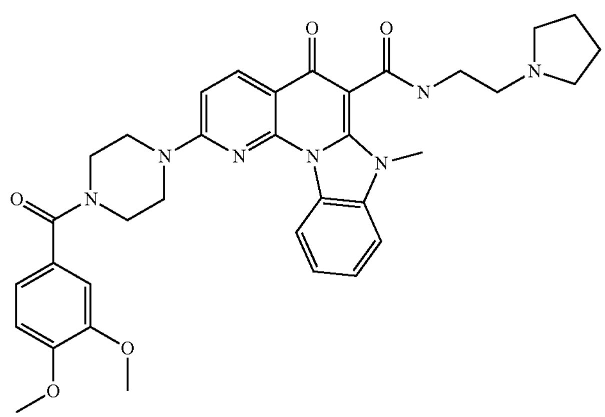 [SMILES: COc1ccc(C(=O)N2CCN(c3ccc4c(=O)c(C(=O)NCCN5CCCC5)c5n(C)c6ccccc6n5c4n3)CC2)cc1OC] | 637.73 | 638 |
| 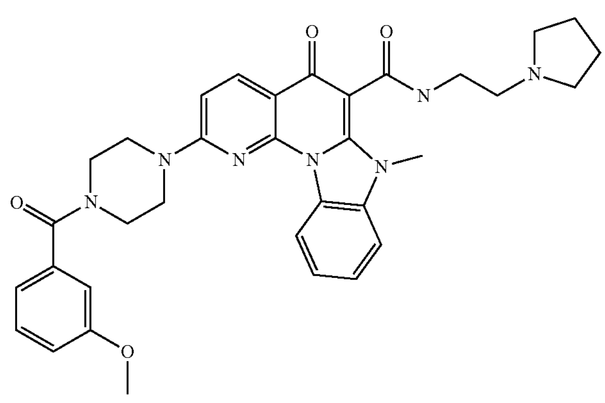 [SMILES: COc1cccc(C(=O)N2CCN(c3ccc4c(=O)c(C(=O)NCCN5CCCC5)c5n(C)c6ccccc6n5c4n3)CC2)c1] | 607.70 | 608 |

TABLE 3-continued

| Structure | MW | LCMS (ES) m/z [M + 1]+ |
|---|---|---|
| 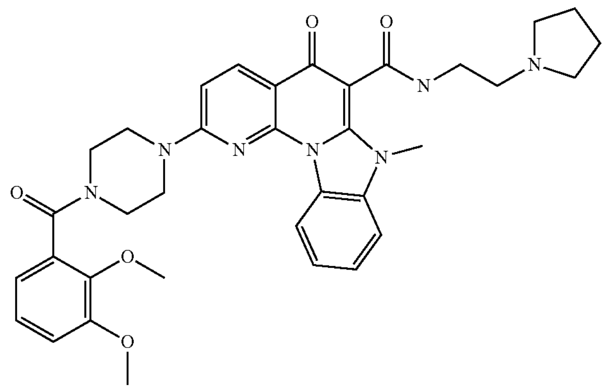 [SMILES: COc1cccc(C(=O)N2CCN(c3ccc4c(=O)c(C(=O)NCCN5CCCC5)c5n(C)c6ccccc6n5c4n3)CC2)c1OC] | 637.73 | 638 |
| 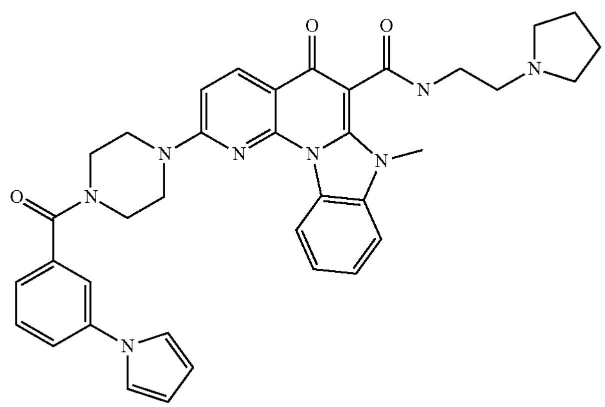 [SMILES: Cn1c2ccccc2n2c3nc(N4CCN(C(=O)c5cccc(-n6cccc6)c5)CC4)ccc3c(=O)c(C(=O)NCCN3CCCC3)c12] | 642.75 | 643 |
| 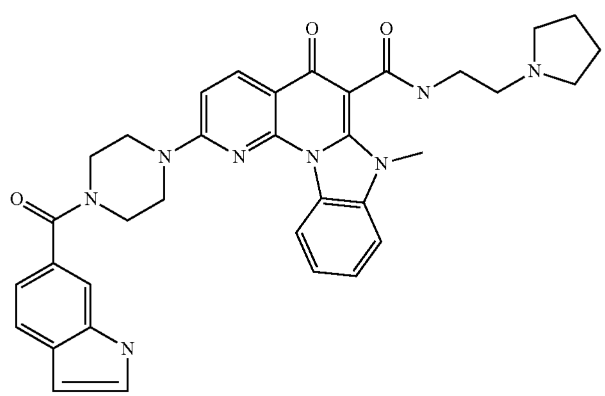 [SMILES: Cn1c2ccccc2n2c3nc(N4CCN(C(=O)c5ccc6cc[nH]c6c5)CC4)ccc3c(=O)c(C(=O)NCCN3CCCC3)c12] | 616.71 | 617 |
| 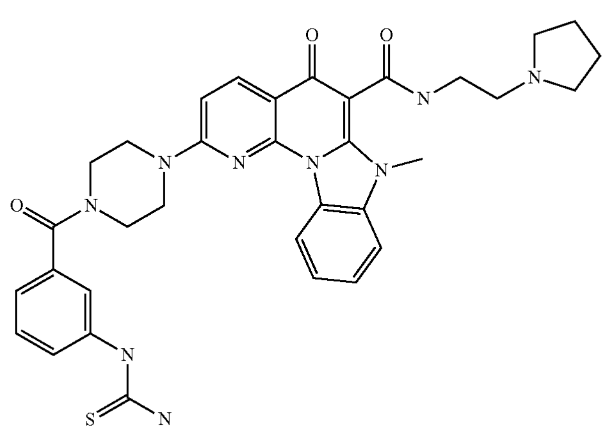 [SMILES: Cn1c2ccccc2n2c3nc(N4CCN(C(=O)c5cccc(NC(N)=S)c5)CC4)ccc3c(=O)c(C(=O)NCCN3CCCC3)c12] | 651.78 | 652 |

TABLE 3-continued
| Structure | MW | LCMS (ES) m/z [M + 1]+ |
|---|---|---|
| 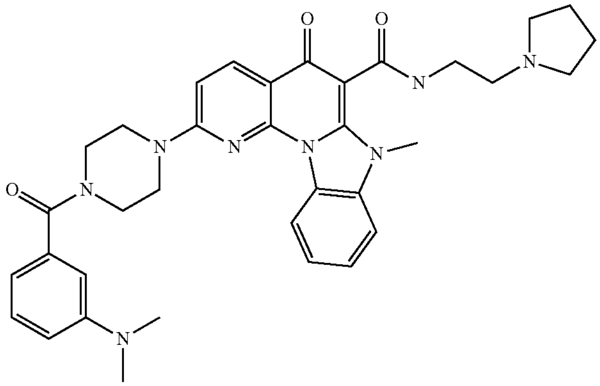 [SMILES: CN(C)c1cccc(C(=O)N2CCN(c3ccc4c(=O)c(C(=O)NCCN5CCCC5)c5n(C)c6ccccc6n5c4n3)CC2)c1] | 620.74 | 621 |
| 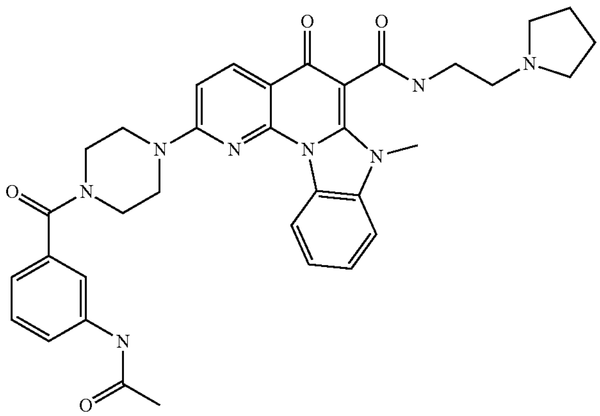 [SMILES: CC(=O)Nc1cccc(C(=O)N2CCN(c3ccc4c(=O)c(C(=O)NCCN5CCCC5)c5n(C)c6ccccc6n5c4n3)CC2)c1] | 634.73 | 635 |
Example 35
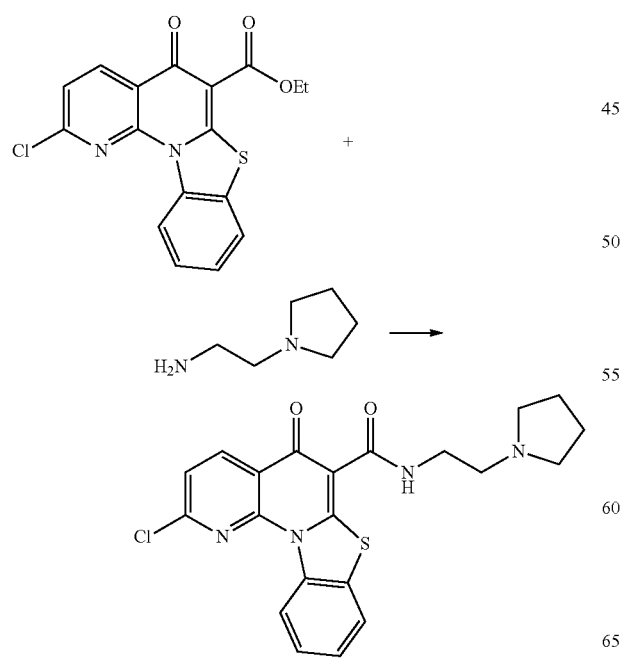
The desired chloroamide was synthesized in 72% yield using the procedure using aluminum chloride condition using chloroester and amine. LCMS (ES): 95% pure, m/z 427 [M+1]+.
Example 36
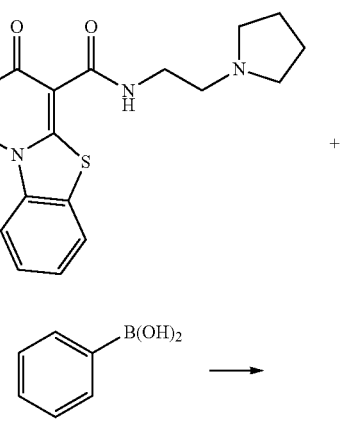

-continued

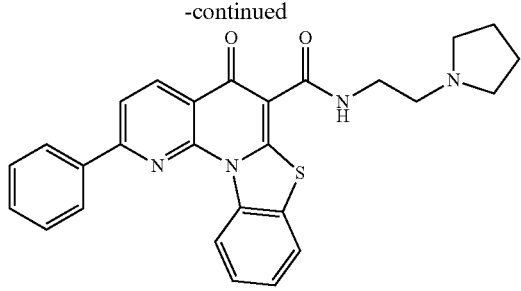

The chloroamide (1.0 eq, 100 mg, 0.23 mmol) and benzeneboronic acid (2.0 eq, 57 mg, 0.47 mmol) were mixed with sodium acetate (3.0 eq, 58 mg, 0.70 mmol) in DMF (1 ml). After adding $PdCl_2(dppf)$ (0.1 eq, 19 mg, 0.02 mmol), the mixture was heated under microwave at 100° C. for 5 min. The solution was filtered through CELITE™ and the material was precipitated by adding ethyl acetate and hexanes. After purification by preparative HPLC, the desired product was isolated as a brown solid (51 mg, 47% yield). LCMS (ES): 95% pure, m/z 469 $[M+1]^+$.

The following analogues in Table 4 were prepared by the same method, using the appropriate chloroamide and boronic acid.

TABLE 4

| Structure | MW | LCMS (ES) m/z $[M + 1]^+$ |
|---|---|---|
| 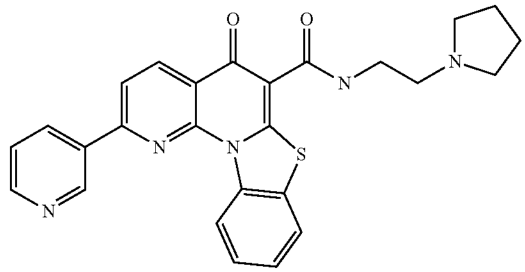 [SMILES: O=C(NCCN1CCCC1)c1c(=O)c2ccc(-c3cccnc3)nc2n2c1sc1ccccc12] | 469.56 | 470 |
| 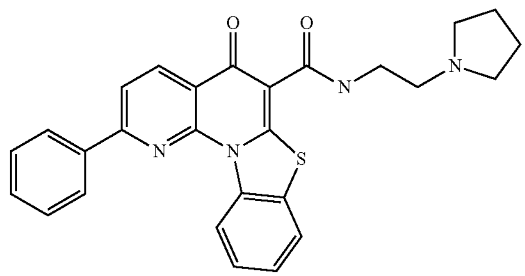 [SMILES: O=C(NCCN1CCCC1)c1c(=O)c2ccc(-c3ccccc3)nc2n2c1sc1ccccc12] | 468.57 | 469 |
| 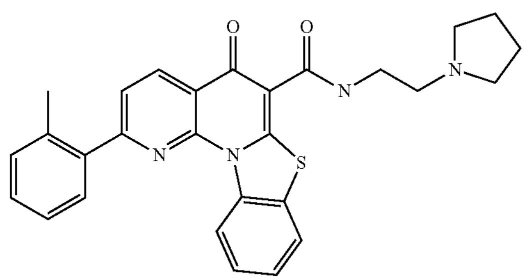 [SMILES: Cc1ccccc1-c1ccc2c(=O)c(C(=O)NCCN3CCCC3)c3sc4ccccc4n3c2n1] | 482.60 | 483 |
| 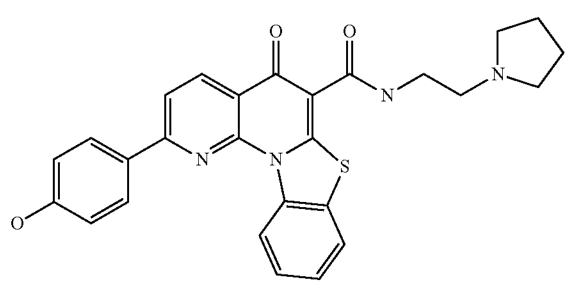 [SMILES: O=C(NCCN1CCCC1)c1c(=O)c2ccc(-c3ccc(O)cc3)nc2n2c1sc1ccccc12] | 484.57 | 485 |

TABLE 4-continued

| Structure | MW | LCMS (ES) m/z [M + 1]+ |
|---|---|---|
| 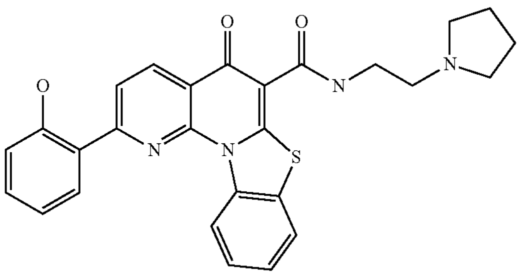 [SMILES: O=C(NCCN1CCCC1)c1c(=O)c2ccc(-c3ccccc3O)nc2n2c1sc1ccccc12] | 484.57 | 485 |
| 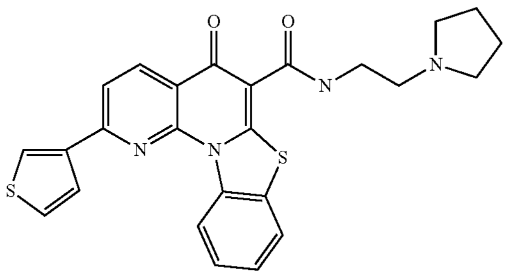 [SMILES: O=C(NCCN1CCCC1)c1c(=O)c2ccc(-c3ccsc3)nc2n2c1sc1ccccc12] | 474.60 | 475 |
| 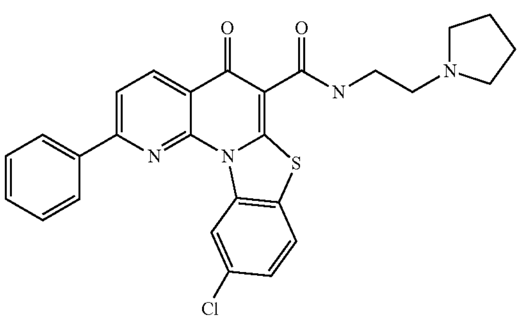 [SMILES: O=C(NCCN1CCCC1)c1c(=O)c2ccc(-c3ccccc3)nc2n2c1sc1ccc(Cl)cc12] | 503.02 | 503 |
| 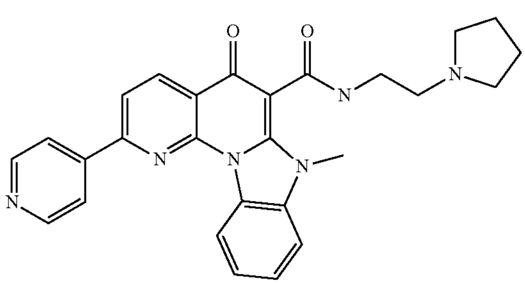 [SMILES: Cn1c2ccccc2n2c3nc(-c4ccncc4)ccc3c(=O)c(C(=O)NCCN3CCCC3)c12] | 466.53 | 467 |
| 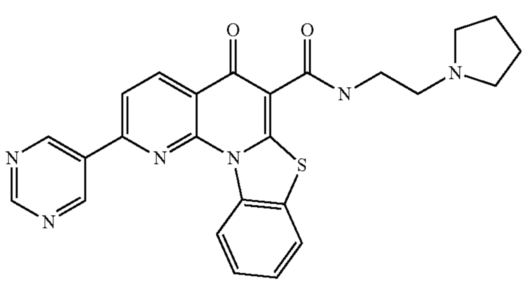 [SMILES: O=C(NCCN1CCCC1)c1c(=O)c2ccc(-c3cncnc3)nc2n2c1sc1ccccc12] | 470.55 | 471 |

TABLE 4-continued

| Structure | MW | LCMS (ES) m/z [M + 1]+ |
|---|---|---|
| 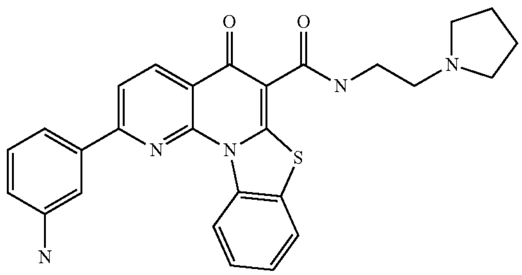 [SMILES: Nc1cccc(-c2ccc3c(=O)c(C(=O)NCCN4CCCC4)c4sc5ccccc5n4c3n2)c1] | 483.58 | 484 |
| 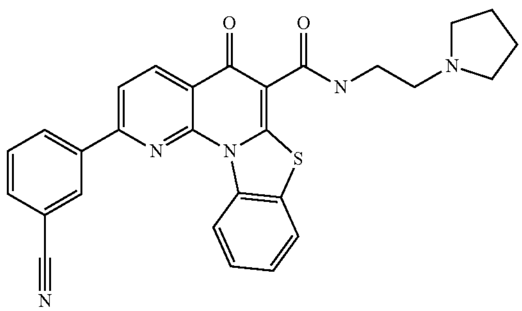 [SMILES: N#Cc1cccc(-c2ccc3c(=O)c(C(=O)NCCN4CCCC4)c4sc5ccccc5n4c3n2)c1] | 493.58 | 494 |
| | 498.60 | 499 |
| | 498.60 | 499 |
| 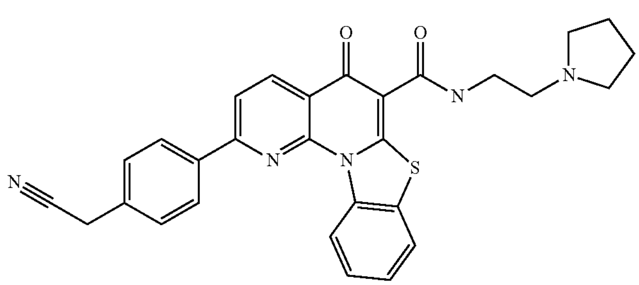 [SMILES: N#CCc1ccc(-c2ccc3c(=O)c(C(=O)NCCN4CCCC4)c4sc5ccccc5n4c3n2)cc1] | 507.61 | 508 |

TABLE 4-continued
| Structure | MW | LCMS (ES) m/z [M + 1]+ |
|---|---|---|
| 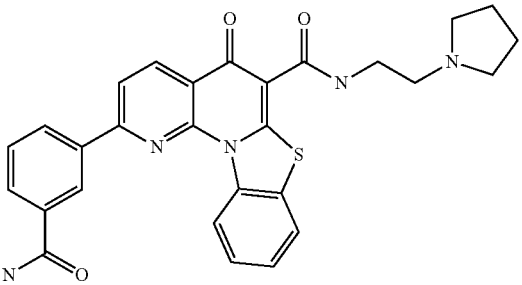 [SMILES: NC(=O)c1cccc(-c2ccc3c(=O)c(C(=O)NCCN4CCCC4)c4sc5ccccc5n4c3n2)c1] | 511.59 | 512 |
| 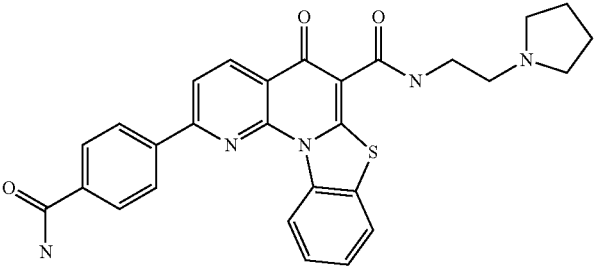 [SMILES: NC(=O)c1ccc(-c2ccc3c(=O)c(C(=O)NCCN4CCCC4)c4sc5ccccc5n4c3n2)cc1] | 511.59 | 512 |
| 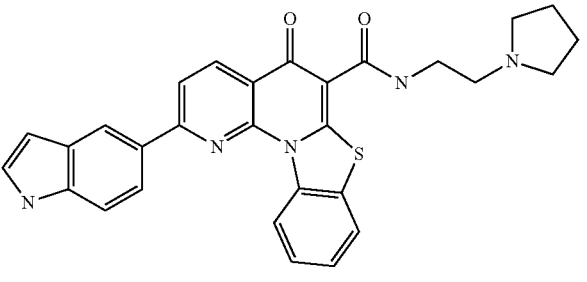 [SMILES: O=C(NCCN1CCCC1)c1c(=O)c2ccc(-c3ccc4[nH]ccc4c3)nc2n2c1sc1ccccc12] | 507.61 | 508 |
| 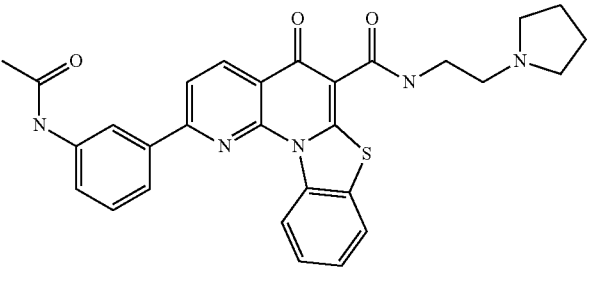 [SMILES: CC(=O)Nc1cccc(-c2ccc3c(=O)c(C(=O)NCCN4CCCC4)c4sc5ccccc5n4c3n2)c1] | 525.62 | 526 |
| 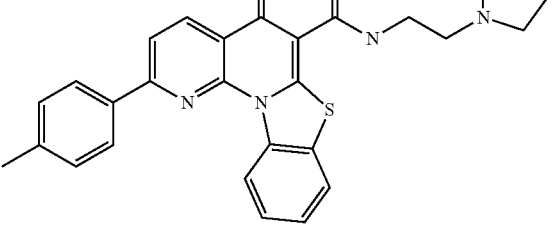 | 482.60 | 483 |

TABLE 4-continued
| Structure | MW | LCMS (ES) m/z [M + 1]+ |
|---|---|---|
| 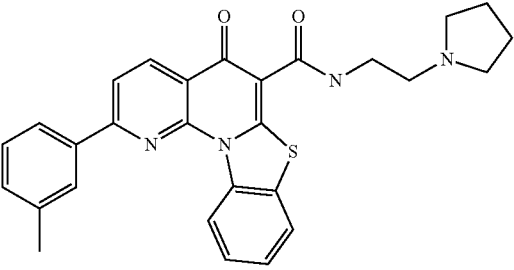 [SMILES: Cc1cccc(-c2ccc3c(=O)c(C(=O)NCCN4CCCC4)c4sc5ccccc5n4c3n2)c1] | 482.60 | 483 |
| 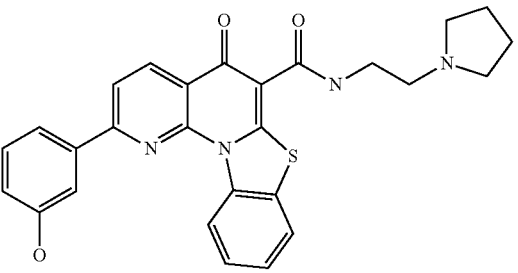 | 484.57 | 485 |
| 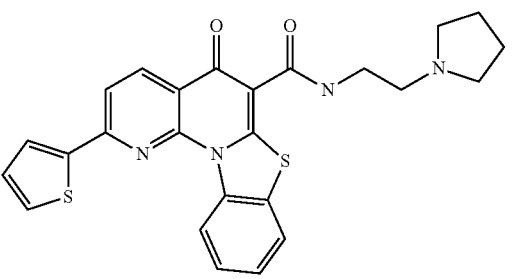 [SMILES: O=C(NCCN1CCCC1)c1c(=O)c2ccc(-c3cccs3)nc2n2c1sc1ccccc12] | 474.60 | 475 |
| 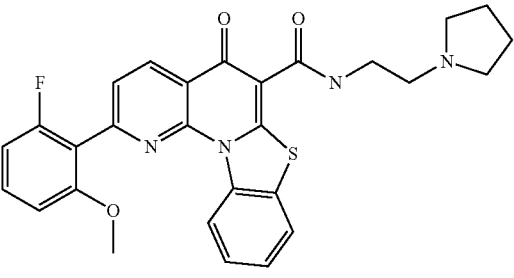 [SMILES: COc1cccc(F)c1-c1ccc2c(=O)c(C(=O)NCCN3CCCC3)c3sc4ccccc4n3c2n1] | 516.59 | 517 |
| 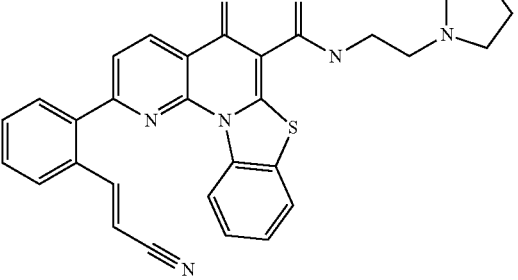 | 519.62 | 520 |

TABLE 4-continued

| Structure | MW | LCMS (ES) m/z [M + 1]+ |
|---|---|---|
| 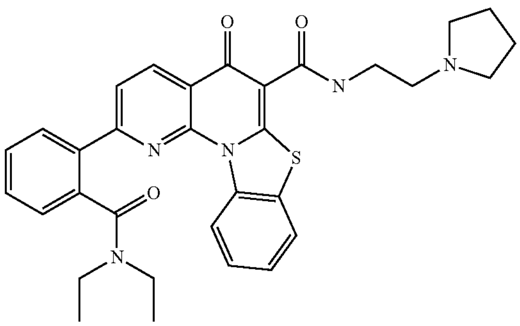 [SMILES: CCN(CC)C(=O)c1ccccc1-c1ccc2c(=O)c(C(=O)NCCN3CCCC3)c3sc4ccccc4n3c2n1] | 567.70 | 568 |
| 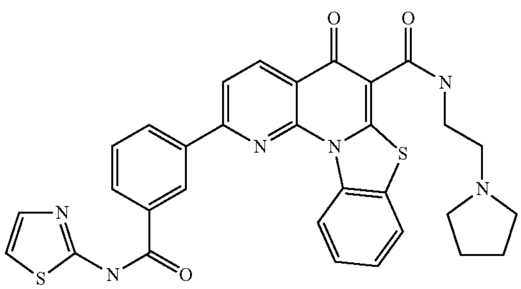 [SMILES: O=C(Nc1nccs1)c1cccc(-c2ccc3c(=O)c(C(=O)NCCN4CCCC4)c4sc5ccccc5n4c3n2)c1] | 594.71 | 595 |
| 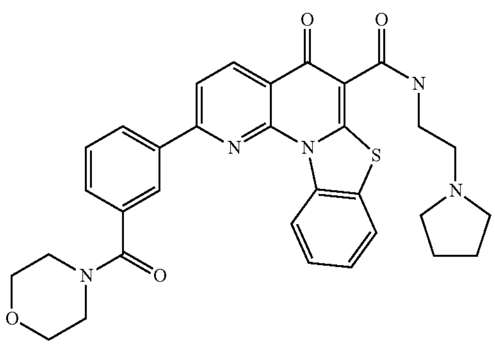 [SMILES: O=C(NCCN1CCCC1)c1c(=O)c2ccc(-c3cccc(C(=O)N4CCOCC4)c3)nc2n2c1sc1ccccc12] | 581.68 | 582 |
| 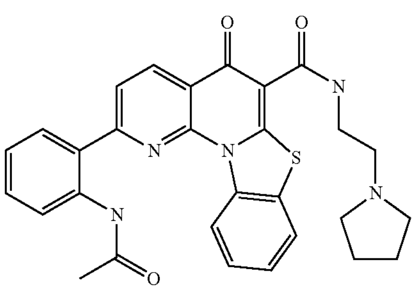 [SMILES: CC(=O)Nc1ccccc1-c1ccc2c(=O)c(C(=O)NCCN3CCCC3)c3sc4ccccc4n3c2n1] | 525.62 | 526 |
| 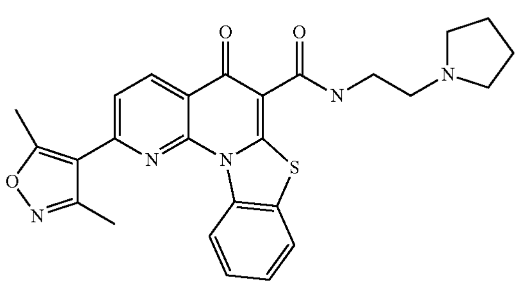 [SMILES: Cc1noc(C)c1-c1ccc2c(=O)c(C(=O)NCCN3CCCC3)c3sc4ccccc4n3c2n1] | 487.57 | 488 |

TABLE 4-continued
| Structure | MW | LCMS (ES) m/z [M + 1]+ |
|---|---|---|
| 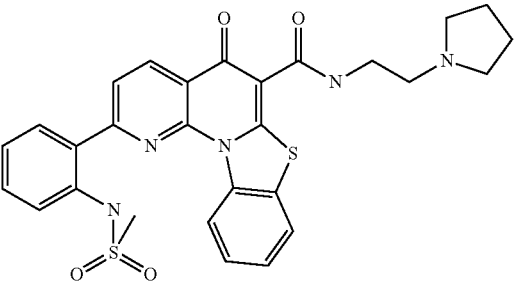 [SMILES: CS(=O)(=O)Nc1ccccc1-c1ccc2c(=O)c(C(=O)NCCN3CCCC3)c3sc4ccccc4n3c2n1] | 561.68 | 562 |
| 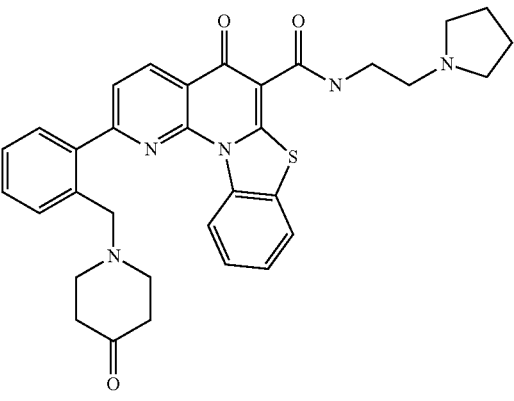 [SMILES: O=C1CCN(Cc2ccccc2-c2ccc3c(=O)c(C(=O)NCCN4CCCC4)c4sc5ccccc5n4c3n2)CC1] | 579.71 | 580 |
| 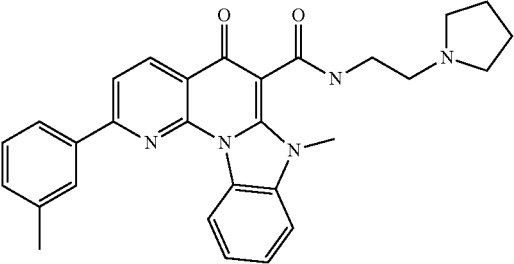 | 479.57 | 480 |
| 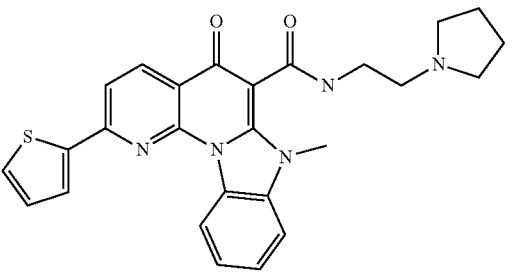 [SMILES: Cn1c2ccccc2n2c3nc(-c4cccs4)ccc3c(=O)c(C(=O)NCCN3CCCC3)c12] | 471.57 | 472 |
| 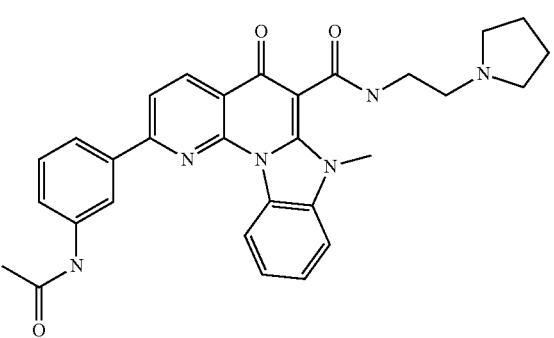 [SMILES: CC(=O)Nc1cccc(-c2ccc3c(=O)c(C(=O)NCCN4CCCC4)c4n(C)c5ccccc5n4c3n2)c1] | 522.60 | 523 |

TABLE 4-continued

| Structure | MW | LCMS (ES) m/z [M + 1]+ |
|---|---|---|
| 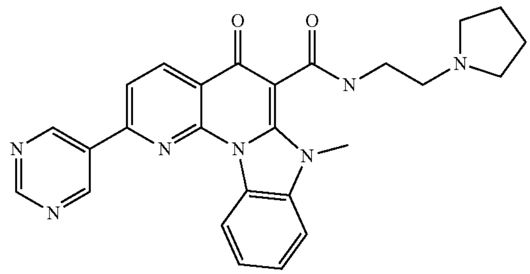 [SMILES: Cn1c2ccccc2n2c3nc(-c4cncnc4)ccc3c(=O)c(C(=O)NCCN3CCCC3)c12] | 467.52 | 468 |
| 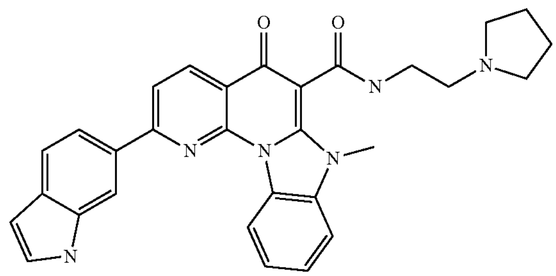 [SMILES: Cn1c2ccccc2n2c3nc(-c4ccc5cc[nH]c5c4)ccc3c(=O)c(C(=O)NCCN3CCCC3)c12] | 504.58 | 505 |
| 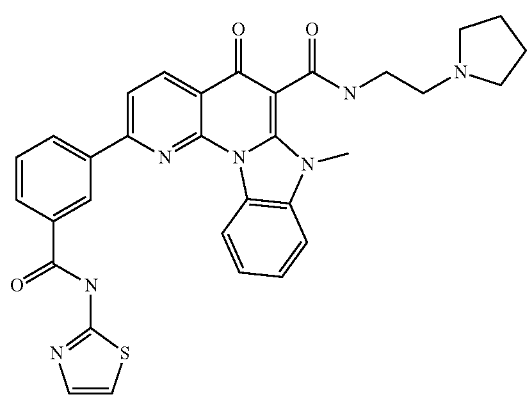 [SMILES: Cn1c2ccccc2n2c3nc(-c4cccc(C(=O)Nc5nccs5)c4)ccc3c(=O)c(C(=O)NCCN3CCCC3)c12] | 591.68 | 592 |
| 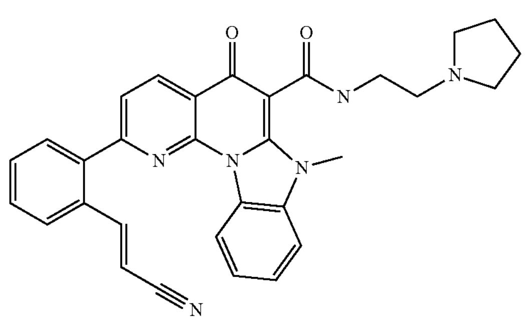 [SMILES: Cn1c2ccccc2n2c3nc(-c4ccccc4/C=C/C#N)ccc3c(=O)c(C(=O)NCCN3CCCC3)c12] | 516.59 | 517 |

TABLE 4-continued
| Structure | MW | LCMS (ES) m/z [M + 1]+ |
|---|---|---|
| 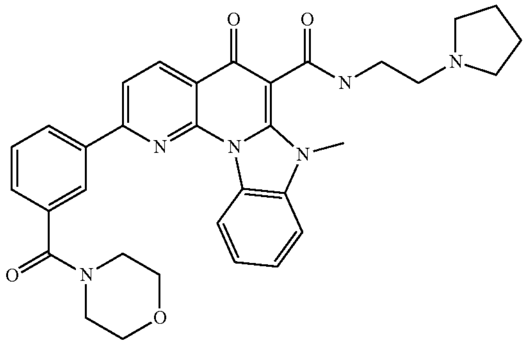 [SMILES: Cn1c2ccccc2n2c3nc(-c4cccc(C(=O)N5CCOCC5)c4)ccc3c(=O)c(C(=O)NCCN3CCCC3)c12] | 578.66 | 579 |
| 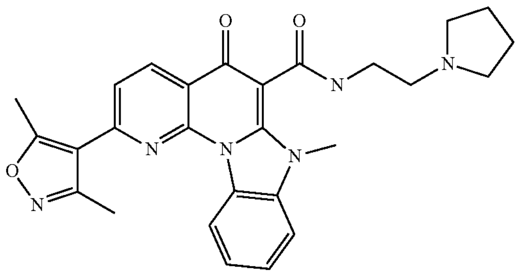 [SMILES: Cc1noc(C)c1-c1ccc2c(=O)c(C(=O)NCCN3CCCC3)c3n(C)c4ccccc4n3c2n1] | 484.55 | 485 |
| 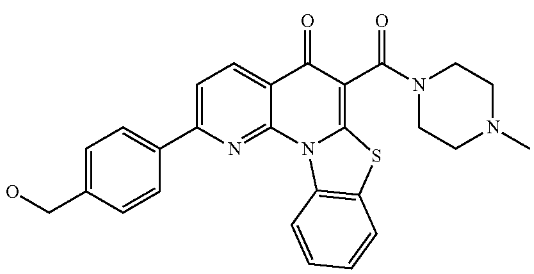 [SMILES: CN1CCN(C(=O)c2c(=O)c3ccc(-c4ccc(CO)cc4)nc3n3c2sc2ccccc23)CC1] | 484.57 | 485 |
| 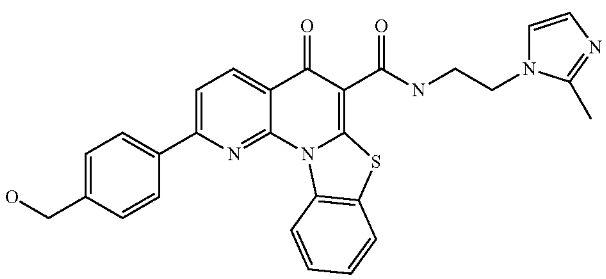 [SMILES: Cc1nccn1CCNC(=O)c1c(=O)c2ccc(-c3ccc(CO)cc3)nc2n2c1sc1ccccc12] | 509.58 | 510 |
Example 37
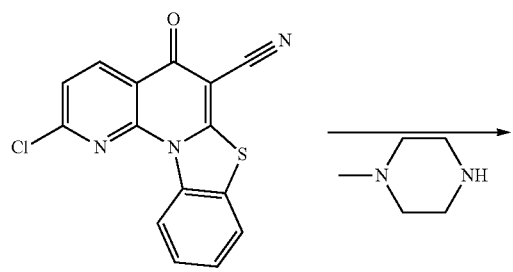
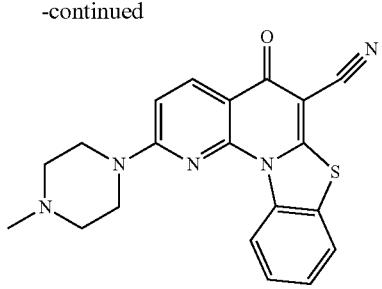
-continued
A solution of chloride (40 mg, 0.13 mmol) and 1-methylpiperazine (0.10 mL) in ACN (1.0 mL) was heated at 120°

C. for 10 min in microwave. The precipitate was collected by filtration and washed with ACN then EtOAc to yield desired product as a solid. LCMS (ES): m/z 376 [M+1]$^+$.

The following analogues in Table 5 were prepared by the same method, using the appropriate chloroquinolones and amines.

TABLE 5

| Structure | MW | LCMS (ES) m/z [M + 1]$^+$ |
|---|---|---|
| (morpholine-substituted structure) | 362.41 | 363 |
| (piperidine-substituted structure) | 360.43 | 361 |
| (isopropylamino-substituted structure) | 334.39 | 335 |
| (hydroxypyrrolidine-substituted structure) | 362.41 | 363 |
| (4-chlorobenzylamino-substituted structure) | 416.88 | 417 |

TABLE 5-continued

| Structure | MW | LCMS (ES) m/z [M + 1]$^+$ |
|---|---|---|
| (tetrahydrofurfurylamino-substituted structure) | 376.43 | 377 |
| (methoxyethylamino-substituted structure) | 350.39 | 351 |
| (methoxyethylamino-substituted structure) | 336.37 | 337 |
| (1,4-oxazepane-substituted structure) | 376.43 | 377 |
| (2,6-dimethylmorpholine-substituted structure) | 390.46 | 391 |

TABLE 5-continued

| Structure | MW | LCMS (ES) m/z [M + 1]+ |
|---|---|---|
| (4-hydroxypiperidinyl derivative) | 376.43 | 377 |
| (3-oxopiperazinyl derivative) | 375.43 | 376 |
| (prolinol derivative) | 376.43 | 377 |
| (4-methylpiperazinyl derivative) | 375.45 | 376 |
| (tert-butylamino derivative) | 348.42 | 349 |

TABLE 5-continued

| Structure | MW | LCMS (ES) m/z [M + 1]+ |
|---|---|---|
| (benzylamino derivative) | 382.44 | 383 |
| (2-methoxybenzylamino derivative) | 412.46 | 413 |
| (pyridin-2-ylmethylamino derivative) | 383.43 | 384 |
| (2-hydroxy-2-phenylethylamino derivative) | 412.46 | 413 |
| (pyridin-4-ylmethylamino derivative) | 383.43 | 384 |

TABLE 5-continued

| Structure | MW | LCMS (ES) m/z [M + 1]⁺ |
|---|---|---|
| 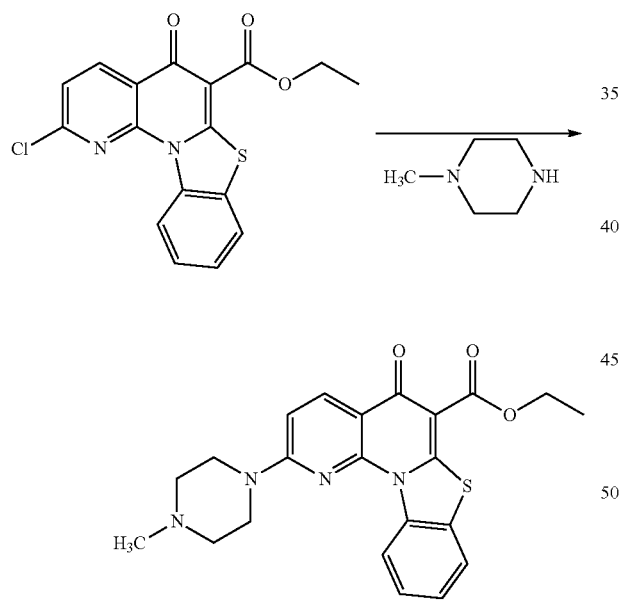 | 412.46 | 413 |

Example 38

Synthesis of Compound A1

To a slurry of the chloroester (5.00 g, 13.94 mmol) in CH₃CN (50 mL) was added N-methylpiperazine (3.10 mL, 27.95 mmol) and the mixture was heated at reflux over night. The reaction was cooled to rt and the product was collected by filtration to yield desired product as a tan solid (4.7 g, 80%). $^1$H NMR (CDCl₃) δ: 9.47 (d, 1H), 8.62 (d, 1H), 7.74 (dd, 1H), 7.51 (m, 1H), 7.43 (m, 1H), 6.89 (d, 1H), 4.50 (q, 2H), 3.85 (t, 4H), 2.62 (t, 4H), 2.40 (s, 3H), 1.49 (t, 3H). LCMS (ES): m/z 423 [M+1]⁺.

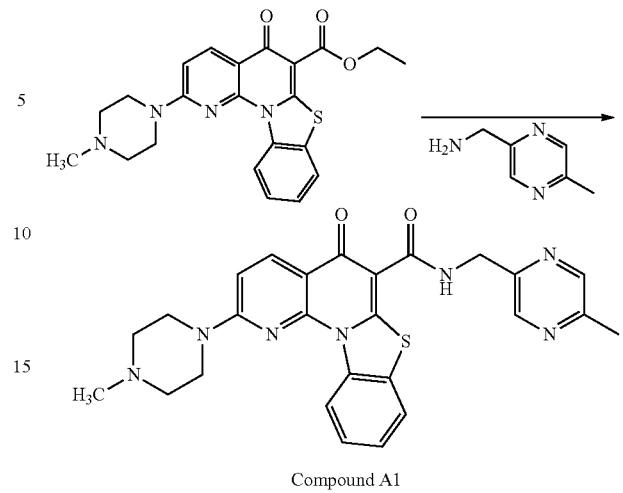

Compound A1

To a solution of ester (72 mg, 0.17 mmol), (5-methylpyrazin-2-yl)methanamine (0.10 mL, 0.81 mmol), and DBU (0.20 mL, 1.34 mmol) in DCM (10 mL) was added AlCl₃ (80 mg, 0.60 mmol). The reaction mixture was stirred at rt for 30 min. The reaction was diluted with DCM (100 mL) and 3N NaOH (25 mL) and stirred for 10 min. The layers were separated and the organic layer was washed with H₂O (2×50 mL), brine (50 mL), and dried over Na₂SO₄. The solvent was removed under reduced pressure and the resulting solid was triturated in ACN to give the desired product as a white solid (60 mg, 71%). LCMS (ES): m/z 500 [M+1]⁺.

Example 39

Synthesis of Compound A2

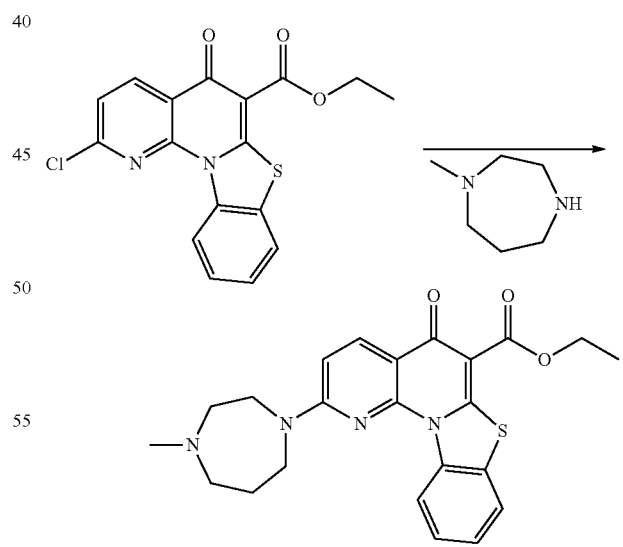

To a slurry of the chloroester (3.51 g, 9.7 mmol) in CH₃CN (50 mL) was added N-methylhomopiperazine (1.34 mL, 10 mmol) and triethyl amine (1.49 ml, 10 mmol). The mixture was heated at reflux over night. The reaction was cooled to rt and the product was collected by filtration to yield desired product as a tan solid (2.85 g). LCMS (ES): m/z 437 [M+1]⁺.

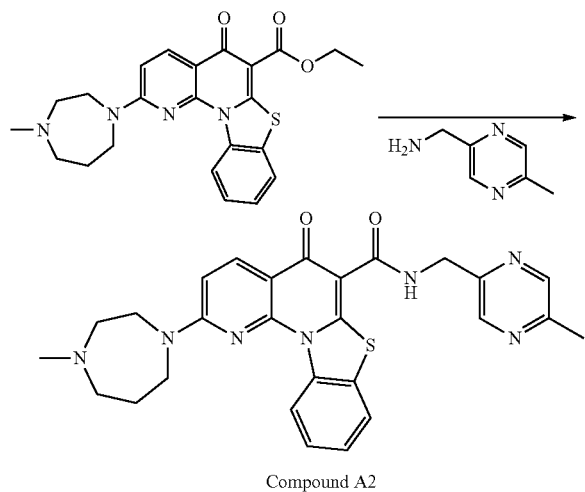

Compound A2

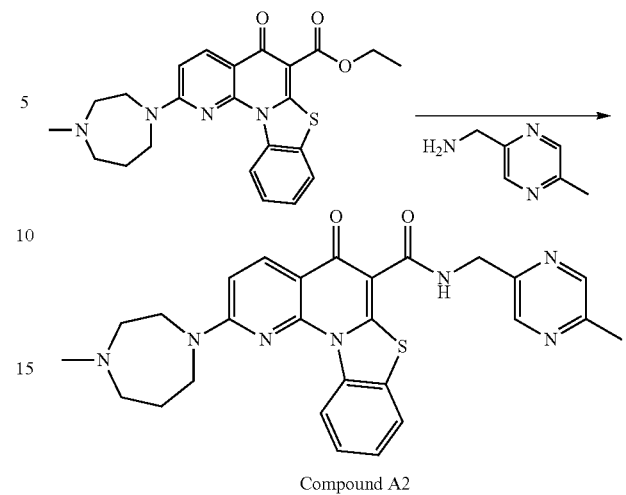

Compound A2

To a solution of ester (2.85 mg, 6.53 mmol), (5-methylpyrazin-2-yl)methanamine (2.45 mL), and DBU (2.93 mL) in DCM (100 mL) was added AlCl$_3$ (2.67 g). The reaction mixture was stirred at rt for 30 min. The reaction was diluted with DCM (100 mL) and 4N NaOH (100 mL) and stirred for 15 min. The layers were separated and the organic layer was washed with H$_2$O (2×100 mL), brine (100 mL), and dried over Na$_2$SO$_4$. The solvent was removed under reduced pressure and the resulting solid was triturated in ACN to give the desired product as a white solid (1.98 g). LCMS (ES): m/z 514 [M+1]$^+$.

Example 40

Large Scale Synthesis of Compound A2

To a solution of ester (2.24 g, 5.15 mmol), 2-(aminomethyl)-5-methylpyrazine (1.27 g, 10.32 mmol) and DBU (2.3 mL, 15.38 mmol) in DCM (50 mL) was added AlCl$_3$ (2.05 g, 15.39 mmol). The reaction mixture was stirred at rt for 30 min. The reaction was diluted with DCM (200 mL) and 3N NaOH (50 mL) and stirred for 10 min. The layers were separated and the organic layer was washed with H$_2$O (2×100 mL), brine (100 mL), and dried over Na$_2$SO$_4$. The solvent was removed under reduced pressure and the resulting solid was triturated in ACN to give the desired product (1.80 g) as a pale yellow solid. $^1$H NMR (CDCl$_3$) δ: 11.28 (t, 1H), 9.52 (d, 1H), 8.57 (m, 2H), 8.45 (d, 1H), 7.74 (m, 1H), 7.44 (m, 2H), 6.78 (d, 1H), 4.86 (d, 2H), 3.90 (br, 4H), 2.86 (m, 2H), 2.65 (m, 2H), 2.56 (s, 3H), 2.42 (s, 3H), 2.15 (m, 2H). LCMS (ES): m/z 485 [M+1]$^+$. LCMS (ES): m/z 514 [M+1]$^+$.

Example 41

Synthesis of Compound A3

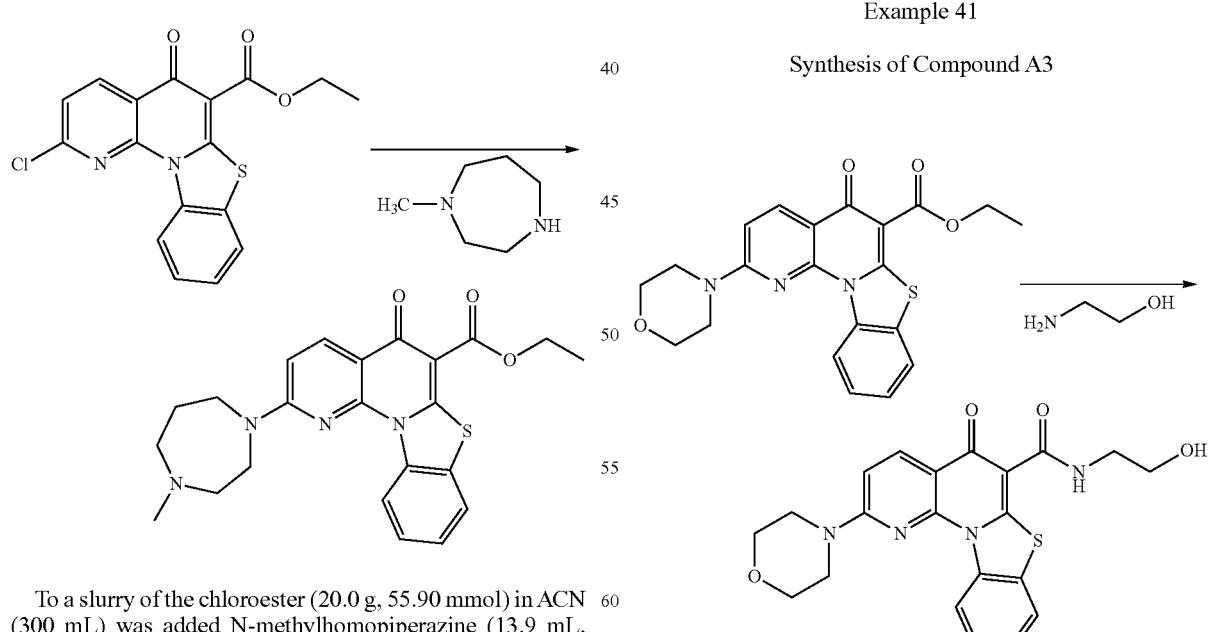

To a slurry of the chloroester (20.0 g, 55.90 mmol) in ACN (300 mL) was added N-methylhomopiperazine (13.9 mL, 111.70 mmol) and the mixture was heated at reflux overnight. The reaction was cooled to rt and the ppt was collected by filtration. The resulting solid was dissolved in CHCl$_3$ (500 mL) and filtered through CELITE™. The solvent was removed under reduced pressure to yield the desired product as a solid (16.07 g, 66%). LCMS (ES): m/z 437 [M+1]$^+$.

A solution of ester (6.53 g, 15.97 mmol) in ethanolamine (30 mL) was stirred at 150° C. over night. The reaction was diluted with H$_2$O (100 mL) and the resulting ppt was collected by filtration. The solid was washed with H$_2$O (2×) and ACN (2×) to yield the desired product as a white solid (5.75 g, 85%). ¹H NMR (DMSO-d⁶) δ: 10.57 (t, 1H), 9.32 (d, 1H), 8.36 (d, 1H), 7.99 (dd, 1H), 7.55 (m, 1H), 7.48 (m, 1H), 7.18 (d, 1H), 4.85 (t, 1H), 3.82 (t, 4H), 3.75 (t, 4H), 3.56 (q, 2H), 3.43 (q, 2H). LCMS (ES): m/z 425 [M+1]⁺.

1H), 6.92 (d, 1H), 3.94 (t, 4H), 3.82 (t, 4H), 3.66 (q, 2H), 3.01 (t, 2H), 2.00 (m, 1H), 0.43 (m, 4H). LCMS (ES): m/z 464 [M+1]⁺

Example 42

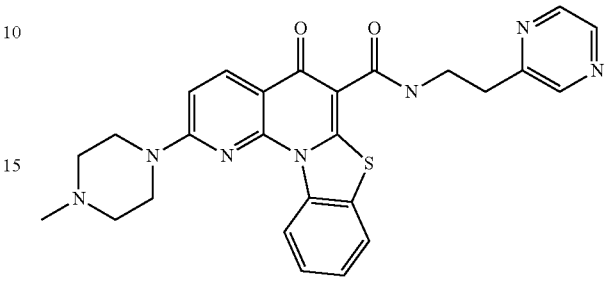

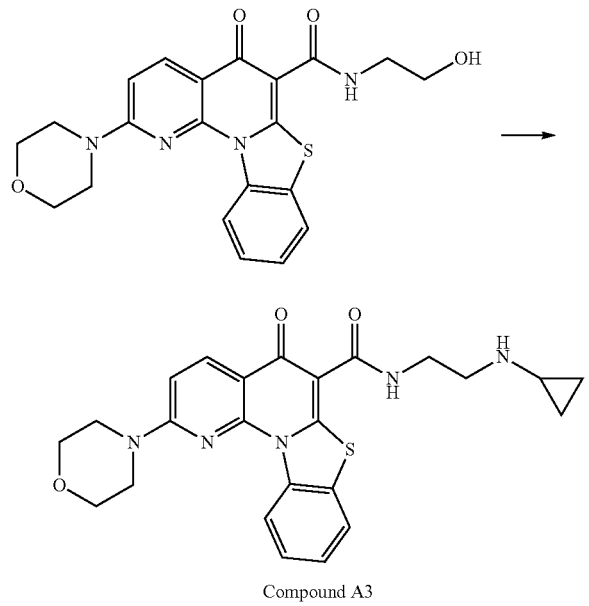

Compound A3

To a solution of alcohol (4.810 g, 11.343 mmol) and TEA (4.75 mL, 34.076 mmol) in DCM (125 mL) was added MsCl (1.70 mL, 21.964 mmol). The reaction mixture was stirred at rt for 2 h, diluted with DCM (200 mL) and satd NH₄Cl (50 mL). The layers were separated and the organic layer was dried over Na₂SO₄. The solvent was removed under reduced pressure and the reaction crude was triturated in ACN to yield the mesylate. A solution of above mesylate, cyclopropylamine (2.20 mL, 33.570 mmol), HCl (1N, 1.0 mL) and TEA (4.75 mL, 34.076 mmol) in ACN (100 mL) was heated at reflux over night. The precipitate was collected by filtration and purified on silica gel column to yield the desired amine as a white solid (1.2 g). ¹H NMR (CDCl₃) δ: 10.64 (t, 1H), 9.45 (d, 1H), 8.63 (d, 1H), 7.77 (dd, 1H), 7.50 (m, 1H), 7.42 (m, The compound of Example 42 was prepared by the same method as compound A1, using the appropriate amine and quinolone ethyl ester.

MW 499.6; LCMS (ES): m/z 500 [M+1]⁺.

Example 43

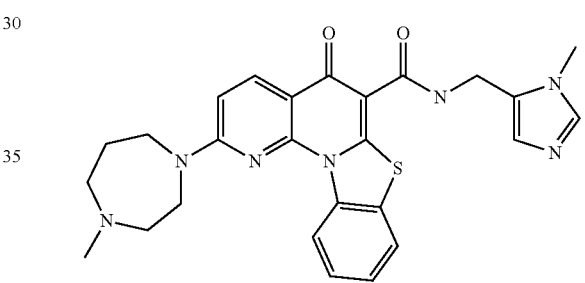

The compound of Example 43 was prepared by the same method as compound A2, using the appropriate amine and quinolone ethyl ester.

MW 501.61; LCMS (ES): m/z 502 [M+1]⁺.

The following analogues in Table 6 were prepared by the same method, using the appropriate amine and quinolone ethyl ester.

TABLE 6

| Structure | MW | LCMS (ES) m/z [M + 1]⁺ |
|---|---|---|
| 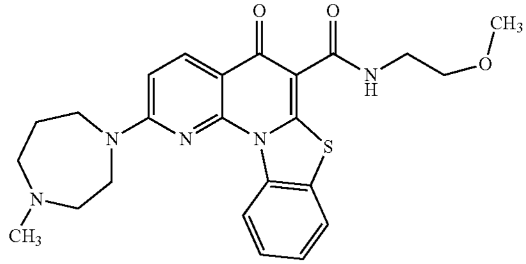 | 465.5 | 466.3 |

TABLE 6-continued
| Structure | MW | LCMS (ES) m/z [M + 1]+ |
|---|---|---|
| 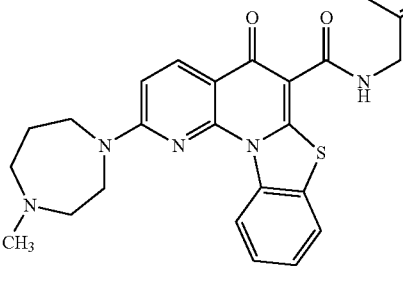 | 573.6 | 574.2 |
| 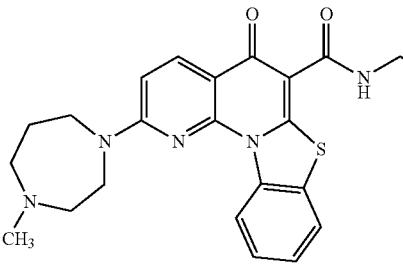 | 493.6 | 494.2 |
| 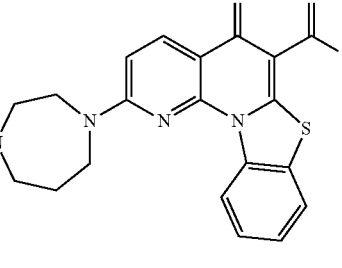 | 541.6 | 542.2 |
| 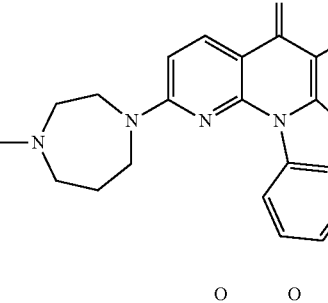 | 581.7 | 582.2 |
| 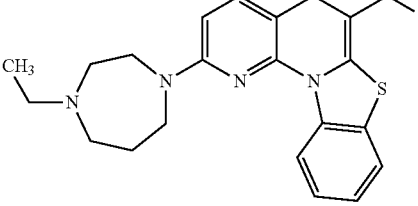 | 527.6 | 528.2 |

TABLE 6-continued

| Structure | MW | LCMS (ES) m/z [M + 1]+ |
|---|---|---|
| 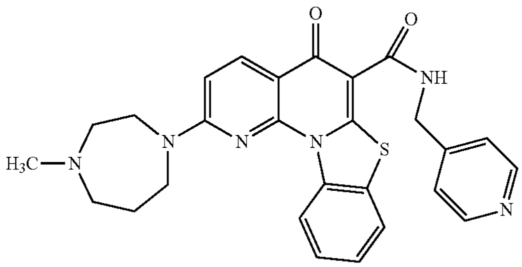 [SMILES: CN1CCCN(c2ccc3c(=O)c(C(=O)NCc4ccncc4)c4sc5ccccc5n4c3n2)CC1] | 498.6 | 499.1 |
| 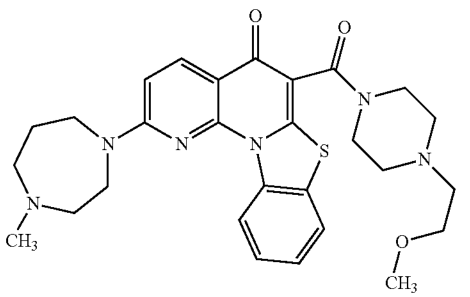 [SMILES: COCCN1CCN(C(=O)c2c(=O)c3ccc(N4CCCN(C)CC4)nc3n3c2sc2ccccc23)CC1] | 534.6 | 535.2 |
| 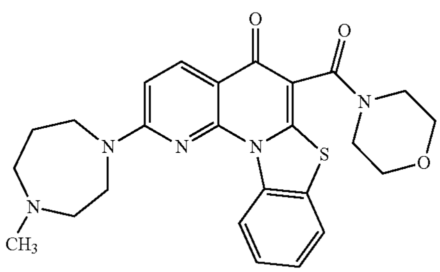 [SMILES: CN1CCCN(c2ccc3c(=O)c(C(=O)N4CCOCC4)c4sc5ccccc5n4c3n2)CC1] | 477.5 | 478.1 |
| 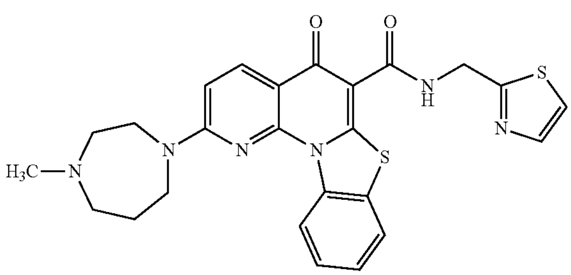 [SMILES: CN1CCCN(c2ccc3c(=O)c(C(=O)NCc4nccs4)c4sc5ccccc5n4c3n2)CC1] | 504.6 | 505.2 |
| 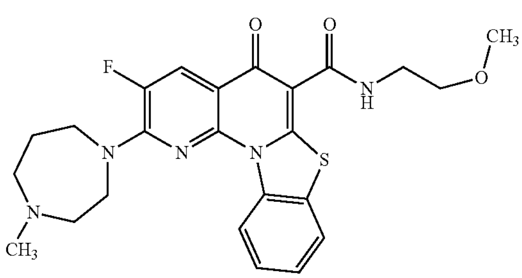 | 483.6 | 484 |

TABLE 6-continued

| Structure | MW | LCMS (ES) m/z [M + 1]+ |
|---|---|---|
| | 516.6 | 517 |
| | 516.6 | 517 |
| | 516.6 | 517 |
| 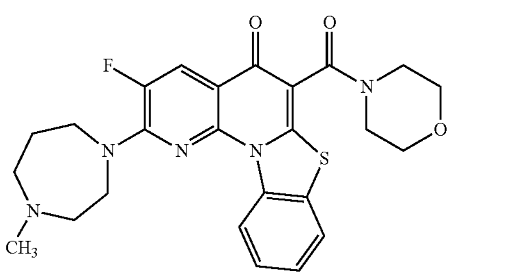 [SMILES: CN1CCCN(c2nc3c(cc2F)c(=O)c(C(=O)N2CCOCC2)c2sc4ccccc4n23)CC1] | 495.6 | 496 |
| 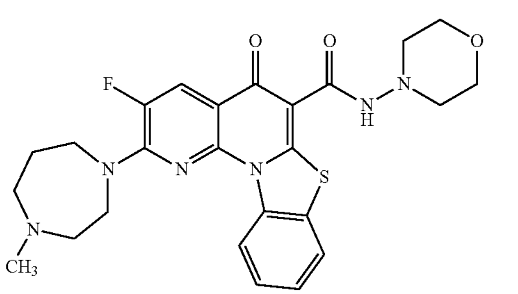 [SMILES: CN1CCCN(c2nc3c(cc2F)c(=O)c(C(=O)NN2CCOCC2)c2sc4ccccc4n23)CC1] | 510.6 | 511 |

TABLE 6-continued
| Structure | MW | LCMS (ES) m/z [M + 1]+ |
|---|---|---|
| 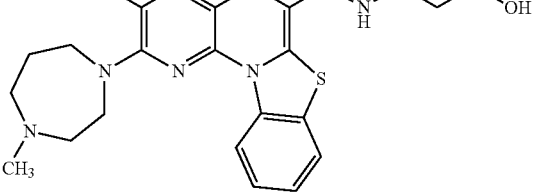 | 483.6 | 484 |
| 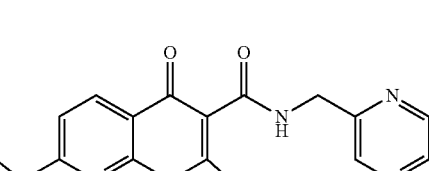 | 499.6 | 500 |
| 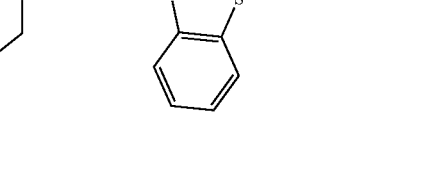 | 451.5 | 452 |
| 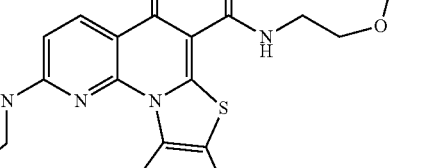 | 463.6 | 464 |
| 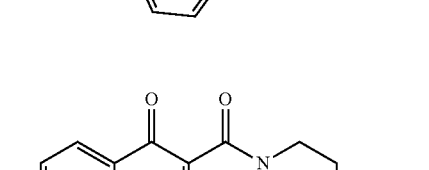 | 531.6 | 532 |

Example 44

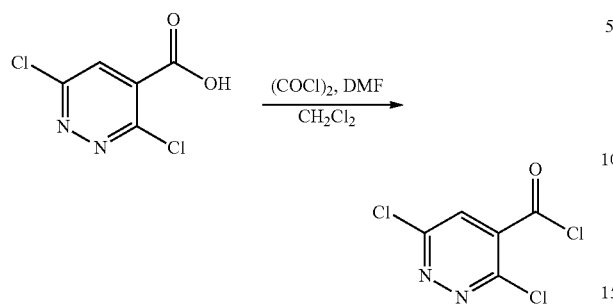

To a solution of the 3,6-dichloropyridazine-4-carboxylic acid (2.5 g, 12.9 mmol) in methylene chloride (25 mL) was added oxalyl chloride (14.2 mmol, 1.1 eq.) followed by 2 drops of DMF and the mixture was allowed to stir overnight at room temperature. The solvent was then removed in vacuo to afford the crude acid chloride as oil which was used without further purification (quantitative).

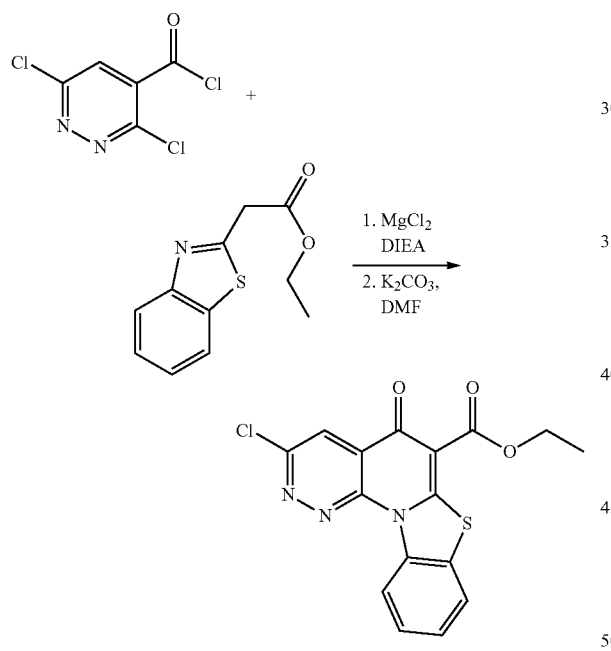

To a solution of the benzothiazole ester (2.53 g, 11.45 mmol) in acetonitrile (25 mL) at 0° C. was added magnesium chloride (1.63 g, 1.5 eq.) and the mixture was stirred for 5 minutes. To this mixture was added the pryidazine-4-carbonyl chloride (2.36 g, 11.45 mmol), dissolved in THF (5.0 mL) via addition funnel and the mixture was stirred for an additional 5 minutes. Triethylamine (3.75 mL, 2.5 eq.) was added slowly and the mixture was allowed to come to room temperature over 1 hour. The solvent was removed in vacuo and replaced with DMF (75 mL) and potassium carbonate (3.16 g, 22.9 mmol) was added and the mixture was heated to 100° C. for 2 hours. Upon cooling the mixture was filtered and the resulting solids were stirred in water (20 mL) then filtered, washing with water (20 mL), methanol (20 mL) and ethyl acetate (20 mL) and dried to afford the pyridazinebenzothiazole ester as a tan solid (2.9 g, 8.08 mmol, 70%).

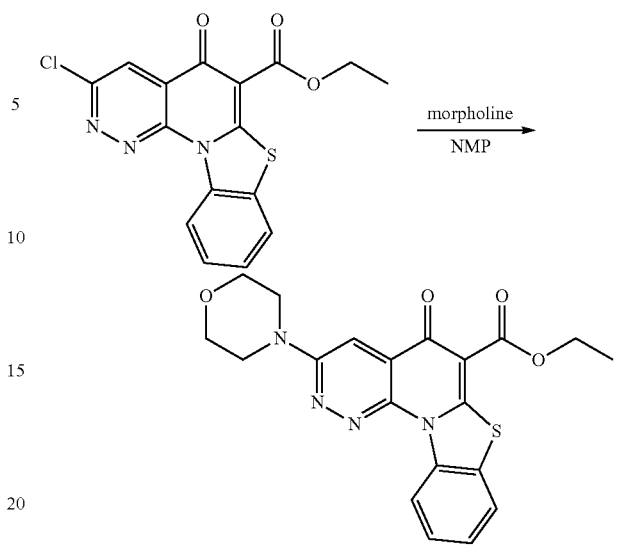

To a slurry of the pyridazinebenzothiazole ester (500 mg) in dry NMP (5 mL) was added morpholine (500 mg) and the mixture was heated to reflux for 4 hours. The mixture was then cooled to room temperature and filtered, washed with acetonitrile and dried to afford the morpholino compound as a tan solid (505 mg).

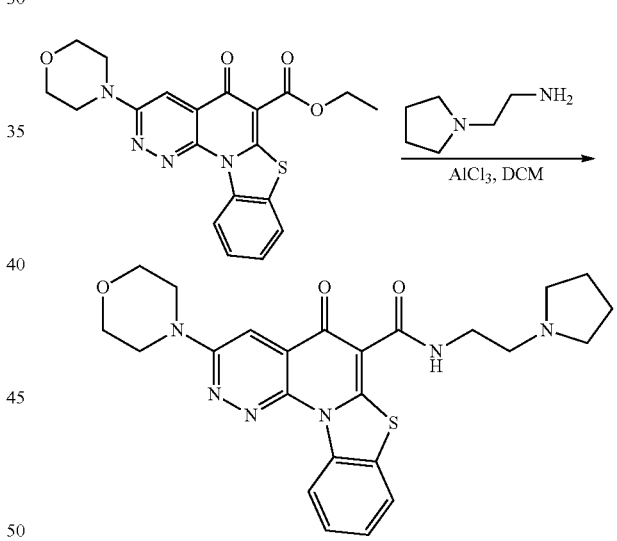

To a mixture of the morpholinopyridazinebenzothiazole ester (100 mg) in and 1-(2-aminoethyl)-pyrrolidine (100 mg) DCM (2 mL) was added aluminum chloride (100 mg) and the mixture was allowed to stir overnight at room temperature. The solvent was removed in vacuo and a saturated L-tartaric acid solution (5 mL) was added and allowed to stir for 30 minutes. The solution was washed with DCM (5 mL) and basified with 1N NaOH. The solid was collected by filtration and dissolved in DCM (20 mL) and methanol (2 mL) and the solution was passed over a pad of alumina. The solvent was removed in vacuo and the resulting solid was triturated with methanol to afford the final compound as a yellow solid.

The following analogues in Table 7 were prepared by the same method, using the appropriate amine and pyridazinebenzothiazole ester.

TABLE 7

| Structure | MW | LCMS (ES) m/z [M + 1]+ |
|---|---|---|
| 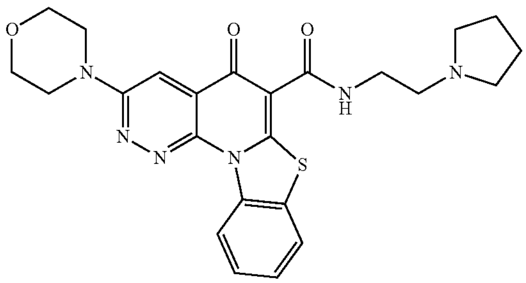 [SMILES: O=C(NCCN1CCCC1)c1c(=O)c2cc(N3CCOCC3)nnc2n2c1sc1ccccc12] | 478.6 | 479.6 |
| 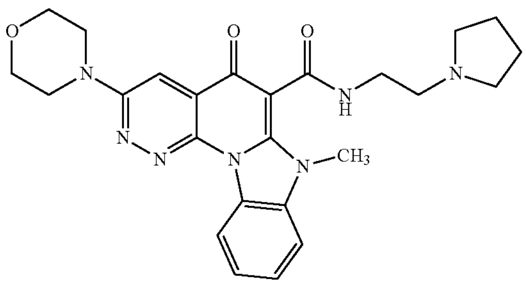 [SMILES: Cn1c2ccccc2n2c3nnc(N4CCOCC4)cc3c(=O)c(C(=O)NCCN3CCCC3)c12] | 475.6 | 476.6 |
| 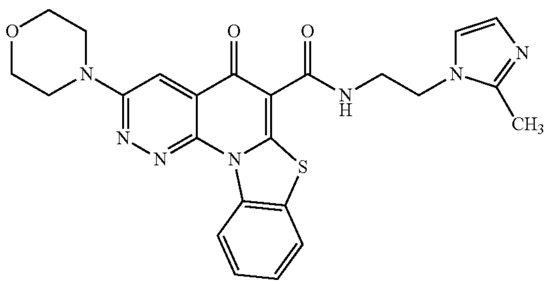 [SMILES: Cc1nccn1CCNC(=O)c1c(=O)c2cc(N3CCOCC3)nnc2n2c1sc1ccccc12] | 489.6 | 490.6 |
| | 475.5 | 476.5 |
| | 475.5 | 476.5 |

TABLE 7-continued

| Structure | MW | LCMS (ES) m/z [M + 1]+ |
|---|---|---|
| 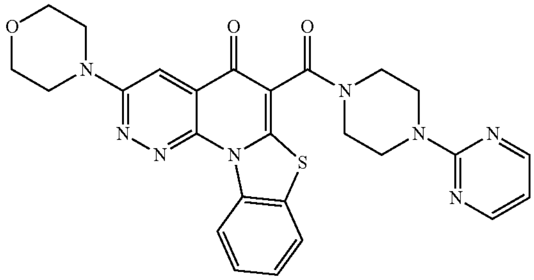 [SMILES: O=C(c1c(=O)c2cc(N3CCOCC3)nnc2n2c1sc1ccccc12)N1CCN(c2ncccn2)CC1] | 528.6 | 529.6 |
| | 464.5 | 465.5 |
| | 464.5 | 465.5 |
| 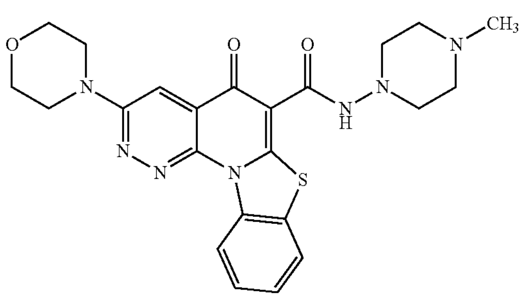 [SMILES: CN1CCN(NC(=O)c2c(=O)c3cc(N4CCOCC4)nnc3n3c2sc2ccccc23)CC1] | 479.6 | 480.6 |
| 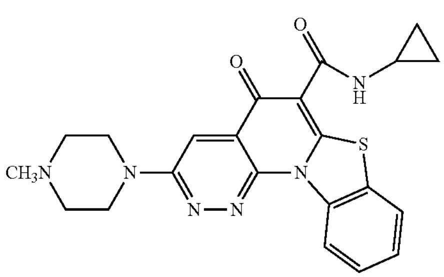 | 434.5 | 435.5 |

TABLE 7-continued

| Structure | MW | LCMS (ES) m/z [M + 1]+ |
|---|---|---|
| 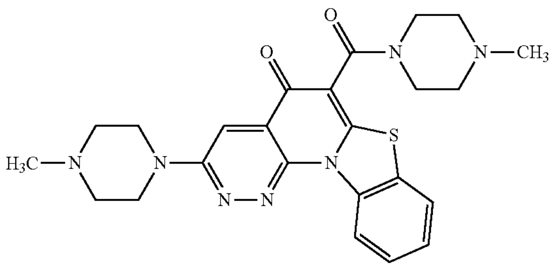 | 477.6 | 478.6 |
| 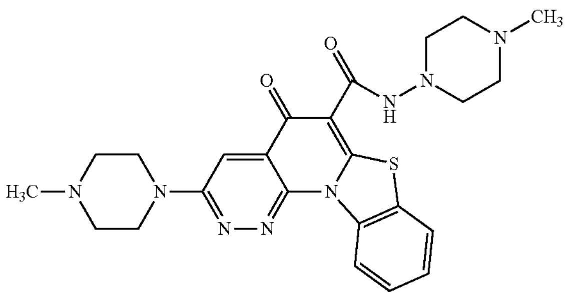 | 492.6 | 493.6 |
| 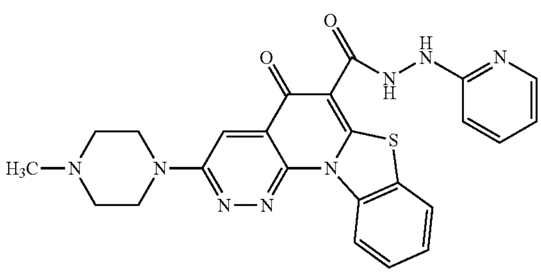 [SMILES: CN1CCN(c2cc3c(=O)c(C(=O)NNc4ccccn4)c4sc5ccccc5n4c3nn2)CC1] | 486.6 | 487.6 |
| 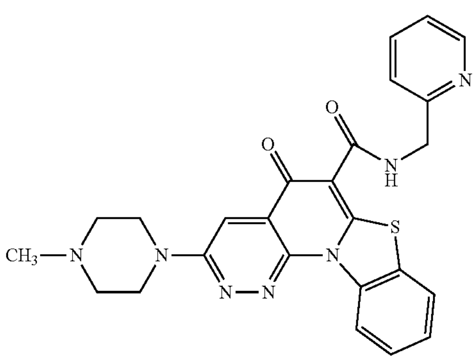 [SMILES: CN1CCN(c2cc3c(=O)c(C(=O)NCc4ccccn4)c4sc5ccccc5n4c3nn2)CC1] | 485.6 | 486.6 |
| 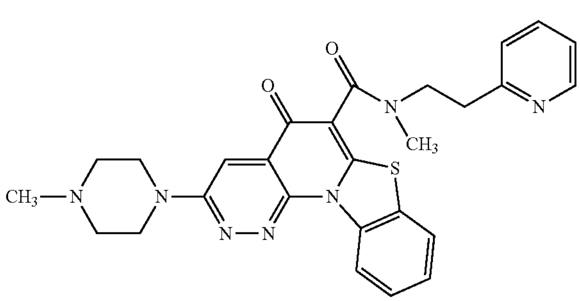 [SMILES: CN1CCN(c2cc3c(=O)c(C(=O)N(C)CCc4ccccn4)c4sc5ccccc5n4c3nn2)CC1] | 513.6 | 514.6 |

TABLE 7-continued

| Structure | MW | LCMS (ES) m/z [M + 1]+ |
|---|---|---|
| 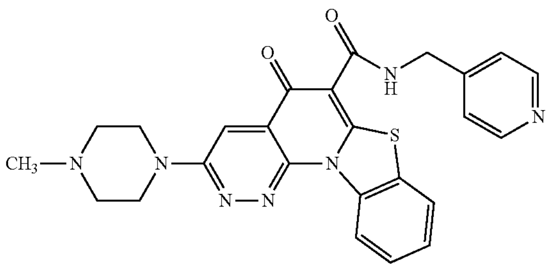 [SMILES: CN1CCN(c2cc3c(=O)c(C(=O)NCc4ccncc4)c4sc5ccccc5n4c3nn2)CC1] | 485.6 | 486.6 |
| 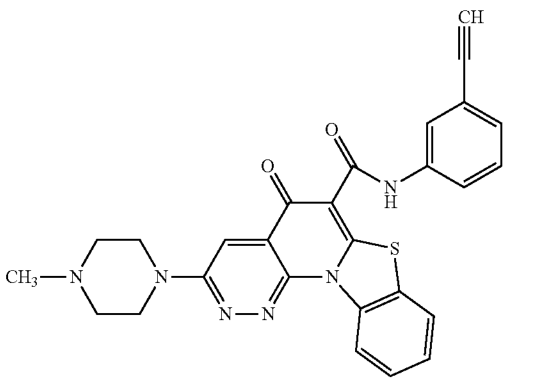 [SMILES: C#Cc1cccc(NC(=O)c2c(=O)c3cc(N4CCN(C)CC4)nnc3n3c2sc2ccccc23)c1] | 494.6 | 495.6 |
| 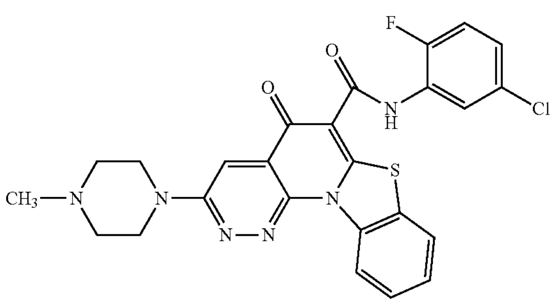 [SMILES: CN1CCN(c2cc3c(=O)c(C(=O)Nc4cc(Cl)ccc4F)c4sc5ccccc5n4c3nn2)CC1] | 523.0 | 524.0 |
| 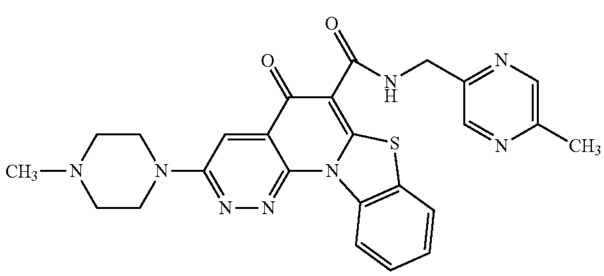 | 500.6 | 501.6 |
| 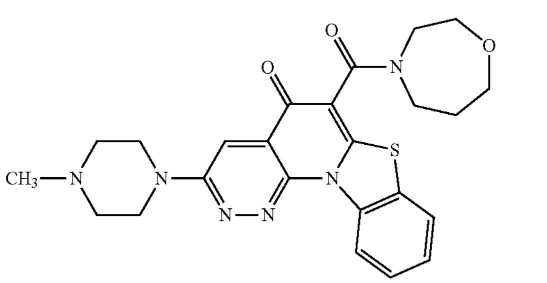 [SMILES: CN1CCN(c2cc3c(=O)c(C(=O)N4CCCOCC4)c4sc5ccccc5n4c3nn2)CC1] | 478.6 | 479.6 |

TABLE 7-continued

| Structure | MW | LCMS (ES) m/z [M + 1]+ |
|---|---|---|
| | 492.6 | 493.6 |
| 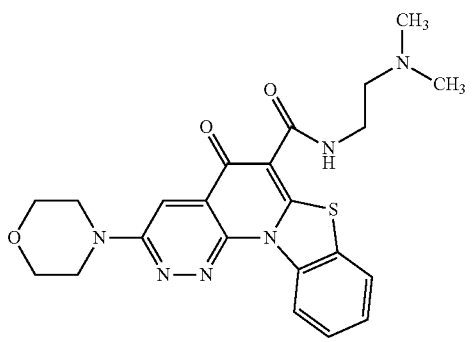 [SMILES: CN(C)CCNC(=O)c1c(=O)c2cc(N3CCOCC3)nnc2n2c1sc1ccccc12] | 452.5 | 453.5 |
| | 492.6 | 493.6 |
| 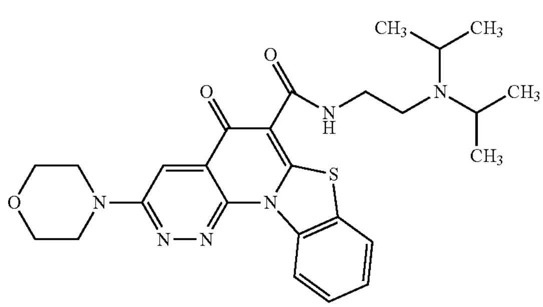 [SMILES: CC(C)N(CCNC(=O)c1c(=O)c2cc(N3CCOCC3)nnc2n2c1sc1ccccc12)C(C)C] | 508.6 | 509.6 |

TABLE 7-continued

| Structure | MW | LCMS (ES) m/z [M + 1]+ |
|---|---|---|
| 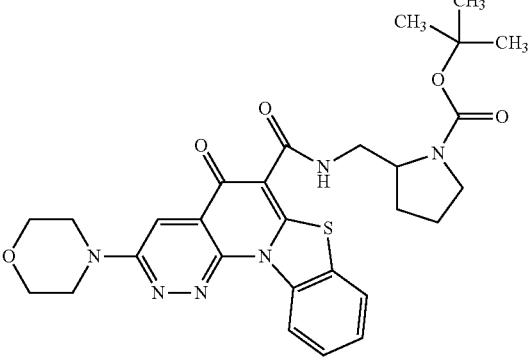 | 564.7 | 565.7 |
| 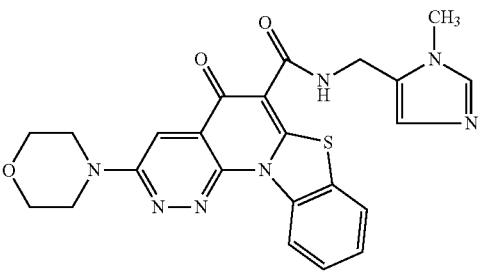 [SMILES: Cn1cncc1CNC(=O)c1c(=O)c2cc(N3CCOCC3)nnc2n2c1sc1ccccc12] | 475.5 | 476.5 |
| 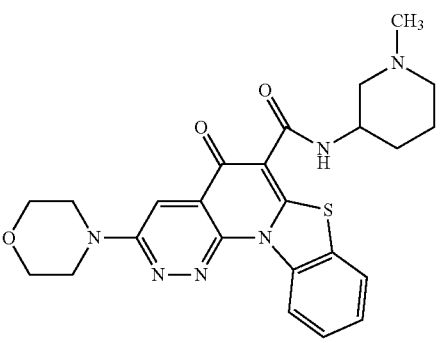 [SMILES: CN1CCCC(NC(=O)c2c(=O)c3cc(N4CCOCC4)nnc3n3c2sc2ccccc23)C1] | 478.6 | 479.6 |
| 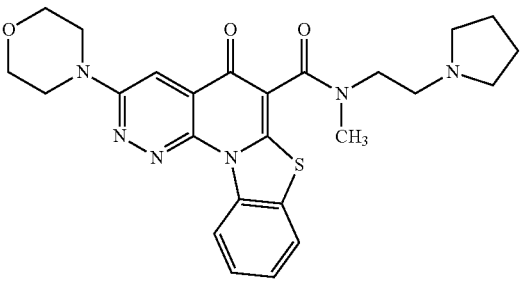 [SMILES: CN(CCN1CCCC1)C(=O)c1c(=O)c2cc(N3CCOCC3)nnc2n2c1sc1ccccc12] | 492.6 | 493.6 |

Example 45

Cell Proliferation Modulatory Activity

A representative cell-proliferation assay protocol using Alamar Blue dye (stored at 4° C., use 20 ul per well) is described hereafter.

96-Well Plate Setup and Compound Treatment a. Split and trypsinize cells.

b. Count cells using hemocytometer.

c. Plate 4,000-5,000 cells per well in 100 µl of medium and seed into a 96-well plate according to the following plate layout. Add cell culture medium only to wells B10 to B12. Wells B1 to B9 have cells but no compound added.

|   | 1 | 2 | 3 | 4 | 5 | 6 | 7 | 8 | 9 | 10 | 11 | 12 |
|---|---|---|---|---|---|---|---|---|---|---|---|---|
| A | | | | | | EMPTY | | | | | | |
| B | | | NO COMPOUND ADDED | | | | | | | Medium Only | | |

-continued

|   | 1 2 3 | 4 5 6 | 7 8 9 | 10 11 12 |         |
|---|-------|-------|-------|----------|---------|
| C | 10 nM | 100 nM | 1 uM | 10 uM | Control |
| D | 10 nM | 100 nM | 1 uM | 10 uM | Comp1   |
| E | 10 nM | 100 nM | 1 uM | 10 uM | Comp2   |
| F | 10 nM | 100 nM | 1 uM | 10 uM | Comp3   |
| G | 10 nM | 100 nM | 1 uM | 10 uM | Comp4   |
| H |       |       | EMPTY |          |         | d. Add 100 µl of 2× drug dilution to each well in a concentration shown in the plate layout above. At the same time, add 100 µl of media into the control wells (wells B10 to B12). Total volume is 200 µl/well.

e. Incubate four (4) days at 37° C., 5% $CO_2$ in a humidified incubator.

f. Add 20 µl Alamar Blue reagent to each well.

g. Incubate for four (4) hours at 37° C., 5% $CO_2$ in a humidified incubator.

h. Record fluorescence at an excitation wavelength of 544 nm and emission wavelength of 590 nm using a microplate reader.

In the assays, cells are cultured with a test compound for approximately four days, the dye then is added to the cells and fluorescence of non-reduced dye is detected after approximately four hours. Different types of cells can be utilized in the assays (e.g., HCT-116 human colorectal carcinoma cells, PC-3 human prostatic cancer cells and MiaPaca human pancreatic carcinoma cells). Anti-proliferative effects of representative compounds are provided hereafter.

Example 46

Measurement of mRNA Values in Cell Assays

Real-time quantitative PCR (QPCR) method may be used to detect the changes of the target c-myc and the endogenous reference GAPDH gene copies in the same tube. Generally, cells (15,000 cells/well) are seeded on 96 well flat bottom plates (Corning, N.Y.) and incubated under normal growth conditions for overnight. The next day, the culture medium is exchanged for that containing anticancer drugs at various concentrations and incubated for 4 hrs in a humidified atmosphere of 5% CO2 at 37° C. Total RNA (tRNA) is extracted using the RNeasy 96 Kit (QIAGEN, CA). The concentration of the tRNA is determined by the RiboGreen RNA Quantitation Reagent (Molecular Probes, OR).

A reverse-transcription (RT) reaction may be conducted using 50 ng of tRNA from each well in a 25 µl reaction containing 1× TaqMan RT buffer, 2.5 uM random hexamers, 5.5 mM $MgCl_2$, 0.5 mM each deoxynucleoside triphosphate (dNTP), 30 U MultiScribe Reverse Transcriptase, and 10 U RNase inhibitor. RT reactions are incubated for 10 min at 25° C., reverse-transcribed for 30 min at 48° C., inactivated for 5 min at 95° C., and placed at 4° C. All RT reagents may be purchased from Applied Biosystems, CA.

Real-Time QPCR reaction may be performed in a 50 µl reaction containing the 5 µl of cDNA, 1× Universal PCR Master Mix, 1× c-myc Pre-Developed Primers and Probe set, and 0.8×GAPDH Pre-Developed Primers and Probe set. Because of the relative abundance of GAPDH gene in Hela, GAPDH primers and probe concentration may be adjusted to get accurate threshold cycles ($C_T$) for both genes in the same tube. The threshold cycle ($C_T$) indicates the fractional cycle number at which the amount of amplified target reaches a fixed threshold. By doing so, the GAPDH amplification is stopped before it can limit the common reactants available for amplification of the c-myc. The ΔRn value represents the normalized reporter signal minus the baseline signal. ΔRn increases during PCR as amplicon copy number increases until the reaction approaches a plateau.

The c-myc probe is labeled with 6FAM™ dye-MGB and the GAPDH probe is labeled with VIC™ dye-MTB. Preincubation is performed for 2 min at 50° C. to activate AmpErase UNG enzyme and then for 10 min at 95° C. to activate AmpliTaq DNA Polymerase. DNA is amplified for 40 cycles of 15 sec at 95° C. and 1 min at 60° C. Human c-myc and GAPDH cDNA are amplified, detected, and quantitated in real time using the ABI Prism 7000 Sequence Detection system (Applied Biosystems, CA), which is set to detect both 6-FAM and VIC reporter dyes simultaneously.

The data may be analyzed using the ABI PRISM Sequence Detection System and Microsoft Excel. Relative quantitation is done using the standard curve and comparative $C_T$ method at the same time, and both methods gave equivalent results. The cycle at which the amplification plot crosses the $C_T$ is known to accurately reflect relative mRNA values. (See, Heid, et al., *Genome Res.* (1996) 6:986-994; Gibson, et al., *Genome Res.* (1996) 6:995-1001). QPCR reactions are set up in triplicate at each cDNA sample and the triplicate $C_T$ values are averaged. All reagents including Pre-Developed Primers and probe set may be purchased from Applied Biosystems, CA.

Example 47

In Vitro Characterization

Various methods may be used for in vitro characterization of the compounds of the present invention, including but not limited to i) stop assays; ii) quadruplex/duplex competition assay; iii) quadrome footprints; and iv) direct assay in the absence of a competitor molecule.

Stop Assays.

Stop assays are high throughput, first-pass screens for detecting drugs that bind to and stabilize the target G-quadruplex. Generally, DNA template oligonucleotide is created, which contains the nucleotide sequence of the "target" quadruplex against which drug screening is desired. A fluorescently labeled primer DNA is then annealed to the 3' end of the template DNA. A DNA polymerase such as Taq polymerase is then introduced to synthesize a complementary strand of DNA by extending from the fluorescently labeled primer. When the progress of the Taq polymerase is unhindered, it synthesizes a full-length copy of the template. Addition of a test drug that merely binds to duplex DNA but does not bind selectively the quadruplex region results in a decrease in synthesis of full length product and a concomitant increase in variable-length DNA copies. If, however, the test drug selectively binds to and stabilizes the quadruplex, the progress of polymerase arrests only at the quadruplex, and a characteristic "Stop Product" is synthesized.

Compounds are initially screened at a single concentration, and "hits" are re-assayed over a range of doses to determine an $IC_{50}$ value (i.e., the concentration of drug required to produce an arrest product/full-length product ratio of 1:1). These products are visualized by capillary electrophoresis.

Quadruplex/Duplex Competitor Assay

The selectivity of compounds for the target quadruplex sequence relative to duplex DNA may be measured using a competition assay (i.e., "selectivity screen"). This selectivity screen uses the stop assay as a reporter system to measure the relative ability of an externally added DNA sequence to compete with the target quadruplex structure formed in the DNA template for binding of the drug. For example, the competitors are the c-myc quadruplex sequence, which is identical to the quadruplex sequence present in the template DNA; or a plasmid DNA which mimics complex genomic duplex DNA. The degree to which each competitor successfully "soaks up" drug in solution is reflected by the quantitative decrease in synthesis of the stop product. In this manner, the relative binding affinities of drug to both the target quadruplex and duplex DNA are determined Quadrome Footprints.

Compounds may also be evaluated for their ability to bind to other native quadruplex structures of biological relevance, including quadruplex control elements that regulate a range of different oncogenes. The resulting data are used to create a Quadrome footprint.

Direct Interaction Assay.

Compounds may be evaluated for their ability to interact directly with nucleic acids capable of forming a quadruplex structure, wherein the nucleic acid is not a telomeric nucleic acid. The assay may be performed in the same or different vessels. For example, a compound may be contacted with each nucleic acid in the same vessel. Alternatively, a compound may be separately contacted with each of the nucleic acids tested in a different vessel. A telomeric nucleic acid as used herein represents a region of highly repetitive nucleic acid at the end of a chromosome. As used herein, a direct interaction is measured without the presence of a competitor nucleic acid.

An interaction between the compound and the nucleic acid may be determined for example, by measuring $IC_{50}$ values, which are indicative of the binding and/or quadruplex stabilization. The selectivity of interactions may be determined, for example, by comparing measured $IC_{50}$ values. For example, the lowest $IC_{50}$ values may be used to indicate a strong interaction between the compound and the nucleic acid, while highest $IC_{50}$ values show a poor interaction; thus, showing selectivity of interaction. The reaction products may be characterized by capillary electrophoresis.

Example 48

Pharmaceutical Properties of RBI Compounds

A cassette dosing procedure was utilized to determine pharmaceutical properties of compounds disclosed herein. In this procedure, compounds are selected for each cassette (i.e., cocktail) on the basis that mass spectrometric signals for each compound will not interfere with one another upon mass spectrometric analysis (e.g., will not overlap). The concentration of each compound in the dosing cassette often is about 20 mg/mL to achieve an oral dose level of 25 mg/kg in ICR mice. Aspects of the cassette dosing procedure are described hereafter.

MS/MS Method Development

Prepare 0.5 mL of 20 mg/mL dosing solution (in PBS or formulation vehicle) of 12 test compounds. Dilute a dosing solution 20 fold by transferring 10 μL of the stock solution into 190 μL acetonitrile containing 0.1% formic acid to achieve a final concentration of 1 mg/mL. Dilute further a 1 mg/mL solution 1,000 fold by transferring 1 μL of the stock solution into 999 μL acetonitrile containing 0.1% formic acid to achieve a final concentration of 1 μg/mL. Use the 1 μg/mL solution for mass spectrometric method development based on direct infusion. Determine parent/daughter mass spectra of each compound using multiple reaction monitoring (MRM). Compare parent/daughter mass spectra of each compound to assure no cross-reaction interference during LC-MS/MS measurements. Based on MRM mass spectra determine the composition of all cassettes.

Dosing Cassette Preparation

Mix 250 μL of four prepared dosing solutions and an oral PK internal standard (20 mg/mL each) according to cassette design to achieve a final concentration of 4 mg/mL. Vortex cassettes rigorously and ultra-sonicate to obtain a clear solution or homogeneous suspension. Use the cassette solutions to dose animals by oral route of administration at 25 mg/kg.

Animals and Dosing

All in vivo experiments follow protocols approved by the Animal Use and Care Committee. Female ICR mice (IcrTac: ICR), 8-10 weeks of age are obtained from Taconic (Hudson, N.Y.). Mice are housed on a 12 h/12 h light/dark cycle with ad libitum access to water and food. After a minimum two week acclimation period, the mice are randomized into groups with a minimum group size of four. The animals used for pharmacokinetic studies have a body-weight range of 25-35 g. A 25 mg/kg (4 mg/ml) dose of a cassette described in Example 1 is orally administered to mice that have been fasted overnight.

Blood Sample Preparation

After compound administration, serial blood samples are collected via retro-orbital puncture with a capillary tube at various time points (15, 30 minutes and 1, 2, 4, 6 and 8 hours). The samples are transferred to a heparinized 0.5 mL microcentrifuge tube and placed on ice. Plasma is separated by centrifugation and samples are stored at −80° C. until assay.

Preparation of Working Standard Solutions

Dilute a cassette dosing solution (4 mg/mL) four fold by transferring 25 μL of the stock solution into 75 μL of 50% acetonitrile containing 0.1% formic acid to achieve the concentration of 1 mg/mL. Dilute this stock solution further by serial dilutions to make 0.01, 0.1, 1 and 5 μg/mL working standard solutions.

Preparation of a Quenching Solution

Prepare 500 mL of 0.5 μg/mL solution of bioanalytical internal standard using 100% acetonitrile with 0.1% formic acid. Store the quenching solution in a tightly sealed bottle at 4° C.

Calibration Standard Preparation for Analysis

Transfer 15 μL of blank mouse plasma to a 96 well plate and precipitate plasma proteins by pipetting of 120 μL of quenching solution to all plasma aliquots. Cover the plate with a matching plate mat and mix well for 30-60 seconds using a vertical multi-tube shaker.

Add 15 μL of the working standard solution of corresponding cassette to quenched plasma and vortex the plate for an additional 30-60 seconds. Then, centrifuge the plate at 4,000 rpm for 10 minutes at 4° C. Without disturbing the plasma protein pellet, transfer 120 μL of the supernatant to a new 96 well plate and dry the sample under nitrogen using a TurboVap® plate evaporator (Caliper Life Sciences; Hopkinton, Mass.). Reconstitute dried residues with 120 μL 20% acetonitrile containing 0.1% formic acid. Vortex the plate for 30-60 seconds and subject to LC-MS/MS analysis (described hereafter).

Study Sample Preparation for Analysis

Transfer 15 μL of blank mouse plasma to a 96 well plate and precipitate plasma proteins by pipetting of 120 μL of quenching solution to all plasma aliquots. Cover the plate with a matching plate mat and mix well for 30-60 seconds using a vertical multi-tube shaker Add 15 μL of the working standard solution of corresponding cassette to quenched plasma and vortex the plate for an additional 30-60 seconds. Add 15 μL of 50% acetonitrile containing 0.1% formic acid to quenched plasma to match the matrix and vortex the plate for an additional 30-60 seconds.

Then, centrifuge the plate at 4,000 rpm for 10 minutes at 4° C. Without disturbing the plasma protein pellet, transfer 120 μl of the supernatant to a new 96 well plate and dry the sample under nitrogen using TurboVap® plate evaporator (Caliper Life Sciences; Hopkinton, Mass.). Reconstitute dried residues with 120 μL 20% acetonitrile containing 0.1% formic acid. Vortex the plate for 30-60 seconds and subject to LC-MS/MS analysis (described hereafter).

LC-MS/MS Analysis

Analyze the reaction mixtures for the amount of each chemical entity in the cassettes for the parent form according to the following HPLC conditions:

Column: PHENOMENEX® Synergi™ Polar RP, 20.0×2.0 mm, 3 μM
Guard Column: PHENOMENEX® C18, 4.0×2.0 mm
Flow Rate: 0.25 mL/min
Column Temperature: 40° C.
Sample Temperature: 10° C.
Injection Volume: 10 μL
Run Time: 3.5 min
Gradient Solvent System:
Solvent A: 0.1% Formic Acid in Water
Solvent B: 0.1% Formic Acid in Acetonitrile
Solvent Gradient Profile:

| Time, min | % A | % B |
|---|---|---|
| 0.0 | 95 | 5 |
| 1.0 | 95 | 5 |
| 1.5 | 5 | 95 |
| 2.0 | 5 | 95 |
| 2.5 | 95 | 5 |
| 3.5 | 95 | 5 |

Mass Spectrometry Parameters:
MS Mode: ESI (+)
Capillary: 3.5 kV
Cone: 40 V
Extractor: 3 V
RF Lens: 0.2 V
Source T: 120° C.
Desolvation T: 300° C.
Gas_Desolvation: 450 L/h
Gas_Cone: 72 L/h
LM Resolution: 15.0
HM Resolution: 15.0
Ion Energy: 0.5
Multiplier: 650

Pharmacokinetic Analysis

Apply noncompartmental pharmacokinetic analysis for oral administration. Record the observed Cmax and Tmax. Use linear trapezoidal rule to compute AUC (0-8) according to Gibaldi, M. and Perrier, D. Pharmacokinetics, Second Edition, Marcel Dekker, Inc., New York, 1982.

Representative cassette dosing and bioavailability data are given in Table 8, along with cell proliferation inhibition (from Alamar Blue (AB) assay (e.g., Example 45 herein) and rRNA inhibition (from quantitative PCR (QPCR) assay (e.g., Example 46 herein).

TABLE 8

Representative Cassette Dosing, Bioavailability Data and Pharmaceutical Activity Data

| Structure | AB: HCT-116 (μM) | QPCR: rDNA (μM) | Selectivity | AUC (8 hr)- Cassette | Bio-availability (% F) |
|---|---|---|---|---|---|
| [structure 1] | 0.307 | 0.318 | 7 | 2002 | |
| [structure 2] | 0.21 | 0.521 | 8 | 1190 | 10.4 |

TABLE 8-continued

Representative Cassette Dosing, Bioavailability Data and Pharmaceutical Activity Data

| Structure | AB: HCT-116 (µM) | QPCR: rDNA (µM) | Selectivity | AUC (8 hr)-Cassette | Bio-availability (% F) |
|---|---|---|---|---|---|
| 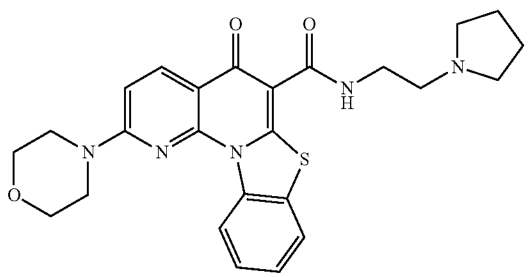 [SMILES: O=C(NCCN1CCCC1)c1c(=O)c2ccc(N3CCOCC3)nc2n2c1sc1ccccc12] | 0.059 | 0.052 | 162 | 2151 | 10.7 |
| 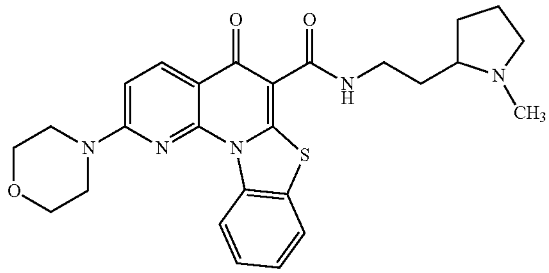 [SMILES: CN1CCCC1CCNC(=O)c1c(=O)c2ccc(N3CCOCC3)nc2n2c1sc1ccccc12] | 0.055 | 0.249 | 42 | 2586 | |
| 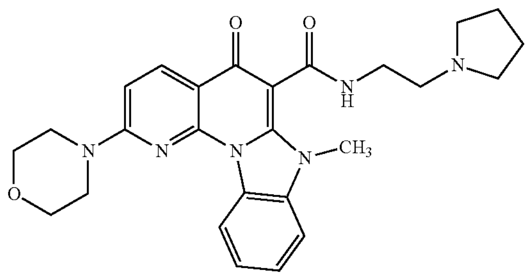 [SMILES: Cn1c2ccccc2n2c3nc(N4CCOCC4)ccc3c(=O)c(C(=O)NCCN3CCCC3)c12] | 0.075 | 0.261 | 3 | 1260 | |
| 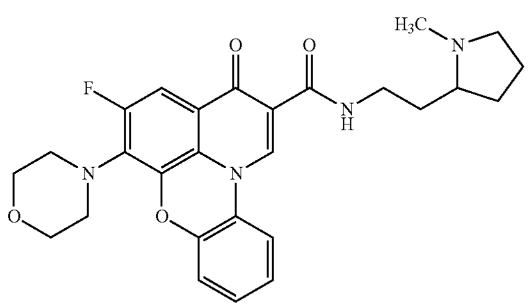 [SMILES: CN1CCCC1CCNC(=O)c1cn2c3c(c(N4CCOCC4)c(F)cc3c1=O)Oc1ccccc1-2] | 0.389 | 0.405 | 12 | 1426 | |
| 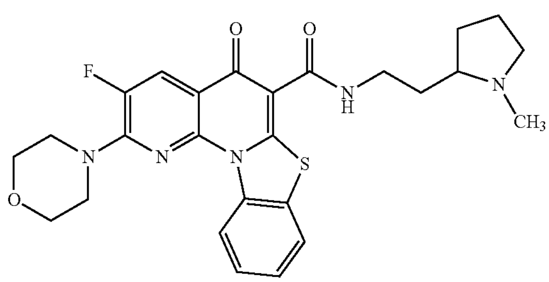 [SMILES: CN1CCCC1CCNC(=O)c1c(=O)c2cc(F)c(N3CCOCC3)nc2n2c1sc1ccccc12] | 0.337 | 0.892 | 10 | 3807 | 22.4 |

TABLE 8-continued

Representative Cassette Dosing, Bioavailability Data and Pharmaceutical Activity Data

| Structure | AB: HCT-116 (μM) | QPCR: rDNA (μM) | Selectivity | AUC (8 hr)-Cassette | Bio-availability (% F) |
|---|---|---|---|---|---|
| 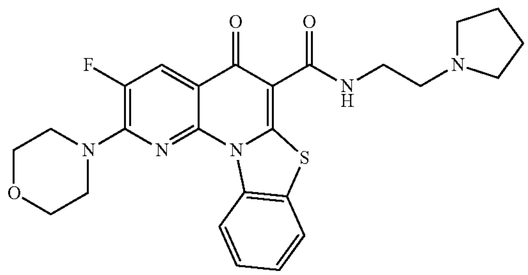 | 0.081 | 0.127 | 70 | 2261 | |
| 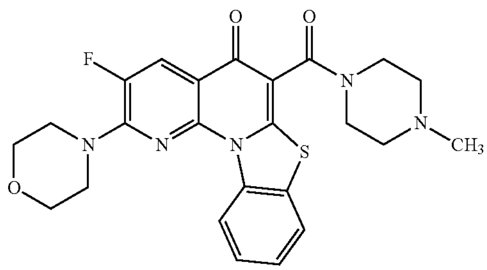 [SMILES: CN1CCN(C(=O)c2c(=O)c3cc(F)c(N4CCOCC4)nc3n3c2sc2ccccc23)CC1] | 0.386 | 1.153 | 7 | 6163 | 30.3 |
| 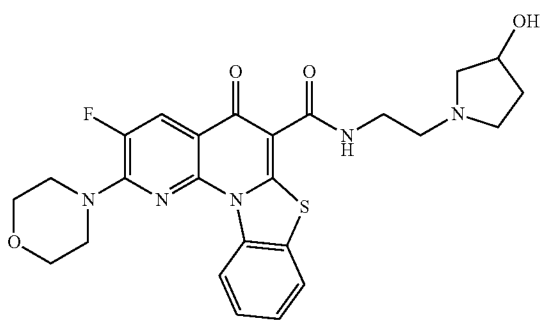 [SMILES: O=C(NCCN1CCC(O)C1)c1c(=O)c2cc(F)c(N3CCOCC3)nc2n2c1sc1ccccc12] | 0.055 | 0.01 | 10 | 1086 | |
| 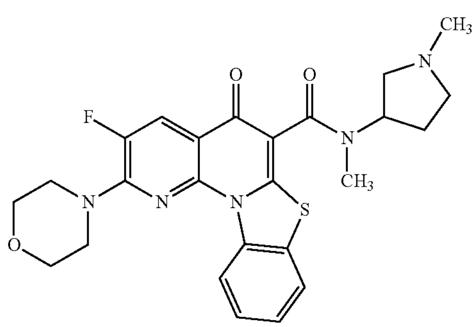 [SMILES: CN1CCC(N(C)C(=O)c2c(=O)c3cc(F)c(N4CCOCC4)nc3n3c2sc2ccccc23)C1] | 0.174 | 0.381 | 5 | 2133 | |
| 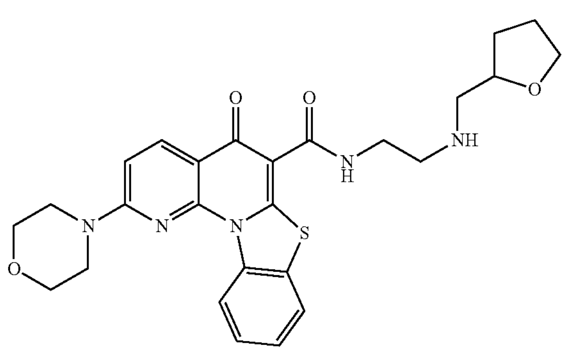 [SMILES: O=C(NCCNCC1CCCO1)c1c(=O)c2ccc(N3CCOCC3)nc2n2c1sc1ccccc12] | 0.116 | 0.04 | 119 | 1904 | 2 |

TABLE 8-continued
Representative Cassette Dosing, Bioavailability Data and Pharmaceutical Activity Data
| Structure | AB: HCT-116 (µM) | QPCR: rDNA (µM) | Selectivity | AUC (8 hr)- Cassette | Bio- availability (% F) |
|---|---|---|---|---|---|
| 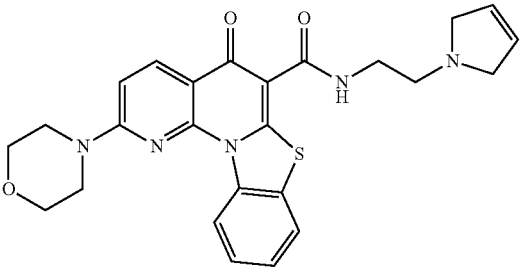 [SMILES: O=C(NCCN1CC=CC1)c1c(=O)c2ccc(N3CCOCC3)nc2n2c1sc1ccccc12] | 0.13 | 0.064 | 22 | 7939 | 27.5 |
| 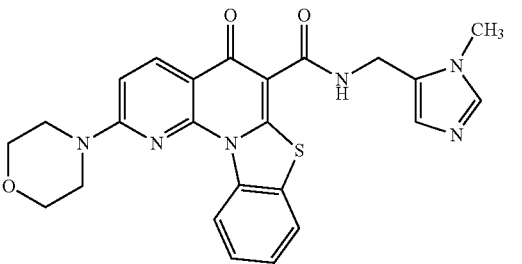 [SMILES: Cn1cncc1CNC(=O)c1c(=O)c2ccc(N3CCOCC3)nc2n2c1sc1ccccc12] | 0.174 | 0.262 | 60 | 2915 | 12.4 |
| 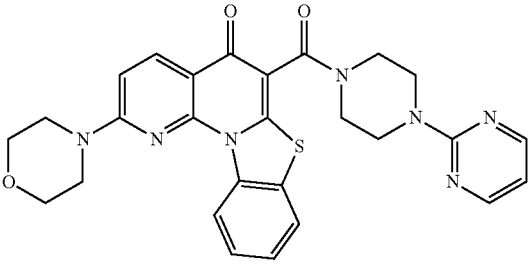 | 0.461 | 0.578 | 13 | 15344 | 31.1 |
| 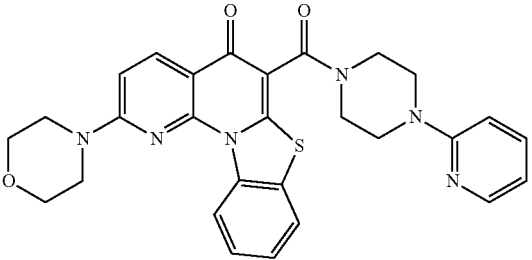 [SMILES: O=C(c1c(=O)c2ccc(N3CCOCC3)nc2n2c1sc1ccccc12)N1CCN(c2ccccn2)CC1] | 0.21 | 0.723 | 17 | 1742 | |
| 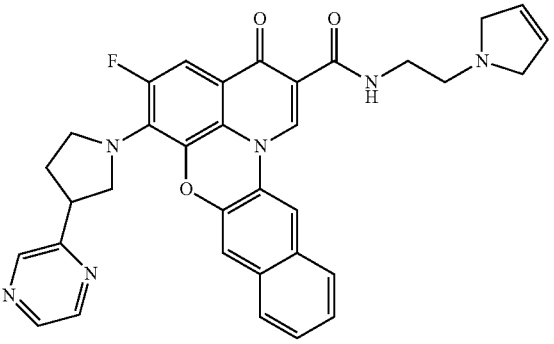 [SMILES: O=C(NCCN1CC=CC1)c1cn2c3c(c(N4CCC(c5cnccn5)C4)c(F)cc3c1=O)Oc1cc3ccccc3cc1-2] | 0.398 | 1.041 | 24 | 8042 | |

TABLE 8-continued

Representative Cassette Dosing, Bioavailability Data and Pharmaceutical Activity Data

| Structure | AB: HCT-116 (μM) | QPCR: rDNA (μM) | Selectivity | AUC (8 hr)-Cassette | Bio-availability (% F) |
|---|---|---|---|---|---|
| *[structure]* | 0.098 | 0.032 | 64 | 632 | |
| *[structure]* | 0.392 | 0.042 | 3 | 1999 | |
| *[structure]* | 0.265 | 0.102 | 89 | 4362 | |
| *[structure]* | 0.135 | 0.059 | 48 | 5015 | |
| *[structure]* | 0.535 | 0.502 | 15 | 9447 | |

TABLE 8-continued
Representative Cassette Dosing, Bioavailability Data and Pharmaceutical Activity Data
| Structure | AB: HCT-116 (μM) | QPCR: rDNA (μM) | Selectivity | AUC (8 hr)- Cassette | Bio-availability (% F) |
|---|---|---|---|---|---|
| 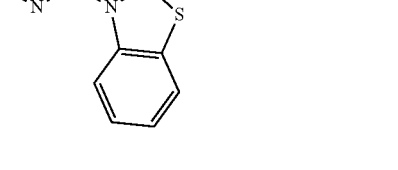 | 0.484 | 0.147 | 70 | 2223 | |
| 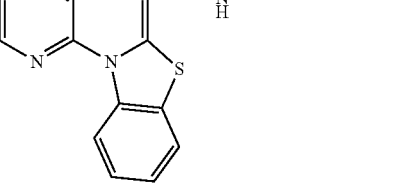 | 0.473 | 0.431 | 24 | 4028 | |
| 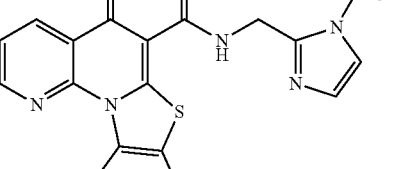 | 0.145 | 0.173 | 9 | 5491 | 17.9 |
| 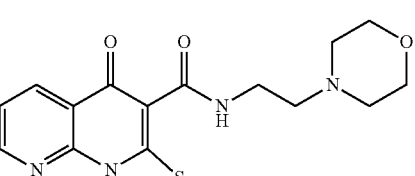 | 0.454 | 0.496 | 16 | 2985 | |
| 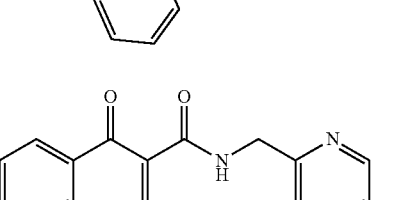 | | 22.632 | 1 | 90599 | |

TABLE 8-continued

Representative Cassette Dosing, Bioavailability Data and Pharmaceutical Activity Data

| Structure | AB: HCT-116 (µM) | QPCR: rDNA (µM) | Selectivity | AUC (8 hr)-Cassette | Bio-availability (% F) |
|---|---|---|---|---|---|
| 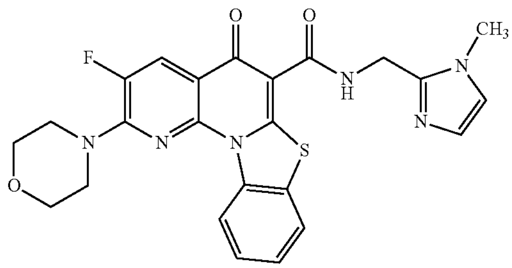 [SMILES: Cn1ccnc1CNC(=O)c1c(=O)c2cc(F)c(N3CCOCC3)nc2n2c1sc1ccccc12] | 0.199 | 0.134 | 11 | 20272 | 15.8 |
| 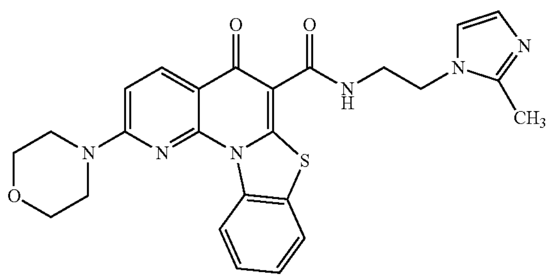 [SMILES: Cc1nccn1CCNC(=O)c1c(=O)c2ccc(N3CCOCC3)nc2n2c1sc1ccccc12] | 0.166 | 0.084 | 21 | 4378 |  |
| 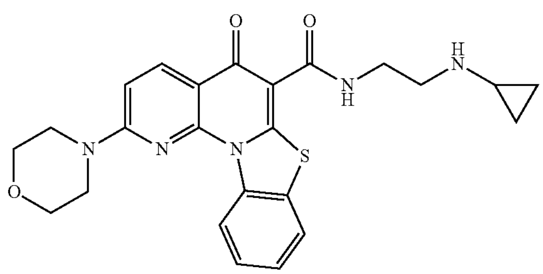 [SMILES: O=C(NCCNC1CC1)c1c(=O)c2ccc(N3CCOCC3)nc2n2c1sc1ccccc12] | 0.065 | 0.1 | 39 | 5372 | 43.3 |
| 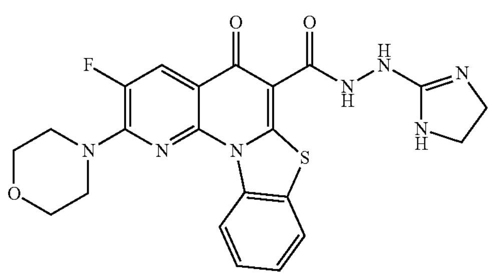 [SMILES: O=C(NNC1=NCCN1)c1c(=O)c2cc(F)c(N3CCOCC3)nc2n2c1sc1ccccc12] | 0.001 | 0.028 | 893 | 2429 | 0.1 |
| 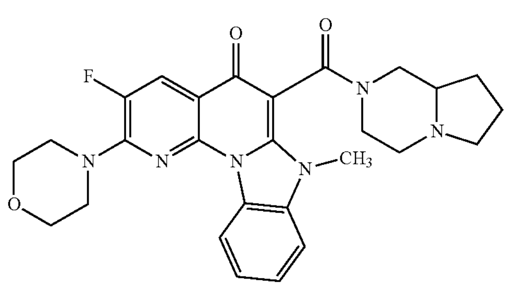 [SMILES: Cn1c2ccccc2n2c3nc(N4CCOCC4)c(F)cc3c(=O)c(C(=O)N3CCN4CCCC4C3)c12] | 0.843 | 0.841 | 10 | 3206 |  |

TABLE 8-continued

Representative Cassette Dosing, Bioavailability Data and Pharmaceutical Activity Data

| Structure | AB: HCT-116 (μM) | QPCR: rDNA (μM) | Selectivity | AUC (8 hr)- Cassette | Bio-availability (% F) |
|---|---|---|---|---|---|
| 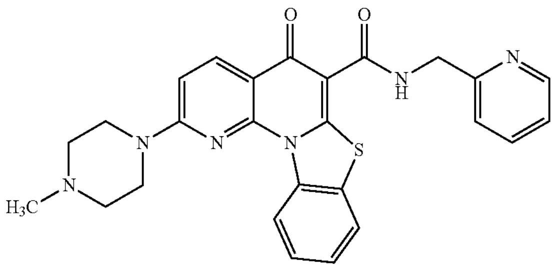 [SMILES: CN1CCN(c2ccc3c(=O)c(C(=O)NCc4ccccn4)c4sc5ccccc5n4c3n2)CC1] | 0.147 | 0.112 | 111 | 51054 | 41.4 |
| 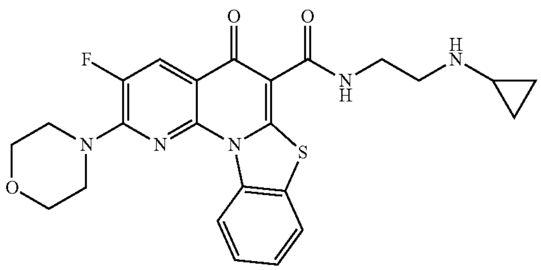 [SMILES: O=C(NCCNC1CC1)c1c(=O)c2cc(F)c(N3CCOCC3)nc2n2c1sc1ccccc12] | 0.132 | 0.248 | 53 | 5154 | |
| 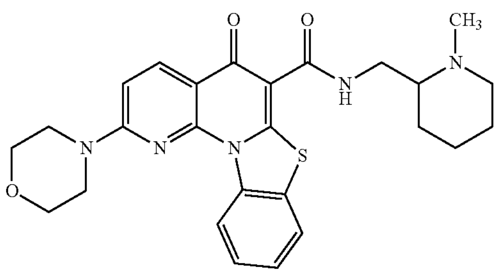 [SMILES: CN1CCCCC1CNC(=O)c1c(=O)c2ccc(N3CCOCC3)nc2n2c1sc1ccccc12] | 0.006 | 0.009 | 2778 | 1048 | |
| 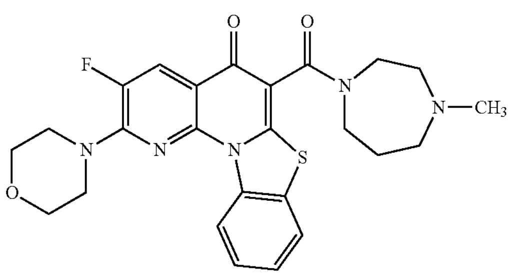 [SMILES: CN1CCCN(C(=O)c2c(=O)c3cc(F)c(N4CCOCC4)nc3n3c2sc2ccccc23)CC1] | 0.3 | 0.233 | 10 | 4226 | |
| 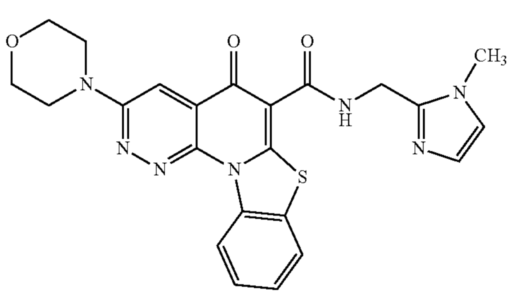 [SMILES: Cn1ccnc1CNC(=O)c1c(=O)c2cc(N3CCOCC3)nnc2n2c1sc1ccccc12] | 0.174 | 0.334 | 53 | 3779 | |

TABLE 8-continued

Representative Cassette Dosing, Bioavailability Data and Pharmaceutical Activity Data

| Structure | AB: HCT-116 (μM) | QPCR: rDNA (μM) | Selectivity | AUC (8 hr)-Cassette | Bio-availability (% F) |
|---|---|---|---|---|---|
| 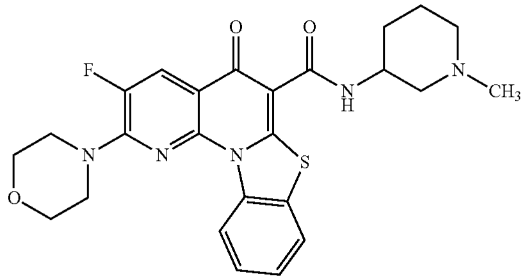 [SMILES: CN1CCCC(NC(=O)c2c(=O)c3cc(F)c(N4CCOCC4)nc3n3c2sc2ccccc23)C1] | 0.027 | 0.029 | 862 | 1026 | |
| 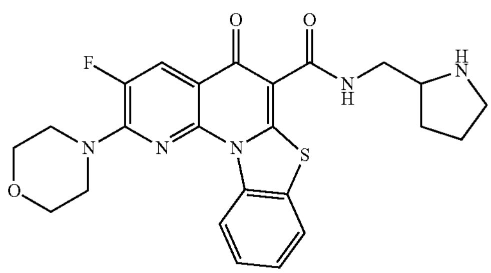 [SMILES: O=C(NCC1CCCN1)c1c(=O)c2cc(F)c(N3CCOCC3)nc2n2c1sc1ccccc12] | 0.009 | 0.016 | 25 | 1049 | |
| 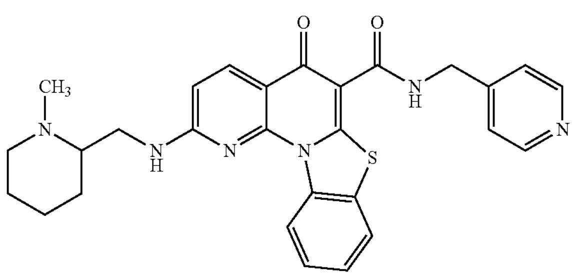 [SMILES: CN1CCCCC1CNc1ccc2c(=O)c(C(=O)NCc3ccncc3)c3sc4ccccc4n3c2n1] | 0.008 | 0.067 | 39 | 790 | |
| 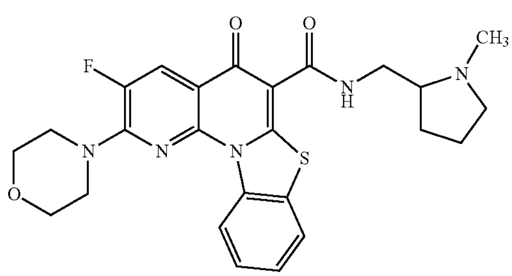 [SMILES: CN1CCCC1CNC(=O)c1c(=O)c2cc(F)c(N3CCOCC3)nc2n2c1sc1ccccc12] | 0.128 | 0.383 | 45 | 3957 | |
| 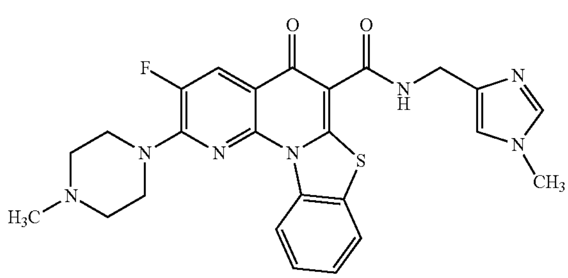 [SMILES: CN1CCN(c2nc3c(cc2F)c(=O)c(C(=O)NCc2cn(C)cn2)c2sc4ccccc4n23)CC1] | 0.303 | 0.139 | 69 | 45116 | |

| Structure | AB: HCT-116 (μM) | QPCR: rDNA (μM) | Selectivity | AUC (8 hr)- Cassette | Bio-availability (% F) |
|---|---|---|---|---|---|
| (structure) | 0.286 | 0.176 | 16 | 3176 | |
| (structure) | 0.202 | 0.127 | 4 | 5195 | |
| (structure) | 0.391 | 0.069 | 13 | 165786 | |

Example 49

Evaluation of Pharmacokinetic Properties

The pharmacokinetics properties of drugs are investigated in ICR mice following an intravenous (IV) bolus and oral (PO) doses of drug at 5 mg/kg and 25 mg/kg respectively. Blood samples are collected at predetermined times and the plasma separated. Plasma is separated from the blood samples collected at 5, 15 and 30 minutes and 1, 2, 4, 8 and 24 hours post-dose.

Drug levels are quantified by the LC/MS/MS method described below. Noncompartmental pharmacokinetic analysis is applied for intravenous administration. A linear trapezoidal rule is used to compute AUC(0-24) or AUC(0-8). The terminal $t_{1/2}$ and $C_0$ are calculated using the last three and the first three data points, respectively Bioanalysis is performed using a Quattro Micro LC/MS/MS instrument in the MRM detection mode, with an internal standard (IS). Briefly, 15 μL plasma samples are prepared for analysis using protein precipitation with 120 μL of acetonitrile. The supernatants are transferred into a 96 well plate and subjected to LC-MS/MS analysis using a PHENOMENEX® Polar-RP HPLC column. The mobile phases are 10 mM $NH_4HCO_3$ in water (Solution-A) and 10 mM $NH_4HCO_3$ in methanol (Solution-B). The column is initially equilibrated with 25% Solution-B and followed with 100% Solution B over 5 minutes. The method has a dynamic range from 1 to 10,000 ng/mL. Quantitation of the analytes is performed in the batch mode with two bracketing calibration curves according to the bioanalytical sample list.

Example 50

Cytochrome P450 (CYP450) Inhibition Assay

The compounds of the present invention may be evaluated for potential inhibitory activity against cytochrome P450 isoenzymes. Generally, six reaction tubes with 100 μL of a solution containing 50 mM potassium phosphate, pH 7.4, 2.6 mM NADP+, 6.6 mM glucose 6-phosphate, 0.8 U of glucose 6-phosphate dehydrogenase/mL and 1:6 serial dilutions of the test compound will be prepared along with six tubes of 1:6 serial dilutions of a suitable positive control inhibitor. The reactions will be initiated by adding 100 μL of a pre-warmed enzyme/substrate solution to the reaction tubes. A zero time-point control reaction will be prepared by adding 50 μL of acetonitrile to 100 μL of cofactor solution to inactivate the enzymes, then adding 100 μL of enzyme/substrate solution. A control reaction with no inhibitor may also be prepared. After a suitable incubation at 37° C., the reactions will be terminated by the addition of 50 μL of acetonitrile. The reactions will be analyzed for the metabolite forms of the probe substrate using LC/MS/MS.

Example 51

Evaluation of Compound Efficacy in Tumor Suppression

A representative experiment for evaluating the efficacy of compounds of the present invention in athymic nude mouse models of human carcinoma may be designed as follows. Male or female animals (mouse, Sim) (NCR, nu/nu) aged five to six weeks and weighing more than 20 grams will be used. The animals will be purposely bred and will be experimentally naïve at the outset of the study. Tumors will be propagated either from injected cells or from the passage of tumor fragments. Cell lines to be used include, but are not limited to, alia Paca-2, HPAC, Hs700T, Panc10.05, Panc 02.13, PL45, SW 190, Hs 766T, CFPAC-1 and PANC-1.

Cell implantation. One to ten million cells suspended in 0.1 ml culture media with or without Matrigel (Collaborative Biomedical Products, Inc, Bedford, Mass.) will be inoculated subcutaneously in the right flank of sixty animals. There will only be one injection per animal. Within 7-14 days of injection tumors will develop to a study use size of approximately 1.0 $cm^3$. A small subset (<10/60) animals will be considered. Donors and tumors will be grown 10-28 days and to a size of 1.5 $cm^3$ in order to be used for serial transplantation.

Fragment transplantation. Donor animals will be euthanized and tumors surgically excised and cut into 2 $mm^3$ size fragments using aseptic technique Animals to be implanted will be lightly anesthetized with isoflurane. The area to be implanted will be cleansed with 70% alcohol and betadine. A single fragment will then be implanted subcutaneously using a trocar.

Efficacy studies. Groups of 50-60 tumor bearing animals will be randomly divided. For example, in a representative study, animals may be randomly divided into three to eight groups containing 7 animals each, as described in Table 9.

Dosing Procedure. Compounds will be administered QD, QOD, Q3D or once weekly via IP, IV (lateral tail vein) or PO. Animals will be dosed in a systematic order that distributes the time of dosing similarly across all groups. For bolus IP and PO dosing, animals will be manually restrained. For IV bolus dosing or short term IV infusion (one minute), animals will be mechanically restrained but not sedated. Disposable sterile syringes will be used for each animal/dose. A test compound in combination with about 10-100 mg/kg (e.g., about 40 mg/kg) chemotherapeutic agent such as gemcitabine also will be tested, normally by IP administration once per week.

Example 52

Evaluation of Maximum Tolerated Doses

A representative experiment for evaluating the maximum tolerate dose (MTD) of compounds of the present invention may be designed as follows.

Acute Toxicity Studies. In a representative study to determine the MTD after a single dose, sixty naive animals, for example, will be randomly divided into groups containing 10 animals (5 male and 5 female) and will receive either one compound via two routes of administration or two compounds via a single route of administration. A single 50 mg/kg IV dose has been shown to be tolerated, and is used as the preliminary low dose levels. The low dose for oral studies is based on projected tolerability and will be adjusted downward if necessary. A representative design of dose levels, dose volumes and dose solution concentration are described in Table 10.

TABLE 10

| Group No. | Number of Males and Females | Dose Level (mg/kg) | Dose Vol. (μL) | Dose Solution Conc. (mg/mL) | Number Euthanized on: Day 7 |
|---|---|---|---|---|---|
| | | Test compound #1 | | | |
| 1 | N = 5 M<br>N = 5 F | 50 IV<br>100 PO | 250 IV<br>500 PO | 5 IV<br>5 PO | all |

TABLE 9

| Group No. | Number of Males/ Females | Dose Level | Dose Vol. (μL) | Dose Solution Conc. (mg/mL) | Number Euthanized on: Day 28-42 |
|---|---|---|---|---|---|
| 1 | N = 7 | Negative Control* | 250 | | all |
| 2 | N = 7 | Positive Control** | 10-400 IP<br>10-250 IV<br>125-500 PO | 2 to 5 IP<br>2.5 to 5 IV<br>≤10 PO | all |
| | | Test Compound | | | |
| Groups 3-8 | N = 7/grp<br><56 total | 1 to 25 IP<br>1 to 50 IV<br>50 to 200 PO | 10-400 IP<br>10-250 IV<br>125-500 PO | 2.5 to 5 IP<br>2.5 to 5 IV<br>10 PO | all |

*Vehicle/Diluent
**Commercially available anticancer compounds including, but not limited to, Taxol, CPT11 and Gemcitabine will be used as positive controls.

TABLE 10-continued

| Group No. | Number of Males and Females | Dose Level (mg/kg) | Dose Vol. (µL) | Dose Solution Conc. (mg/mL) | Number Euthanized on: Day 7 |
|---|---|---|---|---|---|
| | | Test compound #1 | | | |
| 2 | N = 5 M<br>N = 5 F | 75 IV<br>200 PO | 250 IV<br>500 PO | 8.25 IV<br>10 PO | all |
| | | Test compound #1 | | | |
| 3 | N = 5 M<br>N = 5 F | 100 IV<br>300 PO | 250 IV<br>500 PO | 10 IV<br>15 PO | all |
| | | Test compound #2 | | | |
| 4 | N = 5 M<br>N = 5 F | 50 IV<br>100 PO | 250 IV<br>500 PO | 5 IV<br>5 PO | all |
| | | Test compound #2 | | | |
| 5 | N = 5 M<br>N = 5 F | 75 IV<br>200 PO | 250 IV<br>500 PO | 8.25 IV<br>10 PO | all |
| | | Test compound #2 | | | |
| 6 | N = 5 M<br>N = 5 F | 100 IV<br>300 PO | 250 IV<br>500 PO | 10 IV<br>15 PO | all |

Sub-Chronic Studies. In a representative study to characterize dose-response relationships following repeated dosing, twenty-five naive animals, for example, will be randomly divided into groups containing 5 animals each as described in Table 11. Each two week study will test only one compound via a single route of administration at an optimal dose derived from data collected in prior acute toxicity studies.

TABLE 11

| Group No. | Number of Males or Females | Dose Level (mg/kg) | Dose Vol. (µL) | Dose Solution Conc. (mg/mL) | Number Euthanized on: Day 14 |
|---|---|---|---|---|---|
| 1 | N = 5 | Negative Control | 250 IV<br>500 PO | Depends on Dose Level | all |
| 2<br>QD | N = 5 | Test Compound As Determined in MTD Studies | 250 IV<br>500 PO | Depends on Dose Level | all |
| 3<br>QOD | N = 5 | Test Compound As Determined in MTD Studies | 250 IV<br>500 PO | Depends on Dose Level | all |
| 4<br>Q3D | N = 5 | Test Compound As Determined in MTD Studies | 250 IV<br>500 PO | Depends on Dose Level | all |
| 5<br>Q7D | N = 5 | Test Compound As Determined in MTD Studies | 250 IV<br>500 PO | Depends on Dose Level | all |

Dosing Procedure. Compounds will be administered QD, QOD, Q3D or Q7D via IV (lateral tail vein) or PO. Animals will be dosed in a systematic order that distributes the time of dosing similarly across all groups. For PO dosing, animals will be manually restrained. For IV bolus dosing or short term IV infusion (one minute), animals will be mechanically restrained but not sedated. Disposable sterile syringes will be used for each animal/dose.

Example 53

Pharmaceutical Activity of Compounds A1, A2 and A3

Inhibitory activity on cell proliferation of Compounds A1, A2 and A3 was determined using an Alamar Blue cell viability assay (e.g., Example 39 herein) using a variety of cell types that are representative of different cancers Inhibition values ($IC_{50}$) are presented in micromolar concentrations in the following table (Table 12).

TABLE 12

| | | | $IC_{50}$ (micromolar) | | |
|---|---|---|---|---|---|
| Disease | Cell-Line | Cell-type | A1 | A2 | A3 |
| Prostate | LNCAP | Fibroblastoid | 0.077 | 0.029 | 0.045 |
| | PC-3 | Epithelial | 0.600 | 0.089 | 0.563 |
| Colorectal | HCT-116 | Epithelial | 0.097 | 0.032 | 0.093 |
| | HT-29 | Epithelial | 0.073 | 0.042 | 0.102 |
| | COLO-205 | Epithelial | | 0.096 | |
| Lung | H1299 | NSCL | 0.112 | 0.069 | 0.102 |
| | H460 | Epithelial | 0.142 | 0.090 | 0.123 |
| | SK-MES-1 | Sqaumous carcinoma | 0.105 | 0.021 | 0.134 |
| Pancreas | Miapaca-2 | Epithelial | 0.103 | 0.036 | 0.122 |
| | Miapaca-R5 | Epithelial | 0.149 | 0.034 | 0.133 |
| | BXPC3 | Epithelial | 0.056 | 0.035 | 0.071 |
| | PANC-1 | Epithelial | 0.148 | | 0.103 |
| Breast | MCF-7 | Mammary carcinoma | 0.348 | | 0.267 |
| | MDA-MB-231 | Epithelial | 0.105 | 0.052 | 0.139 |
| Hematopoetic | K562 | Lymphoblast | 0.140 | 0.042 | 0.120 |
| | Jurkat | Lymphoma | 0.069 | 0.025 | 0.060 |
| | HL60 | Lymphoma | 0.264 | 0.083 | 0.160 |
| | HL60/MX2 | Lymphoma | 0.244 | 0.147 | 0.219 |
| Skin | A375 | Epithelial | 0.090 | 0.023 | 0.070 |
| Ovary | SK-OV-3 | Epithelial | 0.215 | 0.064 | 0.279 |
| Bone | U2OS | Epithelial | 0.752 | 0.089 | 0.476 |
| | Saos-2 | Epithelial | 0.264 | 0.124 | 0.249 |

Compounds A1, A2 and A3 also were tested for tumor inhibition in xenograft rodents. Rodents having A375 cell xenograft tumors were administered 100 mg/kg, 75 mg/kg and 100 mg/kg doses of Compound A1, A2 and A3, respectively, by oral delivery twice a day. Each of these compounds significantly inhibited A375 tumor growth over a period of seven days relative to an untreated control group. Also, rodents having MiaPaCa xenograft tumors were administered 100 mg/kg doses of Compound A1 and A3 by oral delivery twice per day. Each of these compounds significantly inhibited MiaPaCa tumor growth over a period of twenty-two days relative to an untreated control group.

Example 54

Representative Cell Based $IC_{50}$ Data

Inhibitory activity on cell proliferation of representative compounds of the invention was determined using an Alamar Blue cell viability assay (e.g., Example 39 herein) using a variety of cell types that are representative of different cancers Inhibition values (IC$_{50}$) are presented in micromolar concentrations in Table 13 and Table 14.
TABLE 13
| Structure | AB: MV-4-11 (IC50, μM) | AB: PC3 (IC50, μM) | AB: HCT-116 (IC50, μM) | AB: K-562 (IC50, μM) | M + 1 |
| --- | --- | --- | --- | --- | --- |
| 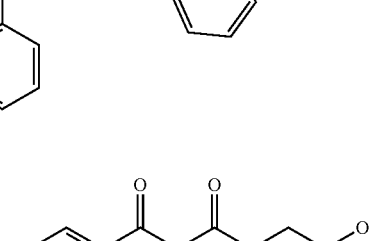 | >10 | >10 | >10 | >10 | 471 |
| 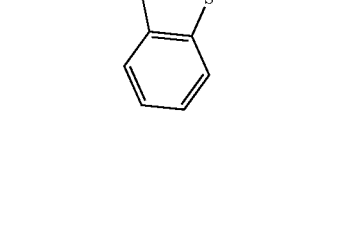 | | 3.736 | 0.133 | | 489 |
| 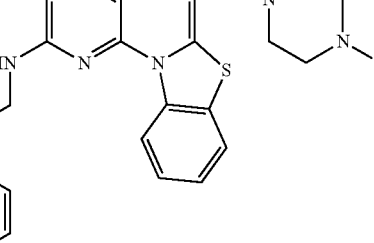 | 0.543 | 6.666 | 2.507 | 3.127 | 514 |
| 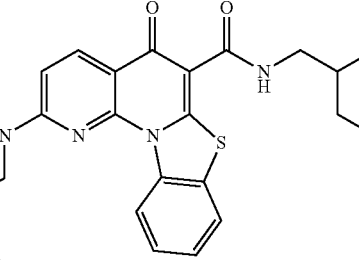 | | 0.633 | 0.267 | | 542 |

TABLE 13-continued
| Structure | AB: MV-4-11 (IC50, μM) | AB: PC3 (IC50, μM) | AB: HCT-116 (IC50, μM) | AB: K-562 (IC50, μM) | M + 1 |
|---|---|---|---|---|---|
| 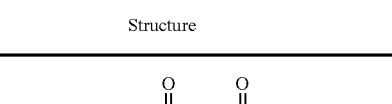 | 5.032 | 6.08 | >10 | >10 | 485 |
TABLE 14
| Structure | AB: MV-4-11 (IC50, μM) | AB: K-562 (IC50, μM) | AB: THP-1 (IC50, μM) | AB: PC3 (IC50, μM) | AB: MiaPaCa (IC50, μM) |
|---|---|---|---|---|---|
| 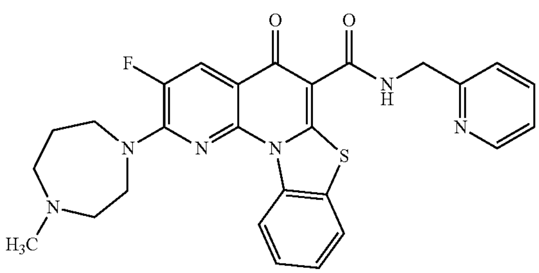 [SMILES: CN1CCCN(c2nc3c(cc2F)c(=O)c(C(=O)NCc2ccccn2)c2sc4ccccc4n23)CC1] | 0.043 | 0.118 | 1.334 | 7.773 | 0.941 |
|  | <3.e-002 | 0.032 | 0.356 | 2.485 | 0.133 |
|  | <3.e-002 | 0.095 | 1.064 | 6.59 | 0.131 |

TABLE 14-continued

| Structure | AB: MV-4-11 (IC50, μM) | AB: K-562 (IC50, μM) | AB: THP-1 (IC50, μM) | AB: PC3 (IC50, μM) | AB: MiaPaCa (IC50, μM) |
|---|---|---|---|---|---|
| (structure 1) | <3.e-002 | 0.11 | 0.59 | 1.212 | 0.352 |
| (structure 2) | 0.124 | 0.267 | 1.317 | 1.804 | 0.359 |
| (structure 3) | 0.032 | 0.051 | 0.571 | 2.645 | <0.12 |
| (structure 4) | 0.084 | 0.101 | | | 0.637 |

Example 55

Representative Embodiments

The following embodiments are offered to illustrate but not to limit the invention 1. A compound of Formula (I),

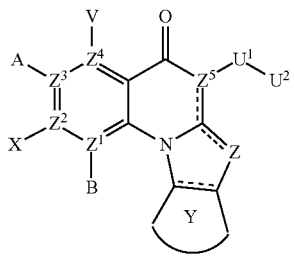

or a pharmaceutically acceptable salt or ester thereof;
wherein ----- indicates an optionally unsaturated bond;
each of B, X, A or V is absent if $Z^1$, $Z^2$, $Z^3$ and $Z^4$, respectively, is N; and
each of B, X, A and V is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$, when each of $Z^1$, $Z^2$, $Z^3$ and $Z^4$, respectively, is C;
Z is O, S, $CR^4{}_2$, $NR^4CR^4$, $CR^4NR^4$, $CR^4$, $NR^4$ or N;
each of $Z^1$, $Z^2$, $Z^3$ and $Z^4$ is independently C or N, provided any three N are non-adjacent;
$Z^5$ is C; or $Z^5$ may be N when Z is N;
Y is an optionally substituted 5-6 membered carbocyclic or heterocyclic ring;
$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when $Z^5$ is N or $U^2$ is H;
$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;
in each —$NR^1R^2$, $R^1$ and $R^2$ together with N may form an optionally substituted azacyclic ring, optionally containing an additional heteroatom selected from N, O and S as a ring member;
$R^1$ is H or C1-C6 alkyl, optionally substituted with one or more halogens, or =O;
$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;
each $R^4$ is independently H, or C1-C6 alkyl; or $R^4$ may be —W, -L-W or -L-N(R)—$W^0$;
each R and $R^0$ is independently H or C1-C6 alkyl;
L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;
W is an optionally substituted 4-7 membered azacyclic ring, optionally containing an additional heteroatom selected from N, O and S as a ring member;
$W^0$ is an optionally substituted 3-4 membered carbocyclic ring, or a C1-C6 alkyl group substituted with from 1 to 4 fluorine atoms;
provided one of $U^2$, V, A, X and B is a secondary amine $A^2$ or a tertiary amine $A^3$, wherein
the secondary amine $A^2$ is —NH—$W^0$, and
the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member;
with the proviso that when $Z^1$ is N, $Z^2$ and $Z^4$ are C, $Z^5$ is C, $U^1$ is —C(O)NH—, $U^2$ is -L-W, and L is an ethylene linker, one of V, A, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

2. The compound of embodiment 1, wherein $Z^1$ is N, and each of $Z^2$, $Z^3$ and $Z^4$ is C.

3. The compound of embodiment 1 or 2, wherein $U^2$ is —W or -L-W, where W is an optionally substituted 5-6 membered unsaturated or aromatic azacyclic ring, optionally containing an additional heteroatom selected from N, O and S; or W is an optionally substituted 5-7 membered saturated azacyclic ring containing an additional heteroatom selected from N and S.

4. The compound of embodiment 1 or 2, wherein $U^2$ is -L-N(R)—$W^0$.

5. The compound of any one of embodiments 1-4, wherein Y is an optionally substituted phenyl ring.

6. A compound of Formula (II),

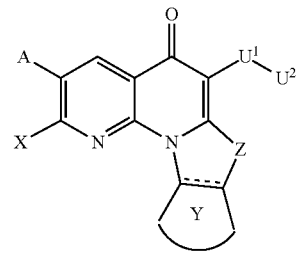

or a pharmaceutically acceptable salt or ester thereof;
wherein ----- indicates an optionally unsaturated bond;
each of A and X is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;
Z is O, S, $CR^4{}_2$, $NR^4CR^4$, $CR^4NR^4$ or $NR^4$;
Y is an optionally substituted 5-6 membered carbocyclic or heterocyclic ring;
$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when $U^2$ is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, A, and X is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member;

with the proviso that when $U^1$ is —C(O)NH—, $U^2$ is -L-W, and L is an ethylene linker, one of A and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

7. The compound of embodiment 6, wherein at least one of A and X is a tertiary amine $A^3$.

8. The compound of embodiment 6 or 7, wherein $A^3$ is selected from the group consisting of imidazole, imidazoline, pyrroline, piperidine, piperazine, morpholine, thiomorpholine and homopiperazine.

9. The compound of embodiment 6, 7 or 8, wherein $U^1$ is —C(=T)N(R)—, T is O, and $U^2$ is -L-W or -L-N(R)—$W^0$.

10. A compound of Formula (III),

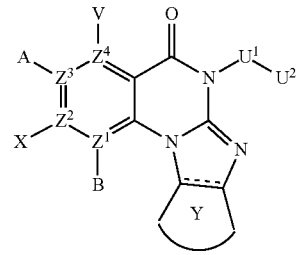

or a pharmaceutically acceptable salt or ester thereof;

wherein ----- indicates an optionally unsaturated bond; and each of B, X, A or V is absent if $Z^1$, $Z^2$, $Z^3$ and $Z^4$, respectively, is N; and each of B, X, A and V is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$, when each of $Z^1$, $Z^2$, $Z^3$ and $Z^4$, respectively, is C;

each of $Z^1$, $Z^2$, $Z^3$ and $Z^4$ is independently C or N, provided any three N are non-adjacent;

Y is an optionally substituted 5-6 membered carbocyclic or heterocyclic ring;

$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when $Z^5$ is N or $U^2$ is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, V, A, X and B is a secondary amine $A^2$ or a tertiary amine $A^3$, wherein
the secondary amine $A^2$ is —NH—$W^0$, and
the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member.

11. A compound of Formula (IV),

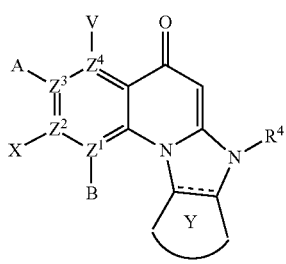

(IV)

or a pharmaceutically acceptable salt or ester thereof;
wherein ---- indicates an optionally unsaturated bond;
each of B, X, A or V is absent if $Z^1$, $Z^2$, $Z^3$ and $Z^4$, respectively, is N; and
each of B, X, A and V is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$, when each of $Z^1$, $Z^2$, $Z^3$ and $Z^4$, respectively, is C;
each of $Z^1$, $Z^2$, $Z^3$ and $Z^4$ is independently C or N, provided any three N are non-adjacent;
Y is an optionally substituted 5-6 membered carbocyclic or heterocyclic ring;
in each —$NR^1R^2$, $R^1$ and $R^2$ together with N may form an optionally substituted azacyclic ring, optionally containing an additional heteroatom selected from N, O and S as a ring member;
$R^1$ is H or C1-C6 alkyl, optionally substituted with one or more halogens, or =O;
$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;
$R^4$ is —W, -L-W or -L-N(R)—$W^0$; and
each R is independently H or C1-C6 alkyl;
L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;
W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

12. A compound of Formula (V),

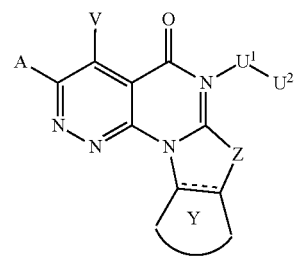

(V)

or a pharmaceutically acceptable salt or ester thereof;
---- indicates an optionally unsaturated bond;
A and V independently are H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;
Z is O, S, $CR^4{}_2$, $NR^4CR^4$, $CR^4NR^4$ or $NR^4$;
Y is an optionally substituted 5-6 membered carbocyclic or heterocyclic ring;
$U^1$ is —C(=T)N(R)—, —C(=T)N(R)O—, —C(=T)-, —$SO_2$N(R)—, —$SO_2$N(R)N($R^0$)—, —$SO_2$—, or —$SO_3$—, where T is O, S, or NH; or $U^1$ may be a bond when $U^2$ is H;
$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W or -L-N(R)—$W^0$, $A^2$ or $A^3$;
in each —$NR^1R^2$, $R^1$ and $R^2$ together with N may form an optionally substituted azacyclic ring, optionally containing an additional heteroatom selected from N, O and S as a ring member;
$R^1$ is H or C1-C6 alkyl, optionally substituted with one or more halogens, or =O;
$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;
each $R^4$ is independently H, or C1-C6 alkyl; or $R^4$ may be —W, -L-W or -L-N(R)—$W^0$;
each R and $R^0$ is independently H or C1-C6 alkyl;
L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;
W is an optionally substituted 4-7 membered azacyclic ring, optionally containing an additional heteroatom selected from N, O and S as a ring member;
$W^0$ is an optionally substituted 3-4 membered carbocyclic ring, or a C1-C6 alkyl group substituted with from 1 to 4 fluorine atoms;

provided one of $U^2$, A, and V is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

13. A compound of Formula (VI), (VI)

or a pharmaceutically acceptable salt or ester thereof; wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that: (i) zero, one or two of $X^2$, $X^3$, $X^4$, $X^5$, $X^6$ and $X^7$ are $NR^4$; (ii) when $X^1$ is N, both of $X^2$ and $X^7$ are not $NR^4$; (iii) when $X^1$ is N, $X^3$ and $X^6$ are not $NR^4$; and (iv) when $X^1$ is CH and two of $X^2$, $X^3$, $X^4$, $X^5$, $X^6$ and $X^7$ are $NR^4$, the two $NR^4$ are located at adjacent ring positions or are separated by two or more other ring positions;

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

14. The compound of embodiment 13, wherein $X^1$ is CH and two of $X^2$, $X^3$, $X^4$, $X^5$, $X^6$ and $X^7$ are $NR^4$.

15. The compound of embodiment 13, wherein $X^1$ is CH and one of $X^2$, $X^3$, $X^4$, $X^5$, $X^6$ and $X^7$ are $NR^4$.

16. The compound of embodiment 13, wherein $X^1$ is CH and none of $X^2$, $X^3$, $X^4$, $X^5$, $X^6$ and $X^7$ are $NR^4$.

17. The compound of embodiment 13, wherein $X^1$ is N and none of $X^2$, $X^3$, $X^4$, $X^5$, $X^6$ and $X^7$ are $NR^4$.

18. The compound of embodiment 13, wherein $X^1$ is N and one of $X^4$ or $X^5$ is $NR^4$.

19. A compound of the formula (VIII), (VIII)

or a pharmaceutically acceptable salt or ester thereof; wherein:

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, $NR^1R^2$, —$SR^2$, —$OR^2$, $R^3$, —W, -L-W, —$W^0$, or -L-N(R)—$W^0$;

in each and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl; or R⁴ may be —W, -L-W or -L-N(R)—W⁰;

each R is independently H or C1-C6 alkyl;

R⁷ is H and R⁸ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —NR⁷R⁸, R⁷ and R⁸ together with N may form an optionally substituted azacyclic ring, optionally containing an additional heteroatom selected from N, O and S as a ring member;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W⁰ is an optionally substituted 3-4 membered carbocyclic ring, or a C1-C6 alkyl group substituted with from 1 to 4 fluorine atoms.

20. The compound of embodiment 19, wherein R⁷ is H and R⁸ is a $C_{1-4}$ alkyl substituted with an optionally substituted aromatic heterocyclic ring.

21. The compound of embodiment 20, wherein the optionally substituted aromatic heterocyclic ring is selected from pyridine, pyrimidine, pyrazine, imidazole, pyrrolidine, and thiazole.

22. The compound of embodiment 19, wherein R⁷ and R⁸ together with N in —NR⁷R⁸ form an optionally substituted azacyclic ring selected from the group consisting of morpholine, thiomorpholine, piperidine or piperazine ring.

23. A compound of Formula (VII), (VII)

or a pharmaceutically acceptable salt or ester thereof;

A and V independently are H, halo, azido, —CN, —CF₃, —CONR¹R², —NR¹R², —SR², —OR², —R³, —W, -L-W, —W⁰, or -L-N(R)—W⁰;

each Q is independently halo, azido, —CN, —CF₃, —CONR¹R², —NR¹R², —SR², —OR², —R³, —W, -L-W, —W⁰, or -L-N(R)—W⁰;

in each —NR¹R², R¹ and R² together with N may form an optionally substituted azacyclic ring, optionally containing an additional heteroatom selected from N, O and S as a ring member;

R¹ is H or C1-C6 alkyl, optionally substituted with one or more halogens, or =O;

R² is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl; or R⁴ may be —W, -L-W or -L-N(R)—W⁰;

each R is independently H or C1-C6 alkyl;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and W⁰ is an optionally substituted 3-4 membered carbocyclic ring, or a C1-C6 alkyl group substituted with from 1 to 4 fluorine atoms.

24. The compound of embodiment 23, wherein A and V are independently H or halo.

25. The compound of embodiment 23 or 24, wherein R⁴ is H or C1-4 alkyl.

26. The compound of embodiment 23, 24, or 25 wherein m and n are each 0.

27. The compound of any one of embodiments 23-26, wherein p is 0 or 1,

28. The compound of any one of embodiments 23-27 having the structure:

or a pharmaceutically acceptable salt or ester thereof.

29. A compound selected from the group consisting of:

;

325
-continued
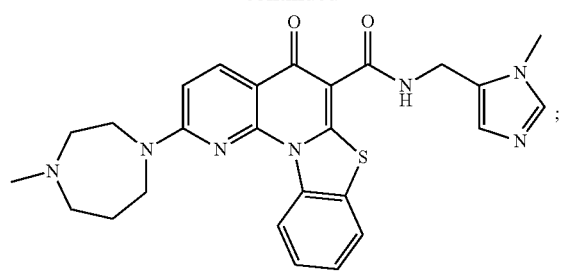
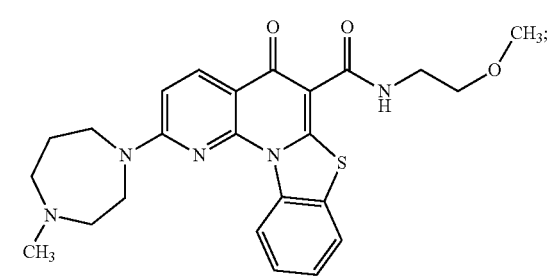
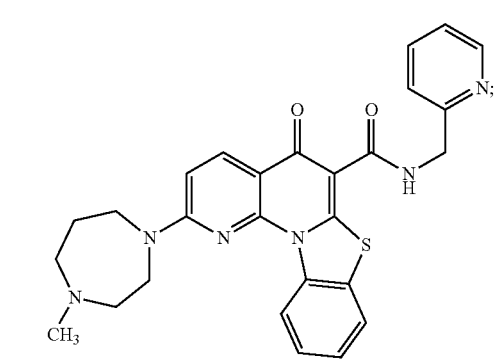
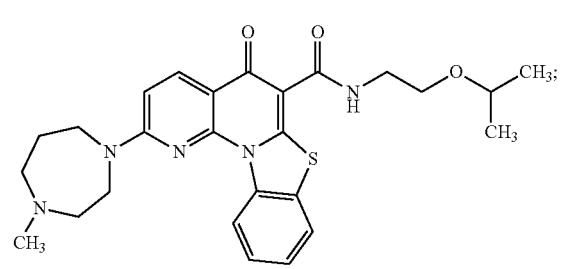
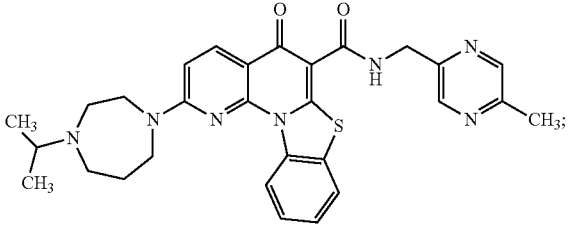
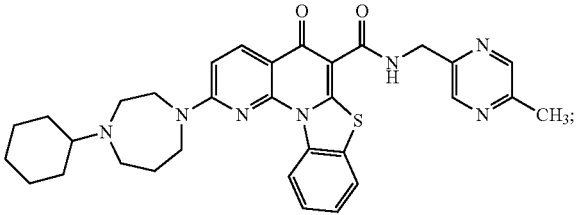
326
-continued
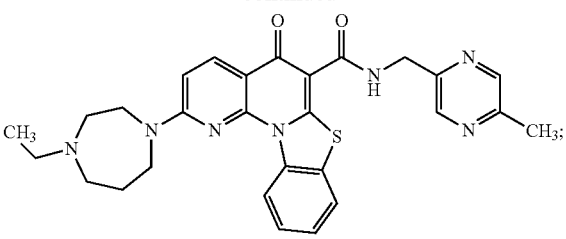
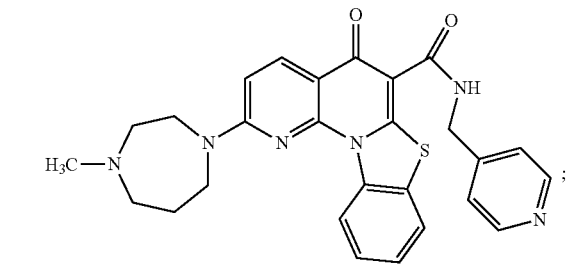
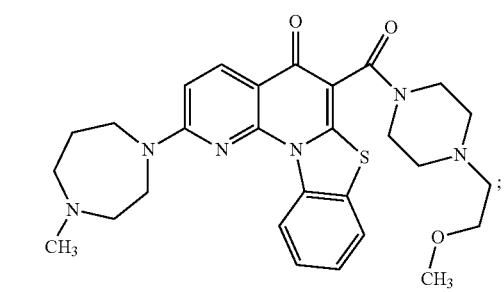
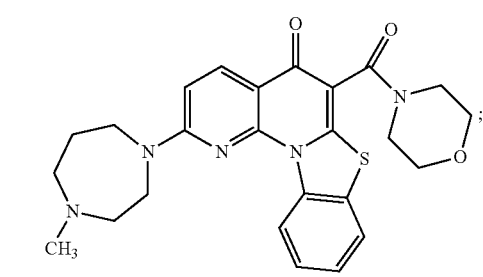
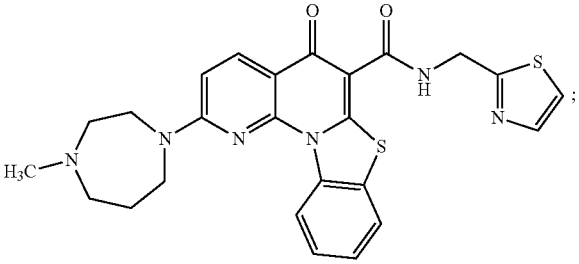
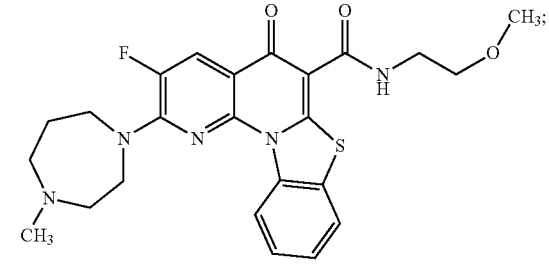

327
-continued

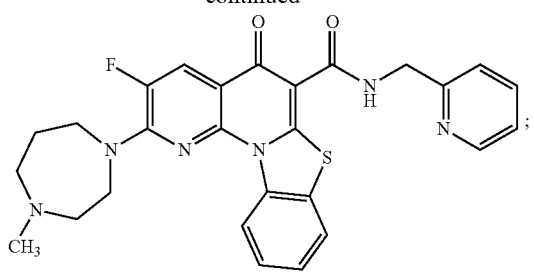

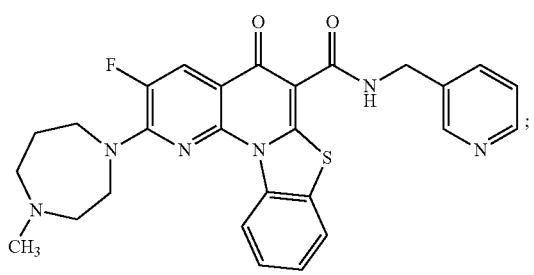

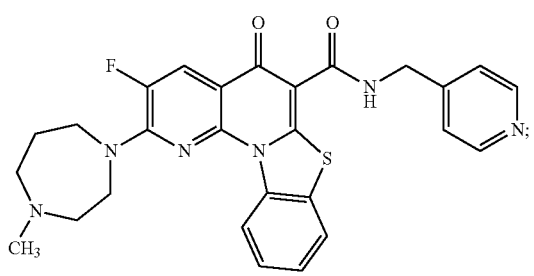

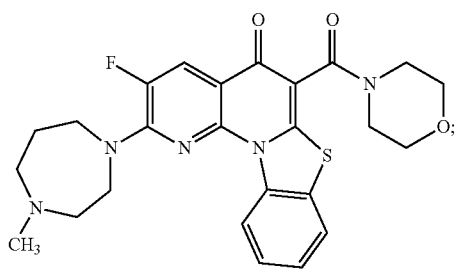

328
-continued

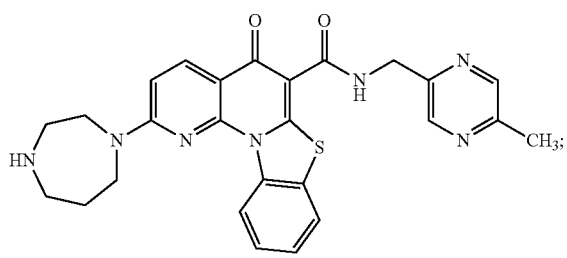

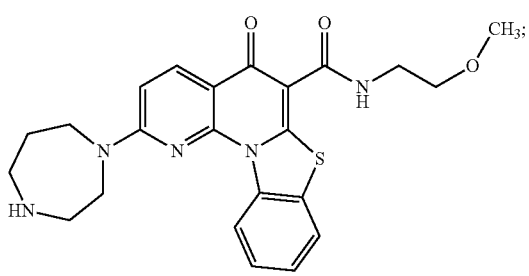

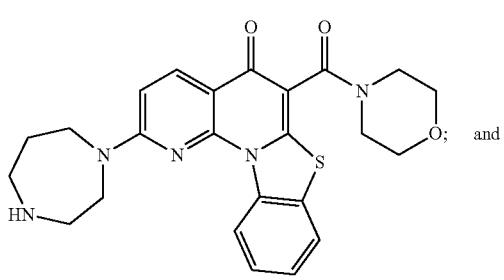

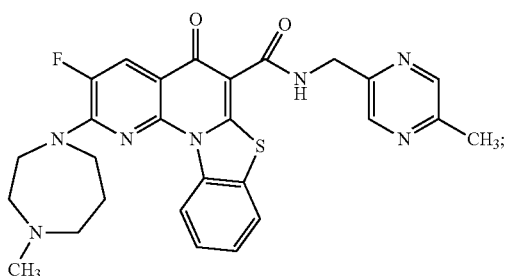

or a pharmaceutically acceptable salt or ester thereof.

30. A compound selected from the group consisting of the compounds in Tables 1-4, and 6-8, and in the Examples, or a pharmaceutically acceptable salt or ester thereof.

31. A pharmaceutical composition comprising a compound of any one of the preceding embodiments, or a pharmaceutically acceptable salt or ester thereof, and a pharmaceutically acceptable excipient.

32. A pharmaceutical composition comprising at least one compound of embodiment 19, or a pharmaceutically acceptable salt or ester thereof, and a pharmaceutically acceptable excipient.

33. A method for treating or ameliorating a cell proliferation disorder in a subject, said method comprising administering to a subject in need thereof a therapeutically effective amount of compound of Formula (I),

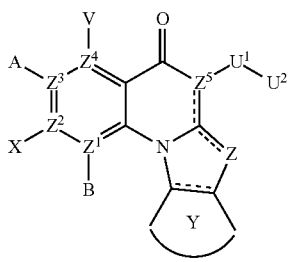

(I)

or a pharmaceutically acceptable salt or ester thereof;

wherein ---- indicates an optionally unsaturated bond; and

A, B, V, X, $Z^1$, $Z^2$, $Z^3$, $Z^4$, $Z^5$, $U^1$, $U^2$, Y and Z are defined as in embodiment 1;

thereby treating or ameliorating said cell proliferation disorder

34. A method for treating or ameliorating a cell proliferation disorder in a subject, said method comprising administering to a subject in need thereof a therapeutically effective amount of a compound of any one of embodiments 1-32; thereby treating or ameliorating a cell proliferation disorder.

35. A method for treating or ameliorating a cell proliferation disorder in a subject, said method comprising administering to a subject in need thereof a therapeutically effective amount of a compound of Formula (VIII),

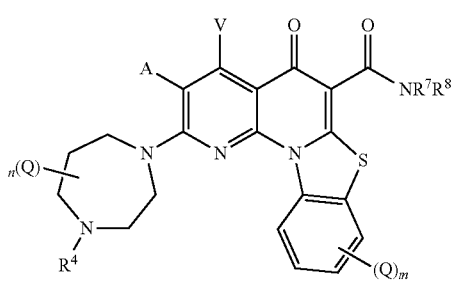

(VIII)

or a pharmaceutically acceptable salt or ester thereof;

wherein A, V, X, Q, m, n, p, $R^4$, $R^7$ and $R^8$ are defined as in embodiment 19;

thereby treating or ameliorating said cell proliferation disorder.

36. A method for treating or ameliorating a cell proliferation disorder in a subject, said method comprising administering to a subject in need thereof a therapeutically effective amount of a compound of any one of embodiments 1-32, thereby treating or ameliorating said cell proliferation disorder.

37. The method of any one of embodiments 33-36, wherein the subject is human.

38. A method for reducing microbial titers and/or ameliorating a microbial infection, comprising contacting a system or a subject in need thereof with an effective amount of a compound of Formula (I),

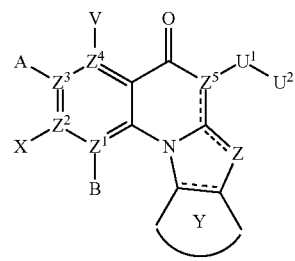

(I)

or a pharmaceutically acceptable salt or ester thereof;

wherein ---- indicates an optionally unsaturated bond; and

A, B, V, X, $Z^1$, $Z^2$, $Z^3$, $Z^4$, $Z^5$, $U^1$, $U^2$, Y and Z are defined as in embodiment 1;

thereby reducing microbial titers.

39. A method for reducing microbial titers and/or ameliorating a microbial infection, comprising contacting a system or a subject in need thereof with an effective amount of a compound of any one of embodiments 1-31, thereby reducing microbial titers.

40. The method of embodiment 38 or 39, wherein the system is a cell or tissue,

41. The method of embodiment 38, 39 or 40, wherein the microbial titers and/or microbial infection are viral, bacterial or fungal titers.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of" and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following aspects.

The invention claimed is:

1. A compound of Formula (I),

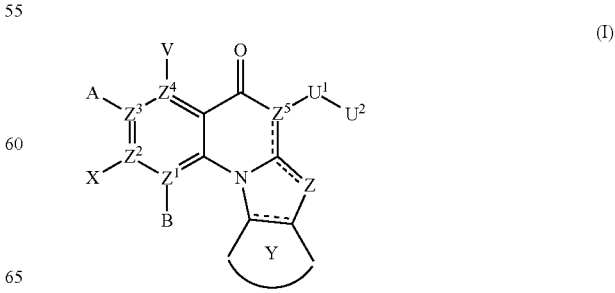

(I)

or a pharmaceutically acceptable salt or ester thereof;
wherein ----- indicates an optionally unsaturated bond;
each of B, X, A or V is absent if $Z^1$, $Z^2$, $Z^3$ and $Z^4$, respectively, is N; and
each of B, X, A and V is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$, when each of $Z^1$, $Z^2$, $Z^3$ and $Z^4$, respectively, is C;
Z is O, S, CR$^4_2$, CR$^4$NR$^4$, or CR$^4$;
each of $Z^1$, $Z^2$, $Z^3$ and $Z^4$ is independently C or N, provided any three N are non-adjacent;
$Z^5$ is C; or $Z^5$ may be N when Z is N;
Y is an optionally substituted 5-6 membered carbocyclic or heterocyclic ring;
$U^1$ is —C(=T)N(R)—, —C(=T)N(R)O—, or —C(=T)-, where T is O, S, or NH; or $U^1$ may be a bond when $Z^5$ is N or $U^2$ is H;
$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic; or $U^2$ is -L-W, -L-N(R)—W$^0$, or A$^2$;
in each —NR$^1$R$^2$, R$^1$ and R$^2$ together with N may form an optionally substituted azacyclic ring, optionally containing an additional heteroatom selected from N, O and S as a ring member;
$R^1$ is H or C1-C6 alkyl, optionally substituted with one or more halogens, or =O;
$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;
$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;
each $R^4$ is independently H, or C1-C6 alkyl; or $R^4$ may be —W, -L-W or -L-N(R)—W$^0$;
each R and R$^0$ is independently H or C1-C6 alkyl;
L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;
W is an optionally substituted 4-7 membered azacyclic ring, optionally containing an additional heteroatom selected from N, O and S as a ring member;
$W^0$ is an optionally substituted 3-4 membered carbocyclic ring, or a C1-C6 alkyl group substituted with from 1 to 4 fluorine atoms;
provided one of V, A, X and B is a secondary amine A$^2$ or a tertiary amine A$^3$, wherein
the secondary amine A$^2$ is —NH—W$^0$, and
the tertiary amine A$^3$ is a fully saturated and optionally substituted six-membered or seven-membered azacyclic ring optionally containing an additional heteroatom selected from N, O or S as a ring member, or the tertiary amine A$^3$ is a partially unsaturated or aromatic optionally substituted five-membered azacyclic ring, optionally containing an additional heteroatom selected from N, O or S as a ring member;
with the proviso that when $Z^1$ is N, $Z^2$ and $Z^4$ are C, $Z^5$ is C, $U^1$ is —C(O)NH—, $U^2$ is -L-W, and L is an ethylene linker, one of V, A, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

2. The compound of claim 1, wherein $Z^1$ is N, and each of $Z^2$, $Z^3$ and $Z^4$ is C.

3. The compound of claim 1, wherein $U^2$ is -L-W, where W is an optionally substituted 5-6 membered unsaturated or aromatic azacyclic ring, optionally containing an additional heteroatom selected from N, O and S; or W is an optionally substituted 5-7 membered saturated azacyclic ring containing an additional heteroatom selected from N and S.

4. The compound of claim 1, wherein $U^2$ is -L-N(R)—W$^0$.

5. The compound of claim 1, wherein Y is an optionally substituted phenyl ring.

6. A compound of Formula (II),

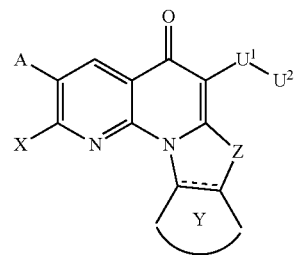

(II)

or a pharmaceutically acceptable salt or ester thereof;
wherein ----- indicates an optionally unsaturated bond;
each of A and X is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$;
Z is O, S, CR$^4_2$, NR$^4$CR$^4$, CR$^4$NR$^4$ or NR$^4$;
Y is an optionally substituted 5-6 membered carbocyclic or heterocyclic ring;
$U^1$ is —C(=T)N(R)—, —C(=T)N(R)O—, or —C(=T)-, where T is O, S, or NH; or $U^1$ may be a bond when $U^2$ is H;
$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic; or $U^2$ is -L-W, -L-N(R)—W$^0$, or A$^2$;
in each —NR$^1$R$^2$, R$^1$ and R$^2$ together with N may form an optionally substituted azacyclic ring, optionally containing an additional heteroatom selected from N, O and S as a ring member;
$R^1$ is H or C1-C6 alkyl, optionally substituted with one or more halogens, or =O;
$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl; or R⁴ may be —W, -L-W or -L-N(R)—W⁰;

each R and R⁰ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

W⁰ is an optionally substituted 3-4 membered carbocyclic ring, or a C1-C6 alkyl group substituted with from 1 to 4 fluorine atoms;

provided X is a secondary amine A² or a tertiary amine A³, wherein the secondary amine A² is —NH—W⁰, and the tertiary amine A³ is a fully saturated and optionally substituted six-membered or seven-membered azacyclic ring optionally containing an additional heteroatom selected from N, O or S as a ring member, or the tertiary amine A³ is a partially unsaturated or aromatic optionally substituted five-membered azacyclic ring optionally containing an additional heteroatom selected from N, O or S as a ring member;

with the proviso that when U¹ is —C(O)NH—, U² is -L-W, and L is an ethylene linker, one of A and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

7. The compound of claim 6, wherein at least one of A and X is a tertiary amine A³.

8. The compound of claim 7, wherein A³ is selected from the group consisting of imidazole, imidazoline, pyrroline, piperidine, piperazine, morpholine, thiomorpholine and homopiperazine.

9. The compound of claim 6, wherein U¹ is a —C(=T)N(R)—, T is O, and U² is -L-W or -L-N(R)—W⁰.

10. The compound of claim 6, which is selected from the group consisting of

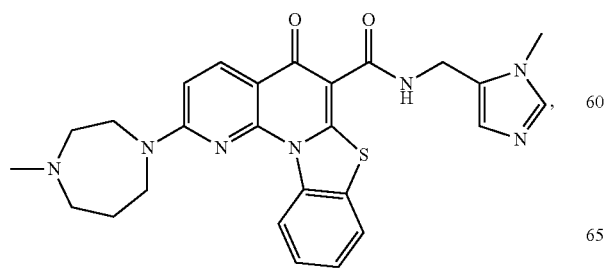

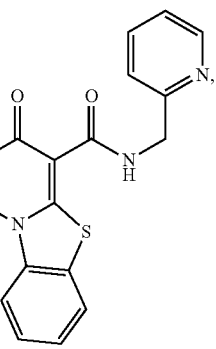

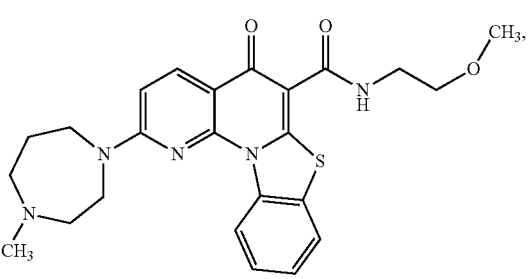

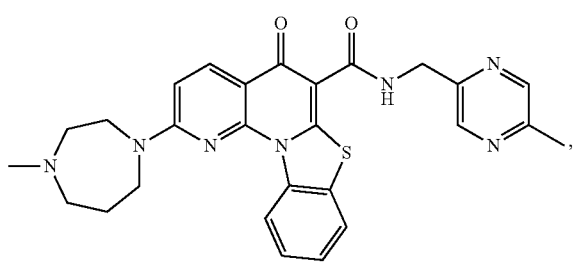

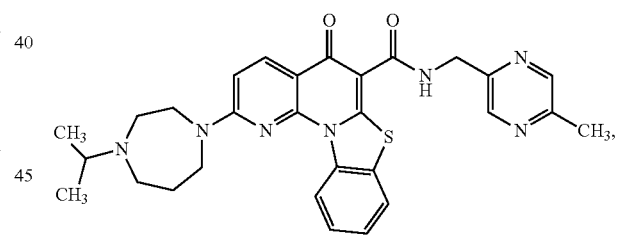

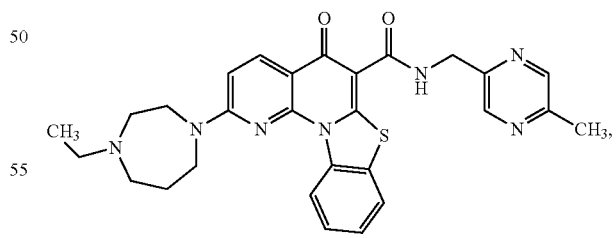

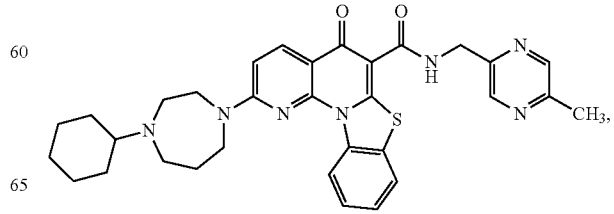

335
-continued
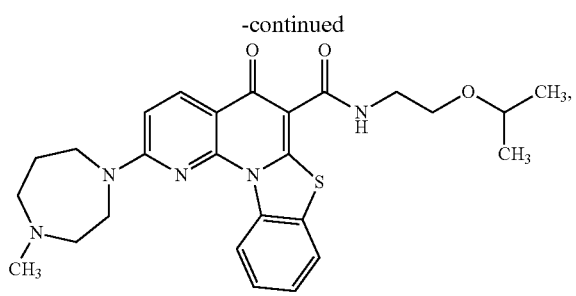
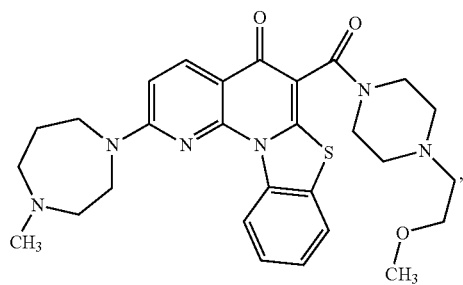
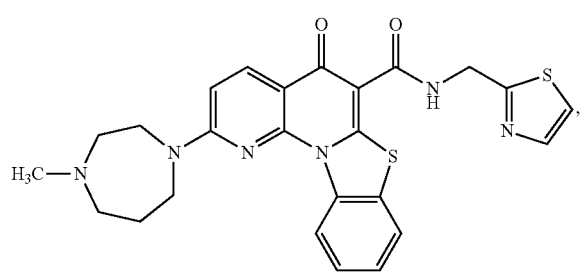
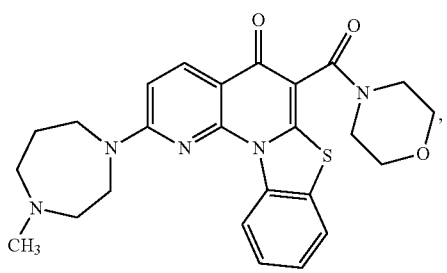
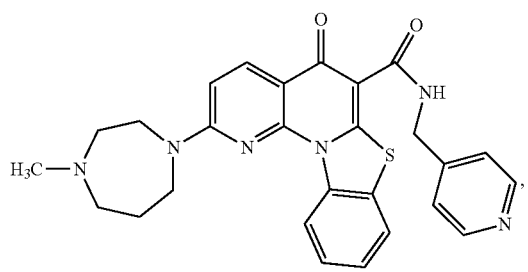
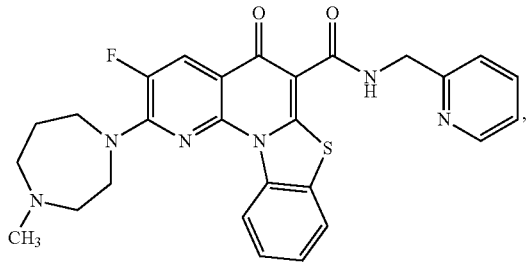
336
-continued
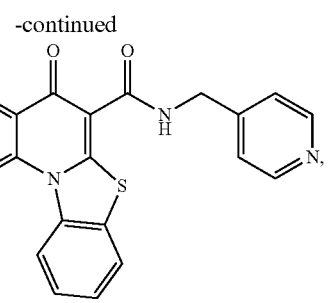
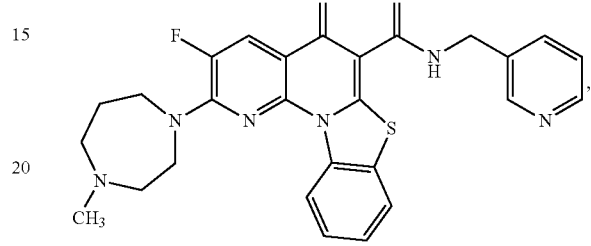
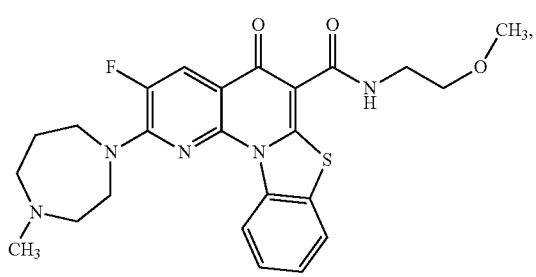
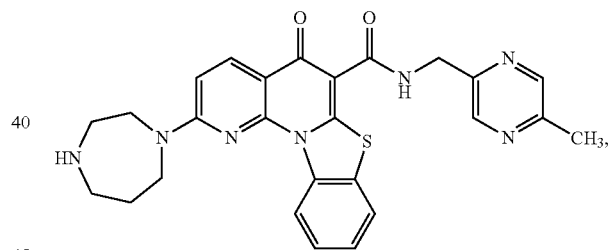
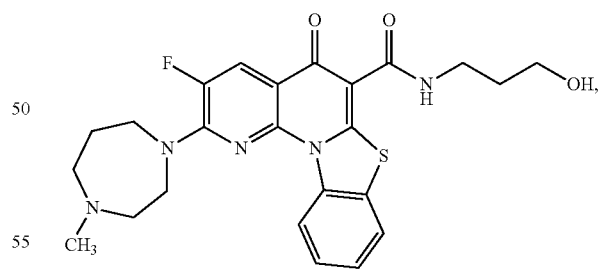
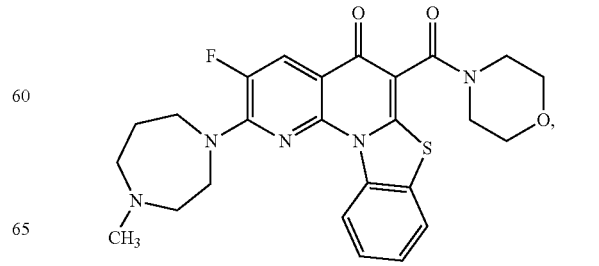

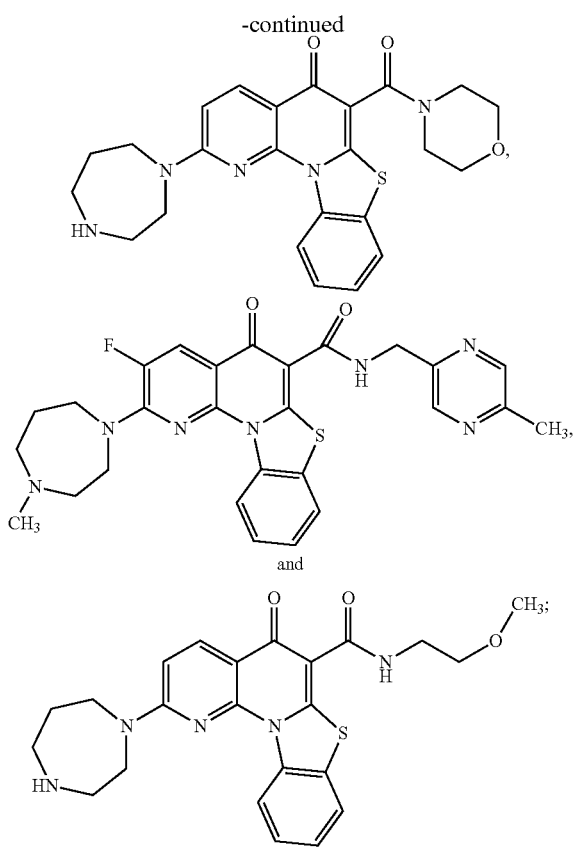

or a pharmaceutically acceptable salt or ester thereof.

11. A pharmaceutical composition comprising a compound of claim 1, or a pharmaceutically acceptable salt or ester thereof, and a pharmaceutically acceptable excipient.

12. The compound of claim 6, wherein X is —NR$^1$R$^2$, and R$^1$ and R$^2$ together with N may form an optionally substituted azacyclic ring, optionally containing an additional heteroatom selected from N, O and S as a ring member.

13. The compound of claim 12, wherein A is H or halo.

14. The compound of claim 13, wherein U$^1$ is a —C(=T)N(R)—, T is O, and R is H or C1-C6 alkyl.

15. The compound of claim 14, wherein U$^2$ is -L-W, where L is a C1-C10 alkylene, and W is an optionally substituted 5-6 membered unsaturated or aromatic azacyclic ring, optionally containing an additional heteroatom selected from N, O and S; or W is an optionally substituted 5-7 membered saturated azacyclic ring containing an additional heteroatom selected from N and S.

16. The compound of claim 15, wherein Z is S.

17. The compound of claim 16, wherein Y is an optionally substituted phenyl ring.

18. A pharmaceutical composition comprising a compound of claim 6, or a pharmaceutically acceptable salt or ester thereof, and a pharmaceutically acceptable excipient.

* * * * *